(12) United States Patent
Tuszynski et al.

(10) Patent No.: US 12,324,799 B2
(45) Date of Patent: Jun. 10, 2025

(54) METHODS AND USES OF COLCHICINE DERIVATIVES

(71) Applicants: Alberta Health Services, Edmonton (CA); Université Laval, Québec (CA)

(72) Inventors: Jack Tuszynski, Edmonton (CA); Maria Fernandes, Québec (CA)

(73) Assignees: Alberta Health Services, Edmonton (CA); Université Laval, Québec (CA)

( * ) Notice: Subject to any disclaimer, the term of this patent is extended or adjusted under 35 U.S.C. 154(b) by 991 days.

(21) Appl. No.: 17/255,414

(22) PCT Filed: Jun. 28, 2019

(86) PCT No.: PCT/CA2019/050903
§ 371 (c)(1),
(2) Date: Dec. 22, 2020

(87) PCT Pub. No.: WO2020/000109
PCT Pub. Date: Jan. 2, 2020

(65) Prior Publication Data
US 2021/0283092 A1    Sep. 16, 2021

Related U.S. Application Data

(60) Provisional application No. 62/691,807, filed on Jun. 29, 2018.

(51) Int. Cl.
*A61K 31/27* (2006.01)
*A61K 31/165* (2006.01)
(Continued)

(52) U.S. Cl.
CPC ............ *A61K 31/27* (2013.01); *A61K 31/165* (2013.01); *A61K 31/4406* (2013.01);
(Continued)

(58) Field of Classification Search
CPC .. A61K 31/165; A61K 31/27; A61K 31/4406; A61K 38/44; A61K 45/06;
(Continued)

(56) References Cited

U.S. PATENT DOCUMENTS 3,997,506 A    12/1976  Dugat
4,533,675 A    8/1985   Brossi et al.
(Continued)

FOREIGN PATENT DOCUMENTS

FR    1344474 A    11/1963
GB    763217 A     12/1956
(Continued)

OTHER PUBLICATIONS

Grivennikov et al. (Cell 140, 883-899, Mar. 19, 2010 (Year: 2010).*
(Continued)

*Primary Examiner* — Savitha M Rao
(74) *Attorney, Agent, or Firm* — Melissa M. Hayworth; E. Joseph Gess; Merchant & Gould, P.C.

(57) ABSTRACT

Colchicine derivative(s), method(s) and use(s) thereof for treatment of inflammation. In certain embodiments, the colchicine derivative is a compound of Formula I: (I)
(Continued)

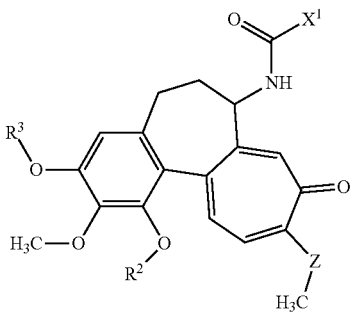

Formula I

22 Claims, 51 Drawing Sheets

(51) Int. Cl.
*A61K 31/4406* (2006.01)
*A61K 38/44* (2006.01)
*A61K 45/06* (2006.01)
*A61P 9/10* (2006.01)

(52) U.S. Cl.
CPC .............. *A61K 38/44* (2013.01); *A61K 45/06* (2013.01); *A61P 9/10* (2018.01)

(58) Field of Classification Search
CPC .. A61K 9/0019; A61K 9/0095; A61K 9/2018; A61K 9/4858; A61P 29/00; A61P 9/10; C07C 2603/34; C07C 323/41
See application file for complete search history.

(56) References Cited

U.S. PATENT DOCUMENTS

| | | | |
|---|---|---|---|
| 5,175,342 | A | 12/1992 | Brossi |
| 5,843,910 | A | 12/1998 | Bombardelli et al. |
| 5,880,160 | A | 3/1999 | Bombardelli et al. |
| 5,973,204 | A | 10/1999 | Bombardelli |
| 7,119,229 | B2 | 10/2006 | Kim et al. |
| 7,601,758 | B1 | 10/2009 | Davis |
| 7,619,004 | B1 | 11/2009 | Davis |
| 7,622,612 | B2 * | 11/2009 | Chang ................... C07C 49/755 564/162 |
| 7,820,681 | B1 | 10/2010 | Davis |
| 7,915,269 | B2 | 3/2011 | Davis |
| 7,964,647 | B2 | 6/2011 | Davis |
| 7,964,648 | B2 | 6/2011 | Davis |
| 7,981,938 | B2 | 7/2011 | Davis |
| 8,093,296 | B2 | 1/2012 | Davis |
| 8,093,297 | B2 | 1/2012 | Davis |
| 8,097,655 | B2 | 1/2012 | Davis |
| 8,415,395 | B1 | 4/2013 | Davis et al. |
| 8,415,396 | B1 | 4/2013 | Davis et al. |
| 8,440,721 | B2 | 5/2013 | Davis |
| 8,440,722 | B2 | 5/2013 | Davis |
| 8,927,760 | B2 | 1/2015 | Han et al. |
| 9,458,101 | B2 | 10/2016 | Tuszynski et al. |
| 2014/0037550 | A1 | 2/2014 | Davis et al. |
| 2014/0107213 | A1 | 4/2014 | Davis |

FOREIGN PATENT DOCUMENTS

| | | |
|---|---|---|
| JP | 0967326 A | 3/1997 |
| JP | H1121277 A | 1/1999 |
| JP | 2013502441 A | 1/2013 |
| KR | 101998081125 | 11/1998 |
| WO | 199611184 A1 | 4/1996 |
| WO | 199701570 A1 | 1/1997 |
| WO | 2004111068 A1 | 12/2004 |
| WO | 2004113281 A1 | 12/2004 |
| WO | 2005007076 A2 | 1/2005 |
| WO | 2011004980 A2 | 1/2011 |
| WO | 2011021397 A1 | 2/2011 |
| WO | 2011022805 A1 | 3/2011 |
| WO | 2011091114 A2 | 7/2011 |
| WO | 2013149109 A1 | 10/2013 |
| WO | 2014066944 A1 | 5/2014 |

OTHER PUBLICATIONS

Anderson et al. ( South African Journal of Science, vol. 110, No. 1 /2 2014, pp. 1-6) (Year: 2014).*
CA Office Action dated Jun. 8, 2023 issued in corresponding Canadian application No. 3,136,489.
EP Supplementary European Search Report dated Mar. 31, 2022 issued in corresponding EP application No. 19824855.1.
Sugio, K., et al., "Separation of tubulin-binding and anti-imflammatory activity in colchicine analogs and congeners", Life Science, vol. 40, No. 1, pp. 35-39 (1987).
Chia, E.W., et al., "Colchicine suppresses neutrophil superoxide production in a murine model of gouty arthritis: a rational for use of low-dose colchicine", British Jr. Pharmacology, vol. 153, No. 6, pp. 1288-1295 (2009).
Sharma Shubhada et al., "Characterization of the Colchicine Binding site on Avian Tubulin Isotype [beta]VI", Biochemistry, vol. 49, No. 13, pp. 2932-2942 (2010).
JP Office Action dated May 16, 2023 issued in corresponding JP application No. 2020-573412 with English Translation.
Dvorak, Zdenik, et al., "Cytotoxicity of colchicine derivatives in primary cultures of human hepatocytes", Biomedical Papers, 2007 151(1), pp. 475-2.
Ben-Chetrit, E., et al., "Mechanism of the anti-inflammatory effect of colchicine in rheumatic diseases: a possible new outlook through microarray analysis", Rheumatoloty(Oxford, United Kingdom) 2006, 45(3), pp. 274-2821.
Khan, I. A. et al., Different Effects of Vinblastine on the Polymerization of Isotypically Purified Tubulins From Bovine Brain, Invest. New Drugs, (2003), vol. 21, pp. 3-13.
Kim, K. Y, et al., A Literature Review of the Epidemiology and Treatment of Acute Gout, Clin Therap, (2003). vol. 25, pp. 1593-1617.
Kuo, C. F. et al., Global Epidemiology of Gout: Prevalence, Incidence and Risk Factors, Nature Reviews Rheumatology, (2015), vol. 11, pp. 649-662.
Laclette, J. P. et al., Inhibition of Tubulin Polymerization by Mebendazole, Biochem Biophys Res Commun., (1980), vol. 92, pp. 417-423.
Lagarde, F. et al., Non-Monotonic Dose-Response Relationships and Endocrine Disruptors: A Qualitative Method of Assessment, Environmental Health Source, (2015), vol. 14, pp. 1-15.
Leandro-Garcia, L. J. et al., Tumoral and Tissue-Specific Expression of the Major Human β-Tubulin Isotypes, Cytoskeleton (2010), vol. 67, pp. 214-223.
Lin, B. et al., Use of Colchicine in Atherosclerotic Heart Disease, Curr Res Integr Med., (2018), vol. 3, pp. 2-4.
Lindahl, F. et al., GROMACS 3.0: A Package for Molecular Simulation and Trajectory Analysis, J Mol. Model, (2001), vol. 7, pp. 306-317.
Löwe, J. et al., Refined Structure of αβ-Tubulin at 3.5 Å Resolution, J. Mol. Biol., (2001), vol. 313, pp. 1045-1057.
Lu, Q. et al., In Vitro Analysis of Microtubule Assembly of Isotypically Pure Tubulin Dimers, J. Biol. Chem., (1994), vol. 269, pp. 2041-2047.
Ludueña, R. F., Multiple Forms of Tubulin: Different Gene Products and Covalent Modifications, Int. Rev. Cytol., (1997), vol. 178, pp. 207-275.
Ludueña, R. F. et al., Interaction of Bovine Brain Tubulin with the 4(1H)-Pyrizinone Derivative IKP104, an Antimitotic Drug with a Complex Set of Effects on the Conformational Stability of the Tubulin Molecule, Biochem., (1995), vol. 34, pp. 15751-15759.

(56) References Cited

OTHER PUBLICATIONS

Martinon, F., Mechanisms of Uric Acid Crystal-Mediated Autoinflammation, Immunol Rev., (2010), vol. 233, pp. 218-232.
Mekori, Y. A. et al., Inhibition of Delayed Hypersensitivity Reactions in Mice by Colchicine, Cell. Immunol., (1989), vol. 120, pp. 330-340.
Minoura, I., Towards an Understanding of the Isotype-Specific Functions of Tubulin in Neurons: Technical Advances in Tubulin Expression and Purification, Neuroscience Research, (2017), vol. 122, pp. 1-8.
Mitroulis, I. et al., Neutrophil Extracellular Trap Formation is Associated with IL-1beta and Autophagy-Related Signaling in Gout, PLoS One, (2011), vol. 6(12), pp. 29318.
Mitroulis, I. et al., Neutrophils, IL-1beta, and Gout: Is there a link? Seminars in Immunopathology, (2013), vol. 35(4), pp. 501-512.
Muzaffar, A. et al., Antitubulin Effects of Derivatives of 3-Demethylthiocolchine, Methylthio Ethers of Natural Colchicinoids and Thioketones Derived from Thiocolchicine Comparison with Colchicinoida, J. Med. Chem., (1990), vol. 33, pp. 567-571.
Nair, A. B. et al., A Simple Practice Guide for Dose Conversion Between Animals and Human, J Basic Clin Pharma, (2016), vol. 7, pp. 27-31.
Nidorf, S. M. et al., Colchicine for Secondary Prevention of Cardiovascular Disease, Curr Atheroscler Rep., (2014), vol. 16:391, pp. 1-8.
Nidorf, S. M. et al., Why Colchicine Should Be Considered for Secondary Prevention of Atherosclerosis: An Overview, Clinical Therapeutics, (2019), vol. 41, pp. 41-48.
Nogales, E. et al., Structure of Tubulin at 6.5 Å and Location of the Taxol-Binding Site, Nature, (1995), vol. 375, pp. 424-427.
Owellen, R. J. et al., The Binding of Vincristine, Vinblastine and Colchicine to Tubulin, Biochem. Biophys. Res. Commun., (1972), vol. 47, pp. 685-691.
Pascart, T. et al., Gout: State of the Art After a Decade of Developments, Rheumatology, (2019), vol. 58, pp. 27-44.
Pascual, E. et al., Therapeutic Advances in Gout, Current Opinion in rheumatology, (2007), vol. 19, pp. 122-127.
Paul, B. D. et al., New Agents for Prostatic Cancer Activated Specifically by Prostatic Acid Phosphatase, Cancer Treatment Reports, (1977), vol. 61, pp. 259-263.
Phelps, P., Polymorphonuclear Leukocyte Motility In Vitro: IV. Colchicine Inhibition of Chemotactic Activity Formation After Phagocytosis of Urate Crystals, Arthritis Rheum., (2008), vol. 58, pp. S25-S33.
Pichichero, M. E. et al., The Evolution of Cellular Movement in Eukaryotes: The Role of Microfilaments and Microtubules, Sub-Cellular Biochemistry, (1973), vol. 2(1), pp. 97-105.
Popa-Nita, O. et al., Crystal-Induced Neutrophil Activation, Immunology and Cell Biology, (2010), vol. 88, pp. 32-40.
Popa-Nita, O. et al., Crystal-Induced Neutrophil Activation: X. Proinflammatory Role of the Tyrosine Kinase Tec. Arthritis Rheum, (2008), vol. 58(6), pp. 1866-1876.
Popa-Nita O. et al., Crystal-induced neutrophil activation. IX. Syk-dependent activation of class la phosphatidylinositol 3-kinase, Journal of leukocyte biology, (2007), vol. 82(3), pp. 763-773.
Ragab, G, et al., Gout: An Old Disease in New Perspective—A Review, Journal of Advanced Research, (2017), vol. 8 (5), pp. 495-511.
Ravanbakhsh, S. et al., Determination of the Optimal Tubulin Isotype Target as a Method for the Development of Individualized Cancer Chemotherapy, Theoretical Biology & Medical Modelling, (2013) vol. 10, pp. 1-18.
Ravelli, R. B. et al., Insight into Tubulin Regulation From a Complex with Colchicine and a Stathmin-Like Domain, Nature, (2004), vol. 428, pp. 198-202.
Richette, P. et al., Novel Drug Discovery Strategies for Gout, Expert Opin. Drug Discov., (2013), vol. 8, pp. 183-189.
Roach, M. C. et al., Preparation of Monoclonal Antibody Specific for the Class I Isotype of β-Tubulin: The β Isotypes of Tubulin Differ in Their Cellular Distributions Within Human Tissues, Cell Motil. Cytoskeleton, (1998), vol. 39, pp. 273-285.
Robinson, P. C., Gout—An Update of Aetiology, Genetics, Co-Morbidities and Management, Maturitas, (2018), vol. 118, pp. 67-73.
Rosenman, S. J. et al., Contact-Dependent Redistribution of Cell Surface Adhesion and Activation Molecules in Lymphocyte-Endothelial Cell Interactions Involves Cytoskeletal Reorganization, F.A.S.E.B. J., (1991), vol. 5, pp. 1603-1609.
Roubille, F. et al., Colchicine: An Old Wine in a New Bottle?, Anti-Inflammatory & Anti-Allergy Agents in Medicinal Chemistry, (2013), vol. 12, pp. 14-23.
Russell, G. J. et al., Inhibition of [3H]Mebendazole Binding to Tubulin by Structurally Diverse Microtubule Inhibitors which Interact at the Colchicine Binding Site, Biochem. Mol. Biol. Int., (1995), vol. 35, pp. 1153-1159.
Ryckman, C. et al., Role of S100A8 and S100A9 in Neutrophil Recruitment in Response to Monosodium Urate Monohydrate Crystals in the Air-Pouch Model of Acute Gouty Arthritis, Arthritis & Rheumatism, (2003), vol. 48, pp. 2310-2320.
Sackett, D. L. et al., Molecular Mechanism of Colchicine Action: Induced Local Unfolding of β-Tubulin, Biochemistry, (1993), vol. 32, pp. 13560-13565.
Schiff, P. B. et al., Promotion of Microtubule Assembly In Vitro by Taxol, Nature, (1979), vol. 277, pp. 665-667.
Schlesinger, N., Management of Acute and Chronic Gouty Arthritis: Present State-of-the-art, Drugs, (2004), vol. 21, pp. 2399-2416.
Schorn, C, et al., Monosodium Urate Crystals Induce Extracellular DNA Traps in Neutrophils, Eosinophils, and Basophils but not in Mononuclear Cells, Frontiers in Immunology, (2012), vol. 3, pp. 1-8.
Schwarz, P. M. et al., β-Tubulin Isotypes Purified from Bovine Brain Have Different Relative Stabilities, Biochem., (1998), vol. 37, pp. 4687-4692.
Scott, C. A. et al., β-Tubulin Epitope Expression in Normal and Malignant Epithelial Cells, Arch. Otolaryngol Head Neck Surg., (1990), vol. 116, pp. 583-589.
Seidemann, P. et al., Psoriatic Arthritis treated with Oral Colchicine, J. Rheumatol, (1987) vol. 14, pp. 777-779.
Seligman, A. M. et al., Design of Spindle Poisons Activated Specifically by Prostatic Acid Phosphatase (PAP) and New Methods for PAP Cytochemistry, Cancer Chemotherapy Report, (1975), Part 1, vol. 59, pp. 233-243.
"What is FMF?", Familial Mediterranean Fever Foundation, (2018) pp. 1-5, https://fmffoundation.org/do-you-have-fmf/.
Meyerhoff, J.O.,"Familial Mediterranean Fever Treatment & Management: Medical Care, Surgical Care, Consultations", Medscape, Apr. 7, 2020, pp. 1-3, https://emedicine.medscape.com/article/330284-treatment.
"Familial Mediterranean fever" Familial Mediterranean fever:MedlinePlus Genetics, National Institutes of Health/U.S. National Library of Medicine, Aug. 11, 2021, pp. 1-6, https://medlineplus.gov/genetics/condition/familial-mediterranean-fever.
Hikma Press Release; "Hikma to launch colchicine 0.6mg capsules", Jan. 12, 2015.
"Prasco and Takeda Enter into Agreement to Market Authorized Generic of Colcrys® (colchicine, USP) in the United States" Takeda Pharmaceuticals North America, Inc., Jan. 11, 2015, pp. 1-4 https://www.takeda.com/en-us/newsroom/news-releases/2015/prasco-and-takeda-enter-into-agreement-to-market--authorized-generic-of-colcrys-colch . . . .
"Key points from the evidence", National Institute for Health and Care Excellence, 2013.
Gaffo, A.G., "Treatment of gout flares" Up to Date, 2021, pp. 1-33, https://www.uptodate.com/contents/treatment-of-gout-flares.
CymaBay Press Release, "CymaBay Therapeutics Announces Successful Completion of Scientific Advice Discussions with the European Medicines Agency for Arhalofenate", Jan. 5, 2017, pp. 1-3 https://ir.cymabay.com/press-releases/detail/390/cymabay-therapeutics-announces-successful-completion-of-scientific-advice-discussions-with-the-eur . . . .

(56) References Cited

OTHER PUBLICATIONS

CAS Registry, ACS on STN, "Acetamide, N-[(7S)-5,6,7,9-tetrahydro-1,2, 10-trimethoxy-9-oxo-3-propoxybenzo[a] heptalen-7-yl]-CN Colchicine, 3-demethyl-O-propyl-".
CAS Registry, ACS on STN, "Acetamide, N-[(7R)-5,6,7,9-tetrahydro-1,2,3-trimethoxy-9-oxo-10-propoxybenzo[a] heptalen-7-yl]".
Abdellatif et al. Management of Gouty Arthritis in Patients with Chronic Kidney Disease, American Journal of Therapeutics, (2014), vol. 21, pp. 523-534.
Alam, A. et al., Applying Linear Interaction Energy Method for Binding Affinity Calculations of Podophyllotoxin Analogues With Tubulin Using Continuum Solvent Model and Prediction of Cytotoxic Activity, Journal of Molecular Graphics and Modelling, (2009), vol. 29, pp. 930-943.
Andreu, J. M. et al., Conformational States of Tubulin Liganded to Colchicine, Tropolone Methyl Ether, and Podophyllotoxin, Biochemistry, (1982), vol. 21, pp. 6465-6476.
Bai, R. et al., Dolastation 10, A Powerful Cytostatic Peptide Derived From a Marine Animal (Inhibition of Tubulin Polymerization Mediated Through the Vinca Alkaloid Binding Domain, Biochem. Pharmacol., (1990), vol. 39, pp. 1941-1949.
Banerjee, A. et al., Kinetics of Colchicine Binding to Purified β-Tubulin Isotypes From Bovine Brain, J. Biol. Chem., (1992), vol. 267, pp. 13335-13339.
Baneljee, A. et al., A Monoclonal Antibody Against the Type II Isotype of β-Tubulin, J. Biol. Chem., (1988), vol. 263, pp. 3029-3034.
Banerjee, A., Increased Levels of Tyrosinated α-, βIII-, and βIV-Tubulin Isotypes in Paclitaxel-Resistant MCF-7 Breast Cancer Cells, Biochem. Biophys. Res. Commun., (2002), vol. 293, pp. 598-601.
Bartusik, D., et al., Derivatives of Thiocolchicine and its Applications to CEM Cells Treatment Using 19F Magnetic Resonance ex vivo, Bioorg Chem., (2010), vol. 28, pp. 1-6.
Bartusik, D., et al., The Efficacy of New Colchicine Derivatives and Viability of the T-Lymphoblastoid Cells in Three-Dimensional Culture Using 19F MRI and HPLC-UV Ex Vivo, Bioorg Chem., (2009), vol. 37, pp. 193-201.
Ben-Chetrit, E. et al., Does the Lack of the p. Glycoprotein Efflux Pump in Neutrophils Explain the Efficacy of Colchicine in Familial Mediterranean Fever and Other Inflammatory Diseases?, Medical hypotheses, (1998), vol. 51 (5), pp. 377-380.
Bollag, D. M. et al., Epothilones, A New Class of Microtubule-Stabilizing Agents With a Taxol-Like Mechanism of Action, Cancer Res., (1995), vol. 55, pp. 2325-2333.
Borisy, G. O. et al., The Mechanism of Action of Colchicine (Colchicine Binding to Sea Urchin Eggs and the Mitotic Apparatus), J. Cell. Biol., (1967), vol. 34, pp. 535-548.
Borisy, G. O. et al., The Mechanism of Action of Colchicine (Binding of Colchincine-3H to Cellular Protein), J. Cell. Biol., (1967), vol. 34, pp. 525-533.
Brooks, B. R. et al., CHARMM: The Biomolecular Simulation Program. J. Comput. Chem., (2009), vol. 30, pp. 1546-1614.
Busso, N, et al., Mechanisms of Inflammation in Gout, Arthritis Res Ther., (2010), vol. 12, pp. 1-8.
Callen, J. P., Colchicine is Effective in Controlling Chronic Cutaneous Leukocytoclastic Vasculitis; J. Am. Acad. Dermatol., (1985), vol. 13, pp. 193-200.
Chappey, O. N. et al., Colchicine Disposition in Human Leukocytes After Single and Multiple Oral Administration, Clinical Pharmacology and Therapeutics, (1993), vol. 54, pp. 360-367.
Chatfield, S. M. et al., Monosodium Urate Crystals Generate Nuclease-Resistant Neutrophil Extracellular Traps via a Distinct Molecular Pathway, J Immunol, (2018), vol. 200, pp. 1802-1816.
Chaudhuri, A. R. et al., The Interaction of the B-Ring of Colchicine with α-Tubulin : A Novel Footprinting Approach, J. Mol. Biol., (2000), vol. 303,pp. 679-692.

Chia, E. W. et al., Colchicine Suppresses Neutrophil Superoxide Production in a Murine Model of Gouty Arthritis: A Rationale for use of Low-Dose Colchicine, British Journal of Pharmacology, (2008), vol. 153, pp. 1288-1295.
Cifuentes, M. et al., Synthesis and Biological Evaluation of B-Ring Modified Colchicine and Isocolchicine Analogs, Bioorganic and Medicinal Chemistry Letters, (2006), vol. 16, pp. 2761-2764.
Cragg, G. M. et al., Anticancer Agents from Natural Products— Introduction, Taylor & Francis Group and CRC Press, (2005) pp. 1, 6-8.
Cronstein, B. N. et al., Colchicine Alters the Quantitative and Qualitative Display of Selectins on Endothelial Cells and Neutrophils, The Journal of Clinical Investigation, (1995), vol. 96, pp. 994-1002.
Cronstein, B. N. et al., Mechanistic Aspects of Inflammation and Clinical Management of Inflammation in Acute Gouty Arthritis, J Clin Rheumatol, (2013), vol. 19, pp. 19-29.
Cucchiarelli, V. et al., β-Tubulin Isotype Classes II and V Expression Patterns in Nonsmall Cell Lung Carcinomas, Cell Motil. Cytoskeleton, (2008), vol. 65, pp. 675-685.
Daniel et al., Attempted Oxidative Deamination of N-Deacetylcolchicinoids With 3,5-Di(Tert-Butyl)-1,2-Benzoquinone: Synthesis of 2H-1,4-Benzoxazine-Type Adducts, Helvetica Chimica Acta, (1999), vol. 82, pp. 7.
Delano, W. L., The PyMOL Molecular Graphics System, (2002)—https://pymol.org/2/.
Ducray, P. et al., Synthesis of Lipid Derivatives of Colchicine, Helvetica Chimica Acta, (1996), vol. 79, pp. 2346-2352.
Dumont, R. et al., A Novel Synthesis of Colchicide and Analogs from Thiocolchicine and Congeners; Reevaluation of Colchicde as a Potential Antitumor Agent, Journal of Medical Chemistry, (1987), vol. 30, pp. 732-735.
Eddy, R. J. et al., Microtubule Asymmetry During Neutrophil Polarization and Migration, Mol Biol Cell, (2002), vol. 13 (12), pp. 4470-4483.
Edwards, J. C. et al., The Formation of a Structure with the Features of Synovial Lining by Subcutaneous Injection of Air: an In Vivo Tissue Culture System, The Journal of Pathology, (1981), vol. 134, pp. 147-156.
Fellous, A., et al., Microtubule Assembly In Vitro, Purification of Assembly-Promoting Factors, Eur. J. Biochem., (1977). vol. 78, pp. 167-174.
Finkelstein, Y. et al., Colchicine Poisoning: The Dart Side of an Ancient Drug, Clinical Toxicology, (2010), vol. 48, pp. 407-414.
Garland, D. L., Kinetics and Mechanism of Colchicine Binding to Tubulin: Evidence for Ligand-Induced Conformational Change, Biochemistry, (1978), vol. 17, pp. 4266-4272.
Gelmi, M. I., N-Deacetyl-N-Aminoacylthiocolchicine Derivatives: Synthesis and biological Evaulation on MDR-Positive and MDR-Negative Human Cancer Cell Lines, J. Med. Chem., (1999), vol. 42, pp. 5272-5276.
Gigant, B. et al., Structural Basis for the Regulation of Tubulin by Vinblastine, Nature, (2005) vol. 435, pp. 519-522.
Harold L., New Developments iIn Gout, Curr Opin Rheumatol, (2013) vol. 25, pp. 304-309.
Hartwig, H. et al., Neutrophils in Atherosclerosis, Hämostaseologie, (2015), vol. 35, pp. 121-127.
Hoebeke, J. et al., Interaction of Onocodazole (R 17934), A New Anti-Tumoral Drug, With Rat Brain Tubulin, Biochem Biophys. Res. Commun., (1976), vol. 69, pp. 319-324.
Huzil, J. T. et al., Comparative Modelling of Human β Tubulin Isotypes and Implications for Drug Binding, Nanotechnology, (2006), vol. 17, pp. S90-S100.
Huzil, J. T. et al., Computer Assisted Design of Second-Generation Colchicine Derivatives, Interdiscip Sci Comput Life Sci., (2010) vol. 2; pp. 169-174.
Huzil, J. T. et al., The Roles of β-Tubulin Mutations and Isotype Expression in Acquired Drug Resistance, Cancer Informatics, (2007), vol. 3, pp. 159-181.
Hyams, J. S. et al., The Mechanism of Microtubule Associated Cytoplasmic Transport. Isolation and Preliminary Characterisation of a Microtubule Transport System, Cell and Tissue Research, (1979), vol. 196, pp. 103-116.

(56) References Cited

OTHER PUBLICATIONS

Janke, C., The Tubulin Code: Molecular Components, Readout Mechanisms, and Functions, The Journal of Cell Biology, (2014), vol. 206, pp. 461-472.
Johnson, L. et al., Novel Colchicine Derivatives and their Anticancer Activity, Current Topics in Medicinal Chemistry, (2017), vol. 17, pp. 2538-2558.
Katsetos, C. D. et al., Differential Distribution of the Neuron-Associated Class III β-Tubulin in Neuroendocrine Lung Tumors, Arch. Pathol. Lab. Med., (2000), vol. 124, pp. 535-544.
Katsetos, C. D. et al., Class III β-Tubulin Isotype: A Key Cytoskeletal Protein at the Crossroads of Developmental Neurobiology and Tumor Neuropathology, J. Child Neurol., (2003), vol. 18, pp. 851-866.
Kavallaris, M. et al., Taxol-Resistant Epithelial Ovarian Tumors are Assoicated with Altered Expression of Specific β-Tubulin Isotypes, J. Clin. Invest., (1997), vol. 100, pp. 1282-1293.
Keenan, R. T. et al., Prevalence of Contraindications and Prescription of Pharmacologic Therapies for Gout, The American Journal of Medicine, (2011), vol. 124, pp. 155-163.
Kerekes, P. et al., Synthesis and Biological Effects of Novel Thiocolchicines. 3. Evaluation of N-Acyldeacetylthiocolchicines, N-(Alkoxycarbonyl) Deacetylthiocolchicines, and O-Ethyldemethylthiocolchicines. New Synthesis of Thiodemecolcine and Antileukemic Effects of 2-Demethyl- and 3-Demethylthiocolchicine, J Med Chem, (1985), vol. 28, pp. 1204-1208.
Tseng, C-Y, et al., "Quantitative analysis of the effect of tubulin isotype expression on sensitivity of cancer cell lines to a set of novel colchicine derivative", Molecular Cancer, 2010, v 9:131, pp. 1/19-19/19.
Darestani, et al., "Screening Anti-Cancer Drugs Against Tubulin", J. Am. Soc. Mass Spectrum, 2016, v. 27, pp. 876-885.
Huzil, et al., "Computational Design and Biological Testing of Highly Cytotoxic Coldhicine Ring A Modification", Chem. Biol. Drug. Des., 2010, v. 75, pp. 541-550.
Mane, et al., "Experimental and Computational study of the Interaction of Novel Colchicinoids with a Recombinant Human αI/βI-Tubulin Heterodimer", Chem. Biol. Drug. Des., 2013, V. 82, pp. 60-70.
Mane, et al., "Free-Energy Calculations on the Binding of Colchicine and Its Derivatives with α/β-Tubulin Isoforms", J. Chem. Inf. Model, 2008, v. 48, pp. 1824-1832.
International Preliminary Report on Patentability mailed Jan. 7, 2021 issued in PCT/CA2019/050903.
International Search Report mailed Aug. 20, 2019 issued in PCT/CA2019/050903.
Seth, R. et al., Preventing Attacks of Acute Gout When Introducing Urate-Lowering Therapy: A Systematic Literature Review; J Rheumatol Suppl.,(2014), vol. 92, pp. 42-47.
Seth, A. K. et al, Excisional Wound Healing is Delayed in a Murine Model of Chronic Kidney Disease, PLOS One, (2013), vol. 8, pp. 1-10.
Shapiro, M. D. et al., From Lipids to Inflammation, Circulation Research, (2016), vol. 118, pp. 732-749.
Singh, J. A., Gout and Comorbidity: A Nominal Group Study of People with Gout, Arthritis Res Ther., (2017), vol. 19, pp. 204.
Slobodnick et al., Colchicine: Old and New, The American Journal of Medicine, (2015), vol. 128, pp. 461-470.
Spasevska, I. et al., Modeling the Colchicum Autumnale Tubulin and a Comparison of Its Interaction with Colchicine to Human Tubulin, International Journal of Molecular Sciences, (2017), vol. 18, pp. 1-14.
Tahir, S. K., Rapid Colchicine Competition-Binding Scintillation Proximity Assay Using Biotin-Labeled Tubulin, Biotechniques, (2000), vol. 29, pp. 156-160.
Terkeltaub, R., Colchicine, Colchicine Update: (2008), pp. 411-419.
Tommasi, S. et al., Cytoskeleton and Paclitaxel Sensitivity in Breast Cancer: The role of β-Tubulins, Int. J. Cancer, (2007), vol. 120, pp. 2078-2085.
Tran, T. H. et al., Role of Interleukin-1 Inhibitors in the Management of Gout, Pharmacotherapy, (2013), vol. 33, pp. 744-753.
Vandenberg, L. N. et al., Hormones and Endocrine-Disrupting Chemicals: Low-Dose Effects and Nonmonotonic Dose Responses, Endocrine Reviews, (2012), vol. 33, pp. 378-455.
Vilar, et al., Probalistic Neutral Network Model for the in Silico Evaluation of Anti-HIV Activity and Mechanism of Action, J. Med. Chem., (2006), vol. 49, pp. 1118-1124.
Walterova et al., Circular Dichroic Spectra and Ionization Processes of Some Tropolonic Alkaloids, Heterocycles, (1987), vol. 25, pp. 9.
Weaver, A. L., Epidemiology of Gout, Cleveland Clinic Journal of Medicine, (2008), vol. 75, pp. S9-S12.
White, W. B. et al., Cardiovascular Safety of Febuxostat or Allopurinol in Patients with Gout, The New England Journal of Medicine, (2018), vol. 378, pp. 1200-1210.
Wu, E. Q. et al., Disease-Related and All-Cause Health Care Costs of Elderly Patients with Gout, J Manag Care Pharm, (2008), vol. 14, pp. 164-175.
Wu, G. et al., Detailed Analysis of Grid-Based Molecular Docking: A Case Study of CDOCKER—A CHARMm-Based MD Docking Algorithm, J. Comput Chem., (2003), vol. 24, pp. 1549-1562.
Xu, K. et al., Interaction of Nocodazole With Tubulin Isotypes, Drug Development Research, (2002), vol. 55, pp. 91-96.
Xu, J. et al., Neutrophil Microtubules Suppress Polarity and Enhance Directional Migration, Proceedings of the National Academy of Sciences of the United States of America, (2005), vol. 102, pp. 6884-6889.
Zhao, C. et al., TNF-α Promotes LPA1- and LPA3-Mediated Recruitment of Leukocytes In Vivo Through CXCR2 Ligand Chemokines, Journal of Lipid Research, (2011), vol. 52, pp. 1307-1318.
Zhu, Y, et al., Prevalence of Gout and Hyperuricemia in the US General Population: The National Health and Nutrition Examination Survey 2007-2008, Arthritis & Rheumatism, (2011), vol. 63, pp. 3136-3141.
Invitation Pursuant to Rule 62(a) EPC and Rule 63(1) EPC from European Application No. 10 811 047.9-1211 dated Dec 6. 2012.
Extended European Search Report from European Application No. 10 811 047.9-1211 dated Feb. 22, 2013.
International Search Report dated Nov. 2, 2010 in counterpart International Application No. PCT/CA2010/001199.
Japanese Office Action (with English Translation) dated Aug. 15, 2014, corresponding to Japanese Application No. 2012-525826.
Australian Examination Report dated Mar. 25, 2024 issued in corresponding application for AU 2019295499, 6 pgs.
Wikipedia, Colchicine, published Jun. 24, 2018, <URL: https://en.wikipedia.org/w/index.php?title=Colchicine&oldid=847278692>; 17 pgs.
Dastoli, S., et al., "Colchicine in Managing Skin Conditions: A Systematic Review", Pharmaceutics, 2022, 14, 294; https://doi.org/10.3390/pharmaceutics14020294; 23 pgs.
Welzel, T., et al., "Colchicine—An Effective Treatment for Children with a Clinical Diagnosis of Autoinflammatory Diseases Without Pathogenic Gene Variants", Pediatric Rheumatology, (2021), 19:142; https://doi.org/10.1186/s12969-021-00588-0; 11 pgs.
Korean Office Action dated Mar. 14, 2024 issued in corresponding application KR 10-2021-7002821 and English-language Translation thereof, 12 pgs.
Yuan, X., et al., "Colchicine Alleviates Rosacea by Inhibiting Neutrophil Inflammation Activated by the TLR2 Pathway", Inflammation, Published Online Jan. 17, 2024, https://doi.org/10.1007/s10753-023-01956-6; 13 pgs.
Australian Examination Report No. 2 for corresponding application No. AU 2019295499, dated Sep. 13, 2024, 3 pgs.
Canadian Office Action for corresponding application No. CA 3,136,489, dated Oct. 21, 2024, 8 pgs.
J. T. Huzil, et al., "Computational Design and Biological Testing of Highly Cytotoxic Colchicine Ring A Modifications", Chem. Biol. Drug Des, 2010; 75; pp. 541-550.
R. Anderson, et al., "Inflammation and Cancer: The Role of the Human Neutrophil", Neutrophils and Cancer, South African Journal of Science; http://www.sajs.co.za; 2014; vol. 110; No. 1/2; 6 pgs.

(56) References Cited

OTHER PUBLICATIONS

Buckland, "The NET is closing in on inflammation in Gout", Nature Reviews Rheumatology; doi: 10.1038/nrrheum.2014.74; vol. 10, 319; 2014; 1 page.
A. Mantovani, et al., "Neutrophils in the Activation and Regulation of Innate and Adaptive Immunity", Nature Reviews; Immunology; www.nature.com/reviews/immunol; vol. 11; Aug. 2011; pp. 519-531.
Original Korean Decision to Refusal for corresponding application No. KR 10-2021-7002821, dated Nov. 26, 2024, 8 pgs.
English-language Translation of Korean Decision to Refusal for corresponding application No. KR 10-2021-7002821, dated Nov. 26, 2024, 8 pgs.

* cited by examiner (4) R = CH₂CH₃

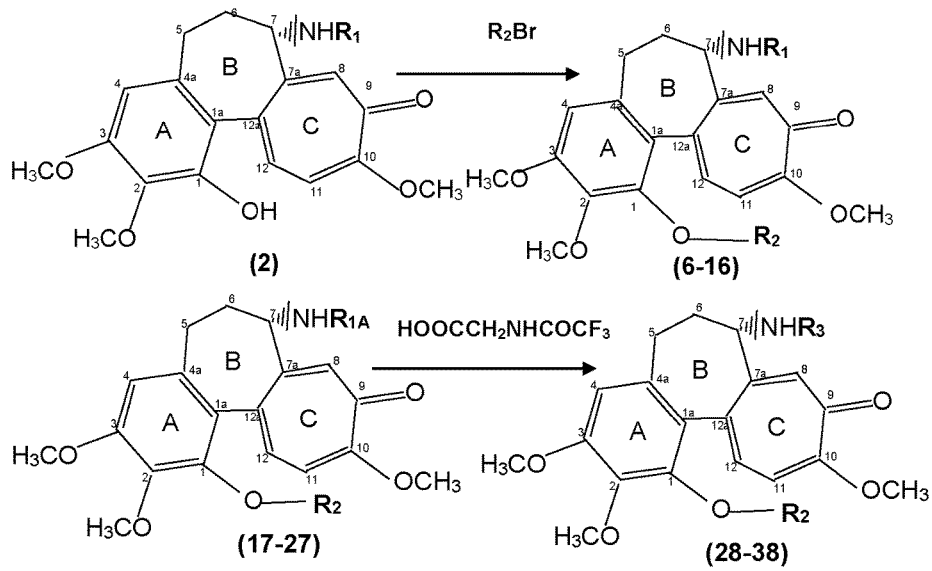

| (6) $R_2= CH_2CH_3; R_1= COCH_3$ | (15) $R_2 = CH_2(C_6H_4)$-p-Cl; $R_1= COCH_3$ | (27) $R_2 = CH_2(C_6H_{11}); R_{1A} = H$ |
|---|---|---|
| (6a) $R_2= CH_3; R_1= COCH_3$ | (16) $R_2 = CH_2(C_6H_{11}); R_1= COCH_3$ | (28) $R_2= CH_2CH_3; R_3= COCH_2NHCOCF_3$ |
| (7) $R_2 = CH(CH_3)_2; R_1= COCH_3$ | (17) $R_2= CH_2CH_3; R_{1A}=H$ | (28a) $R_2= CH_3; R_3= COCH_2NHCOCF_3$ |
| (7a) $R_2 = CH_2CH(CH_3)_2; R_1= COCH_3$ | (17a) $R_2= CH_3; R_{1A}=H$ | (29) $R_2 = CH(CH_3)_2; R_3= COCH_2NHCOCF_3$ |
| (7b) $R_2 = CH_2(CH_2)_2CH_3; R_1= COCH_3$ | (18) $R_2 = CH(CH_3)_2; R_{1A} =H$ | (30) $R_2 = (CH_2)_2CH_3; R_3= COCH_2NHCOCF_3$ |
| (7c) $R_2 = CH_2CH_2CH=CH_2; R_1= COCH_3$ | (19) $R_2 = (CH_2)_2CH_3; R_{1A} =H$ | (31) $R_2 = CH_2CH=CH_2; R_3= COCH_2NHCOCF_3$ |
| (8) $R_2 = (CH_2)_2CH_3; R_1= COCH_3$ | (20) $R_2 = CH_2CH=CH_2; R_{1A} =H$ | (32) $R_2 = CH_2(C_6H_5); R_3= COCH_2NHCOCF_3$ |
| (9) $R_2 = CH_2CH=CH_2; R_1= COCH_3$ | (21) $R_2 = CH_2(C_6H_5); R_{1A} =H$ | (33) $R_2 = CH_2CH_2OCH_3;; R_3= COCH_2NHCOCF_3$ |
| (10) $R_2 = CH_2(C_6H_5); R_1= COCH_3$ | (22) $R_2 = CH_2CH_2OCH_3;; R_{1A} =H$ | (34) $R_2 = CH_2(C_6H_4)$-m-Cl; $R_3= COCH_2NHCOCF_3$ |
| (11) $R_2 = CH_2CH_2OCH_3; R_1= COCH_3$ | (23) $R_2 = CH_2(C_6H_4)$-m-Cl; $R_{1A} =H$ | (35) $R_2=CH_2(C_5H_4N); R_3= COCH_2NHCOCF_3$ |
| (12) $R_2 = CH_2(C_6H_4)$-m-Cl; $R_1= COCH_3$ | (24) $R_2= CH_2(C_5H_4N); R_{1A} =H$ | (36) $R_2= CH_2(C_6H_4)$-o-Cl; $R_3= COCH_2NHCOCF_3$ |
| (13) $R_2 = CH_2(C_5H_4N); R_1= COCH_3$ | (25) $R_2= CH_2(C_6H_4)$-o-Cl; $R_{1A} =H$ | (37) $R_2 = CH_2(C_6H_4)$-p-Cl; $R_3= COCH_2NHCOCF_3$ |
| (14) $R_2= CH_2(C_6H_4)$-o-Cl; $R_1= COCH_3$ | (26) $R_2= CH_2(C_6H_4)$-p-Cl; $R_{1A} =H$ | (38) $R_2= CH_2(C_6H_{11}); R_3= COCH_2NHCOCF_3$ |

(50) R = (—OH); R₁ = (—COCH₃)

(51) R = (—OCH₂CH₂CH=CH₂); R₁ = (—COCH₃)

(52) R = (—OCH₂CH(CH₃)₂); R₁ = (—COCH₃)

(53) R = (—OCH₂CH₂CH₃); R₁ = (—COCH₃)

(54) R = (—OCH₂(CH₂)₂CH₃); R₁ = (—COCH₃)

(39) R = (—OCH$_3$); R$_1$ = (—COCH$_3$)

(40) R = (—OH); R$_1$ = (—COCH$_3$)

(41) R = (—OCH$_2$CH=CH$_2$); R$_1$ = (—COCH$_3$)

(42) R = (—OCH$_2$CH$_3$); R$_1$ = (—COCH$_3$)

(43) R = (—OCH$_2$CH$_2$CH$_3$); R$_1$ = (—COCH$_3$)

(44) R = (—OH); R$_1$ = (—H)

(45) R = (—OCH$_2$CH=CH$_2$); R$_1$ = (—H)

(46) R = (—OCH$_2$CH$_3$); R$_1$ = (—H)

(47) R = (—OH); R$_1$ = (—COCH$_2$NHCOCF$_3$)

(47a) R = (—OCH$_3$); R$_1$ = (—COCH$_2$NHCOCF$_3$)

(48) R = (—OCH$_2$CH=CH$_2$); R$_1$ = (—COCH$_2$NHCOCF$_3$)

(49) R = (—OCH$_2$CH$_3$); R$_1$ = (—COCH$_2$NHCOCF$_3$)

FIG. 4A

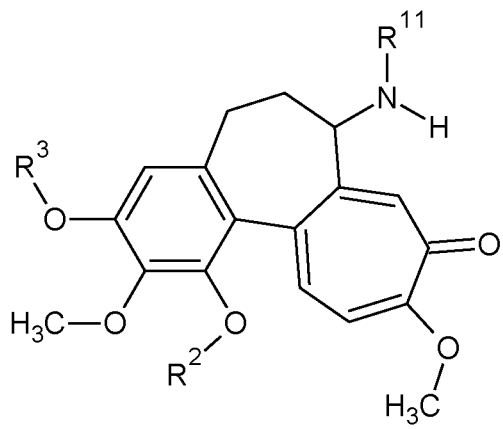

(55) $R^3$ = $CH_3$; $R^2$ = $CH_2CH_2CH_3$; $R^{11}$ = (C=O)H

(56) $R^3$ = $CH_3$; $R^2$ = $CH_2CH_2CH_3$; $R^{11}$ = $OCH_3$

(57) $R^3$ = $CH_3$; $R^2$ = $CH_2CH_2CH_3$; $R^{11}$ = H

(58) $R^3$ = $CH_3$; $R^2$ = $CH(CH_3)_2$; $R^{11}$ = (C=O)H

(59) $R^3$ = $CH_3$; $R^2$ = $CH(CH_3)_2$; $R^{11}$ = $OCH_3$

(60) $R^3$ = $CH_3$; $R^2$ = $CH(CH_3)_2$; $R^{11}$ = H

(61) $R^3$ = $CH_3$; $R^2$ = $CH_2CH(CH_3)_2$; $R^{11}$ = (C=O)H

(62) $R^3$ = $CH_3$; $R^2$ = $CH_2CH(CH_3)_2$; $R^{11}$ = $OCH_3$

(63) $R^3$ = $CH_3$; $R^2$ = $CH_2CH(CH_3)_2$; $R^{11}$ = H

(64) $R^3$ = $CH_3$; $R^2$ = $CH_2CH=CH_2$; $R^{11}$ = (C=O)H

(65) $R^3$ = $CH_3$; $R^2$ = $CH_2CH=CH_2$; $R^{11}$ = $OCH_3$

(66) $R^3$ = $CH_3$; $R^2$ = $CH_2CH=CH_2$; $R^{11}$ = H

(67) $R^3$ = H; $R^2$ = CH$_3$; $R^{11}$ = (C=O)H

(68) $R^3$ = H; $R^2$ = CH$_3$; $R^{11}$ = OCH$_3$

(69) $R^3$ = H; $R^2$ = CH$_3$; $R^{11}$ = H

(70) $R^3$ = CH$_2$CH$_3$; $R^2$ = CH$_3$; $R^{11}$ = (C=O)H

(71) $R^3$ = CH$_2$CH$_3$; $R^2$ = CH$_3$; $R^{11}$ = OCH$_3$

(72) $R^3$ = CH$_2$CH$_3$; $R^2$ = CH$_3$; $R^{11}$ = H

(73) $R^3$ = CH$_2$CH$_2$CH$_3$; $R^2$ = CH$_3$; $R^{11}$ = (C=O)H

(74) $R^3$ = CH$_2$CH$_2$CH$_3$; $R^2$ = CH$_3$; $R^{11}$ = OCH$_3$

(75) $R^3$ = CH$_2$CH$_2$CH$_3$; $R^2$ = CH$_3$; $R^{11}$ = H

(83) $R^3 = CH_3$; $R^2 = CH_2CH_3$; $R^{10} = CH_3$

(84) $R^3 = CH_3$; $R^2 = CH_2CH_2OCH_3$; $R^{10} = CH_3$

(85) $R^3 = CH_3$; $R^2 = CH_2(C_5H_4N)$; $R^{10} = CH_3$

(89) $R^3$ = H; $R^2$ = $CH_3$; $R^{10}$ = $CH_3$

(90) $R^3$ = $CH_2CH=CH_2$; $R^2$ = $CH_3$; $R^{10}$ = $CH_3$

(91) $R^3$ = $CH_2CH_3$; $R^2$ = $CH_3$; $R^{10}$ = $CH_3$

A)

```
236                          312     348    367   Residue
VTTCLRFPGQLNADLRKLAVNMV      TVAAVF  NVKTAV FIG   Type I
- -       - -   --   --      ----I   - ---  -     Type II
- S       - -   --   --      ---T-   - -V-  -     Type III
```

B)

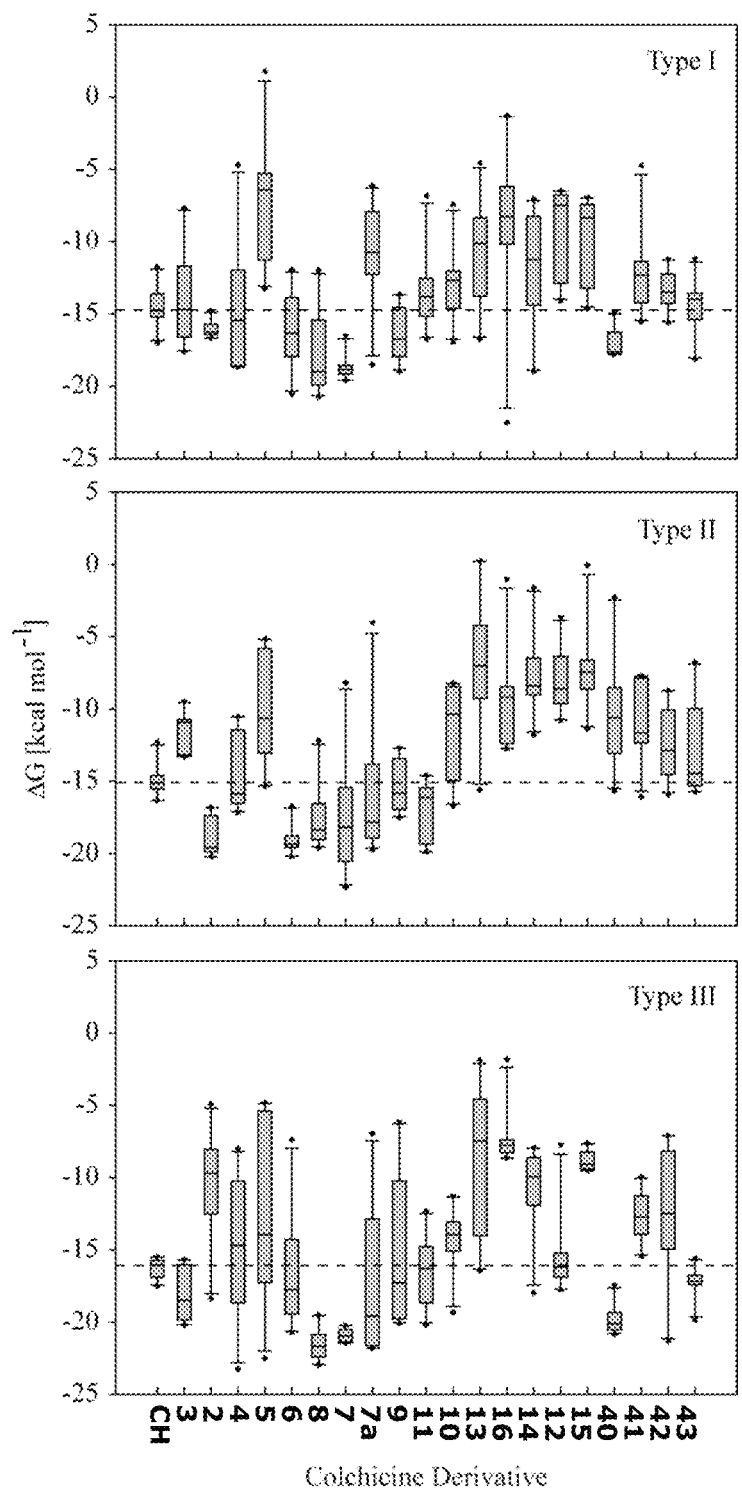

FIG. 7A-B
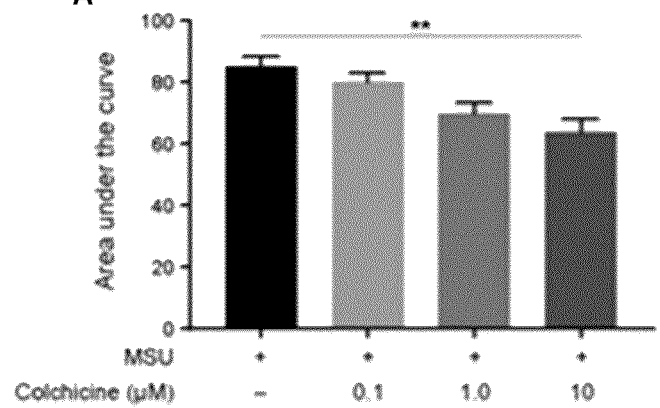
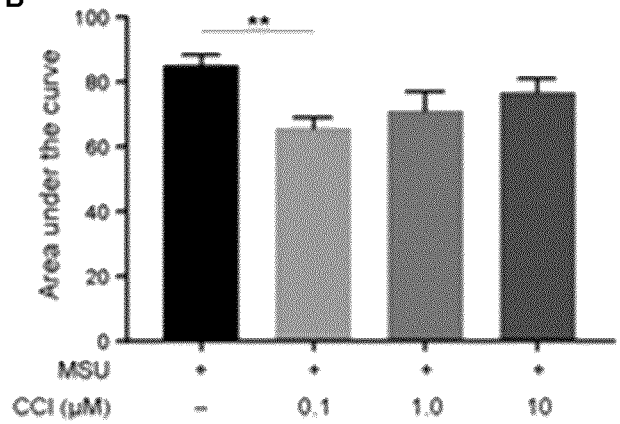

FIG. 7D-E
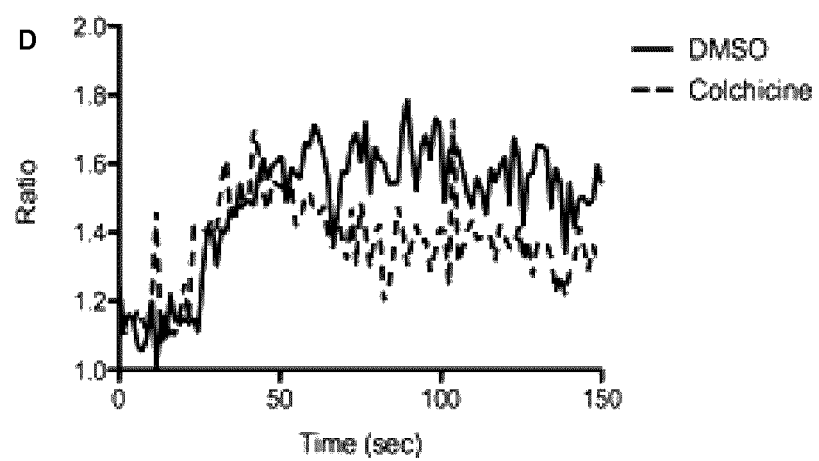
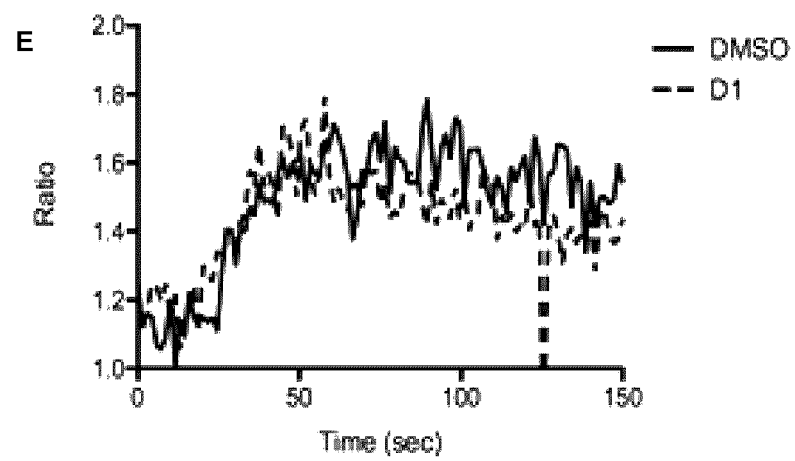

FIG. 7F-G
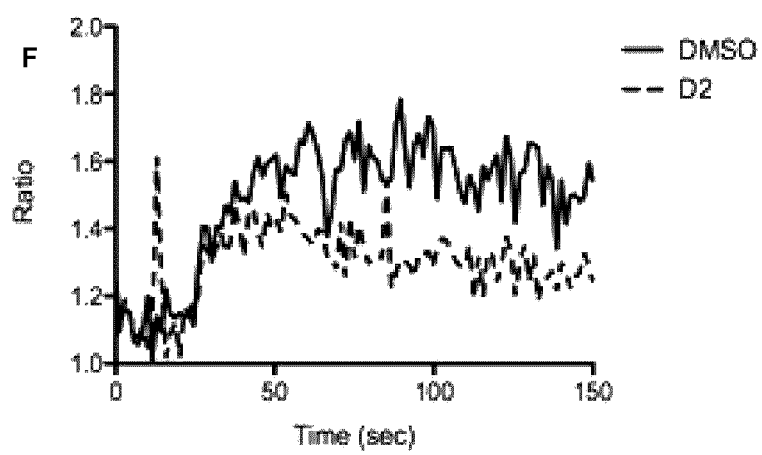
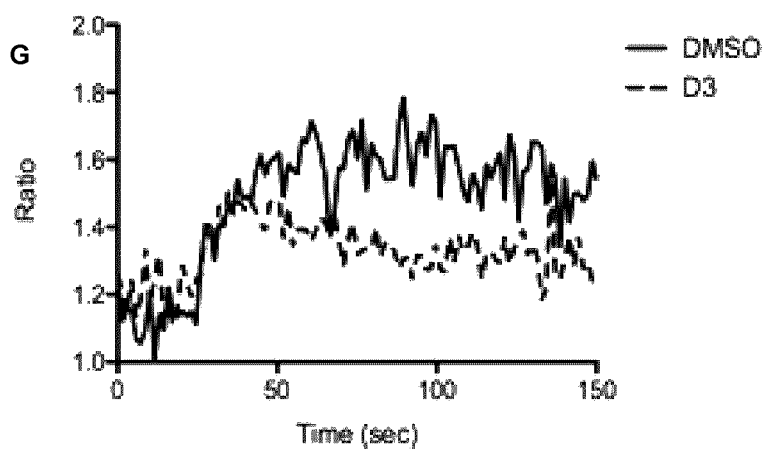

FIG. 7H-I
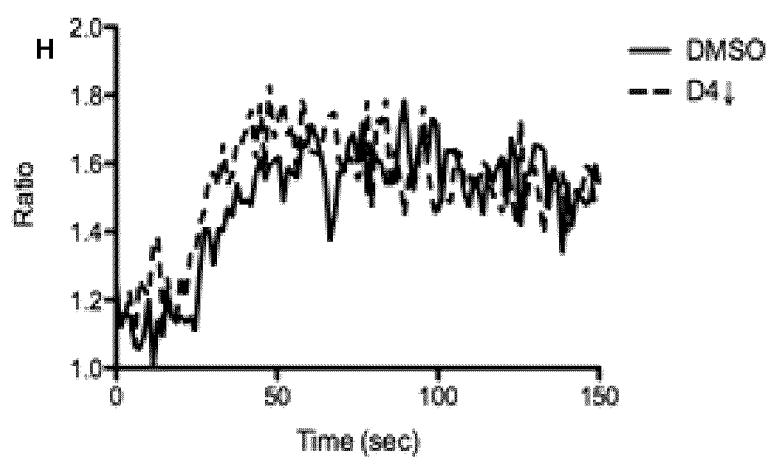
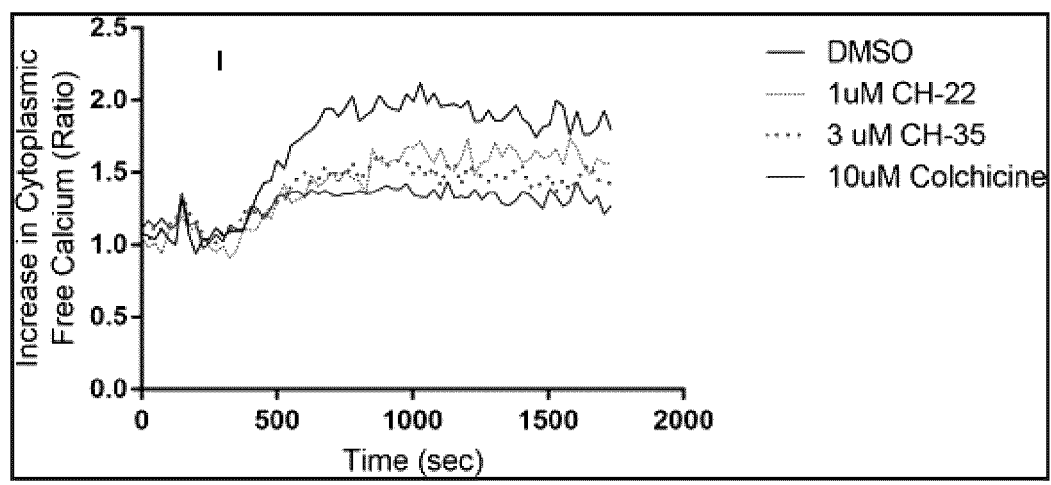

FIG. 7K-L
K
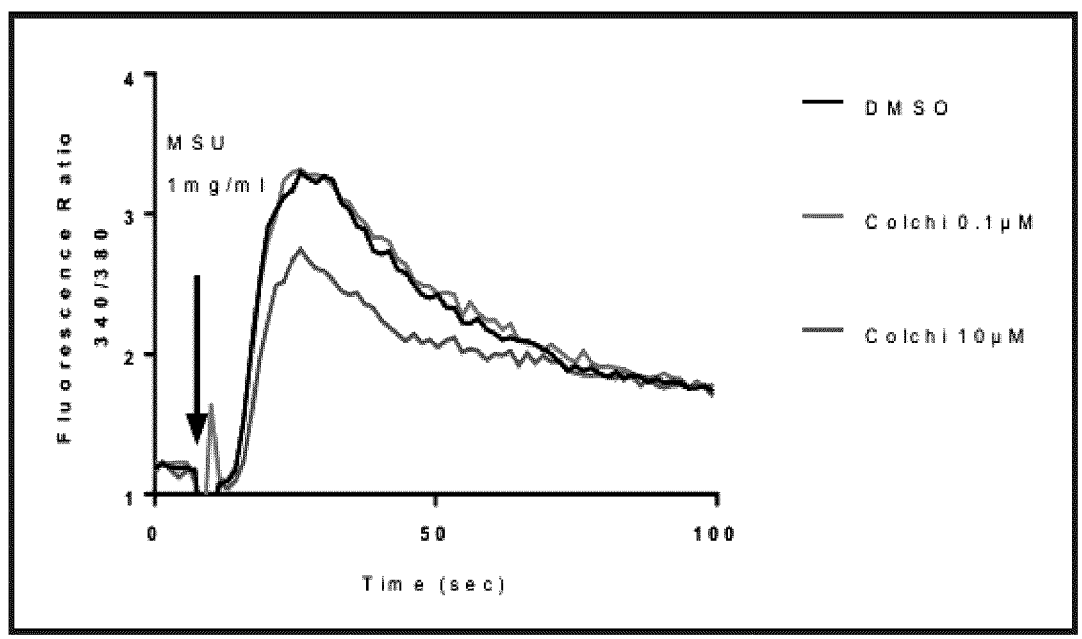
L
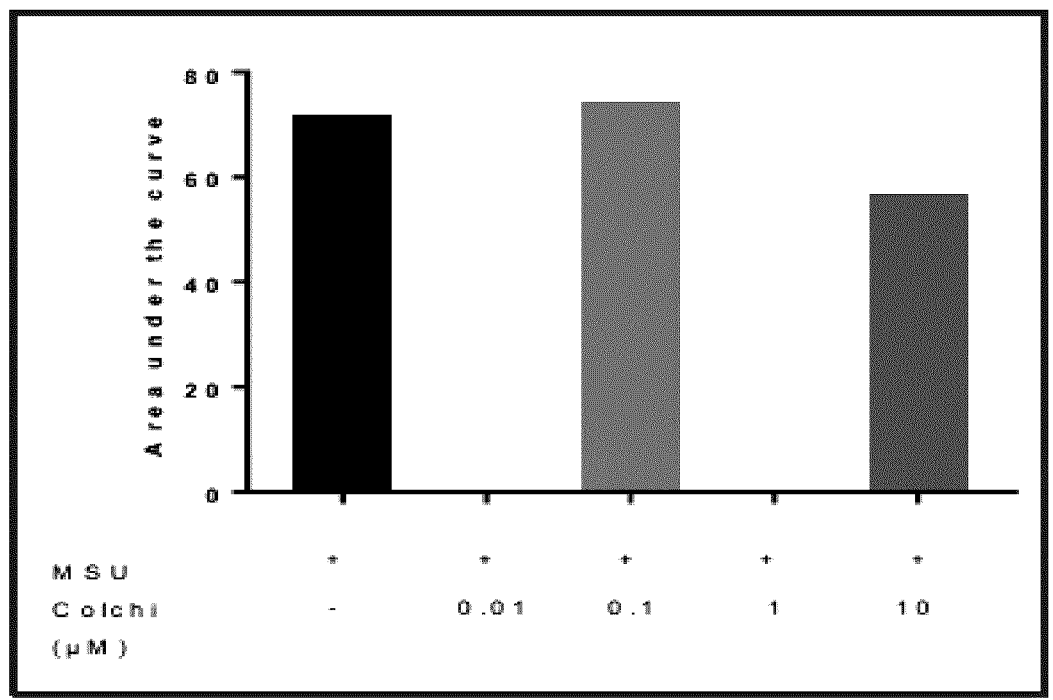

FIG. 7O-P
O
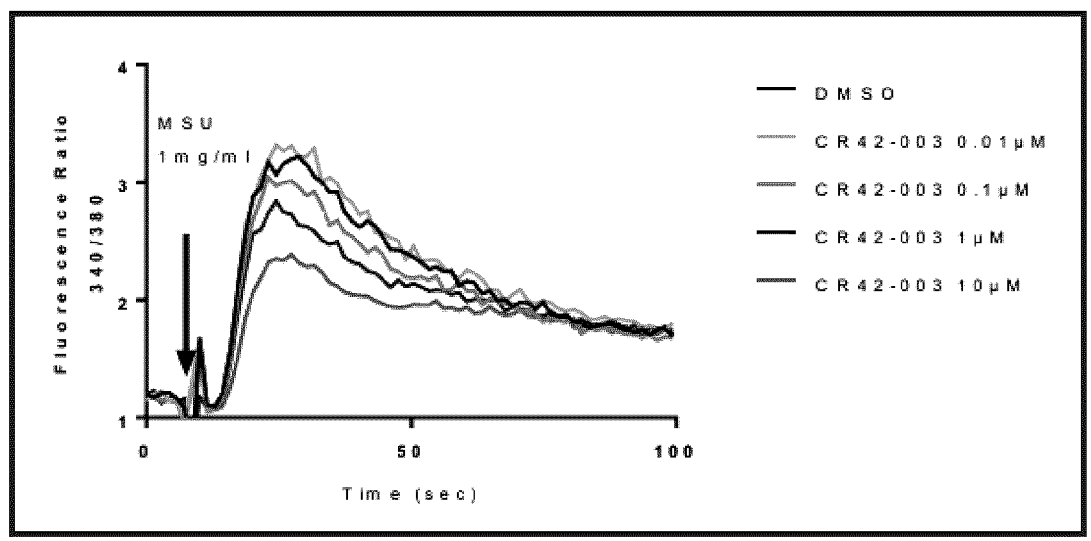
P
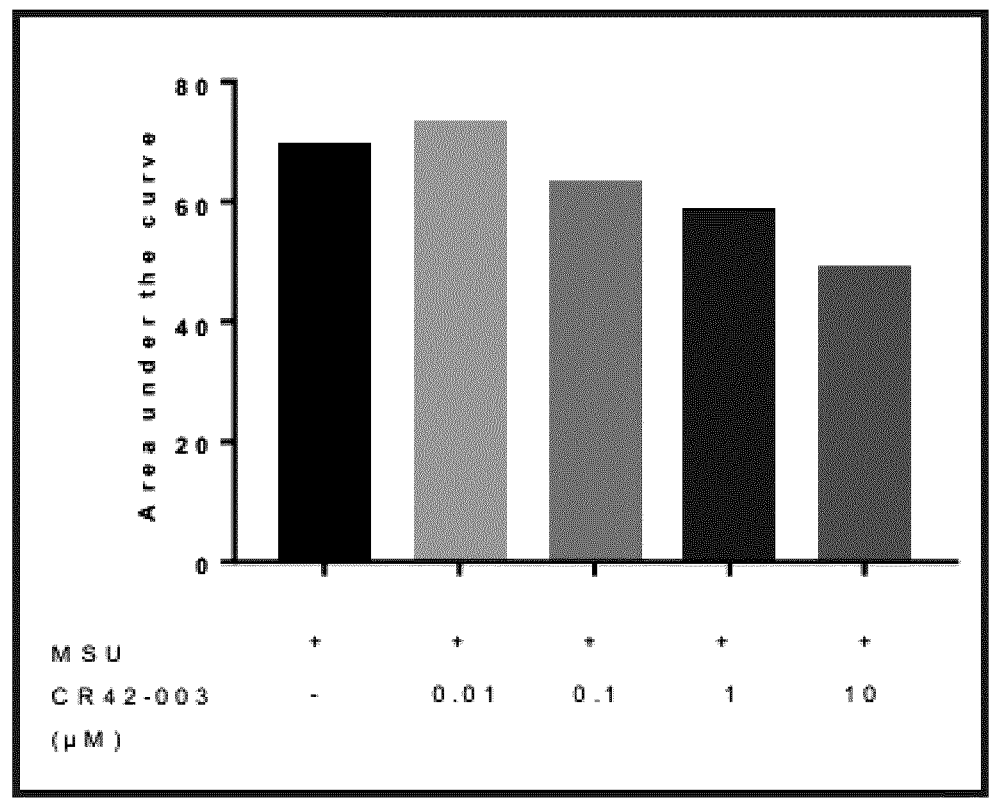

FIG. 7Q-R
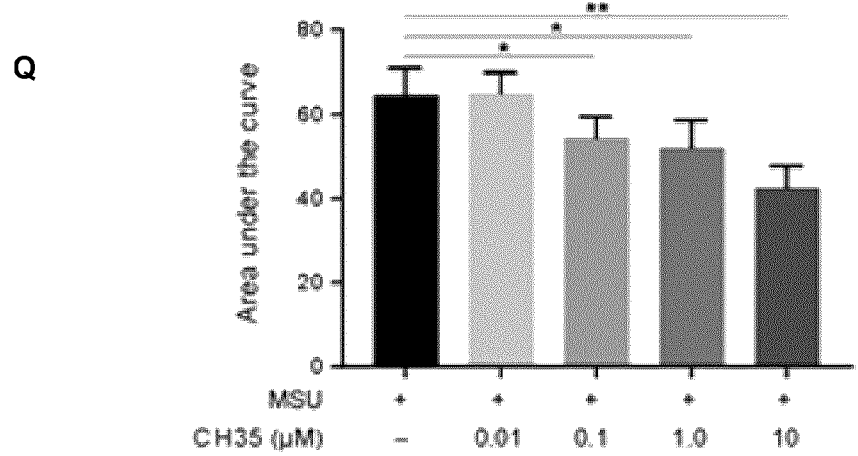
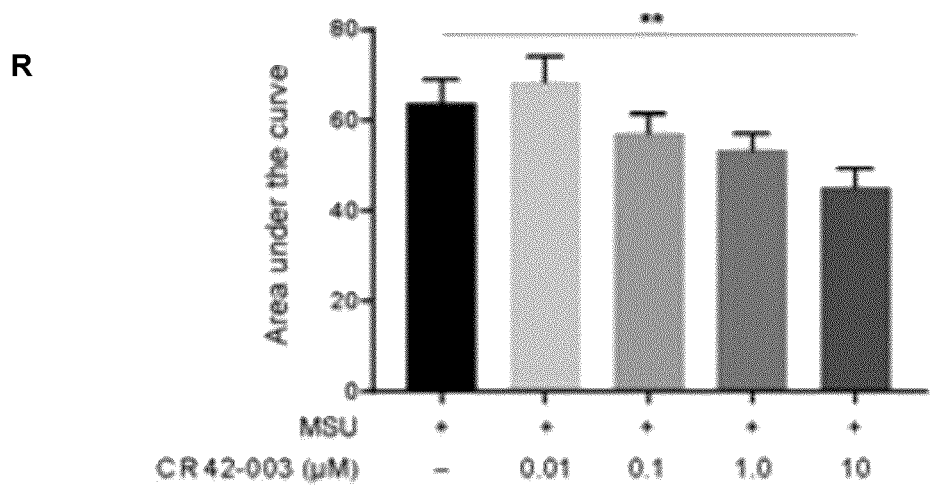

FIG. 7T-U
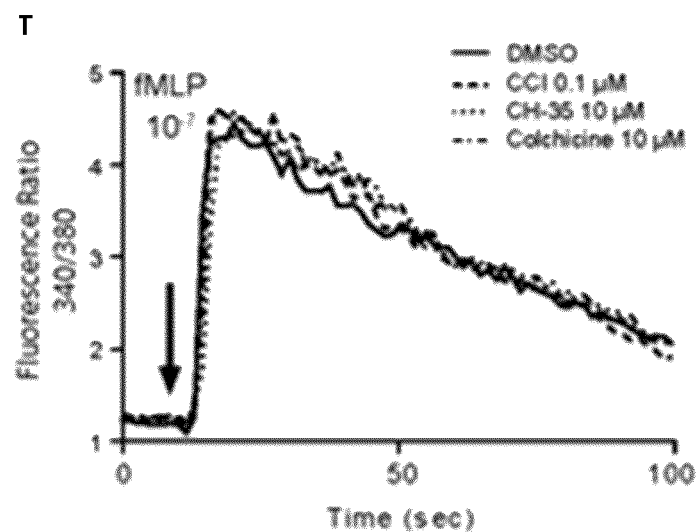
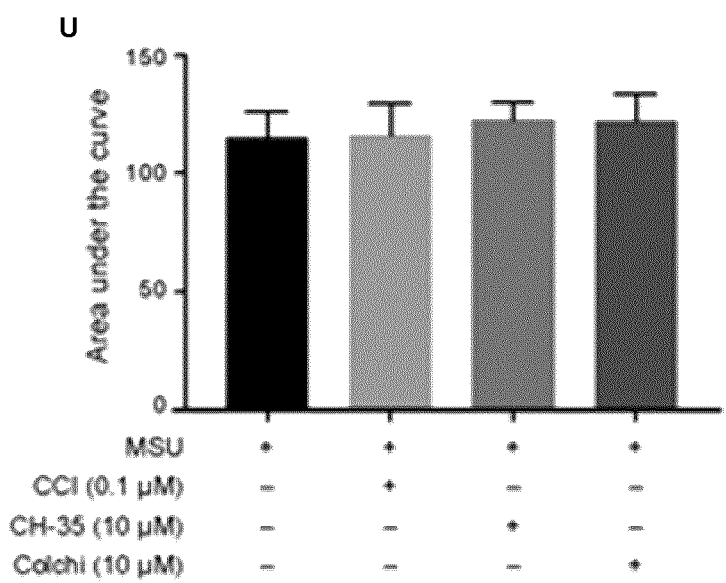

FIG. 7V-W
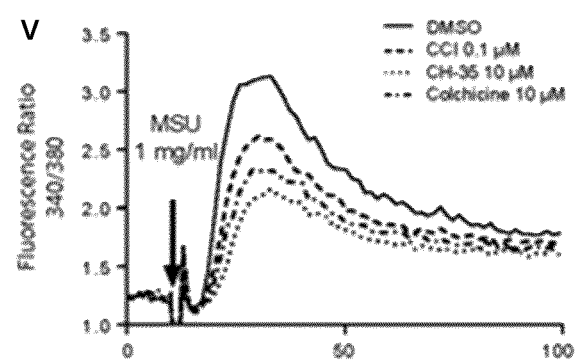
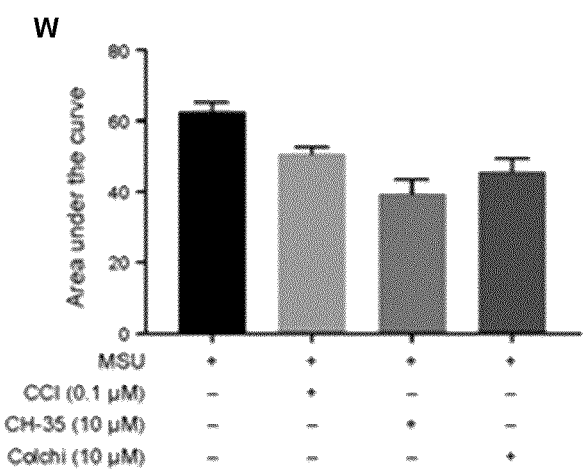

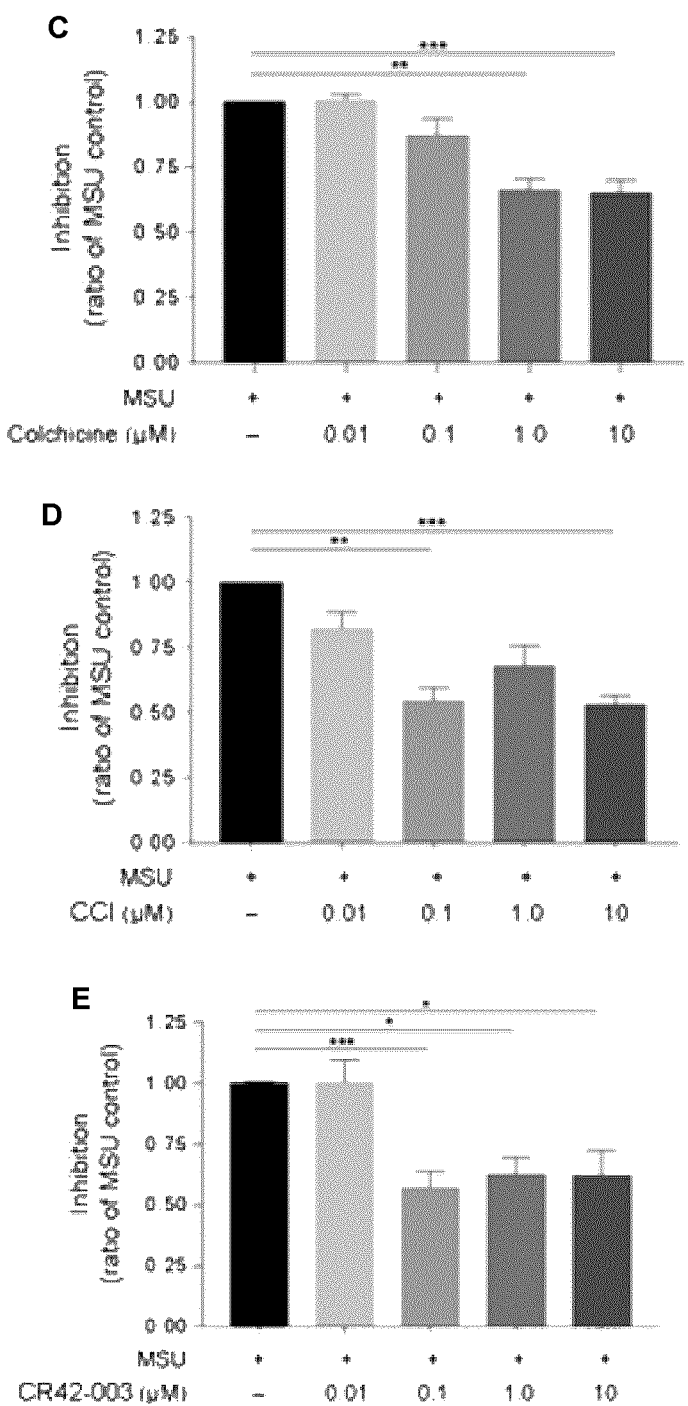
FIG. 8C-E

FIG. 8F-G
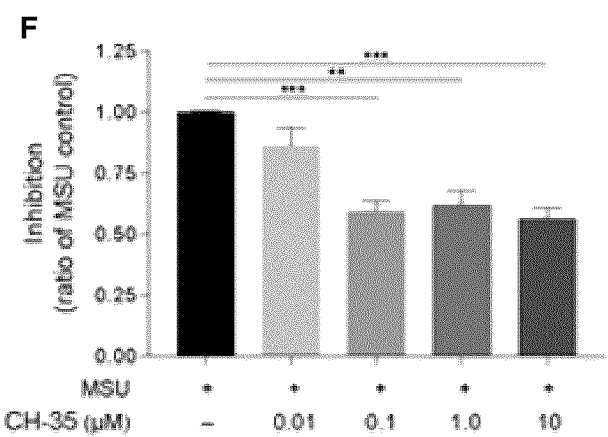
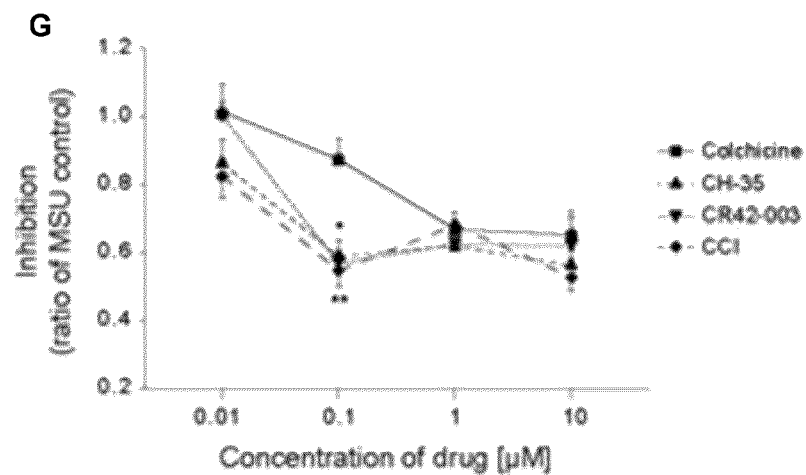

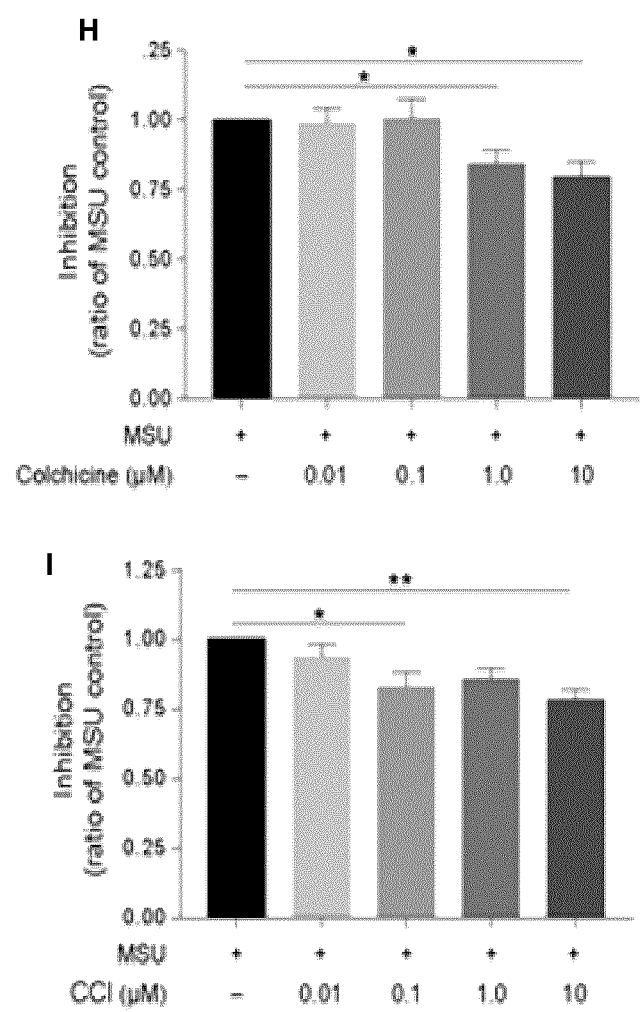
FIG. 8H-I

FIG. 8J-K
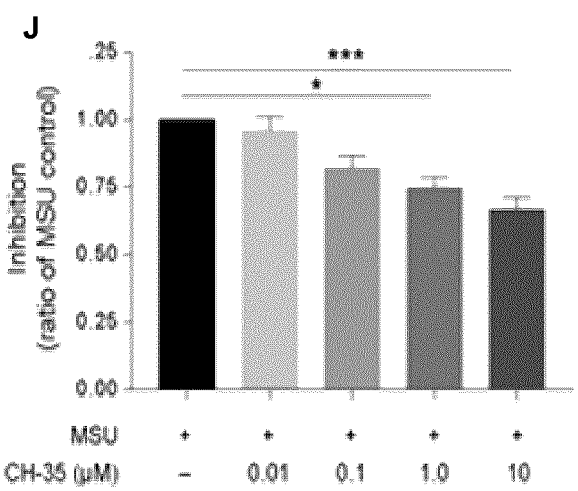
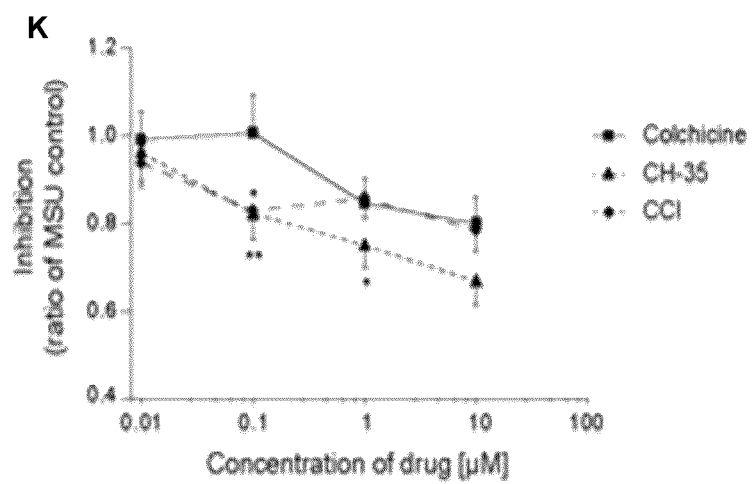

FIG. 9A-B
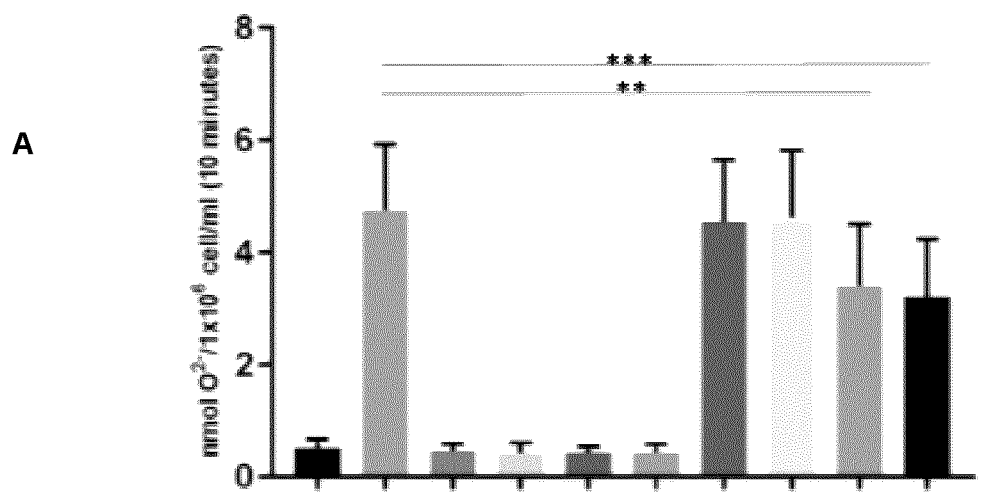
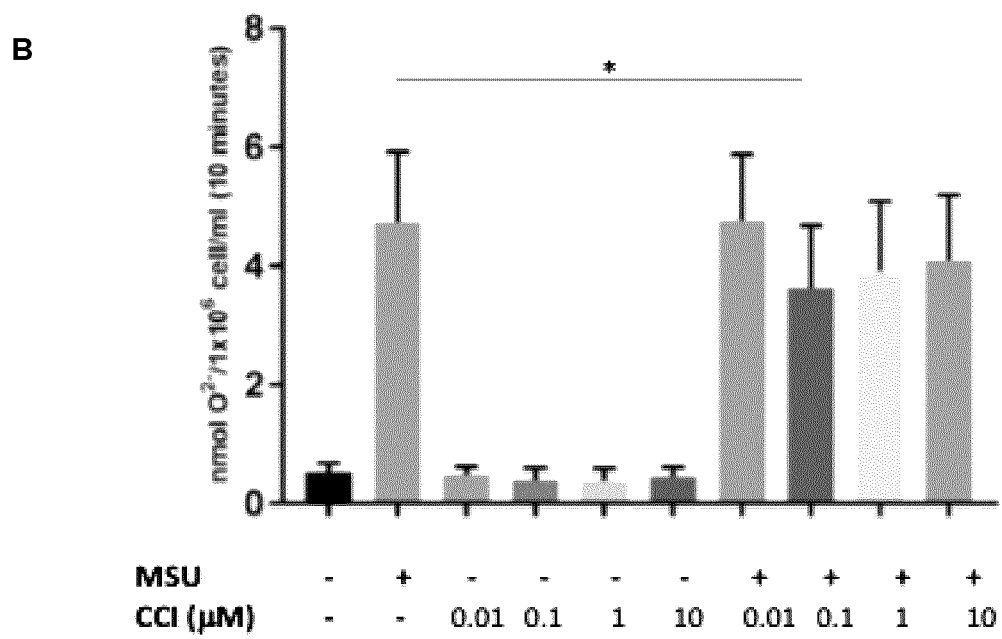

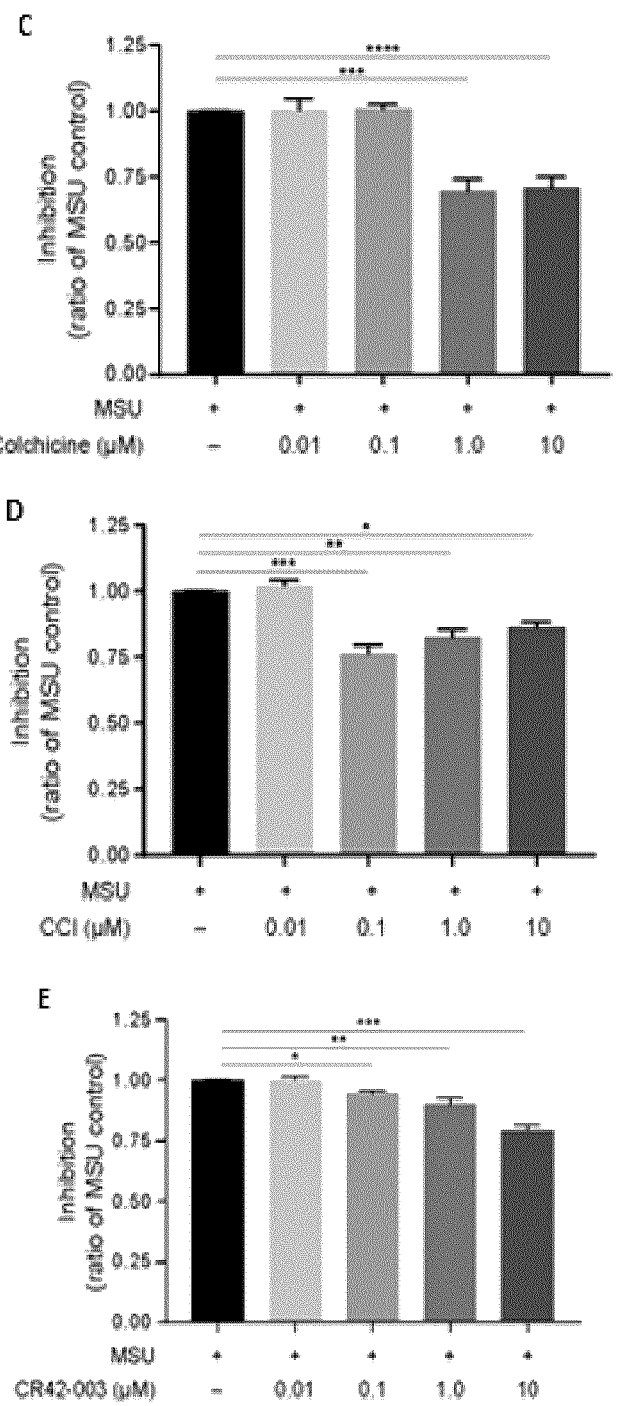
FIG. 9C-E

FIG. 9F-G
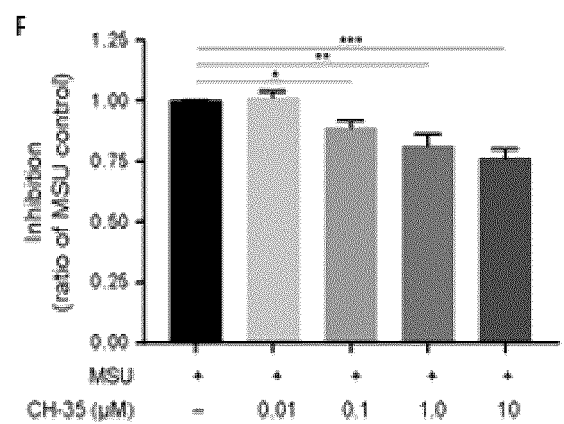
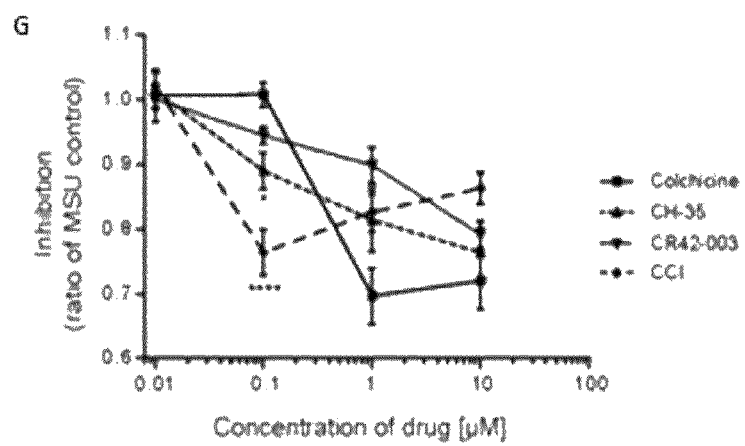

FIG. 10A-B
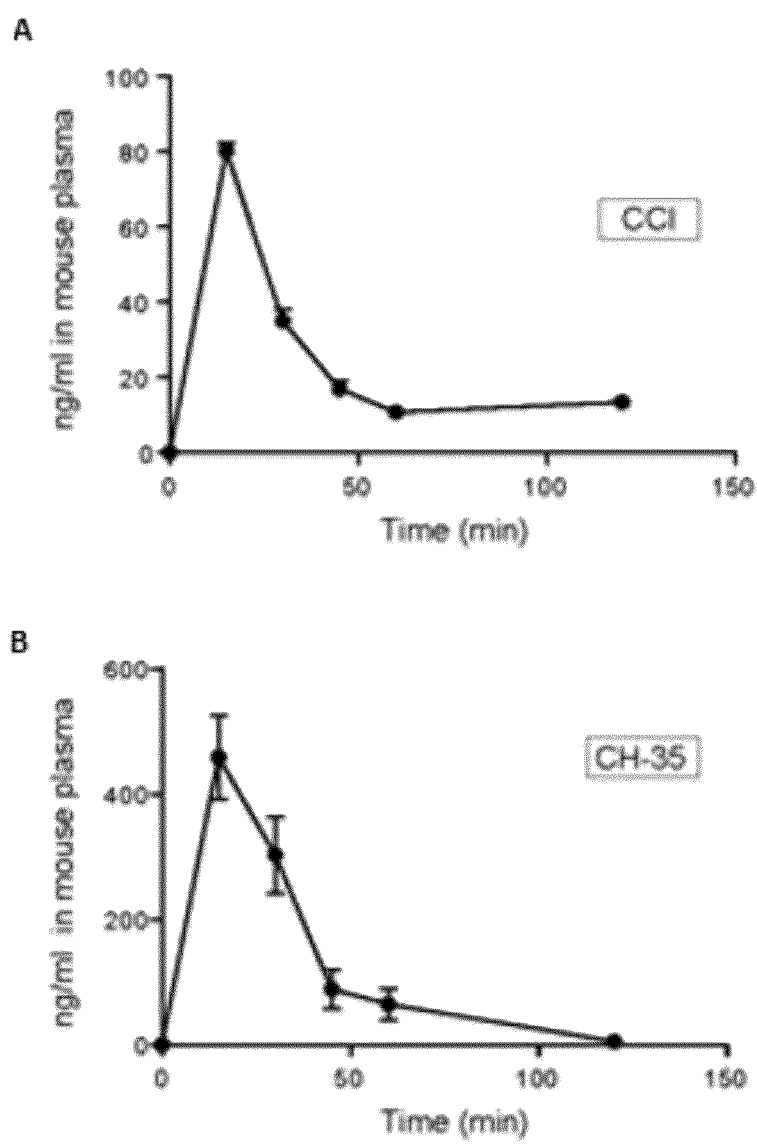

FIG. 11A-B
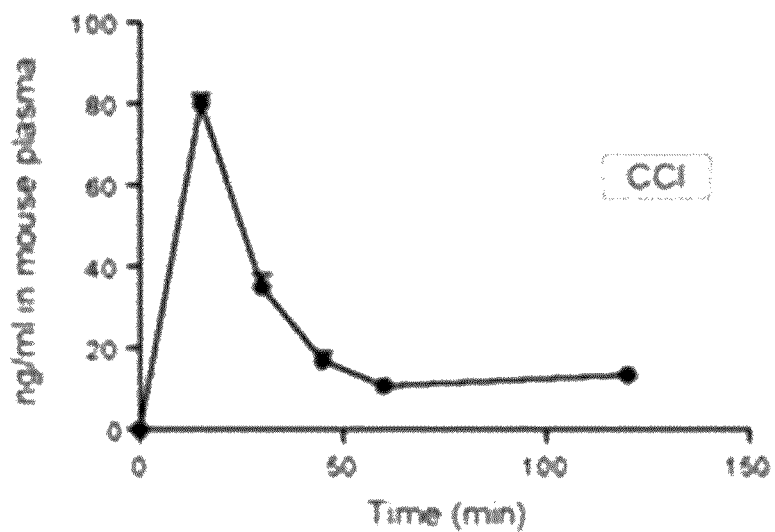
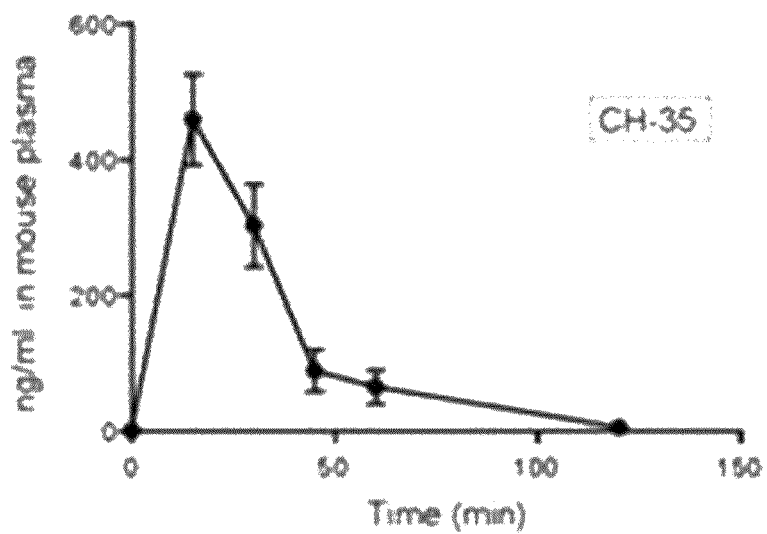

FIG. 14A-B
A
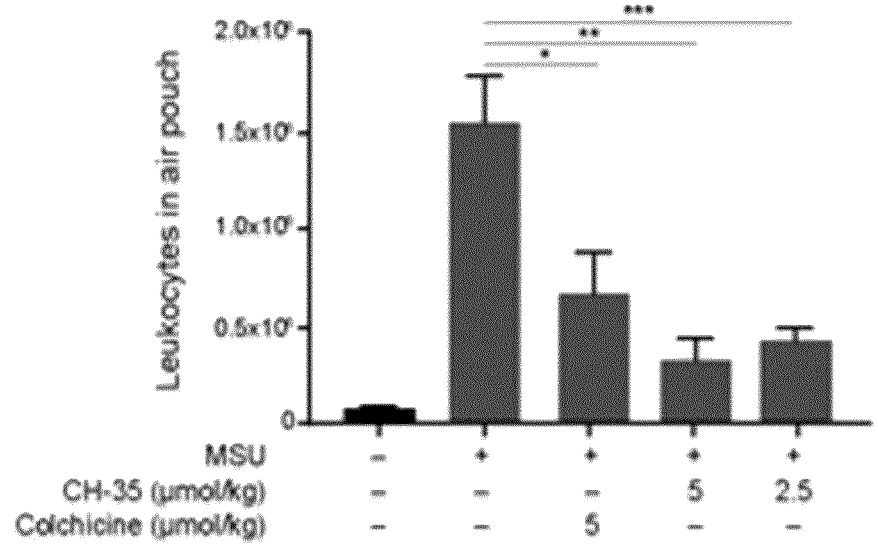
B
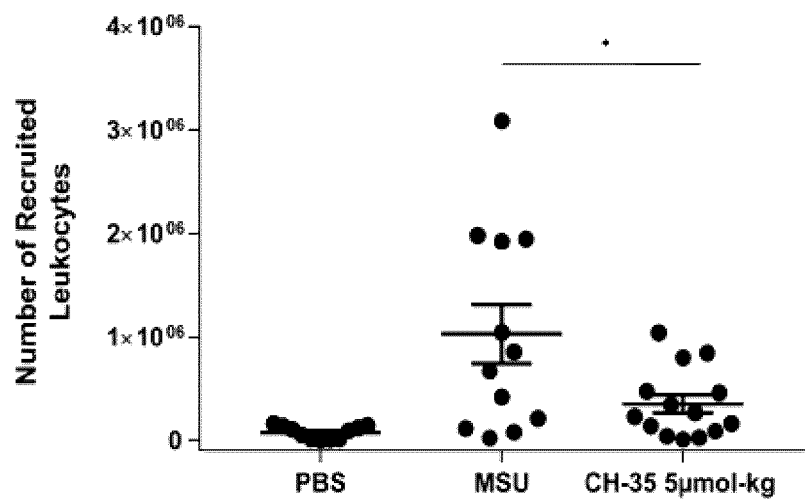

METHODS AND USES OF COLCHICINE DERIVATIVES

RELATED APPLICATIONS

The present application is a U.S. National Stage filing under 35 U.S.C. § 371 of International Application No. PCT/CA2019/050903 filed 28 Jun. 2019, which claims priority to U.S. Application No. 62/691,807 filed 29 Jun. 2018, the contents of which are incorporated herein by reference in their entireties.

FIELD

The subject application relates generally to colchicine derivatives, methods and uses thereof.

BACKGROUND

Inflammatory conditions affect millions of people worldwide and targeted molecular medicine has been aimed at developing safer and more effective drugs and treatment therapies in this area. Colchicine is an antimitotic agent that has been widely used in the treatment of inflammatory diseases as it can target molecular pathways involved in inflammation. For example, beneficial effects were reported in the treatment of psoriatic arthritis (P. Seidemann, B. Fjellner, A. Johannesson, J. Rheumatol. 14 (1987) 777-779) and leukocyte-cytoclastic vasculitis (J. P. Callen, J. Am. Acad. Dermatol. 13 (1987) 193-200). Furthermore, recent studies have shown that colchicine inhibits leukocyte-endothelial cell adhesion (S. J. Rosenman, A. A. Ganji, W. M. Gallatin, F.A.S.E.B. J. 5 (1991)1603-1609) and T cell activation (Y. A. Mekory, D. Baram, A. Goldberg, A. Klajman, Cell. Immunol. 120 (1989) 330-340) by binding to intracellular tubulin monomers, which prevents their polymerization (G. O. Borisy, E. W. Taylor, J. Cell. Biol. 34 (1967) 533-548).

Common uses for colchicine are in the treatment of gout and Familial Mediterranean Fever (FMF). Indeed, patients with FMF are typically on lifelong colchicine therapy. However, the use of colchicine remains challenging due to its low therapeutic index between efficacy and treatment-limiting side effects.

A need, therefore, exists for the development of drugs, as well as uses and/or methods of use thereof that obviate or mitigate at least one of the disadvantages described above or that provide a useful alternative.

SUMMARY

In an aspect, there is provided a compound of Formula I:

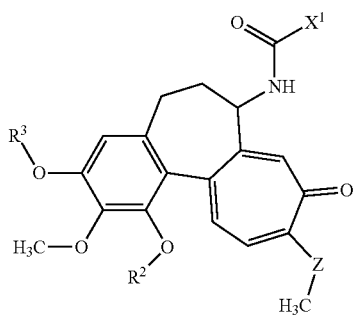

Formula I wherein: Z is O or S; $X^1$ is selected from a substituted or unsubstituted hydrocarbon group, or a substituted or unsubstituted heterogeneous group; $R^2$ and $R^3$ are each independently selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic group, or a substituted or unsubstituted heteroaromatic group; a pharmaceutically-acceptable salt thereof, hydrate thereof, solvate thereof, tautomer thereof, optical isomer thereof, or combination thereof.

In another aspect, wherein $R^2$ and $R^3$ are each independently selected from a substituted or unsubstituted alkyl, a substituted or unsubstituted alkenyl, a substituted or unsubstituted alkynyl, a substituted or unsubstituted aromatic group, a substituted or unsubstituted heteroaromatic group, a substituted or unsubstituted carbocyclic group, or a substituted or unsubstituted heterocyclic group. In another aspect, wherein $R^2$ and $R^3$ are each independently selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted $C_1$-$C_6$ alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In another aspect, wherein $R^2$ and $R^3$ are each independently selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl. In another aspect, wherein $R^2$ and $R^3$ are each independently selected from a substituted or unsubstituted alkyl, a substituted or unsubstituted aryl, or a substituted or unsubstituted alkylaryl. In another aspect, wherein $R^2$ and $R^3$ are each independently selected from a substituted or unsubstituted alkyl, or a substituted or unsubstituted alkylaryl. In another aspect, wherein $R^2$ and $R^3$ are each independently selected from a substituted or unsubstituted alkyl. In another aspect, wherein $R^2$ and $R^3$ are each independently selected from a substituted or unsubstituted $C_1$-$C_6$ alkyl. In another aspect, wherein $R^2$ and $R^3$ are each independently selected from an unsubstituted $C_1$-$C_6$ alkyl. In another aspect, wherein $R^2$ and $R^3$ are each independently selected from methyl, ethyl or propyl. In another aspect, wherein $R^2$ is methyl. In another aspect, wherein $R^3$ is ethyl to propyl.

In another aspect, wherein $X^1$ is a substituted or unsubstituted hydrocarbon group. In another aspect, wherein $X^1$ is selected from a substituted or unsubstituted alkyl, a substituted or unsubstituted alkenyl, or a substituted or unsubstituted alkynyl. In another aspect, wherein $X^1$ is selected from a substituted or unsubstituted $C_1$-$C_6$ alkyl. In another aspect, wherein $X^1$ is selected from an unsubstituted $C_1$-$C_6$ alkyl. In another aspect, wherein $X^1$ is selected from methyl or ethyl. In another aspect, wherein $X^1$ is methyl. In another aspect, wherein $X^1$ is $OR^{10}$ and $R^{10}$ is selected from a substituted or unsubstituted hydrocarbon group, or a substituted or unsubstituted heterogeneous group. In another aspect, wherein $R^{10}$ is selected from a substituted or unsubstituted alkyl group, a substituted or unsubstituted alkenyl, a substituted or unsubstituted alkynyl, a substituted or unsubstituted aromatic group, a substituted or unsubstituted heteroaromatic group, a substituted or unsubstituted carbocyclic group, or a substituted or unsubstituted heterocyclic group. In another aspect, wherein $R^{10}$ is selected from a substituted or unsubstituted alkyl, $CH_2OH$, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In another aspect, wherein $R^{10}$ is selected from a substituted or unsubstituted alkyl, a substituted or unsubstituted alkenyl, or a substituted or unsubstituted alkynyl. In another aspect, wherein $R^{10}$ is selected from a substituted or unsubstituted $C_1$-$C_6$ alkyl, or a substituted or unsubstituted $C_2$-$C_6$ alkenyl, or $C_2$-$C_6$ alkynyl. In another aspect, wherein $R^{10}$ is selected from a substituted or unsubstituted alkyl. In another aspect, wherein $R^{10}$ is selected from a substituted or unsubstituted $C_1$-$C_6$ alkyl. In another aspect, wherein $R^{10}$ is selected from an unsubstituted $C_1$-$C_6$ alkyl. In another aspect, wherein $R^{10}$ is selected from methyl or ethyl. In another aspect, wherein $R^{10}$ is methyl.

In another aspect, wherein $X^1$ is a substituted or unsubstituted heterogeneous group. In another aspect, wherein $X^1$ is selected from —$CR^4R^5R^6$, wherein $R^4$, $R^5$, and $R^6$ are each independently selected from H, a substituted or unsubstituted hydrocarbon group, or a substituted or unsubstituted heterogeneous group. In another aspect, wherein $R^4$, $R^5$, and $R^6$ are each independently selected from an substituted or unsubstituted amido group. In another aspect, wherein $R^4$ and $R^5$ are each independently selected from H, or substituted or unsubstituted alkyl, and $R^6$ is —$NR(CO)CR^7R^8R^9$, wherein R is selected from H and a substituted or unsubstituted alkyl, and $R^7$, $R^8$, and $R^9$ are each selected from H, halo group, a substituted or unsubstituted alkyl. In another aspect, wherein $R^7$, $R^8$, and $R^9$ can be selected from a fluoro group. In another aspect, wherein $X^1$ is —$CH_2NH(CO)CF_3$.

In another aspect, wherein Z is O. In another aspect, wherein Z is S.

In another aspect, wherein the compound is:

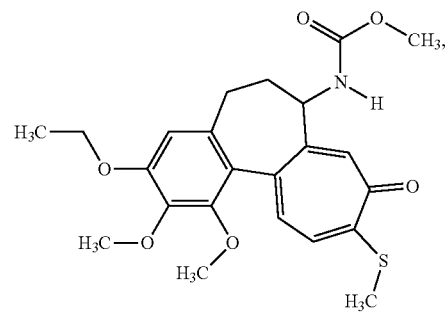 [SMILES: CCOc1cc2c(c(OC)c1OC)-c1ccc(SC)c(=O)cc1C(NC(=O)OC)CC2]

a pharmaceutically-acceptable salt thereof, hydrate thereof, solvate thereof, tautomer thereof, optical isomer thereof, or combination thereof.

In another aspect, wherein the compound is:

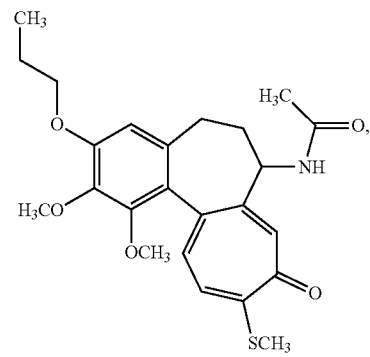 [SMILES: CCCOc1cc2c(c(OC)c1OC)-c1ccc(SC)c(=O)cc1C(NC(C)=O)CC2]

a pharmaceutically-acceptable salt thereof, hydrate thereof, solvate thereof, tautomer thereof, optical isomer thereof, or combination thereof.

In another aspect, wherein the compound is:

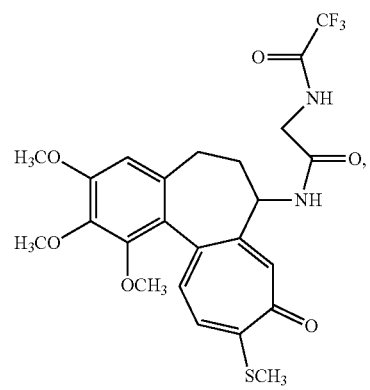

a pharmaceutically-acceptable salt thereof, hydrate thereof, solvate thereof, tautomer thereof, optical isomer thereof, or combination thereof.

In another aspect, wherein the compound is:

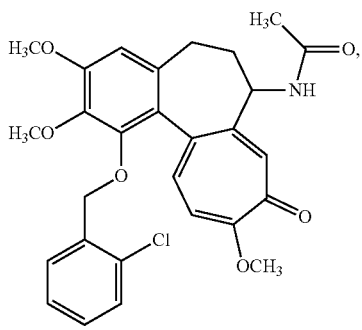 [SMILES: COc1cc2c(c(OCc3ccccc3Cl)c1OC)-c1ccc(OC)c(=O)cc1C(NC(C)=O)CC2]

a pharmaceutically-acceptable salt thereof, hydrate thereof, solvate thereof, tautomer thereof, optical isomer thereof, or combination thereof.

In another aspect, wherein the compound is:

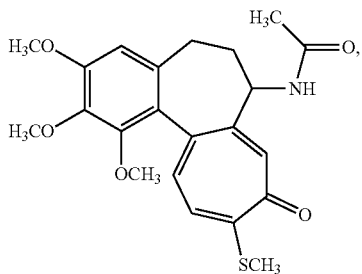

a pharmaceutically-acceptable salt thereof, hydrate thereof, solvate thereof, tautomer thereof, optical isomer thereof, or combination thereof.

In another aspect, wherein the compound is:

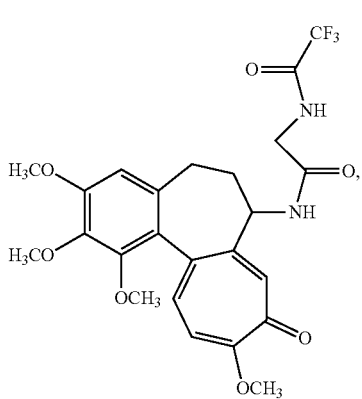 [SMILES: COc1cc2c(c(OC)c1OC)-c1ccc(OC)c(=O)cc1C(NC(=O)CNC(=O)C(F)(F)F)CC2]

a pharmaceutically-acceptable salt thereof, hydrate thereof, solvate thereof, tautomer thereof, optical isomer thereof, or combination thereof.

In another aspect, wherein the compound is Formula I and/or a pharmaceutically-acceptable salt thereof. In another aspect, wherein the configuration at C7 is S-configuration. In another aspect, wherein the compound binds to β-tubulin at a colchicine-binding site. In another aspect, wherein the β-tubulin is β-VI, β-V, and/or β-I. In another aspect, wherein the β-tubulin is β-VI. In another aspect, wherein the compound has a binding energy that is less than the binding energy of colchicine. In another aspect, wherein the compound is less toxic than colchicine. In another aspect, wherein the compound more specifically targets neutrophils compared to colchicine. In another aspect, wherein the compound inhibits the increase in intracellular calcium concentration at a lower dose than colchicine. In another aspect, wherein the compound inhibits the increase in intracellular calcium concentration at a dose that is at least about 10-fold lower than colchicine. In another aspect, wherein the compound inhibits the increase in intracellular calcium concentration at a dose that is about 10-fold to about 100-fold lower than a dose for colchicine. In another aspect, wherein the compound inhibits the increase in intracellular calcium concentration at a dose of about 0.1 μM. In another aspect, wherein the compound inhibits the production of an inflammatory mediator at a lower dose than colchicine. In another aspect, wherein the compound inhibits the production of the inflammatory mediator at a dose that is at least about 10-fold lower than colchicine. In another aspect, wherein the compound inhibits the production of the inflammatory mediator at a dose that is about 10-fold to about 100-fold lower than a dose for colchicine. In another aspect, wherein the compound inhibits the production of the inflammatory mediator at a dose of about 0.1 μM. In another aspect, wherein the inflammatory mediator is selected from IL-8, IL-1, superoxide, or a combination thereof. In another aspect, wherein the compound exhibits a monotonic or non-monotonic dose response in respect of inhibition of at least one of intracellular calcium concentration and inflammatory mediator production. In another aspect, wherein the inflammatory mediator is selected from IL-8, Il-1, superoxide production, or a combination thereof. In another aspect, wherein the compound inhibits recruitment of leukocytes.

In another aspect, there is provided a compound described herein for treatment of inflammation. In another aspect, wherein the inflammation is selected from an inflammatory disease, an inflammatory condition, an inflammatory disorder, or combinations thereof. In another aspect, wherein the inflammation comprises neutrophil-driven inflammation. In another aspect, wherein the neutrophil-driven inflammation is inflammation associated with pseudogout, gout, cardiovascular disease, vasculitis, or combinations thereof. In another aspect, wherein the neutrophil-driven inflammation is associated with cardiovascular disease. In another aspect, wherein the cardiovascular disease is coronary atherosclerosis. In another aspect, wherein the neutrophil-driven inflammation is associated with gout.

In another aspect, there is provided a compound described herein for treatment of gout. In another aspect, wherein the compound has an inhibitory effect on immune function in response to monosodium uric acid (MSU)-induced inflammation. In another aspect, wherein the inhibitory effect on immune function is effected through a mediator selected from intracellular calcium production, IL-1 production, IL-8 production, superoxide production, or combinations thereof. In another aspect, wherein the immune function is in respect of a neutrophil. In another aspect, wherein the inhibitory effect is more potent than that of colchicine. In another aspect, wherein the inhibitory effect is at least about 10-fold greater than that of colchicine. In another aspect, wherein the inhibitory effect occurs at a concentration of about 0.1 μM. In another aspect, there is provided a compound described herein for treatment of cardiovascular disease. In another aspect, wherein the cardiovascular disease is coronary atherosclerosis.

In another aspect, there is provided a pharmaceutical composition comprising the compound described herein. In another aspect, wherein the composition further comprising an anti-gout agent. In another aspect, wherein the anti-gout agent is selected from non-steroidal anti-inflammatory drug (NSAIDS), intraarticular glucocorticoids, xanthine oxidase inhibitors, recombinant non-human uricase enzyme, uric acid excretion promoters, uricosuric agents, or combinations thereof. In another aspect, further comprising at least one pharmaceutically acceptable carrier and/or diluent. In another aspect, wherein the composition comprises two or more compounds described herein. In another aspect, there is provided a pharmaceutical composition comprising the compound described herein for the treatment of inflammation. In another aspect, wherein the inflammation is selected from an inflammatory disease, an inflammatory condition, an inflammatory disorder, or combinations thereof. In another aspect, wherein the inflammation comprises neutrophil-driven inflammation. In another aspect, wherein the neutrophil-driven inflammation is inflammation associated with pseudogout, gout, cardiovascular disease, vasculitis, or combinations thereof. In another aspect, wherein the neutrophil-driven inflammation is associated with cardiovascular disease. In another aspect, wherein the cardiovascular disease is coronary atherosclerosis. In another aspect, wherein the neutrophil-driven inflammation is associated with gout. In another aspect, there is provided a pharmaceutical composition comprising the compound described herein for treatment of gout.

In another aspect, there is provided a method for treating inflammation in a mammal, comprising administering to the mammal a therapeutically effective amount of the compound described herein. In another aspect, wherein there are two or more compounds described herein. In another aspect, wherein the compound is administered orally and/or parenterally. In another aspect, wherein the compound is administered intravenously and/or intraperitoneally. In another aspect, there is provided a method for treating inflammation in a mammal, comprising administering to the mammal a therapeutically effective amount of the composition described herein. In another aspect, wherein the composition is administered orally and/or parenterally. In another aspect, wherein the composition is administered intravenously and/or intraperitoneally. In another aspect, wherein the inflammation is selected from an inflammatory disease, an inflammatory condition, an inflammatory disorder, or combinations thereof. In another aspect, wherein the inflammation comprises neutrophil-driven inflammation. In another aspect, wherein the neutrophil-driven inflammation is inflammation associated with pseudogout, gout, cardiovascular disease, vasculitis, or combinations thereof. In another aspect, wherein the neutrophil-driven inflammation is associated with cardiovascular disease. In another aspect, wherein the cardiovascular disease is coronary atherosclerosis. In another aspect, wherein the neutrophil-driven inflammation is associated with gout. In another aspect, wherein the mammal is a human.

In another aspect, there is provided use of a therapeutically effective amount of the compound described herein for treatment of inflammation in a mammal. In another aspect, wherein there are two or more compounds described herein. In another aspect, wherein the compound is administrable orally and/or parenterally. In another aspect, wherein the compound is administrable intravenously and/or intraperitoneally. In another aspect, there is provided use of a therapeutically effective amount of the composition described herein for treatment of inflammation in a mammal. In another aspect, wherein the composition is administrable orally and/or parenterally. In another aspect, wherein the composition is administrable intravenously and/or intraperitoneally. In another aspect, wherein the inflammation is selected from an inflammatory disease, an inflammatory condition, an inflammatory disorder, or combinations thereof. In another aspect, wherein the inflammation comprises neutrophil-driven inflammation. In another aspect, wherein the neutrophil-driven inflammation is inflammation associated with pseudogout, gout, cardiovascular disease, vasculitis, or combinations thereof. In another aspect, wherein the neutrophil-driven inflammation is associated with cardiovascular disease. In another aspect, wherein the cardiovascular disease is coronary atherosclerosis. In another aspect, wherein the neutrophil-driven inflammation is associated with gout. In another aspect, wherein the mammal is a human.

In another aspect, there is provided a method for treating gout in a mammal, comprising administering to the mammal a therapeutically effective amount of the compound described herein. In another aspect, wherein there are two or more compounds described herein. In another aspect, wherein the compound is administered orally and/or parenterally. In another aspect, wherein the compound is administered intravenously and/or intraperitoneally. In another aspect, there is provided a method for treating gout in a mammal, comprising administering to the mammal a therapeutically effective amount of the composition described herein. In another aspect, wherein the composition is administered orally and/or parenterally. In another aspect, wherein the composition is administered intravenously and/or intraperitoneally. In another aspect, wherein the mammal is a human. In another aspect, wherein the gout is selected from chronic gout and/or acute gout. In another aspect, wherein treatment of gout comprises treatment of at least one gouty symptom. In another aspect, wherein said at least one gouty symptom is selected from gout attack, tophus formation, gouty arthritis, gout-associated inflammation, and/or joint destruction associated with gout. In another aspect, wherein said at least one gouty symptom is selected from gouty inflammation and/or pain associated with inflammation.

In another aspect, there is provided use of a therapeutically effective amount of the compound described herein for treatment of gout in a mammal. In another aspect, wherein there are two or more compounds described herein. In another aspect, wherein the compound is administrable orally and/or parenterally. In another aspect, wherein the compound is administrable intravenously and/or intraperitoneally. In another aspect, there is provided use of a therapeutically effective amount of the composition described herein for treatment of gout in a mammal. In another aspect, wherein the composition is administrable orally and/or parenterally. In another aspect, wherein the composition is administrable intravenously and/or intraperitoneally. In another aspect, wherein the mammal is a human. In another aspect, wherein the gout is selected from chronic gout and/or acute gout. In another aspect, wherein treatment of gout comprises treatment of at least one gouty symptom. In another aspect, wherein said at least one gouty symptom is selected from gout attack, tophus formation, gouty arthritis, gout-associated inflammation, and/or joint destruction associated with gout. In another aspect, wherein said at least one gouty symptom is selected from gouty inflammation and/or pain associated with inflammation.

In another aspect, there is provided there is provided a method of treating inflammation, the method comprising administering a βVI-tubulin inhibitor. In another aspect, wherein the βVI-tubulin inhibitor is a compound or composition described herein. In another aspect, wherein the inflammation is associated with leukocyte infiltration. In another aspect, wherein the leukocyte infiltration comprises infiltration of neutrophils and/or monocytes. In another aspect, wherein the inflammation is associated with gout. In another aspect, wherein the inflammation is associated with atherosclerosis.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments will now be described, by way of example only, with reference to the Figures.

FIG. 3 shows a synthetic scheme for making compounds (6) to (38);

FIGS. 4A to 4D show examples of colchicine and thiocolchicine derivatives;

FIG. 5 shows differences between residues found within the colchicine binding site.

FIG. 6 shows calculated ΔG [kcal mol$^{-1}$] of colchicine and its derivatives binding to the type-I (top), type-II (middle) and type-III (bottom) β-tubulin binding sites and box plots for each of the derivatives ((3)-D-20) and colchicine (CH) were generated from energy evaluations of the ten independent docked poses, whiskers are shown for 5% and 95% confidence values;

FIG. 7 shows the effect of colchicine and colchicine derivatives on the mobilization of calcium stores by monosodium uric acid (MSU) stimulated human neutrophils. FIGS. 7A and 7D show the effect of colchicine. FIG. 7B shows the effect of colchicine derivative (91). FIGS. 7E-J show the effect of colchine derivatives 28a, 39, 47a, 89, 14 and 43 in comparison to colchicine (FIG. 7D). FIGS. 7K-L show the effect of colchicine at varying doses. FIGS. 7M-P show the effect of colchicine derivatives (43) (FIGS. 7M-N) and (47a) (FIGS. 7O-P) at varying doses in comparison to colchicine at varying doses (FIG. 7K-L). FIGS. 7Q and 7R show the effect of colchicine derivatives (47a) and (43), respectively. FIGS. 7T and 7U show the effect colchicine and derivatives (91) and (43) on fMLP-induced increase in the concentration of cytoplasmic calcium. FIGS. 7V and 7W colchicine and derivatives (91) and (43) on the MSU-induced increase in the concentration of cytoplasmic calcium;

FIG. 8 shows the effect of colchicine and colchicine derivatives on the release of IL-8 (FIGS. 8A to 8G and 8L) or IL-1 (FIGS. 8H to 8K) by monosodium uric acid (MSU) stimulated human neutrophils. FIG. 8C shows the effect of colchicine. FIG. 8D shows colchicine derivative (91). FIG. 8E shows colchicine derivative (47a). FIG. 8F shows the effect of colchicine derivative (43). FIG. 8G shows a comparison of the inhibitory activity of the compounds tested in FIGS. 8C to F. FIG. 8H shows the effect of colchicine. FIG. 8I shows colchicine derivative (91). FIG. 8J shows the effect of colchicine derivative (43) FIG. 8K shows a comparison of the inhibitory activity of the compounds tested in FIGS. 8H to J.

FIG. 9 shows the effect of colchicine and a colchicine derivative on the production of superoxide by monosodium uric acid (MSU) stimulated human neutrophils. FIG. 9A shows the effect of colchicine. FIG. 9B shows the effect of colchicine derivative (91). FIG. 9C shows the effect of the effect of colchicine. FIG. 9D shows colchicine derivative (91). FIG. 9E shows colchicine derivative (47a). FIG. 9F shows the effect of colchicine derivative (43). FIG. 9G shows a comparison of the inhibitory activity of the compounds in FIGS. 9C to F.

FIG. 10 shows the plasma concentration of colchicine derivative (91) (FIG. 10A) or colchicine derivative (43) (FIG. 10B) over a period of two hours in mice injected subcutaneously with (91) or colchicine derivative (43), respectively;

FIG. 11 shows the concentration of colchicine derivative (91) (FIG. 11A) or colchicine derivative (43) (FIG. 11B) in circulating leukoctyes of mice over a period of two hours after the subcutaneous injection of (91) or colchicine derivative (43), respectively;

FIG. 14 shows the therapeutic effect of colchicine derivative (43) on leukocyte recruitment to the dorsal air-pouch of mice injected with monosodium uric acid (MSU);

Figure 20:
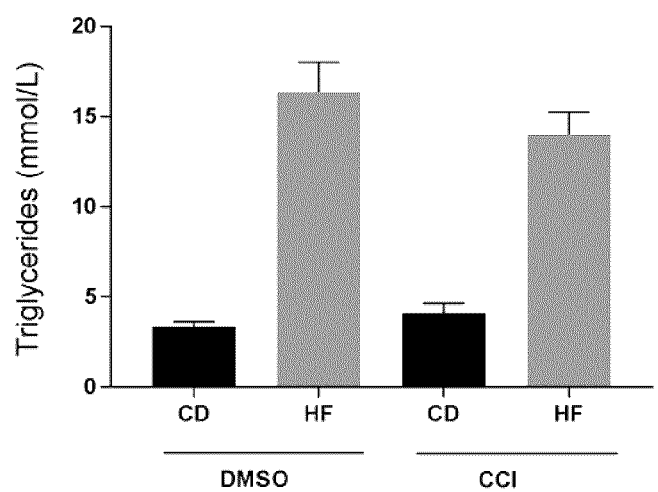
Figure 21:
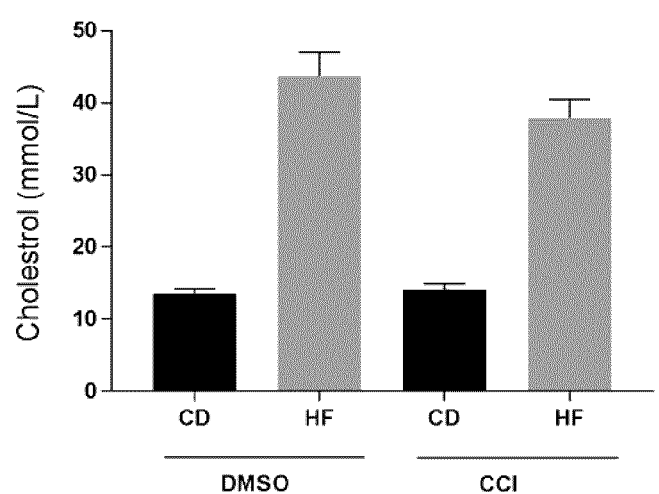
Figure 22A:
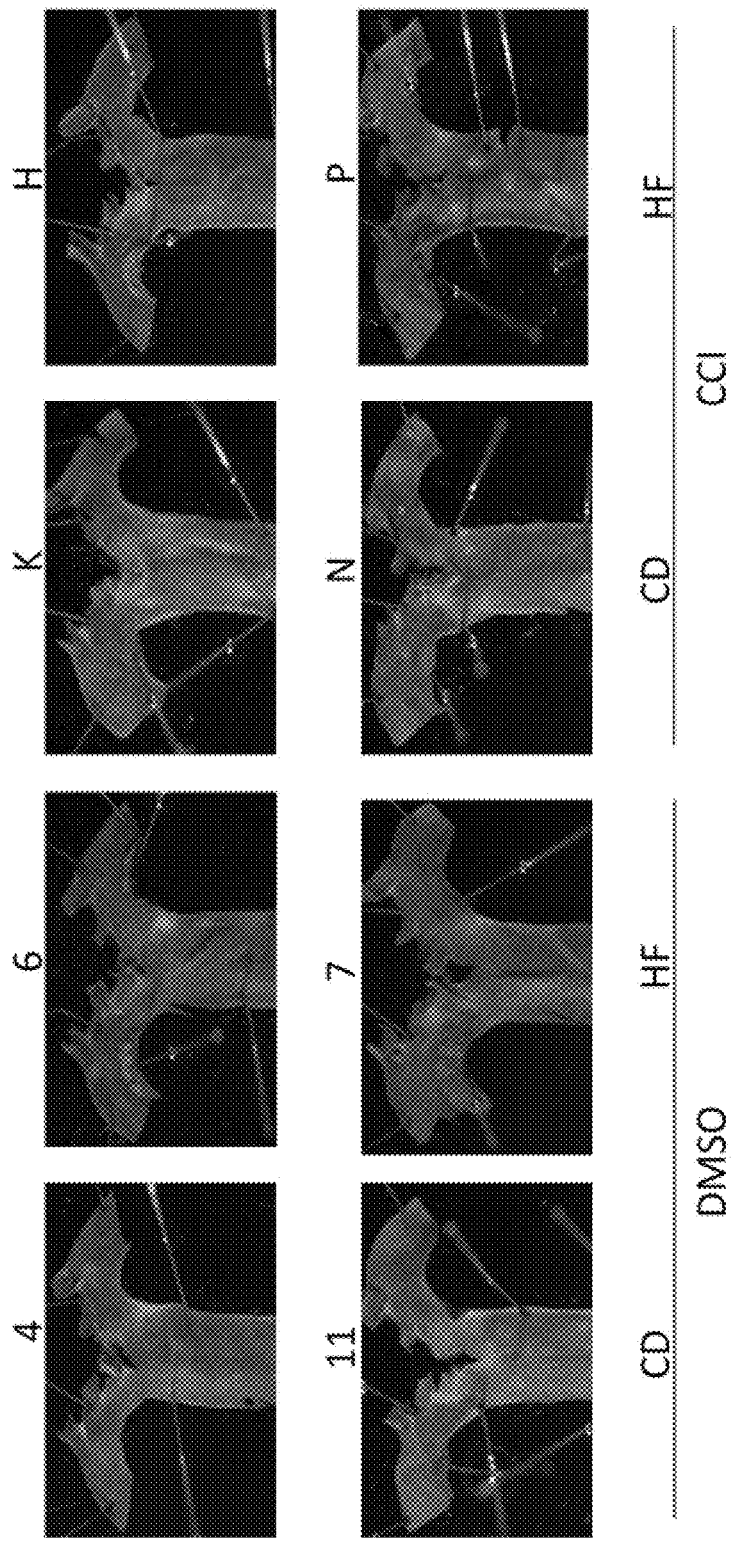
Figure 22B:
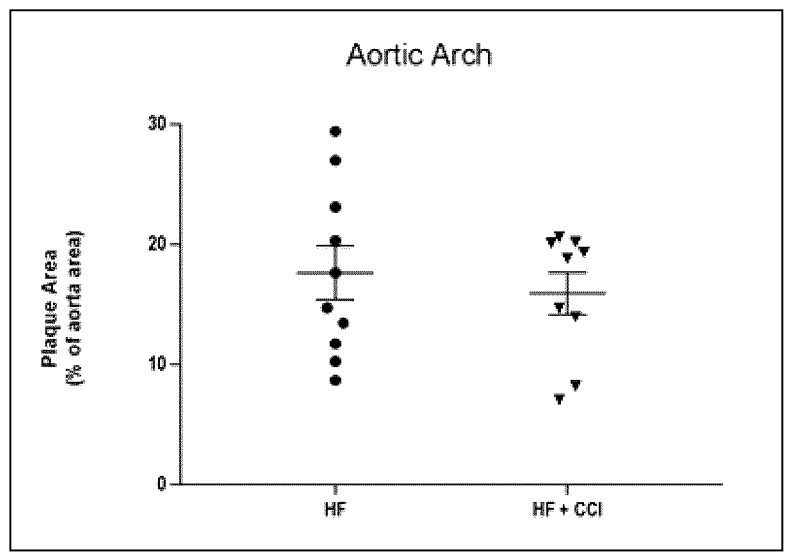
Figure 22C:
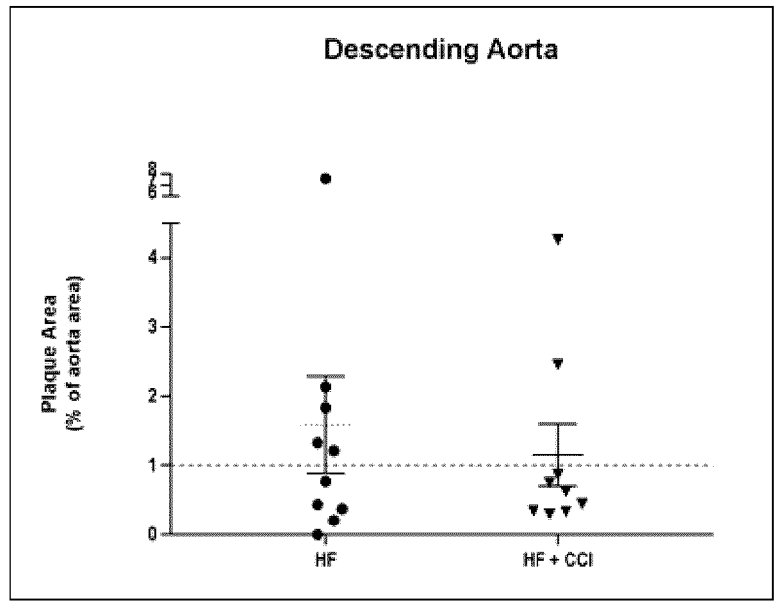

FIG. 20 shows the effect of CCI on the levels of triglycerides in the serum of wild-type and LDLR KO mice fed a high-fat diet: C57BL/6 mice were fed a control diet (CD) or a high-fat diet (HF) for 8 weeks and subcutaneously injected with 0.5 μmol/kg CCI or vehicle (DMSO), 3 times a week. Blood was drawn after the 8-week diet and serum prepared and frozen until analysis;

FIG. 21 shows the effect of CCI on the levels of cholesterol in the serum of wild-type and LDLR KO mice fed a high-fat diet: C57BL/6 mice were fed a control diet (CD) or a high-fat diet (HF) for 8 weeks and subcutaneously injected with 0.5 μmol/kg CCI or vehicle (DMSO), 3 times a week. Blood was drawn after the 8-week diet and serum prepared and frozen until analysis;

FIG. 22 shows the effect of CCI on the development of atherosclerotic lesions in the aortas of LDLR KO mice fed a high-fat diet. FIG. 22A: C57BL/6 mice were fed a control diet (CD) or a high-fat diet (HF) for 8 weeks and subcutaneously injected with 0.5 μmol/kg CCI or vehicle (DMSO), 3 times a week. Aortas were harvested and dissected to perform the aortic lesion en face assay with Sudan IV staining. Sudan IV is a fat-soluble dye that stains lipids, triglycerides and lipoproteins; FIG. 22B shows the percent of the total area of the aortic arch covered by the plaques stained in the 'en face assay'; FIG. 22C shows the percent of the total area of the descending aorta covered by the plaques stained in the 'en face assay'; and FIG. 23 the effect of CCI on the serum levels of cytokines in LDLR KO mice fed a high-fat diet: C57BL/6 mice were fed a control diet (CD) or a high-fat diet (HF) for 8 weeks and subcutaneously injected with 0.5 μmol/kg CCI or vehicle (DMSO), 3 times a week. Blood was drawn after the 8-week diet and serum prepared and frozen until analysis by Luminex assay.

DETAILED DESCRIPTION OF CERTAIN EMBODIMENTS

Any references cited herein are incorporated by reference.

Definitions

When describing the compounds, compositions, methods and uses of this invention, the following terms have the following meanings unless otherwise indicated.

The term "colchicines derivatives" as used herein may include any of the derivatives described herein, for example, it may also include thiocolchicine derivatives, where appropriate.

The term "therapeutically effective amount" as used herein means that amount of active compound or pharmaceutical agent that elicits the biological or medicinal response in a tissue, system, animal, such as a mammal (e.g. human) that is being sought by a researcher, veterinarian, medical doctor or other clinician. When given to treat a disorder, condition, and/or disease, it is an amount that may, when administered to a subject, including a mammal, achieve a desired result, such as treat symptom(s).

The compounds of the present invention may have asymmetric centers, chiral axes, and chiral planes (as described, for example, in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof.

Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are mono-haloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring.

Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N, N-dimethyl-aminoethyl, N, N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S—$).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The present invention includes pharmaceutically acceptable salts, solvates and prodrugs of the compounds of the invention and mixtures thereof.

The term "condition" indicates, for example, a physical status of a mammal (as a whole or as one or more of its parts), that does not conform to a standard physical status associated with a state of well-being for the mammal. Conditions herein described include but are not limited to disorders and diseases wherein the term "disorder" indicates, for example, a condition of the mammal that is associated to a functional abnormality of the mammal or of any of its parts, and the term "disease" indicates, for example, a condition of the mammal that impairs normal functioning of the body of the mammal or of any of its parts and is typically manifested by distinguishing signs and symptoms. Typically, the compounds and compositions described herein are useful for treating inflammatory conditions and, typically, the inflammatory conditions treated have a neutrophil-driven inflammatory component.

The term "neutrophil-driven" inflammation means that the inflammation is associated with neutrophils. Given the multifactorial nature of inflammation, by using this term, the neutrophil is understood to be a driver or mediator of the inflammation, and not necessarily the sole driver or mediator, contributing to at least part of the inflammation/inflammatory pathogenesis. For example, in many cases, other immune cells such as monocytes and/or macrophages may also be drivers of the inflammation. The neutrophil-driven inflammation may be selected from a neutrophil-driven inflammatory disease, a neutrophil-driven inflammatory disorder, a neutrophil-driven inflammatory condition, or combinations thereof. For example, neutrophil-driven inflammation may refer to conditions in which cytokines secreted by neutrophils have a pathological effect, such as IL-1 and/or IL-8.

Examples of such conditions include psoriasis, inflammatory bowel disease, asthma, cardiac and renal reperfusion injury, adult respiratory distress syndrome, thrombosis, glomerulonephritis, rheumatoid arthritis, osteoarthritis, meningitis, stroke including ischemic stroke and hemorrhagic stroke, neurotrauma/closed head injury, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, gout, traumatic arthritis, rubella arthritis, acute synovitis, diabetes, pancreatic β cells disease, Alzheimer's disease, pseudogout, cardiovascular disease, and vasculitis. Typically, the condition is gout, pseudogout, cardiovascular disease, vasculitis, or atherosclerosis. As used herein, "treatment", "treating" or "therapy" is an approach for obtaining a beneficial or desired clinical result. For the purposes described herein, beneficial or desired clinical results may include, but are not limited to, alleviation of symptom(s), diminishment of extent of disease, stabilized (i.e., not worsening) state of disease, delay or slowing of disease progression, and/or amelioration or palliation of the disease state, whether detectable or undetectable. Thus, "treatment" or "therapy" may be considered an intervention performed with the intention of altering the pathology of a disorder. Specifically, the treatment or therapy may directly prevent, slow down or otherwise decrease the pathology of a disease or disorder, or may render the subject more susceptible to treatment or therapy by other therapeutic agents.

The term "chronic gout" includes gout present in a subject having recurrent or prolonged gout attack (also referred to colloquially as a "gout flare"), tophus formation, chronic inflammatory arthritis and/or joint destruction associated with gout.

The term "acute gout" includes gout present in a subject that has had or is having at least one gouty symptom, such as a gout attack.

The term "gout-associated inflammation" or "gouty arthritis" refers to local or systemic inflammation, which may be subclinical, due to immune response to urate crystals.

The term "administration" (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., an anti-gout agent, etc.), "administration" and its variants are each understood to include concurrent and sequential introduction of the compound or prodrug thereof and other agents.

The term "treating gout" or "treatment of gout" refers to administration to a mammal afflicted with a gouty condition and refers to an effect that alleviates the gouty arthritic condition by limiting inflammation and/or alleviating pain associated with inflammation.

The term "pseudogout", also known as calcium pyrophosphate crystal deposition (CPPD) disease, is a type of arthritis that causes spontaneous, painful swelling in joints. It occurs when CPP crystals form in the synovial fluid, causing inflammation and pain.

The terms "comprising", "having" and "including", and various endings thereof, are meant to be open ended, including the indicated component but not excluding other elements.

The term "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

When introducing elements disclosed herein, the articles "a", "an", "the", and "said" are intended to mean that there are one or more of the elements. As used herein, the term "and/or" includes any and all combinations of one or more of the associated listed items.

It will be understood that any component defined herein as being included may be explicitly excluded from the claimed invention by way of proviso or negative limitation. For example, in aspects, particular functional groups may be explicitly excluded from the compounds described herein.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In addition, all ranges given herein include the end of the ranges and also any intermediate range points, whether explicitly stated or not. Thus, as used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Colchicine Derivatives

Colchicine derivative(s), a composition comprising the derivative(s), method(s) of administration thereof, and use(s) thereof are provided for the treatment of inflammation.

Colchicine derivatives are represented by a compound of Formula I:

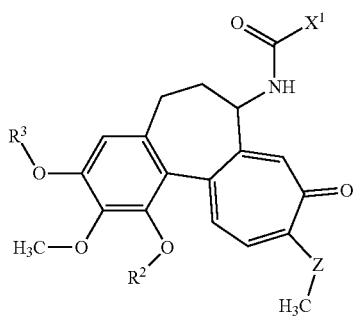

Formula I wherein: Z is O or S; $X^1$ is selected from a substituted or unsubstituted hydrocarbon group, or a substituted or unsubstituted heterogeneous group; $R^2$ and $R^3$ are each independently selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic group, or a substituted or unsubstituted heteroaromatic group; a pharmaceutically-acceptable salt thereof, hydrate thereof, solvate thereof, tautomer thereof, optical isomer thereof, or combination thereof.

In other embodiments, when $R^2$ and $R^3$ are both methyl, $X^1$ is not methyl.

In specific embodiments of Formula I, $R^2$ and $R^3$ are each independently selected from a substituted or unsubstituted alkyl, a substituted or unsubstituted alkenyl, a substituted or unsubstituted alkynyl, a substituted or unsubstituted aromatic group, a substituted or unsubstituted heteroaromatic group, a substituted or unsubstituted carbocyclic group, or a substituted or unsubstituted heterocyclic group. In more particular embodiments, $R^2$ and $R^3$ are each independently selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted $C_1$-$C_6$ alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In other embodiments, $R^2$ and $R^3$ are each independently selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl. In more particular embodiments, $R^2$ and $R^3$ are each independently selected from a substituted or unsubstituted alkyl, a substituted or unsubstituted aryl, or a substituted or unsubstituted alkylaryl. In further embodiments, $R^2$ and $R^3$ are each independently selected from a substituted or unsubstituted alkyl, or a substituted or unsubstituted alkylaryl. In additional embodiments, $R^2$ and $R^3$ are each independently selected from a substituted or unsubstituted alkyl. In further embodiments, $R^2$ and $R^3$ are each independently selected from a substituted or unsubstituted $C_1$-$C_6$ alkyl.

In an embodiment, $X^1$ is a substituted or unsubstituted hydrocarbon group. In further embodiments, $X^1$ is selected from a substituted or unsubstituted alkyl, a substituted or unsubstituted alkenyl, or a substituted or unsubstituted alkynyl. In particular embodiments, $X^1$ is selected from a substituted or unsubstituted alkyl, such as a substituted or unsubstituted $C_1$-$C_6$ alkyl, and in particular, an unsubstituted $C_1$-$C_6$ alkyl. In more specific embodiments, $X^1$ is selected from methyl or ethyl.

In another embodiment, $X^1$ is a substituted or unsubstituted heterogeneous group. In further embodiments, $X^1$ is selected from —$CR^4R^5R^6$, wherein $R^4R^5R^6$ are each independently selected from H, a substituted or unsubstituted hydrocarbon group, a substituted or unsubstituted heterogeneous group. In particular, $R^4R^5R^6$ can each be independently selected from substituted or unsubstituted amido groups. In a specific embodiment $R^4$ and $R^5$ are each independently selected from H, substituted or unsubstituted alkyl, and $R^6$ is —$NR(CO)CR^7R^8R^9$, wherein R is selected from H, and a substituted or unsubstituted alkyl and R⁷, R⁸, and R⁹ are each selected from H, halo group, and a substituted or unsubstituted alkyl. R⁷, R⁸, and R⁹ can be selected from a halo. More specifically, R⁷, R⁸, and R⁹ can be selected from a fluoro group.

In a further embodiment, $X^1$ is $OR^{10}$; $R^{10}$ is selected from a substituted or unsubstituted hydrocarbon group, or a substituted or unsubstituted heterogeneous group. In further embodiment, $R^{10}$ is selected from a substituted or unsubstituted alkyl group, a substituted or unsubstituted alkenyl, a substituted or unsubstituted alkynyl, a substituted or unsubstituted aromatic group, a substituted or unsubstituted heteroaromatic group, a substituted or unsubstituted carbocyclic group, or a substituted or unsubstituted heterocyclic group. In particular, $R^{10}$ is selected from a substituted or unsubstituted alkyl, $CH_2OH$, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl.

In other embodiments, $R^{10}$ is selected from a substituted or unsubstituted alkyl, a substituted or unsubstituted alkenyl, or a substituted or unsubstituted alkynyl. In other embodiments, $R^{10}$ is selected from a substituted or unsubstituted $C_1$-$C_6$ alkyl, or a substituted or unsubstituted $C_2$-$C_6$ alkenyl, or $C_2$-$C_6$ alkynyl.

In further embodiments, $R^{10}$ is selected from a substituted or unsubstituted alkyl, such as a substituted or unsubstituted $C_1$-$C_6$ alkyl, and in particular, an unsubstituted $C_1$-$C_6$ alkyl. In more specific embodiments, $R^{10}$ is selected from methyl or ethyl.

In certain embodiments, the colchicine derivative comprises a compound of Formula IA:

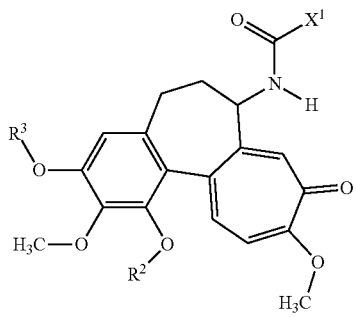

Formula IA

For Formula IA, $R^2$, $R^3$ and $X^1$ can be as noted above with respect to Formula I.

In certain embodiments, the colchicine derivative comprises a compound of Formula IB:

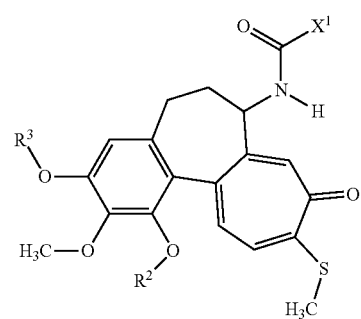

Formula IB

For Formula IB, $R^2$, $R^3$ and $X^1$ can be as noted above with respect to Formula I.

In other embodiments, the colchicine derivative comprises a compound of Formula IC:

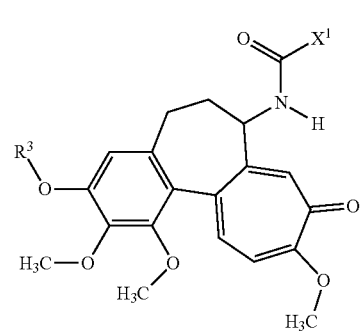

Formula IC

For Formulae IC, $R^3$ and $X^1$ can be as noted above with respect to Formula I.

In other embodiments, the colchicine derivative comprises a compound of Formula ID:

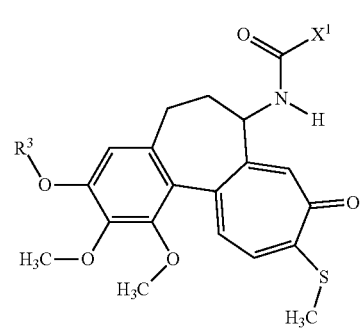

Formula ID

For Formulae ID, $R^3$ and $X^1$ can be as noted above with respect to Formula I.

In certain embodiments of Formulae I and IA to ID, $X^1$ is methyl or methoxy. In another embodiment, $R^3$ is selected from a substituted or unsubstituted alkyl. In further embodiments, $R^3$ is selected from a substituted or unsubstituted $C_1$-$C_6$ alkyl and more specifically, $R^3$ is ethyl.

The colchicine derivatives described herein can be in the form of a pharmaceutically-acceptable salt thereof, a hydrate thereof, a solvate thereof, a tautomer thereof, an optical isomer thereof, or a combination thereof. In more specific embodiments, the compounds of Formulae I and IA to ID have the S-configuration at C7. Certain examples of the compounds of Formulae I and IA to ID are shown in FIGS. 1 to 4 and 4A to 4D.

Certain compounds described herein can be prepared, for example, as follows:

a) reacting a compound of Formula IV with ROCl:

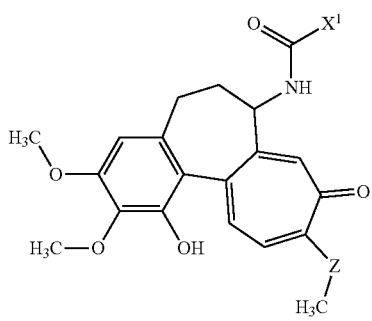

Formula IV to form:

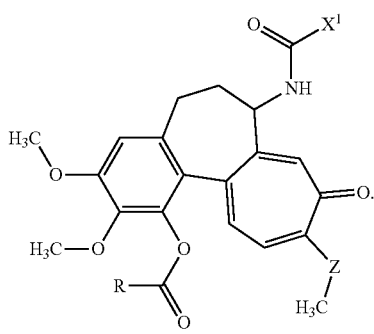

Formula V wherein: R can be selected from a substituted or unsubstituted alkyl and $X^1$ can be as defined above.

Certain compounds described herein can also be prepared as follows:

a) reacting a compound of Formula IV with $R^2Br$:

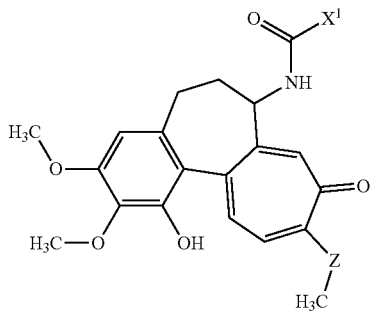

Formula IV to form:

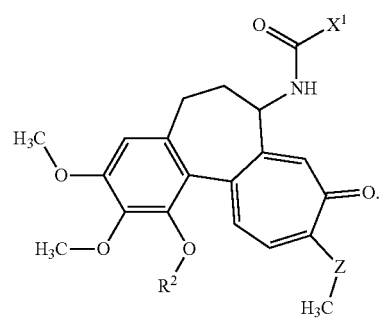

Formula VI wherein: $X^1$ and $R^2$ can be as defined above.

Certain compounds described herein can also be prepared as follows:

a) reacting a compound of Formula VII with $R^2Br$:

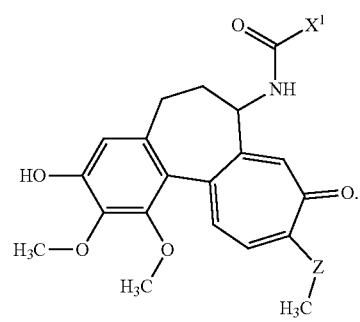

Formula VII to form:

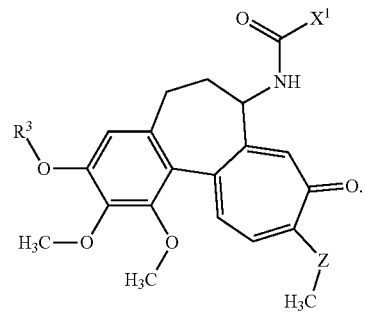

Formula VIII wherein: $X^1$ and $R^3$ can be as defined above.

More specific $X^1$ groups can be added by, for example, reacting Formula VI or VIII, wherein —(CO)$X^1$ is —(CO) OR with HO(CO)CR$^4$R$^5$R$^6$, wherein R$^4$R$^5$R$^6$ are each independently selected from H, a substituted or unsubstituted hydrocarbon group, a substituted or unsubstituted heterogeneous group. In particular, R$^4$R$^5$R$^6$ can each be independently selected from substituted or unsubstituted amido groups. In a specific embodiment R$^4$ and R$^5$ are each independently selected from H, substituted or unsubstituted alkyl group, and R$^6$ is —NR(CO)CR$^7$R$^8$R$^9$, wherein R$^7$, R$^8$, and R$^9$ are each selected from H, halo group, a substituted or unsubstituted alkyl group. $R^1$, $R^8$, and $R^9$ can be selected from a halo group. More specifically, $R^7$, $R^8$, and $R^9$ can be selected from a fluoro group.

Certain compounds described herein can also be prepared, for example, as follows:
a) reacting a compound of Formula VIA with 1-ethyl-3-(3-dimethylaminopropyl) carbodiimide (EDCI), hydroxybenzotriazole (HOBt) and $CF_3NHCH_2COOH$ ($F_3CglyOH$)

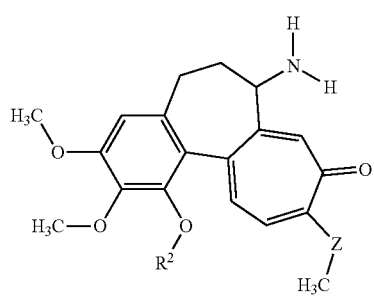

Formula VIA to form:

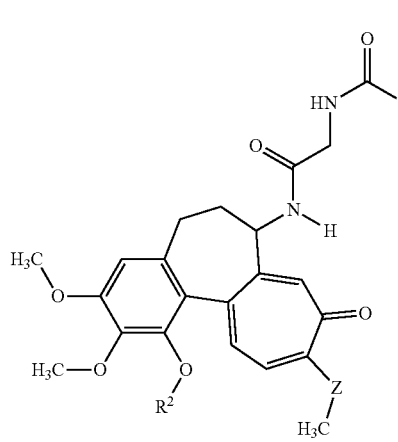

Formula VIB wherein: $R^2$ can be as defined above.

Certain compounds described herein can also be prepared as follows:
a) protecting the hydroxyl group of a compound of Formula VIIA

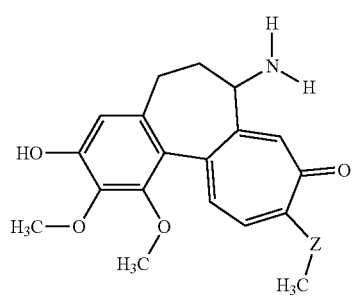

Formula VIIA to form (PG=protecting group):

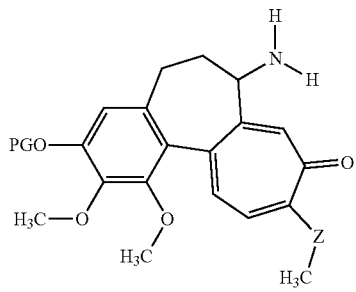

Formula VIIB b) reacting a compound of Formula VIIB with 1-ethyl-3-(3-dimethylaminopropyl) carbodiimide (EDCI), hydroxybenzotriazole (HOBt) and $CF_3NHCH_2COOH$ ($F_3CglyOH$), followed by deprotection to form:

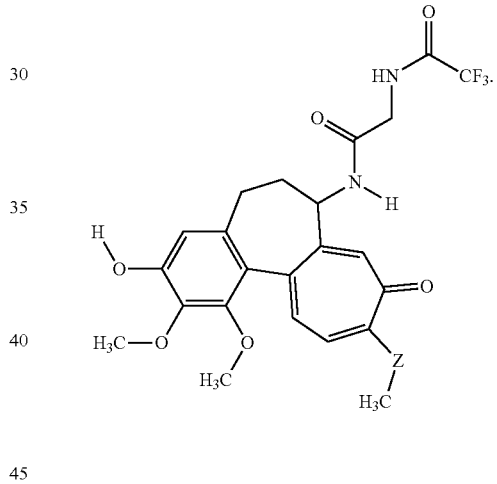

Formula VIIC

Certain compounds described herein can be prepared, for example, as follows:
a) reacting a compound of Formula XX with $RO(C=O)Cl$:

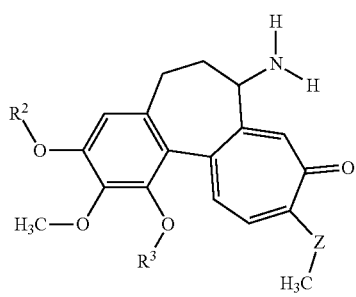

Formula XX to form:

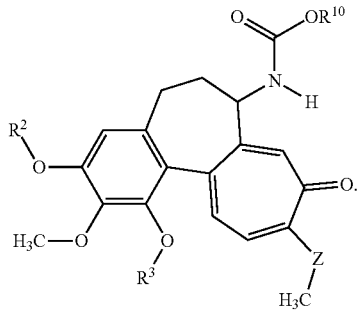

Formula XXI wherein: R², R³ and R¹⁰ can be as defined above.

Certain compounds described herein can also be prepared as follows:

a) protecting the hydroxyl group of a compound of Formula XXII

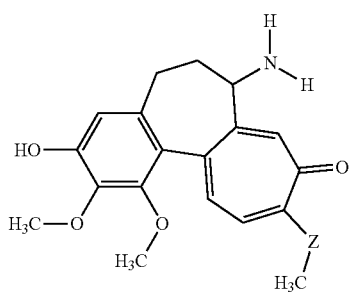

Formula XXII to form (PG=protecting group):

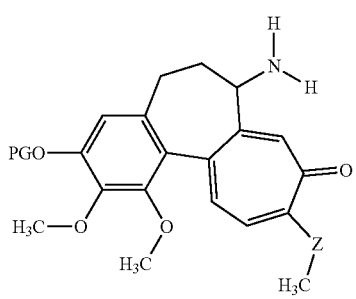

Formula XXIIB b) reacting a compound of Formula XXIIB with R¹⁰O(C=O)Cl, followed by deprotection to form:

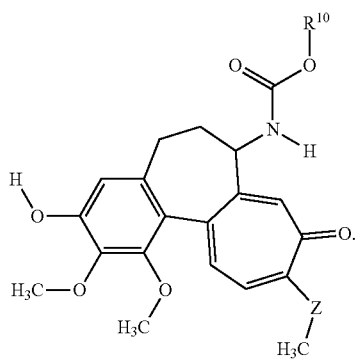

Formula XXIIC

In general, the compounds described herein may be prepared by employing reactions and standard manipulations that are known in the literature or exemplified herein.

The compounds described herein are useful in the treatment of inflammatory condition(s), disease(s) and/or disorder(s), such as gout. The gout treated may be, for example, chronic gout and/or acute gout. In particular, the compounds described herein can treat at least one gouty symptom such as gout attacks, joint destruction associated with gout. For example, the compounds described herein can limit gouty inflammation and/or alleviate pain associated with inflammation.

Gout is known as one of the most painful and common forms of inflammatory arthritis. Its prevalence (3-6% in Western countries), is increasing worldwide due to a rise in conditions that promote the key risk factor for gout, hyperuricemia, including obesity and renal failure. Monosodium urate (MSU) crystals are the etiological agents of gouty arthritis, forming in joints and soft tissues when the concentration of uric acid in circulation exceeds its solubility (>6 mg/mL) triggering a robust, innate immune response that causes excruciating pain.

The initial events of a gout attack involve the MSU-induced activation of tissue resident macrophages as well as cell death within the joint. These cellular events lead to the release of pro-inflammatory cytokines that drive and amplify the inflammatory reaction. IL-1 and IL-8 have been identified as cytokines in the pathogenesis of gout. IL-1 orchestrates the initial molecular events of a gout attack including the increase in the expression of adhesion molecules on the surface of endothelial cells (e.g. E-selectin) and the release of chemokines. IL-8 is one of the most potent chemoattractants for neutrophils and promotes the massive influx of neutrophils that causes the typical symptoms of gout including severe pain and swelling of the affected joint. The recruited neutrophils become themselves activated by MSU and in turn release pro-inflammatory cytokines, reactive oxygen species (ROS), proteases and neutrophil extracellular traps (NETs) that amplify the inflammatory reaction. At high neutrophil concentrations, NETs interact with MSU forming complexes named aggregated NETs contributing to the resolution of the gout attack.

The treatment of gout targets two key facets of its pathogenesis, namely, the development of MSU crystals and inflammation. Medications used for the former include xanthine oxidase inhibitors (XOI) and for the latter, colchicine, non-steroidal anti-inflammatory drugs or corticosteroids. Colchicine is also used to prevent gout attacks with urate-lowering therapy initiation, in some patients who are intolerant to XOI and for prophylaxis for varying periods of time. Although the frequency and occurrence of gout attacks are unpredictable, it is not uncommon for patients to suffer from gout attacks over a period of approximately four years after starting urate-lowering therapy. On average 60% of patients suffer from a gout attack within one or two years of their first attack.

The treatment of gout is challenging since many patients suffer from multiple co-morbidities that are associated with relative contraindications to the available anti-inflammatory drugs. Also, most anti-inflammatory drugs lack specificity for the molecular mechanisms underlying MSU-induced inflammation. In contrast, colchicine exhibits a certain degree of specificity towards the molecular pathways involved in gout since it inhibits the MSU-induced activation of neutrophils but not certain responses of neutrophils induced by the bacterial peptide fMLP. Nevertheless, the range of therapeutically safe doses for colchicine is very small and it exhibits major toxicity in the gastrointestinal system which is the major reason for poor compliance for this drug.

The colchicine derivatives described herein are less toxic and more specific for hematopoietic cells, such as neutrophils; inflammatory cells that are abundant in gout attacks. It was demonstrated in PCT Publication No. WO2011022805 (Tuszynski et al.) that analogues of the anti-mitotic drug, colchicine, were less toxic for the treatment of cancer.

Advantageously, the anti-inflamatory activity of the colchicine derivatives described herein is not only comparable to that of colchicine but can be preserved at doses where colchicine lacks anti-inflammatory properties (e.g. the colchicine derivatives described herein may provide anti-inflammatory effects at lower doses than that of colchicine (e.g. at least about 10 fold lower) and are thus, in aspects, more potent that colchicine). As shown in the examples below, compounds (91), 43 and 47a are able to inhibit the increase in intracellular calcium concentration at a dose as low as 0.1 µM. In contrast, colchicine induced a similar inhibition in the mobilization of calcium at a concentration of 10 µM (FIGS. 7A, E, K and L). Unexpectedly, colchicine derivatives (91), (47a) and (43) are thus able to significantly reduce the mobilization of intracellular calcium stores at about 10 to about 100-fold lower concentration compared to colchicine; doses at which colchicine was shown to be ineffective (FIG. 7).

The effect of colchicine on other inflammatory diseases has been shown in the treatment of recurrent pericarditis and Familial Mediterranean Fever (FMF) (Slobodnock et al. The American Journal of Medicine (2015)). Patients with FMF, an inherited disorder that primarily affects 1 in 200 to 1,000 people in populations originating in the Mediterranean region, benefit from lifelong treatment with colchicine. Colchicine is the gold standard treatment for FMF (https://www.fmffoundation.org/fmf). With regard to pericarditis, current European guidelines recommend colchicine given at 2 mg daily for 1 to 2 days, followed by a maintenance dose (Slobodnock et al. The American Journal of Medicine (2015)). Other secondary markets for colchicine derivatives include, but are not limited to, diseases involving neutrophil-mediated inflammation such as pseudogout, coronary atherosclerosis, vasculitis, or combinations thereof. In particular, with respect to pseudogout, colchicine has been suggested for prophylaxis and acute treatment of CPP arthritis (Slobodnock et al. The American Journal of Medicine (2015)). Moreover, in coronary atherosclerosis where complex immune-inflammatory pathways involving neutrophils are implicated in the development, growth, and instability of atherosclerotic plaque, colchicine has been reported to suppress blood levels of inflammatory mediators and prevent cholesterol-crystal-induced neutrophil-mediated inflammation implicated in the progression and instability of atherosclerosis (Nidorf et al. 2014). With respect to the results presented herein, CCI and other colchicine derivatives would be expected to find use in the treatment of gout as well as other inflammatory diseases, conditions, and/or disorders, such as, for example, recurrent pericarditis, FMF, psoriasis, inflammatory bowel disease, asthma, cardiac and renal reperfusion injury, adult respiratory distress syndrome, thrombosis, glomerulonephritis, rheumatoid arthritis, osteoarthritis, meningitis, stroke including ischemic stroke and hemorrhagic stroke, neurotrauma/closed head injury, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, gout, traumatic arthritis, rubella arthritis, acute synovitis, diabetes, pancreatic p cells disease, Alzheimer's disease, pseudogout, cardiovascular disease, and vasculitis. Typically, the condition is gout, pseudogout, cardiovascular disease, vasculitis, or atherosclerosis.

With respect to treating gout, colchicine exhibits the most specificity with respect to the pathogenesis of this inflammatory disease since it dampens most of the inflammatory actions of neutrophils, a principal leukocyte involved in gout attacks. Nevertheless, the administration of this alkaloid remains challenging due to its low therapeutic index between efficacy and treatment-limiting side effects. Indeed, and unexpectedly, the colchicine derivatives described herein can provide increased specificity, as compared to colchicine, for neutrophils and also have anti-inflammatory activity similar to colchicine at lower doses. In other words, the colchicine derivatives described herein were found to produce the same anti-inflammatory effect as colchicine, however, and surprisingly, they were significantly more potent than colchicine. These unexpected results provide the advantage of allowing the colchicine derivatives described herein to be administered at lower doses, while their increased specificity diminishes the likelihood of toxicity and undesirable secondary effects. This is of particular relevance for gout patients that suffer from chronic kidney disease since these patients have contraindications to the majority of anti-inflammatory drugs used to treat gout attacks including colchicine. The same applies to patients with advanced hepatic impairment. Since the colchicine derivatives described herein can be administered at lower doses and have higher specificity, thereby diminishing the likelihood of toxicity, they can be associated with less of the troublesome side effects caused by colchicine administration such as gastrointestinal complications.

The compounds of this invention may be administered to animals such as mammals, typically humans, either alone or, in combination with pharmaceutically acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, and subcutaneous routes of administration.

As noted, compounds of the present invention may be administered orally. For oral use of a compound or composition according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention may also be combined and/or co-administered with other therapeutic agents that are selected for their particular usefulness against gout that is being treated. For example, the compounds of the present invention may be combined and/or co-administered with anti-gout agent(s), simultaneously or sequentially.

Examples of anti-gout agents include, without being limited thereto, the following: non-steroidal anti-inflammatory drug (NSAIDS), intraarticular glucocorticoids, xanthine oxidase inhibitors, recombinant non-human uricase enzyme, uric acid excretion promoters, uricosuric agents, and combinations thereof. The present compounds may also be useful with other therapies such as when co-administered with ingredients for treating other related indications.

Xanthine oxidase inhibitors include compounds which reduce serum uric acid levels by inhibiting the enzyme xanthine oxidase. Examples of xanthine oxidase inhibitors include, but are not limited thereto, febuxostat, propolis, oxypurinol, tisopurine or an inositol and allopurinol.

Recombinant non-human uricase enzyme include rasburicase or pegloticase.

Uric acid excretion promoters or uricosuric agents refers to compounds which accelerate the rapid excretion of uric acid accumulated in the body by preventing the reuptake of urate back into the bloodstream in the kidney, leading to a net increase in excretion. Examples of such uric acid excretion promoters or uricosuric agents include probenecid, benzbromarone, sulfinpyrazone, guaifenesin, losartan, atorvastatin, amlodipine, adrenocorticotropic hormone or fenofibrate.

NSAIDS include, but are not limited to, diclofenac, indomethacin, naproxen, sulindac, lumiracoxib or a Cox-2 selective inhibitor. The Cox-2 selective inhibitor includes, but it is not limited to, etoricoxib, celecoxib (SC-58635), 5-bromo-2-(4-fluorophenyl)-3-(4-(methylsulfonyl)phenyl)-thiophene (DUP-697), flosulide (CGP-28238), meloxicam, 6-methoxy-2 naphthylacetic acid (6-MNA), MK-966 (Vioxx), nabumetone (6-MNA prodrug), nimesulide, N-[2-(cyclohexyloxy)-4-nitrophenyl]-methanesulfonamide (NS-398), SC-5766, SC-58215, or 3-Formylamino-7-methylsulfonylamino-6-phenoxy-4H-1-benzopyran-1-one (T-614).

The anti-inflammatory agent may be a corticosteroid. The corticosteroid includes, but is not limited to, prednisone, methyl prednisolone, prednisolone, dexamethasone, fluticasone propionate, 6α, 9α-difluoro-17-[(2-furanylcarbonyl) oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17.alpha.-propionyloxy-androsta-1,4-diene-17β-carbothioic acid S-(2-oxo-tetrahydro-furan-3S-yl)ester, beclomethasone esters, the 17-propionate ester or the 17,21-dipropionate ester, budesonide, flunisolide, mometasone esters, the furoate ester, triamcinolone acetonide, rofleponide, ciclesonide, butixocort propionate, RPR-106541, ST-126, fluticasone propionate, 6α,9α-difluoro-11β-hydroxy-16α-methyl-17α-[(-4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, or 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

If formulated as a fixed dose, such combination products employ the compounds of this invention within the dosage range described below and the other pharmaceutically active agent(s) within its approved dosage range. Compounds of described herein may alternatively be used sequentially with known pharmaceutically acceptable agent(s) when a combination formulation is inappropriate.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for gout. Administration occurs in an amount from about 0.001 mg/kg of body weight to greater than about 100 mg/kg of body weight per day; from about 0.001 mg/kg of body weight to about 500 mg/kg of body weight per day; from about 0.001 mg/kg of body weight to about 250 mg/kg of body weight per day; or 0.001 mg/kg of body weight to about 100 mg/kg of body weight per day. These dosages can be more particularly used orally.

Any combination of doses may be used. The combination may be used sequentially or simultaneously.

β-Tubulin Colchicine Binding Sites

Models of the five most prevalent human β-tubulin isotypes have been determined and the colchicine-binding site identified herein as the most promising for drug design based on isotype specificity. Using this binding site as a template, the colchicine derivatives described in PCT Publication No. WO2011022805 were engineered to preferentially bind to β-tubulin isotypes of interest based on their inherent variation between isotypes and the fact that colchicine binding sites on each β-tubulin isotype differ in both their geometrical and biochemical properties. As described therein, colchicine analogues that preferentially bind β-III tubulin, an isotype of tubulin overexpressed in cancer cells were generated and it was found that those derivatives were more potent than Taxol at inhibiting tumour growth at lower doses.

Using the approach described above, colchicine's structure was modified to increase its ability to bind the β-VI tubulin isotype. The β-VI tubulin is important as the target since it is one of the principal β-tubulin isotypes expressed in immune cells, such as neutrophils (see, FIG. 15). Moreover, binding to β-VI tubulin minimizes off-target effects with non-hematopoietic cells since this isotype is specific to hematopoietic cells. The β-VI tubulin isotype is very distinct from others, especially in the colchicine binding area, and has a narrow distribution in the human body offering a high level of specificity and selectivity for the drugs that bind it.

The colchicine derivatives described herein preferentially bind to βVI, βV and with less affinity to βI tubulin. The computational methods described herein provide colchicine derivatives that have increased specificity for cells involved in inflammatory conditions, such as gouty inflammation, and can also unexpectedly be active at much lower concentrations than colchicine, such that undesired side effects of colchicine may be avoided.

Colchicine binding has been examined. The sequence of residues making up the colchicine binding site shows the greatest variation (77.8% identity) among all of the human tubulin isotypes (Huzil J. T. et al., Nanotechnology. 2006: 17:S90-S100). This binding site has previously been shown to interact with several natural compounds including colchicinoids, the benzimidazoles (Laclette J. P. et al., Biochem Biophys Res Commun. 1980; 92:417-23; Tahir S. K., Biotechniques. 2000; 29:156-60; Russell G. J. et al., Biochem. Mol. Biol. Int. 1995; 35:1153-9; and Hoebeke J. et al., Biochem Biophys. Res. Commun. 1976; 69:319-24) and podophyllotoxin (Ravelli R. B. et al., Nature. 2004; 428: 198-202) making it amenable to several binding conformations (Garland D. L., Biochemistry. 1978; 17:4266–72; Sackett D. L. et al., Biochemistry, 1993; 32:13560-5; Andreu J. M. et al., Biochemistry. 1982; 21:6465-76; Chaudhuri A. R. et al., J. Mol. Biol., 2000; 303:679-92). Colchicine has extremely strong anti-mitotic activity that is only observed at toxic or near toxic levels which, while limiting its use as a treatment for gout, is used herein as a standard for comparison of similar compounds with increased selectivity towards tubulin isotypes expressed in hematopoietic cells.

Computational screening was used to determine colchicine derivatives that may have better anti-inflammatory properties based on their β-tubulin isotype affinities (in particular their affinity to β-VI). The anti-inflammatory properties of these derivatives (for example derivatives 91, 47a and 43) were then validated using in vitro and in vivo testing described herein. For example, colchicine derivatives with a higher affinity for certain β-tubulin isotypes, such as compound 91 described herein (see, e.g., FIG. 7), were found to be better than colchicine in their effects against inflammatory cells (e.g., for example in the inhibition of calcium mobilization at about 10 to about 100-fold lower concentration), without the disadvantage of colchicine toxicity. The anti-inflammatory properties of the derivatives described herein are outlined in the Examples below.

While there is a plethora of structural information regarding tubulin's interactions with several ligands, tubulin's conformation decays over time and the binding of a drug can itself cause significant conformational changes within the protein itself (Luduena R. F. et al., Biochem. 1995; 34:15751-9; Chaudhuri A. R. et al., J. Mol. Biol., 2000; 303:679-92; and Schwarz P. M. et al., Biochem. 1998; 37:4687-92). Modeling predictions using a particular, fixed, conformation of a binding site may therefore be unreliable. This is especially true for colchicine binding, where β-tubulin in its unbound form shows a complete absence of the colchicine binding cavity (Nogales E. et al., Nature. 1995; 375:424-7). In order to overcome this limitation, firstly, three representative models of the colchicine binding site as it is found throughout the human β-tubulin isotypes has been created. Secondly, a systematic docking procedure has been performed, which attempts to sample the conformational space of the colchicine binding site through a simulated annealing method.

Using computational modeling methods, several modifications to colchicine have been introduced in an attempt to design a model system capable of increasing specificity for β-tubulin isotypes expressed in hematopoietic cells. To examine the differences between isotypes, a cavity was probed located below the bound colchicine in the crystal structure. In particular, several C3-demethylthiocolchicine derivatives and C1-demethylcolchicine derivatives were synthesized.

Ultimately tubulin-isotype specific drugs should exhibit fewer side effects than their currently prescribed counterparts. This is because they will bind to and disrupt those microtubules only in cells expressing a particular β-tubulin isotype associated with inflammation. These results also suggest that modeling is likely to generate better drugs and that rational drug design is possible with tubulin.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Synthesis and Analysis of Colchicine Derivatives

Material and Methods

All chemical compounds and colchicine, N-[(7S)-1,2,3, 10-tetramethoxy-9-oxo-5,6,7,9-tetrahydrobenzo[α]heptalen-7-yl]acetamide (1), used in the studies were purchased from Sigma-Aldrich (Oakville, ON, Canada).

Synthesis of the Colchicine Compounds

Figure 1:
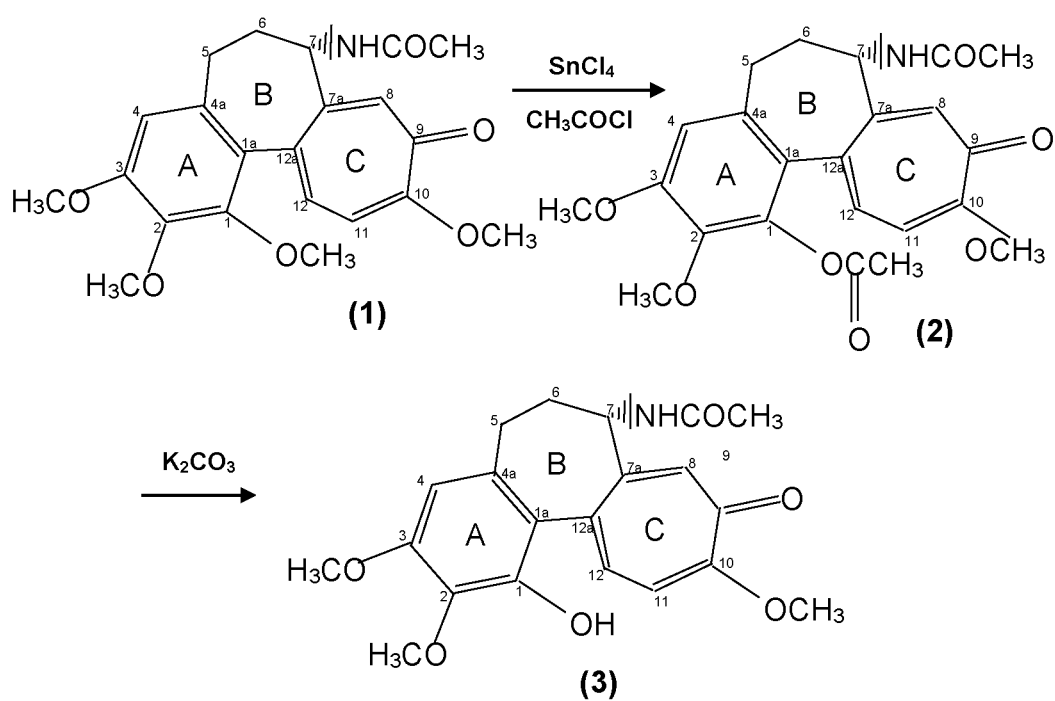
FIG. 1 shows a synthetic scheme for making compounds (2) and (3)
Figure 2:
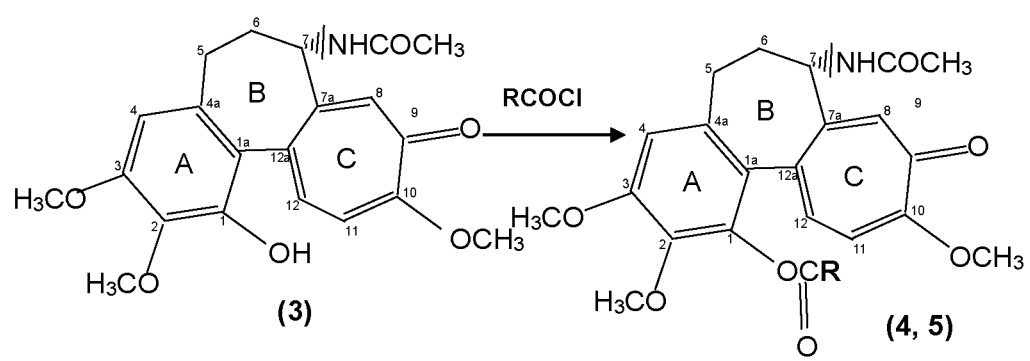
FIG. 2 shows a synthetic scheme for making compounds (4) and (5)

See FIGS. 1-3 for Synthetic Schemes.
N-[(7S)-2,3,10-trimethoxy-1-((methyl)carbonyloxy)-9-oxo-5,6,7,9-tetrahydrobenzo[α]heptalen-7-yl]acetamide (2) and N-[(7S)-1-hydroxy-2,3,10-trimethoxy-9-oxo-5,6,7,9-tetrahydrobenzo[α]heptalen-7-yl]acetamide (3). The synthesis of (2) and (3) was adapted from Blade-Font (A. Blade-Font, Afinidad, 36 (1979) 329-331) and is presented in FIG. 1.
N-[(7S)-1-((ethyl)carbonyloxy)-2,3,10-trimethoxy-9-oxo-5,6,7,9-tetrahydrobenzo[α]heptalen-7-yl]cetamide (4) and N-[(7S)-1-(((methyl)ethyl)carbonyloxy)-2,3,10-trimethoxy-9-oxo-5,6,7,9-tetrahydrobenzo[α]heptalen-7-yl] acetamide (5).
1 mmol of (2) was dissolved in 2.5 mL of sodium hydroxide solution. The solution was cooled to 0° C. 1 mmol of $CH_3CH_2COCl$ or $(CH_3)CH(CH_3)COCl$ was dissolved in 3.5 mL acetone, and added to compounds (4) or (5). The solution was allowed to stand for 15 h and then 25 mL of alkaline water was added. Chloroform was used to extract the resulting product and drying over magnesium sulfate. The syntheses of (4) and (5) are presented in FIG. 2.
N-[(7S)-1-(ethoxy)-2,3,10-trimethoxy-9-oxo-5,6,7,9-tetrahydrobenzo[α]heptalen-7-yl]acetamide (6);
N-[(7S)-1-(ethoxy-1-methyl)-2,3,10-trimethoxy-9-oxo-5,6, 7,9-tetrahydrobenzo[α]heptalen-7-yl]acetamide (7);
N-[(7S)-2,3,10-trimethoxy-1-(2-methylpropoxy)-9-oxo-5,6, 7,9-tetrahydrobenzo[α]heptalen-7-yl]acetamide (7a);
N-[(7S)-1-(butoxy)-2,3,10-trimethoxy-9-oxo-5,6,7,9-tetrahydrobenzo[α]heptalen-7-yl]acetamide (7b);
N-[(7S)-1-((but(3-en)oxy)-2,3,10-trimethoxy-9-oxo-5,6,7, 9-tetrahydrobenzo[α]heptalen-7-yl]acetamide (7c);

N-[(7S)-2,3,10-trimethoxy-9-oxo-1-(pro(2-en)oxy)-5,6,7,9-tetrahydrobenzo[α]heptalen-7-yl]acetamide (8);

N-[(7S)-2,3,10-trimethoxy-9-oxo-1-((prop(2-en)oxy)-5,6,7,9-tetrahydrobenzo[α]heptalen-7-yl]acetamide (9);

N-[(7S)-2,3,10-trimethoxy-9-oxo-1-((phenyl)methoxy)-5,6,7,9-tetrahydrobenzo[α]heptalen-7-yl]acetamide (10);

N-[(7S)-2,3,10-trimethoxy-9-oxo-1-(((3-methoxy)propan)oxy)(3-methoxy))-5,6,7,9-tetrahydrobenzo[α]heptalen-7-yl]acetamide (11);

N-[(7S)-2,3,10-trimethoxy-9-oxo-1-((phenyl(3-chloro))methoxy)-5,6,7,9-tetrahydrobenzo[α]heptalen-7-yl]acetamide (12); N-[(7S)-2,3,10-trimethoxy-9-oxo-1-((pyridin(3))yl)-5,6,7,9-tetrahydrobenzo[α]heptalen-7-yl]acetamide (13);

N-[(7S)-2,3,10-trimethoxy-9-oxo-1-((phenyl(2-chloro))methoxy)-5,6,7,9-tetrahydrobenzo[α]heptalen-7-yl]acetamide (14);

N-[(7S)-2,3,10-trimethoxy-9-oxo-1-(((phenyl(4-chloro))methoxy)-5,6,7,9-tetrahydrobenzo[α]heptalen-7-yl]acetamide (15);

N-[(7S)-2,3,10-trimethoxy-1-((methyl)cyclohexane)-9-oxo-5,6,7,9-tetrahydrobenzo[α]heptalen-7-yl]acetamide (16).

1 mmol of (2) compound was dissolved in 2.5 mL of sodium hydroxide solution and solution was cooled to 0° C. 1 mmol of bromide derivatives (e.g. 1-bromoethane for (6), 2-bromopropane for (7), 1-bromo-2-methylpropane for (7a), 1-bromo-butane for (7b), 4-bromobut-1-ene for (7c), 1-bromopropane for (8), 3-bromoprop-1-ene for (9), (bromomethyl)benzene for (10), 1-methoxy-2-bromoethane for (11), 1-bromomethyl-3-chlorobenzene for (12), 3-(bromomethyl)pyridine for (13), 1-bromomethyl-2-chlorobenzene for (14), 1-bromomethyl-4-chlorobenzene for (15), and (bromomethyl)cyclohexane for (16)) was dissolved in 3.5 mL acetone. Each solution was allowed to stand for 15 h. Then 25 mL of alkaline water was added. Chloroform was used to extract the compound, which was dried over magnesium sulfate. The syntheses of (6-16) are presented in FIG. 3.

General Procedure for the Preparation of N-deacetyl-N-(N-trifluoroacetylaminoacyl) colchicine 3 mmol of the derivative (6-16) in methanol (50 mL) and 2N HCl (25 mL) was heated at 90° C. with stirring for 1 day. The reaction mixture was cooled and was neutralized with NaHCO$_3$. Product was extracted with methylene chloride and washed with brine. The extract was dried over Na$_2$SO$_4$ and was evaporated. The deacetylated compounds (17-27) were crystallized from CH$_2$Cl$_2$.

1 mmol of deacetylated compound (17-27) and [(trifluoroacetyl)amino]acetic acid (1 mmol) was dissolved at room temperature in dichloromethane (6 mL).

Dicyclohexylcarbodiimide (1 mmol) was added. After 2 h the suspension was cooled to 0° C. and filtrated. Products (28-38) were chromatographed on silica gel column eluting with dichloromethane/methanol (1:0 to 0:1). Crystallization of (28-38) were performed with dichloromethane:ethyl ether (1:1).

Analytical Analysis (2) C(23)H(25)O(7)N(1); requires M, 427, found EIMS m/e 427.1 (M$^+$); (3) C(21)H(23)O(6)N(1); requires M, 385, found EIMS m/e 385.1 (M$^+$); (4) C(24)H(27)O(7)N(1); requires M, 441, found EIMS m/e 441.1 (M$^+$); (5) C(25)H(29)O(7)N(1); requires M, 455 found EIMS m/e 455.0 (M$^+$); (6) C(23)H(27)O(6)N(1); requires M, 413, found EIMS m/e 413.1 (M$^+$); Anal. Calc. C % 66.83, H % 6.55, N % 23.22 found: C % 66.82, H % 6.54, N % 23.22; (7) C(24)H(29)O(6)N(1); requires M, 427, found EIMS m/e 427.1 (M$^+$); Anal. Calc. C % 67.44, H % 6.77, N % 3.22, found: C % 67.41, H % 6.73, N % 3.21; (8) C(24)H(29)O(6)N(1); requires M, 427, found EIMS m/e 427.1 (M$^+$); Anal. Calc. C % 67.44, H % 6.79, N % 32.78, found: C % 67.44, H % 6.80, N % 32.77; (9) C(24)H(27)O(6)N(1); requires M, 425, found EIMS m/e 425.1 (M$^+$); Anal. Calc. C % 67.76, H % 6.35, N % 3.29 found: C % 67.77, H % 6.33, N % 3.28; (10) C(28)H(28)O(6)N(1); requires M, 475, found EIMS m/e 475.2 (M$^+$); Anal. Calc. C % 70.88, H % 5.91, N % 2.95 found: C % 70.87, H % 5.92, N % 2.93; (11) C(24)H(29)O(7)N(1); requires M, 443, found EIMS m/e 443.1 (M$^+$); Anal. Calc. C % 65.01, H % 6.54, N % 3.16 found: C % 65.02, H % 6.53, N % 3.11; (12) C(28)H(27)O(6)N(1)Cl(1); requires M, 509, found EIMS m/e 509.1 (M$^+$); Anal. Calc. C % 71.04, H % 6.13, N % 2.93 found: C % 71.05, H % 6.12, N % 2.95; (13) C(27)H(28)O(6)N(2); requires M, 476, found EIMS m/e 476.1 (M$^+$); Anal. Calc. C % 68.06, H % 5.88, N % 5.88, found: C % 68.09, H % 5.86, N 5.89%; (14) C(28)H(28)O(6)N(1)Cl(1); requires M, 509, found EIMS m/e 509.1 (M$^+$); Anal. Calc. C % 66.01, H % 5.50, N % 2.94, Cl % 6.87 found: C % 66.03, H % 5.51, N % 2.95, Cl % 6.88; (15) C(24)H(29)O(7)N(1); requires M, 509, found EIMS m/e 509.1 (M$^+$); Anal. Calc. C % 65.01, H % 6.09, N % 3.16, Cl % 7.90, found: C % 65.02, H % 6.07, N % 3.10, Cl % 7.92; (16) C(28)H(34)O(6)N(1); requires M, 495, found EIMS m/e 495.2 (M$^+$); Anal. Calc. C % 70.02, H % 7.09, N % 2.91 found: C % 70.04, H % 7.08, N % 2.93; (17) C(21)H(25)O(5)N(1); Anal. Calc. C % 67.92, H % 7.27, N % 3.77 found: C % 67.93, H % 7.28, N % 3.78; (18) C(22)H(27)O(5)N(1) Anal. Calc. C % 68.57, H % 7.01, N % 3.77 found: C % 68.59, H % 7.03, N % 3.79; (19) C(22)H(27)O(5)N(1); Anal. Calc. C % 68.63, H % 7.04, N % 3.78 found: C % 68.62, H % 7.05, N % 3.79; (20) C(22)H(25)O(5)N(1); Anal. Calc. C % 68.92, H % 6.52, N % 3.65 found: C % 68.94, H % 6.53, N % 3.67; (21) C(26)H(26)O(5)N(1); Anal. Calc. C % 72.22, H % 6.01, N % 3.24 found: C % 72.21, H % 6.04, N % 3.23; (22) C(22)H(27)O(6)N(1); Anal. Calc. C % 65.83, H % 6.73, N % 3.49 found: C % 65.82, H % 6.73, N % 3.48; (23) C(26)H(25)O(5)N(1)Cl(1); Anal. Calc. C % 66.95, H % 5.36, N % 3.02, Cl 7.51 found: C % 66.93, H % 5.34, N % 3.01, Cl 7.53; (24) C(22)H(26)O(5)N(1); Anal. Calc. C % 81.25, H % 6.77, N % 3.64 found: C % 81.26, H % 6.78, N % 3.66; (25) C(26)H(26)O(5)N(1)Cl(1); Anal. Calc. C % 66.80, H % 5.56, N % 2.99, Cl % 7.49, found: C % 66.81, H % 5.55, N % 2.98, Cl % 7.48; (26) C(22)H(27)O(5)N(1); Anal. Calc. C % 77.92, H % 7.01, N % 3.63, found: C % 77.93, H % 7.03, N % 3.65; (27) C(26)H(32)O(5)N(1); Anal. Calc. C % 71.23, H % 7.30, N % 3.19 found: C % 71.22, H % 7.32, N % 3.20; (28) C(25)H(27)O(7)N(2)F(3); Anal. Calc. C % 57.25, H % 5.15, N % 5.18, F % 10.85, found: C % 57.25, H % 4.99, N % 5.34, F % 10.86; (29) C(26)H(29)O(7)N(2)F(3); Anal. Calc. C % 57.99, H % 5.39, N % 5.20, F % 10.59 found: C % 56.38, H % 5.3, N % 5.3, F % 10.87; (30) C(26)H(29)O(7)N(2)F(3); Anal. Calc. C % 57.99, H % 5.39, N % 5.20, F % 10.59, found: C % 57.58, H % 5.32, N % 5.28, F % 10.59; (31) C(26)H(27)O(7)N(2)F(3); Anal. Calc. C % 57.99, H % 5.39, N % 5.20, F % 10.56, found: C % 57.99, H % 5.88, N % 5.28, F % 10.55; (32) C(30)H(28)O(7)N(2)F(3); Anal. Calc. C % 59.92, H % 4.66, N % 4.65, F % 9.46, found: C % 59.71, H % 4.65, N % 4.37, F % 9.49; (33) C(26)H(29)O(7)N(2)F(3); Anal. Calc. C % 57.99, H % 5.39, N % 5.20, F % 10.59 found: C % 56.38, H % 5.21, N % 4.68, F % 9.55; (34) C(30)H(27)O(7)N(2)Cl(1)F(3); Anal. Calc. C % 56.77, H % 4.28, N % 4.13, F % 8.41, found: C % 56.74, H % 4.29, N % 4.12, F % 8.43; (35)

C(26)H(27)O(7)N(2)F(3); Anal. Calc. C % 58.20, H % 4.86, N % 4.69, F % 9.56, found: C % 58.12, H % 4.87, N % 4.69, F % 9.57; (36) C(30)H(28)O(7)N(2)Cl(1)F(3); Anal. Calc. C % 58.06, H % 4.15, N % 4.12, F % 8.41 found: C % 58.06, H % 4.14, N % 4.13, F % 8.40; (37) C(26)H(28)O(7)N(2)Cl(1)F(3); Anal. Calc. C % 54.54, H % 4.87, N % 4.73, F % 9.25, found: C % 54.53, H % 4.88, N % 4.72, F % 9.26; (38) C(30)H(34)O(7)N(2)F(3); Anal. Calc. C % 60.91, H % 5.75, N % 4.73, F % 9.64, found: C % 60.79, H % 5.67, N % 4.63, F %9.67.

Figure 4:
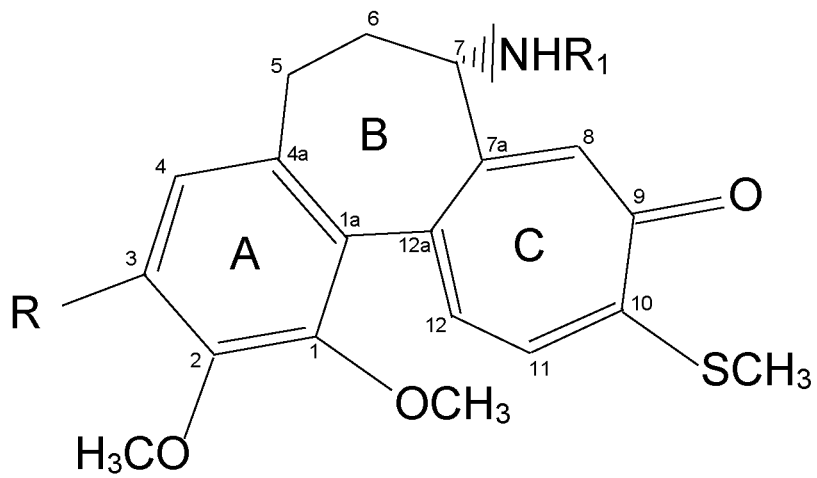
FIG. 4 shows the structure of thiocolchicine with modifications (39), (3 a-c), (4 a-c) and (5 a-c) to thiocolchicine at the R and $R_1$ positions.
Figure 4B:
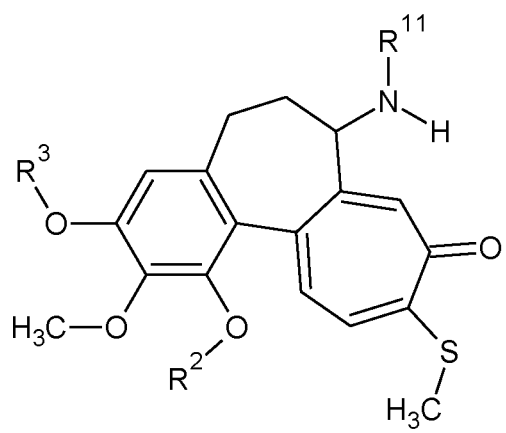
Figure 4C:
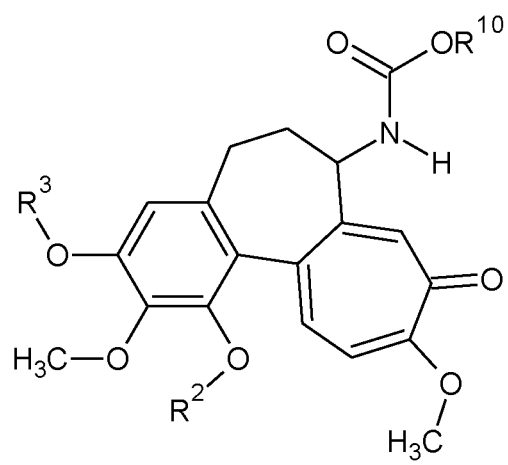
Figure 4D:
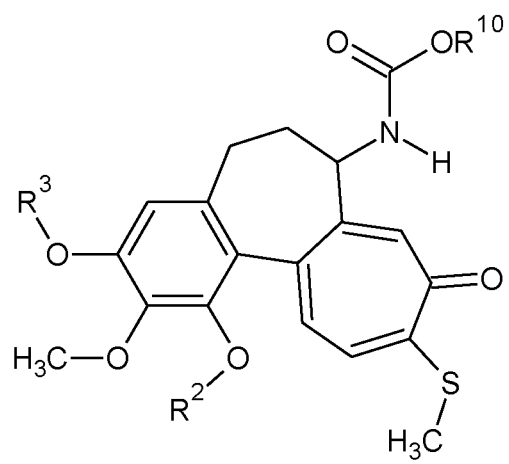

Synthesis of the Thiocolchicine Compounds (FIG. 4)

Thiocolchicine, N-[(7S)-1,2,3-trimethoxy-10-methylsulfanylo-9-oxo-5,6,7,9-tetrahydrobenzo [α]heptalen-7-yl]acetamide (39): Colchicine (1) (1 mmol) was dissolved in 10 mL of methanol/dimethylformamide (1:1) at 70-80° C. The solution was cooled to room temperature and sodium methanethiolate (2 mmol) was added.

The mixture solution was stirred overnight. Water (20 mL) was added, and the reaction mixture was extracted with $CH_2Cl_2$ (10 mL), was dried over $Na_2SO_4$ and concentrated. Crystallization of the residue from ethyl ether/acetone (1:1) gave product (39) with 71% yield.

N-[(7S)-3-hydroxy-1,2-dimethoxy-3-hydroxy-10-methylsulfanyl-9-oxo-5,6,7,9-tetrahydrobenzo[α]heptalen-7-yl] acetamide (40): 10 mL of methanol was used to dissolve 1 mmol of thiocolchicine (39) and 30 mL of 0.2N of hydrochloric acid was added. The methanol was evaporated, cooled and sodium hydroxide solution was added until pH value was 11 and the resulting alkaline solution was extracted with chloroform in order to free it from non-phenolic substances. The sodium hydroxide solution, (color red), was acidified with hydrochloric acid and was extracted with chloroform. After drying and evaporation, the yield of (40) was 58%.

N-[(7S)-1,2-dimethoxy-10-methylsulfanyl-9-oxo-3-(prop (2-en)oxy)-5,6,7,9-tetrahydrobenzo[α]heptalen-7-yl]acetamide (41), N-[(7S)-3-ethoxy-1,2-dimethoxy-10-methylsulfanyl-9-oxo-5,6,7,9-tetrahydrobenzo [α]heptalen-7-yl] acetamide (42), and N-[(7S)-3-propoxy-1,2-dimethoxy-10-methylsulfanyl-9-oxo-5,6,7,9-tetrahydrobenzo [α]heptalen-7-yl]acetamide (43): 1 mmol of (40) compound was dissolved in 2.5 mL of 1N sodium hydroxide solution. The resulting solution was cooled to 0° C. and 3-bromoprop-1-ene (1 mmol) to obtain compound (41); 1-bromoethane (1 mmol) to obtain compound (42); or 1-bromopropane (1 mmol) to obtain compound (43), was dissolved in 3.5 mL acetone and added to the cooled solution. The solution was allowed to stand for 15 h and then 25 mL of alkaline water was added. Chloroform was used to extract the resulting product and drying over magnesium sulfate. The yield of (41) was 68% and the yield of (42) was 71%.

A Preparation of the N-deacetyl-N-(N-trifluoroacetylaminoacyl) thiocolchicine

N-[(7S)-3-hydroxy-1,2-dimethoxy-10-methylsulfanyl-9-oxo-5,6,7,9-tetrahydrobenzo [α]heptalen-7-yl]amine (44)

N-[(7S)-1,2-dimethoxy-10-methylsulfanyl-9-oxo-3-(prop (2-en)oxy)-5,6,7,9-tetrahydrobenzo [α]heptalen-7-yl] amine (45);

N-[(7S)-3-ethoxy-1,2-dimethoxy-10-methylsulfanyl-9-oxo-5,6,7,9-tetrahydrobenzo [α]heptalen-7-yl]amine (46);

N-[(7S)-3-hydroxy-1,2-dimethoxy-10-methylsulfanyl-9-oxo-5,6,7,9-tetrahydrobenzo [α]heptalen-7-yl]-N-[(trifluoroacetyl)glycyl]acetamide (47);

N-[(7S)-1,2-dimethoxy-10-methylsulfanyl-9-oxo-3-(prop-2-enoxy)-5,6,7,9-tetrahydrobenzo[α]heptalen-7-yl]-N-[(trifluoroacetyl)glycyl]acetamide (48);

N-[(7S)-3-ethoxy-1,2-dimethoxy-10-methylsulfanyl-9-oxo-5,6,7,9-tetrahydrobenzo [α]heptalen-7-yl]-N-[(trifluoroacetyl)glycyl]acetamide (49).

Each derivate (44-46), and (47-49) was prepared in a similar way. 1 mmol of appropriate derivative (40) or (41) or (42) was dissolved in methanol (20 mL) with 2N HCl (10 mL) and heated at 90° C. and stirred for a 24 h. The reaction mixture was cooled, neutralized with $NaHCO_3$ and extracted with $CH_2Cl_2$. Extract was dried over $Na_2SO_4$ and evaporated. The crystallization was from (1:1) $CH_2Cl_2/CH_3OH$. The yield of deacetylated compound (44), (45), (46) was 58%, 63% and 71%, respectively.

1 mmol of deacetylated compound of (44) or (45) or (46) and N-trifluoroacetylamino acid (1 mmol) were dissolved at room temperature and dichloromethane (6 mL) was added with stirring. Dicyclohexylcarbodiimide (1 mmol) was added to the suspension and, after 2 h cooled to 0° C. and filtrated. Each compound (47) or (48) or (49) was crystalized from dichloromethane: ethyl ether (1:1) solution. The yield of (47), (48), and (49) was 64%, 67% and 75%, respectively.

Analysis of (39), (40-42), (44-46) and (47-49) Compounds

Colchicine (1): M.p. 275° C.; (39): M.p. 250° C. −252° C.; Anal. Calc. for C(22)H(25)N(1)O(5)S(1): C % 63.60, H % 6.06, N % 3.37, S %7.72; found: C % 63.71, H % 6.15, N % 3.42, S % 7.79; (40): M.p. 306° C.; Anal. Calc. for C(21)H(23)O(5)N(1)S(1): C % 62.8, H % 5.8, N % 3.5, S % 8.0, found: C % 62.9, H % 5.8, N % 3.3, S % 7.5; Requires M, 401.1, found EIMS m/e 401.1 (M+); (41): M.p. 306° C.; Anal. Calc. for C(24)H(27)O(5)N(1)S(1), C % 65.3, H % 6.12, N % 3.17, S % 7.24, found: C % 65.07, H % 6.59, N % 3.21, S % 7.28; Requires M, 454.5, found EIMS 454.5 (M+Na+); 442.5; (42): M.p. 273° C.; Anal. Calc. for C(23)H(27)O(5)N(1)S(1), C % 64.33, H % 18.64, N % 3.26, S % 7.45, found: C % 64.4, H %18.9, N % 3.27, S % 7.61; Requires M, 452.6, found EIMS 452.6 (M+Na+); (44):M.p. 281° C.; Anal. Calc. for C(19)H(21)O(4)N(1)S(1), C % 63.51, H % 5.91, N % 3.88, S % 8.92, found: C % 63.55, H % 5.83, N % 3.75, S % 8.93; (45): M.p. 254° C.; Anal. Calc. for C(22)H(25)O(4)N(1)S(1), C % 65.8, H % 6.77, N % 3.52, S % 7.99, found: C % 65.83, H % 6.49, N % 3.63, S % 8.31; (46): M.p. 276° C.; Anal. Calc. for C(21)H(25)O(4)N(1)S(1), C % 65.81, H % 6.50, N % 3.6, S % 8.24, found: C % 65.12, H % 6.54, N % 3.57, S % 8.27; (47): M.p. 284° C.; Anal. Calc. for C(23)H(23)O(6)N(2)S(1)F(3), C % 55.42, H % 4.61, N % 2.92, S % 6.42, F % 11.44 found: C % 55.43, H % 4.62, N % 2.91, S % 6.42, F % 11.44; (48):

M.p. 324° C.; Anal. Calc. for C(26)H(27)O(6)N(2)S(1)F(3), C % 56.52, H % 4.89, N % 5.07, S % 5.79, F % 10.32 found: C % 56.52, H % 4.87, N % 7.01, S % 5.79, F % 10.32; (49): M.p. 256° C.; Anal. Calc. for C(25)H(27)O(6)N(2)S(1)F(3), C % 57.03, H % 5.13, N % 5.32, S % 6.08, F % 10.87 found: C % 53.67, H % 4.5, N % 5.32, S % 6.05; F % 10.85.

Specific Syntheses of the Colchicine Derivatives

Compound (2)

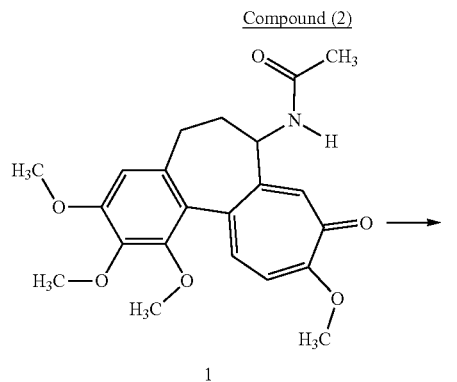

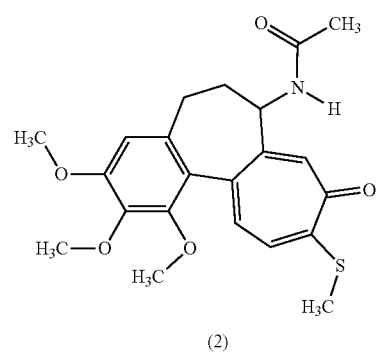

A solution of 1 (30.0 g) and sodiumthiomethoxide (30.0 mL) in water (2000 mL) was stirred at rt overnight. The reaction solution was extracted with dichloromethane and the organic layer was concentrated to give the crude product. The crude product was purified by silica gel column chromatography to give the desired product (20.0 g, 65%).

Compounds (6), (17) and (28)

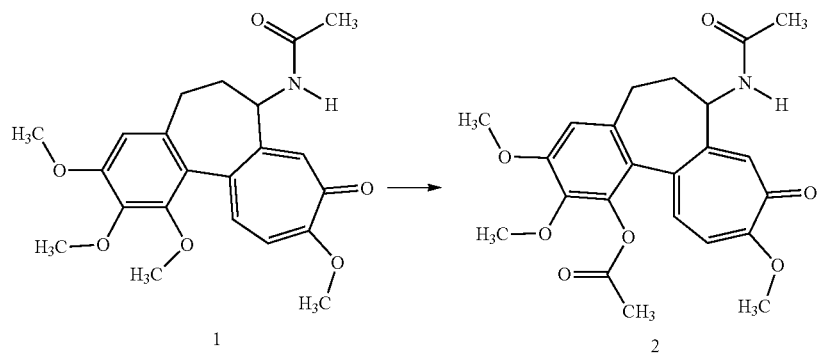

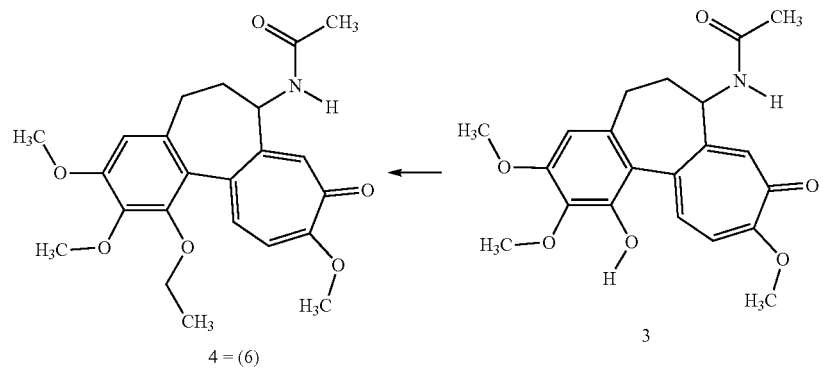

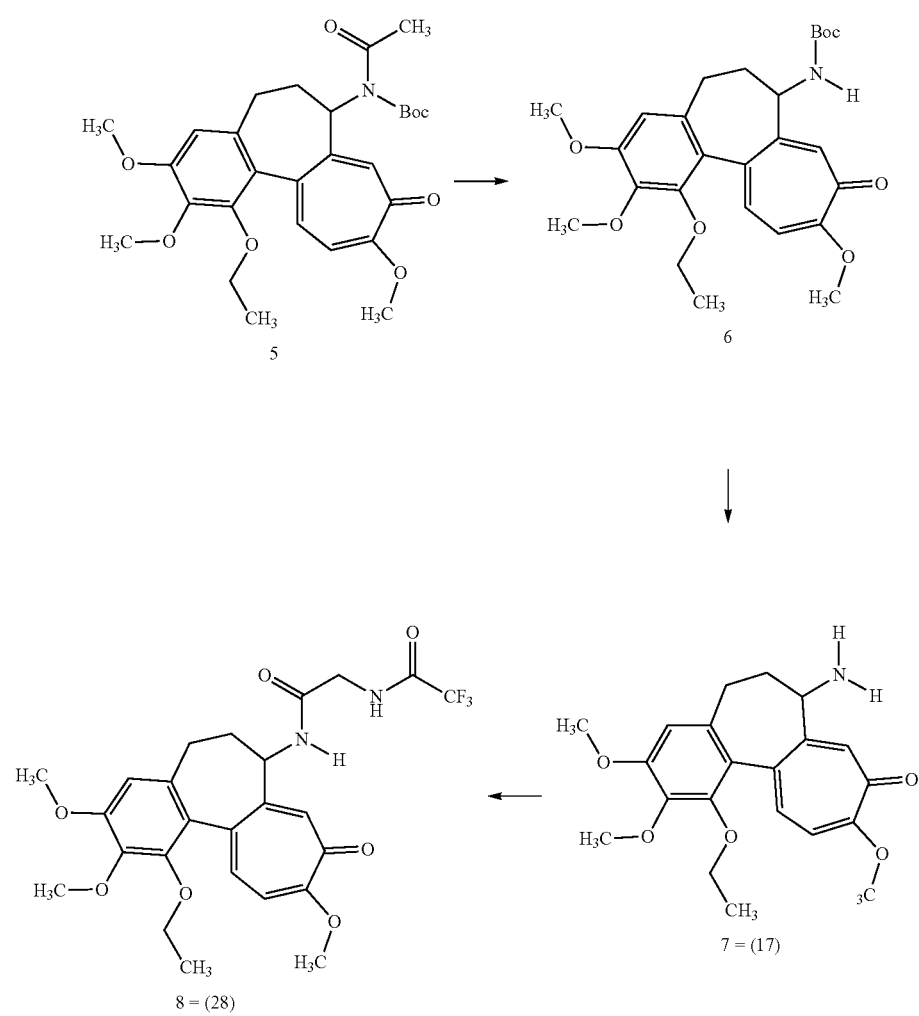

To a solution of 1 (1.0 g, 2.51 mmol) and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), bromoethane (450 mg, 4.16 mmol) and potassium carbonate (1.2 g, 8.31 mmol) in DMF (20 mL) was stirred at 90° C. for 2 h. The reaction mixture was poured in water, extracted with ethyl acetate and concentrated to give the crude product. The crude product was purified by silica gel column chromatography to give the desired product (0.5 g, 60%).

A mixture of 4 (700 mg, 1.69 mmol), (Boc)2O (3.7 g, 16.95 mol) and DMAP (83 mg, 0.68 mmol) in THF (15 mL) was refluxed overnight. The reaction mixture was washed with water, dried and concentrated to give the crude product which was used directly for the next step.

A solution of 5 (crude) and sodium methoxide (365.0 mg, 6.76 mmol) in methanol (15 mL) was stirred at rt for 2 h. Then water was added and extracted with dichloromethane. The extracts were concentrated to give the crude product. The crude product was purified by silica gel column chromatography to give the desired product (0.6 g).

A solution of 6 (600 mg, 1.27 mmol) and trifluoroacetic acid (5 mL) in dichloromethane (5 mL) was stirred at rt for 3 hours. The reaction solution was concentrated to give the product (0.45 g, 96%).

A solution of 7 (50 mg, 0.13 mmol), EDCI (39 mg, 0.20 mmol), HOBT (27 mg, 0.20 mmol), F₃CGlyOH (28 mg, 0.16 mmol) and triethylamine (54 mg, 0.54 mmol) in dichloromethane (3 mL) was stirred at rt overnight. The reaction mixture was washed with water, dried and concentrated to give the crude product. The crude product was purified by chromatography to give the desired product (22 mg, 31%).

Compounds (11), (22) and (33)
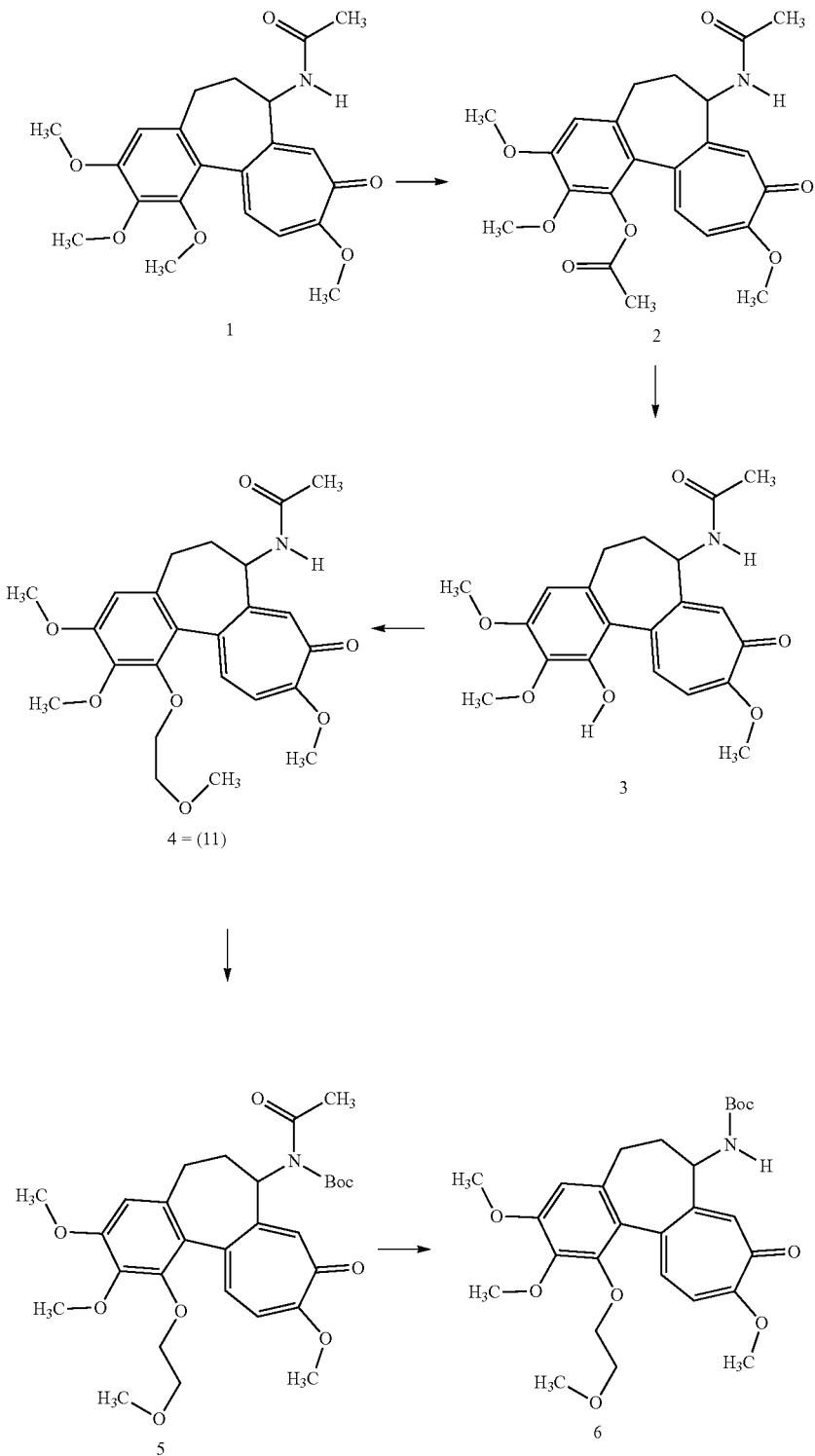

-continued

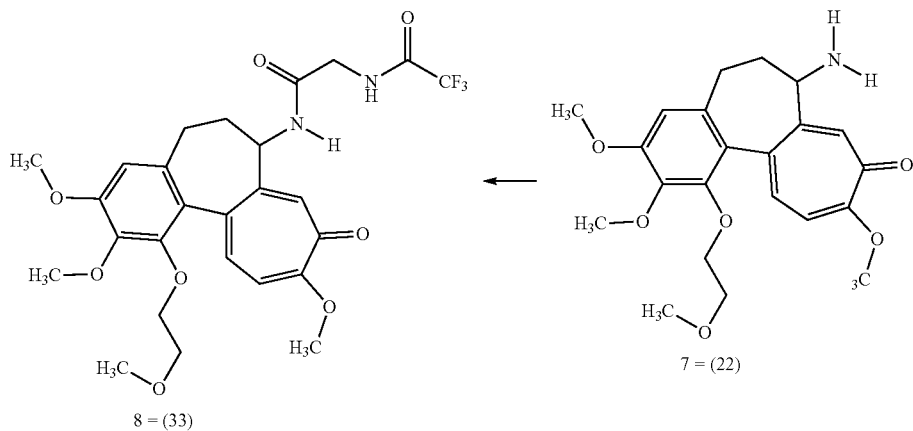

8 = (33)   7 = (22)

To a solution of 1 (1.0 g, 2.51 mmol), and acetylchloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), 1-bromo-2-methoxyethane (580 mg, 4.16 mmol) and potassium carbonate (1.15 g, 8.31 mmol) in DMF (20 mL) was stirred at 75° C. for 3 h. The reaction mixture was poured in water, extracted with ethyl acetate and concentrated to give the crude product. The crude product was purified by silica gel column chromatography to give the desired product (0.5 g, 54%).

A mixture of 4 (500 mg, 1.13 mmol), (Boc)2O (2.5 g, 11.29 mmol) and DMAP (55 mg, 0.45 mmol) in THF (10 mL) was refluxed overnight. The reaction mixture was washed with water, dried and concentrated to give the crude product which was used directly for the next step.

A solution of 5 (crude) and sodium methoxide (244.0 mg, 4.52 mmol) in methanol (15 mL) was stirred at rt for 2 h. Then water was added and extracted with dichloromethane. The extract were concentrated to give the crude product. The crude product was purified by silica gel column chromatography to give the desired product (0.45 g).

A solution of 6 (0.6 g, 1.20 mmol) and trifluoroacetic acid (5 mL) in dichloromethane (5 mL) was stirred at rt for 3 hours. The reaction solution was concentrated to give the product (0.45 g, 94%).

A solution of 7 (65 mg, 0.16 mmol), EDCI (46 mg, 0.24 mmol), HOBT (32 mg, 0.24 mmol), F$_3$CGlyOH (42 mg, 0.24 mmol) and triethylamine (65 mg, 0.65 mmol) in dichloromethane (3 mL) was stirred at rt overnight. The reaction mixture was washed with water, dried and concentrated to give the crude product. The crude product was purified by chromatography to give the desired product (25 mg, 28%).

Compounds (13), (24) and (35)

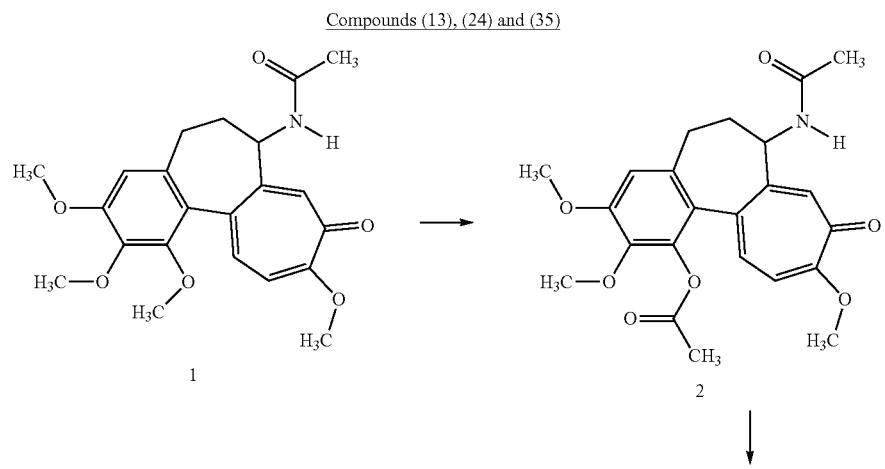

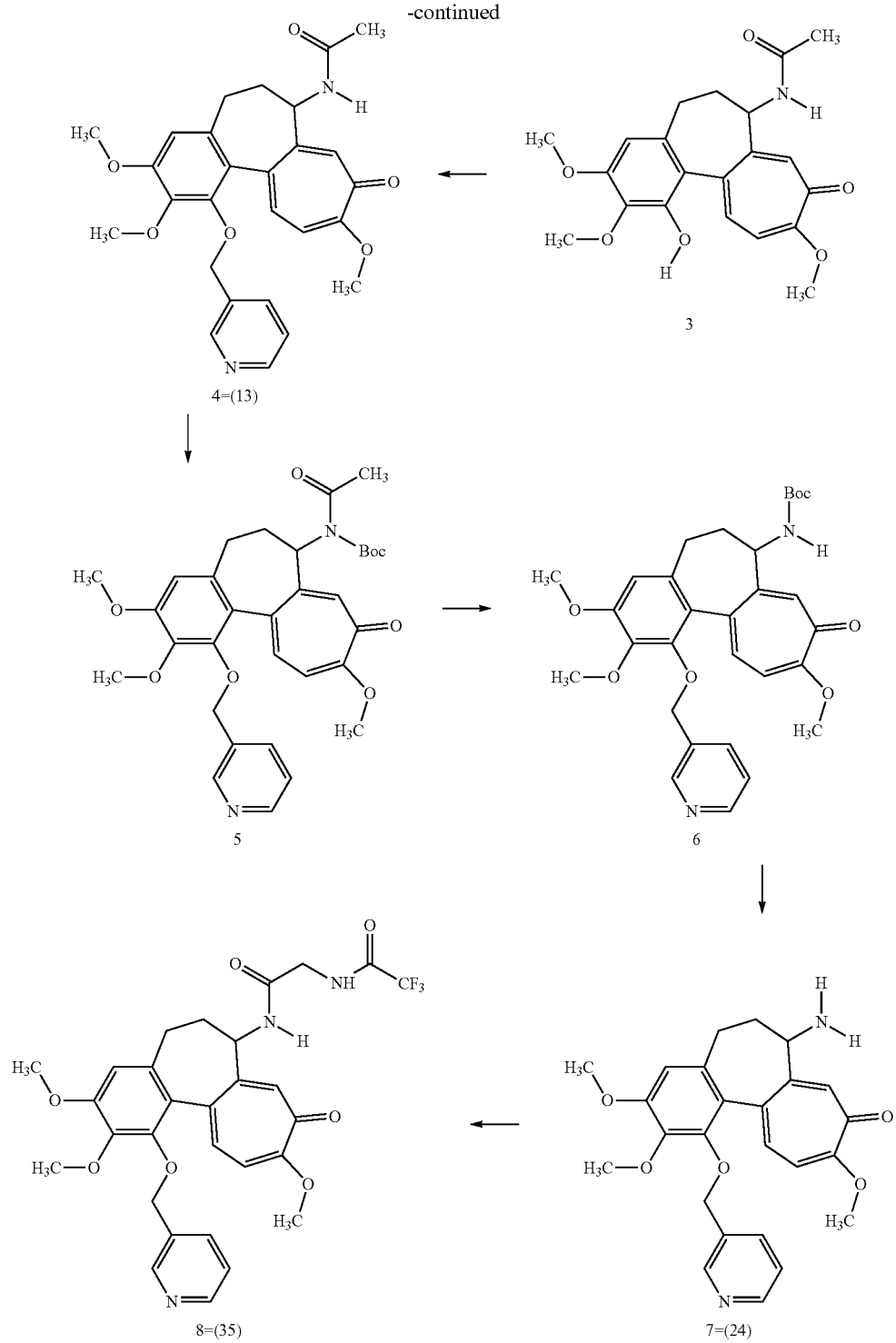

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (1.0 g, 2.6 mmol), 3-(chloromethyl) pyridine (0.64 g, 3.9 mmol) and potassium carbonate (1.08 g, 7.8 mmol) in DMF (20 mL) was stirred at 90° C. for 8 h. The reaction mixture was poured in water, extracted with ethyl acetate and concentrated to give the crude product. The crude product was purified by silica gel column chromatography to give the desired product (0.7 g, 58%).

A mixture of 4 (700 mg, 1.47 mmol), (Boc)2O (3.2 g, 14.71 mol) and DMAP (72 mg, 0.59 mmol) in THF (20 mL)

was refluxed overnight. The reaction mixture was washed with water, dried and concentrated to give the crude product which was purified by silica gel column chromatography to give the product (0.7 g, 87%).

A solution of 5 (0.7 g, 1.22 mmol) and sodium methoxide (131.0 mg, 2.43 mmol) in methanol (10 mL) was stirred at rt for 1 h. The reaction mixture was poured into water, extracted with dichloromethane, dried and concentrated to give the crude product which was used directly for the next step.

A solution of 6 (crude) and trifluoroacetic acid (10 mL) in dichloromethane (10 mL) stirred at rt for 2 hours. The reaction solution was concentrated to give the product (0.3 g).

A solution of 7 (50 mg, 0.13 mmol), EDCI (44 mg, 0.23 mmol), HOBT (31 mg, 0.23 mmol), F₃CGlyOH (39 mg, 0.23 mmol) and triethylamine (47 mg, 0.46 mmol) in dichloromethane (3 mL) was stirred at rt overnight. The reaction mixture was washed with water, dried and concentrated to give the crude product. The crude product was purified by chromatography to give the desired product (22 mg, 32%).

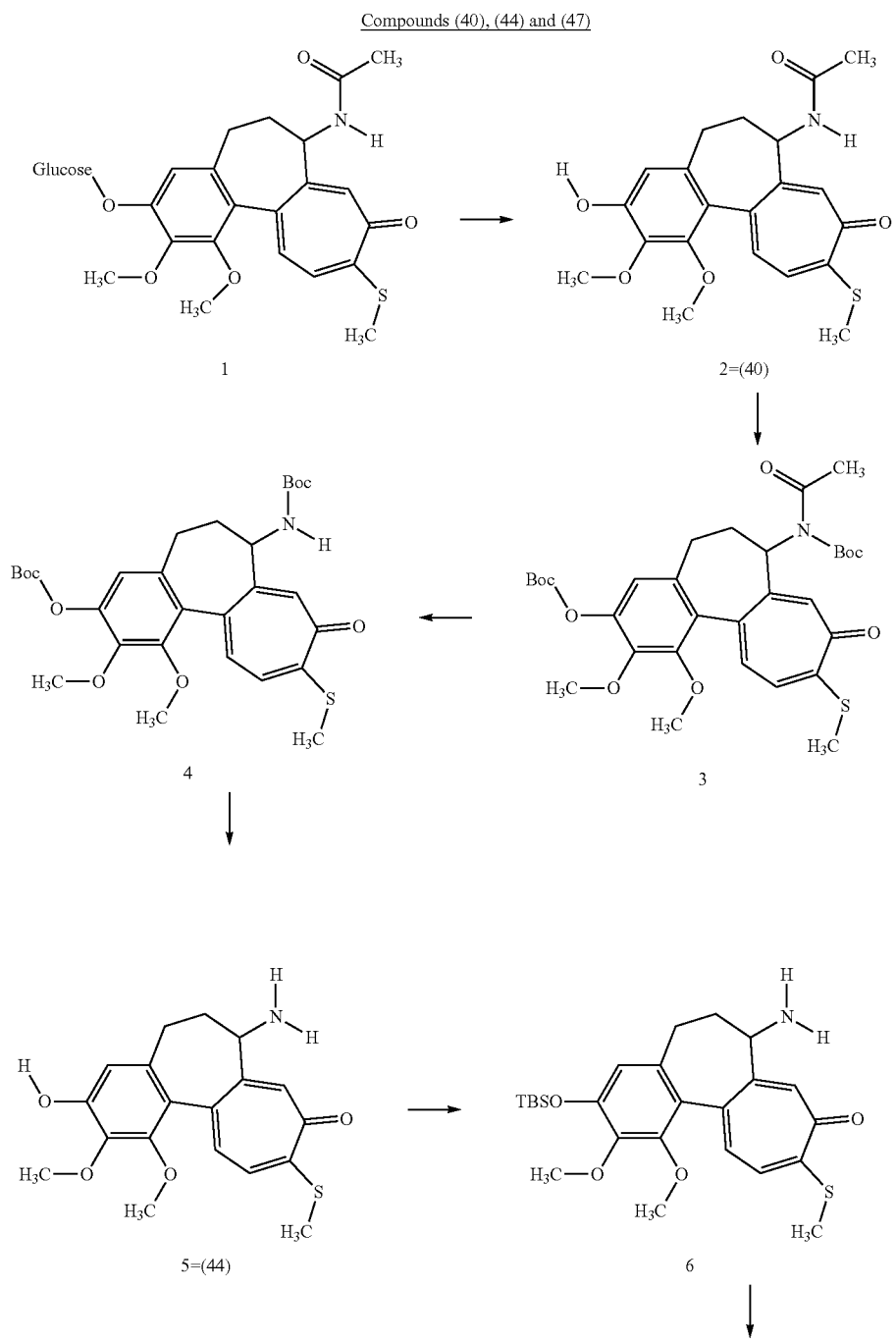

Compounds (40), (44) and (47)

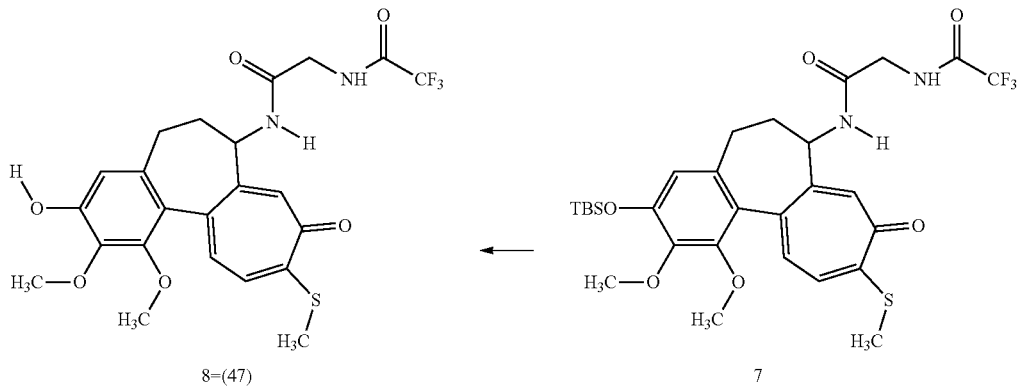

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallization with acetone to afford the title compound (1.8 g, 67%).

A mixture of 2 (600 mg, 1.50 mmol), (Boc)2O (3.3 g, 14.96 mmol) and DMAP (73 mg, 0.60 mmol) in THF (20 mL) was refluxed overnight. The reaction mixture was washed with water, dried and concentrated to give the crude product which was directly used for the next step.

A solution of 3 (crude) and sodium methoxide (120.0 mg, 2.3 mmol) in methanol (10 mL) was stirred at rt for 1 h. The reaction mixture was poured into water, extracted with dichloromethane, dried and concentrated to give the crude product which was used directly for the next step.

A solution of 4 (crude) and trifluoroacetic acid (10 mL) in dichloromethane (10 mL) was stirred at rt for 2 hours. The reaction solution was concentrated to give the product (0.4 g).

To a solution of 5 (50 mg, 0.14 mmol) and imidazole (9 mg, 0.14 mmol) in dichloromethane (3 mL) cooled to 0° C. was added tert-butyldimethylsilyl chloride (21 mg, 0.14 mmol). The resulting mixture was stirred at rt for 10 min. The reaction mixture was washed with water and concentrated to give the crude product. The crude product was purified by chromatography desired product (30 mg, 45%).

A solution of 6 (30 mg, 0.06 mmol), EDCI (24 mg, 0.13 mmol), HOBT (17 mg, 0.13 mmol), F₃CGlyOH (22 mg, 0.13 mmol) and triethylamine (26 mg, 0.26 mmol) in dichloromethane (3 mL) was stirred at rt overnight. The reaction mixture was washed with water, dried and concentrated to give the crude product which was directly used for the next step without further purification.

To a solution of 7 (crude) in THF (3 mL) was added TBAF (28 mg, 0.11 mmol). The resulting mixture was stirred at rt for 30 min. The reaction mixture was concentrated and purified by chromatography to give the desired product (20 mg).

Compound 47a

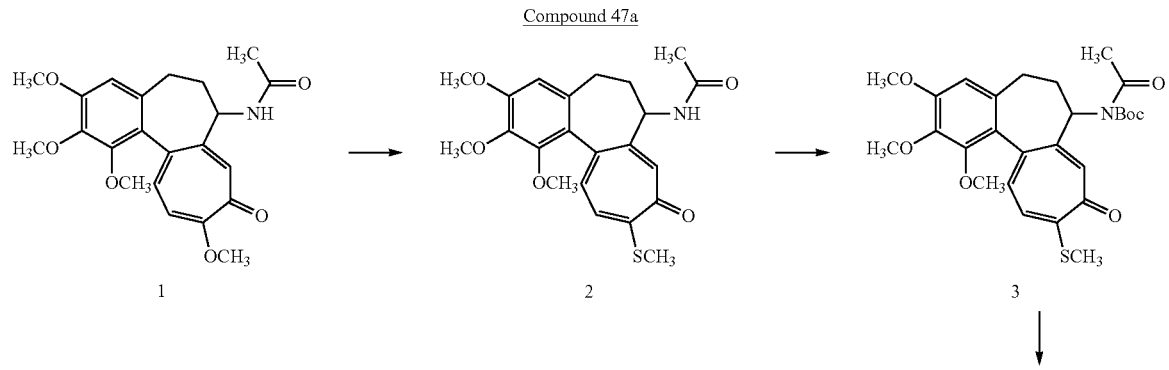

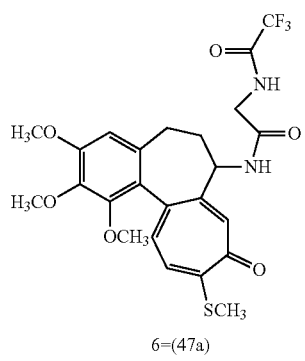
6=(47a)

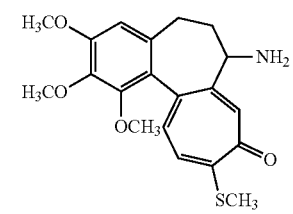
5

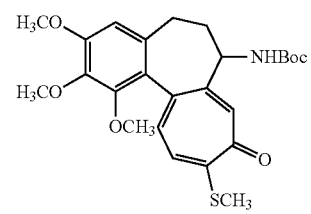
4

A solution of 1 (30.0 g) and sodium thiomethoxide (30.0 mL) in water (2000 mL) was stirred at room temperature overnight. The reaction solution was extracted with dichloromethane and the organic layer was concentrated to give the crude product. The crude product was purified by silica gel column chromatography to give the desired product (20.0 g, 65%).

A mixture of 2 (15.0 g, 36.0 mmol), (Boc)2O (79.0 g, 361.0 mmol) and DMAP (1.8 g, 14.0 mmol) in THF (220 ml) was refluxed overnight. The reaction mixture was washed with water, dried and concentrated to give the crude product which was used directly to next step.

A solution of 3 (crude) and sodium methoxide (4.0 g, 74.0 mmol) in methanol (400 mL) was stirred at room temperature for 2 h. Then water was added and extracted with dichloromethane. The extracts were concentrated to give the crude product. The crude product was purified by silica gel column chromatography to give the desired product (15.0 g).

A solution of 4 (15.0 g, 31.8 mmol) and trifluoroacetic acid (20 ml) in dichloromethane (20 mL) was stirred at room temperature for 1 hour. The reaction solution was concentrated to give the product (11.0 g, 85%).

A solution of 5 (11.0 g, 29.0 mmol), EDCI (11.3 g, 59.0 mmol), HOBT (2.0 g, 59.0 mmol), F₃COGlyOH (7.6 g, 44.0 mmol) and triethylamine (11.9 g, 118.0 mmol) in dichloromethane (200 mL) was stirred at room temperature overnight. The reaction mixture was washed with water to give the crude product. The crude product was purified by silica gel column chromatography to give the desired product (12.0 g, 77%).

Compounds (40), (41), (45) and (48)

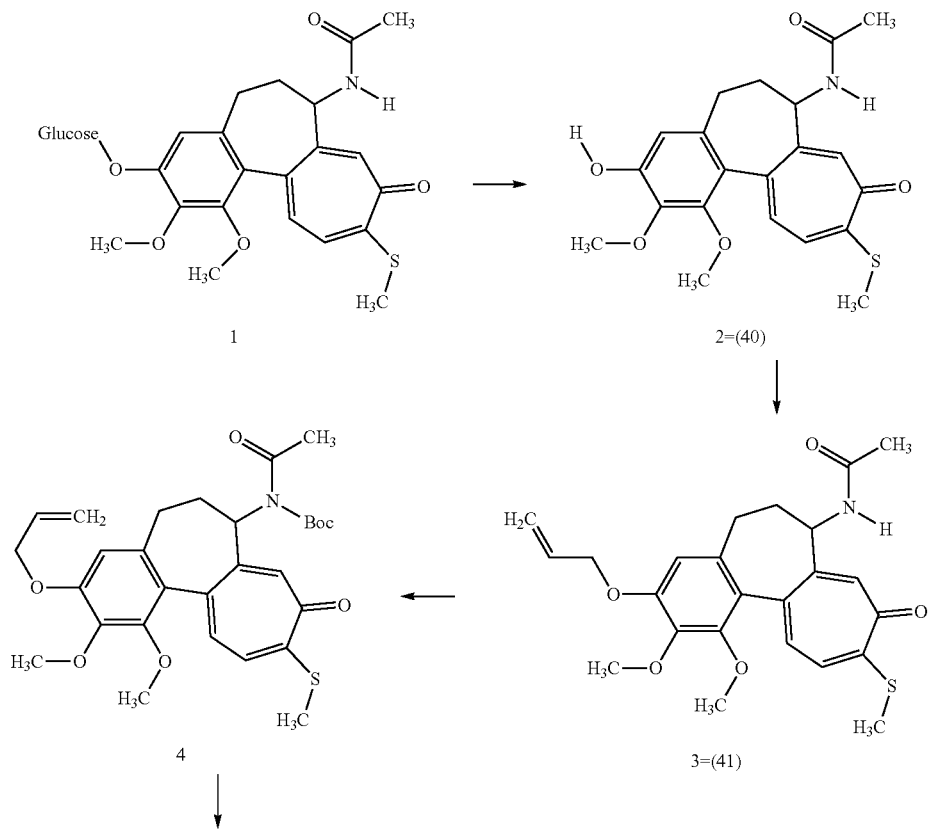

-continued

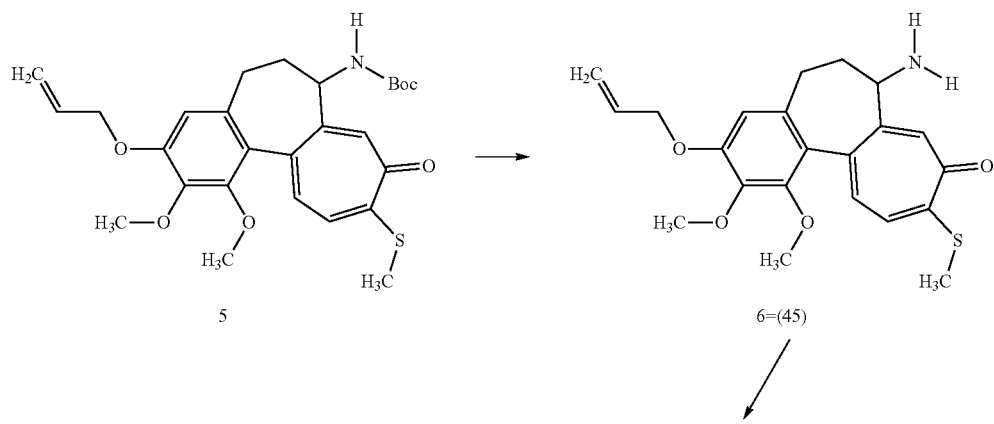

5

6=(45)

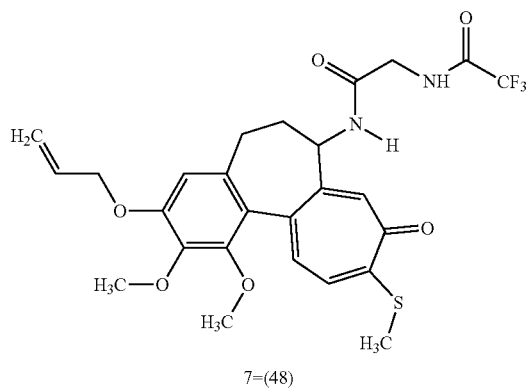

7=(48)

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallization with acetone to afford the title compound (1.8 g, 67%).

A mixture of 2 (50 mg, 0.12 mmol), 3-bromoprop-1-ene (23 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (30 mg, 55%).

A mixture of 3 (500 mg, 1.13 mmol), (Boc)2O (2.5 g, 11.31 mol) and DMAP (55 mg, 0.45 mmol) in THF (20 mL) was refluxed overnight. The reaction mixture was washed with water, dried and concentrated to give the crude product which was directly used for the next.

A solution of 4 (crude) and sodium methoxide (120.0 mg, 2.21 mmol) in methanol (10 mL) was stirred at rt for 1 h. The reaction mixture was poured into water, extracted with dichloromethane, dried and concentrated to give the crude product which was used directly for the next.

A solution of 5 (crude) and trifluoroacetic acid (10 mL) in dichloromethane (10 mL) was stirred at rt for 2 hours. The reaction solution was concentrated to give the product (0.4 g).

A solution of 6 (50 mg, 0.13 mmol), EDCI (48 mg, 0.25 mmol), HOBT (34 mg, 0.25 mmol), F3CGlyOH (43 mg, 0.25 mmol) and triethylamine (63 mg, 0.63 mmol) in dichloromethane (3 mL) was stirred at rt overnight. The reaction mixture was washed with water, dried and concentrated to give the crude product. The crude product was purified by chromatography to give the desired product (25 mg, 36%).

Compounds (40), (42), (46) and (49)
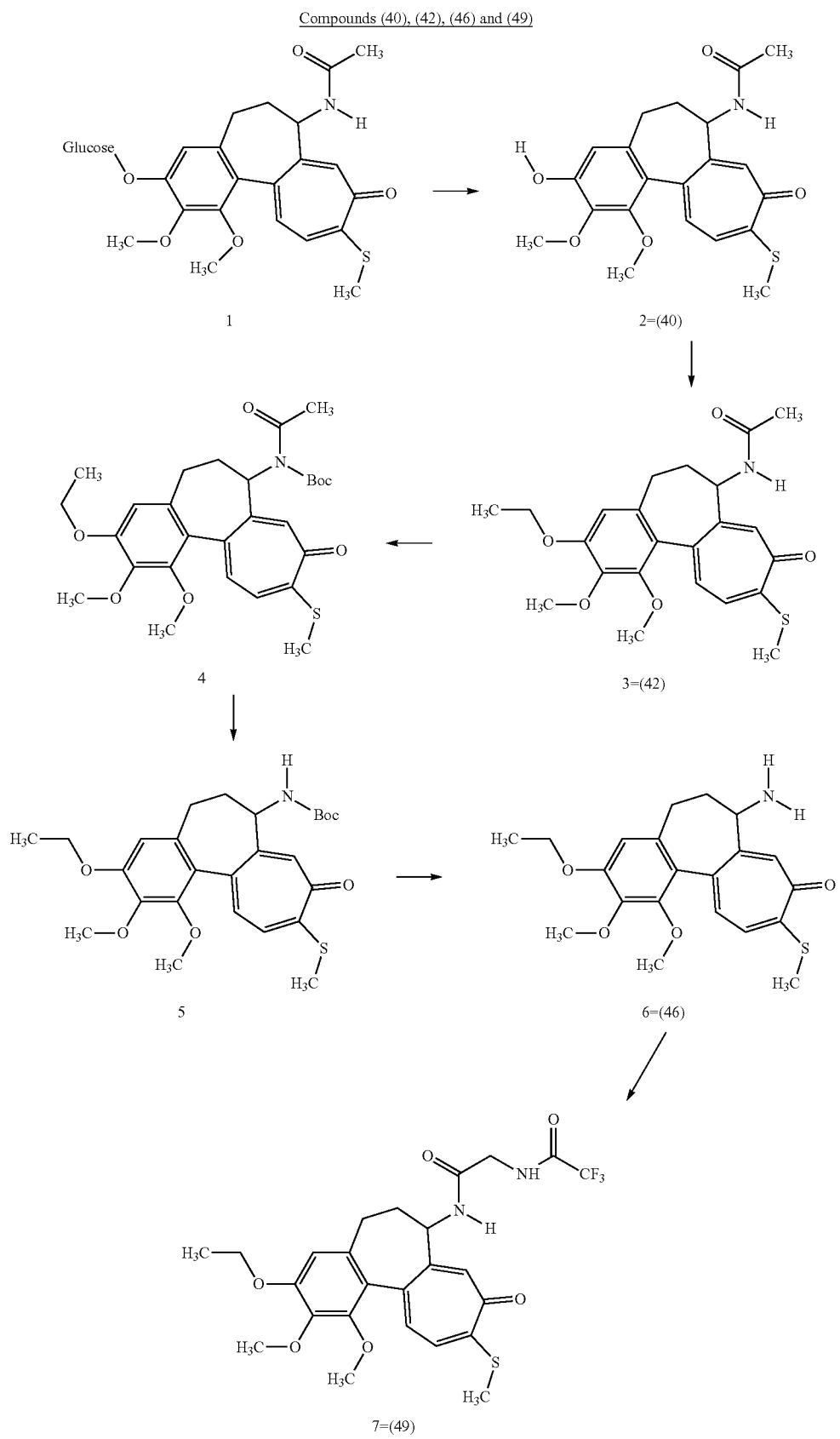

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (50 mg, 0.12 mmol), bromoethane (21 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (35 mg, 65%).

A mixture of 3 (500 mg, 1.16 mmol), (Boc)2O (2.5 g, 11.63 mol) and DMAP (57 mg, 0.47 mmol) in THF (20 mL) was refluxed overnight. The reaction mixture was washed with water, dried and concentrated to give the crude product which was directly used for the next step.

A solution of 4 (crude) and sodium methoxide (122.0 mg, 2.26 mmol) in methanol (10 mL) was stirred at rt for 1 h. The reaction mixture was poured into water, extracted with dichloromethane, dried and concentrated to give the crude product which was used directly for the next step.

A solution of 5 (crude) and trifluoroacetic acid (10 ml) in dichloromethane (10 mL) was stirred at rt for 2 hours. The reaction solution was concentrated to give the product (0.4 g).

A solution of 6 (50 mg, 0.13 mmol), EDCI (49 mg, 0.26 mmol), HOBT (35 mg, 0.26 mmol), F$_3$CGlyOH (44 mg, 0.26 mmol) and triethylamine (65 mg, 0.65 mmol) in dichloromethane (3 mL) was stirred at rt overnight. The reaction mixture was washed with water, dried and concentrated to give the crude product. The crude product was purified by chromatography to give the desired product (25 mg, 36%).

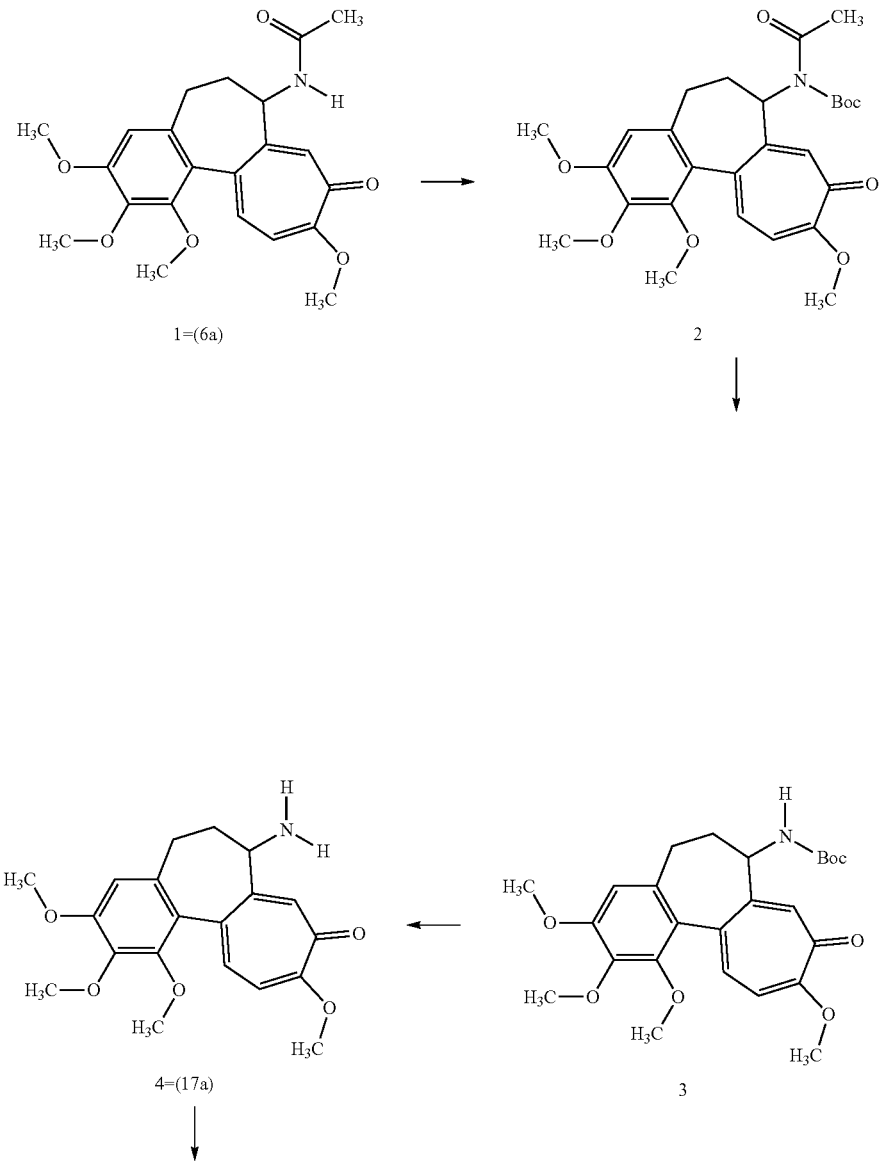

Compounds (6a), (17a) and (28a)

-continued

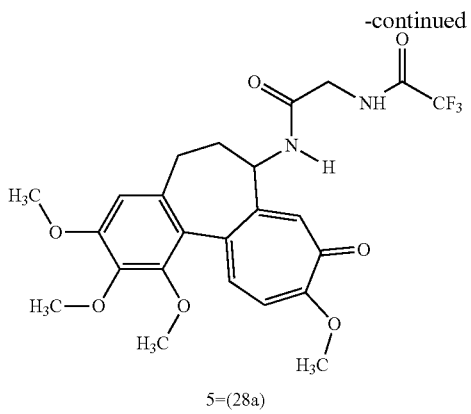
5=(28a)

A mixture of 1 (20.0 g, 0.05 mmol), (Boc)2O (109.3 g, 0.50 mol) and DMAP (2.4 g, 0.02 mol) in THF (300 mL) was refluxed overnight. The reaction mixture was washed with water, dried and concentrated to give the crude product which was used directly to next step.

A solution of 2 (crude) and sodium methoxide (5.4 g, 0.1 mol) in methanol (400 mL) was stirred at rt for 2 h. Then water was added and extracted with dichloromethane. The extracts were concentrated to give the crude product which was purified by silica gel column chromatography (20.0 g, 87%).

A solution of 3 (2.95 g, 6.46 mmol) and trifluoroacetic acid (10 mL) in dichloromethane (10 mL) was stirred at rt for 3 hr. The reaction solution was concentrated to give the product (2.1 g, 91%).

A solution of 4 (200 mg, 0.56 mmol), DCC (138 mg, 0.67 mmol), DMAP (82 mg, 0.67 mmol), and triethylamine (115 mg, 1.12 mmol) in dichloromethane (5 mL) was stirred at rt overnight. The reaction mixture was washed with water and concentrated to give the crude product. The crude product was purified by silica gel column chromatography to give they desired product (110 mg, 39%).

Compound (83)

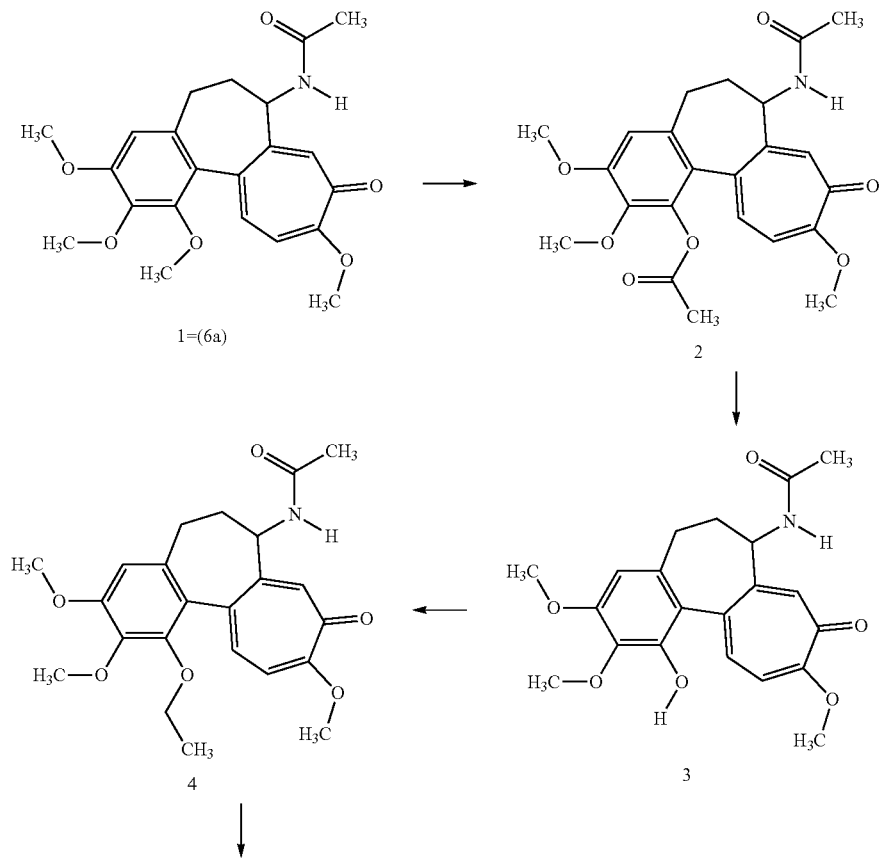

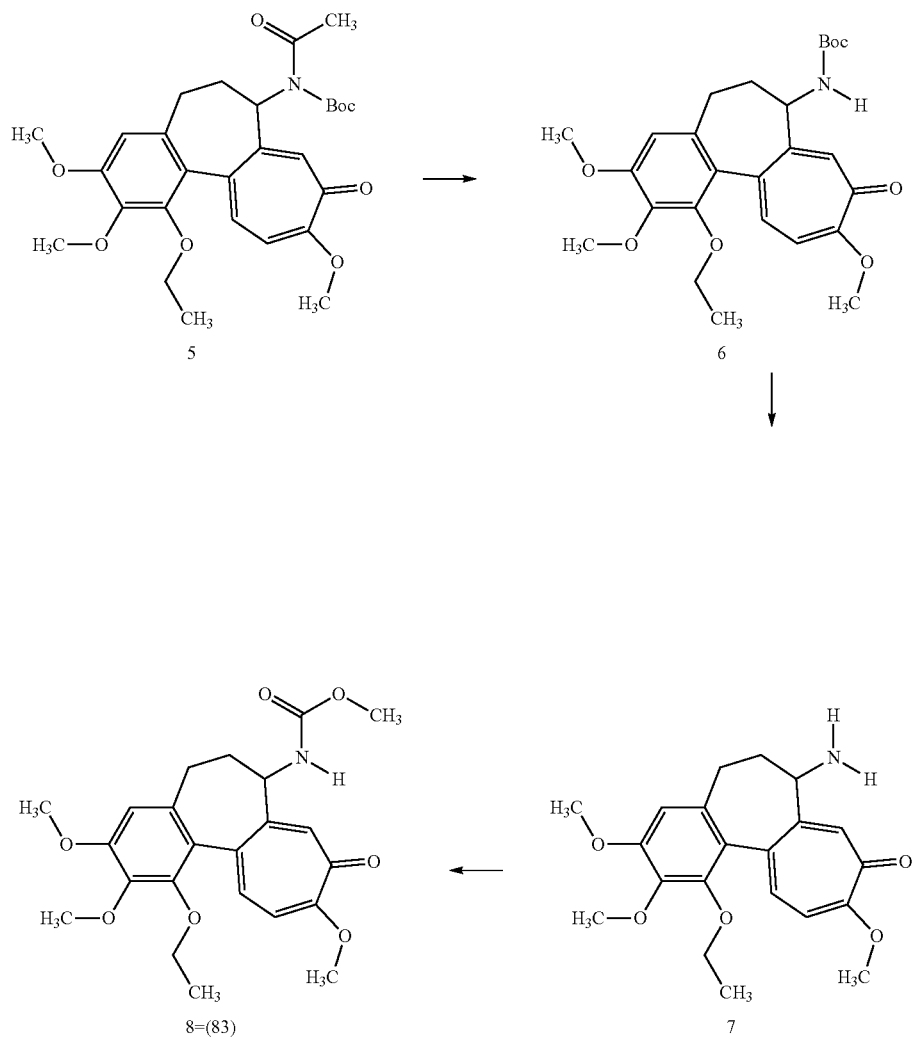

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), bromoethane (450 mg, 4.16 mmol) and potassium carbonate (1150 mg, 8.31 mmol) in DMF (20 mL) was stirred at 90° C. for 2 h. The reaction mixture was poured in water, extracted with ethyl acetate and concentrated to give the crude product. The crude product was purified by silica gel column chromatography to give the desired product (0.5 g, 60%)

A mixture of 4 (700 mg, 1.69 mmol), (Boc)2O (3.7 g, 16.95 mol) and DMAP (83 mg, 0.68 mmol) in THF (15 mL) was refluxed overnight. The reaction mixture was washed with water, dried and concentrated to give the crude product which was used directly for the next step.

A solution of 5 (crude) and sodium methoxide (365.0 mg, 6.76 mmol) in methanol (15 mL) was stirred at rt for 2 h. Then water was added and extracted with dichloromethane. The extracts were concentrated to give the crude product. The crude product was purified by silica gel column chromatography to give the desired product (0.6 g).

A solution of 6 (600 mg, 1.27 mmol) and trifluoroacetic acid (5 mL) in dichloromethane (5 mL) was stirred at rt for 3 h. The reaction solution was concentrated to nine the product (0.45 g, 96%).

To a solution of 7 (50 mg, 0.13 mmol) and triethylamine (27 mg. 0.27 mmol) in dichloromethane (3 mL) was added methyl carbonochloridate (19 mg, 0.20 mmol) at 0° C. The resulting solution was stirred at rt for 1 h. The reaction mixture was washed with water and concentrated to give the crude product. The crude product was purified by chromatography to give the desired product (15 mg, 26%).

Compound (84)
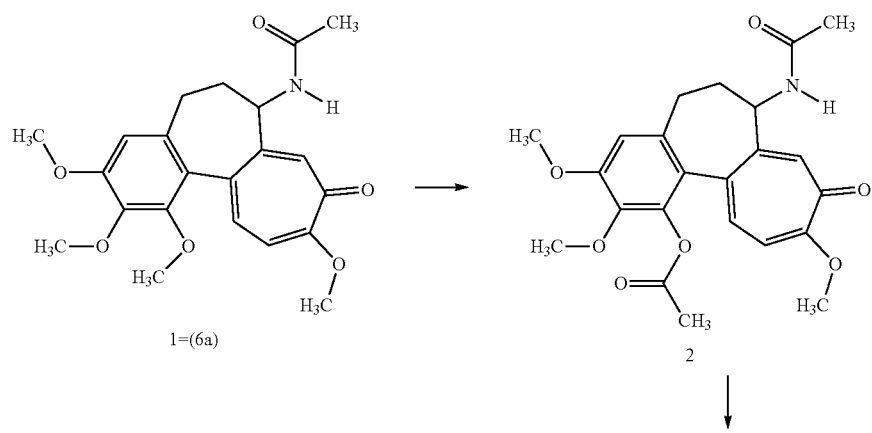
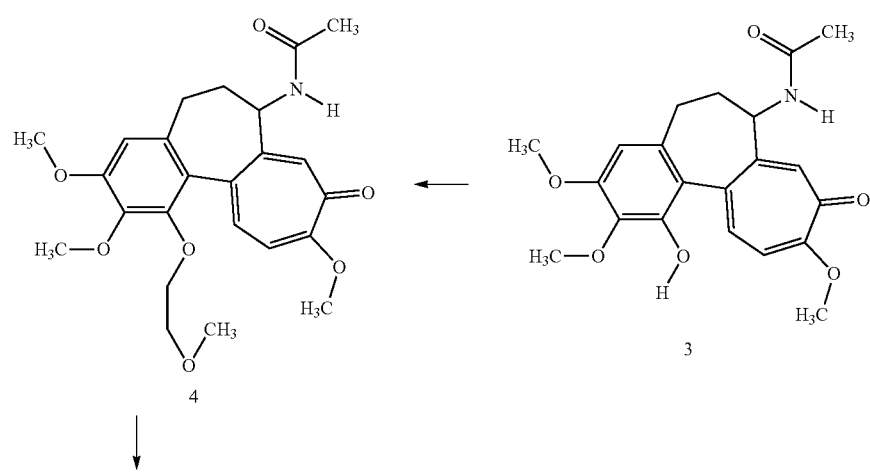
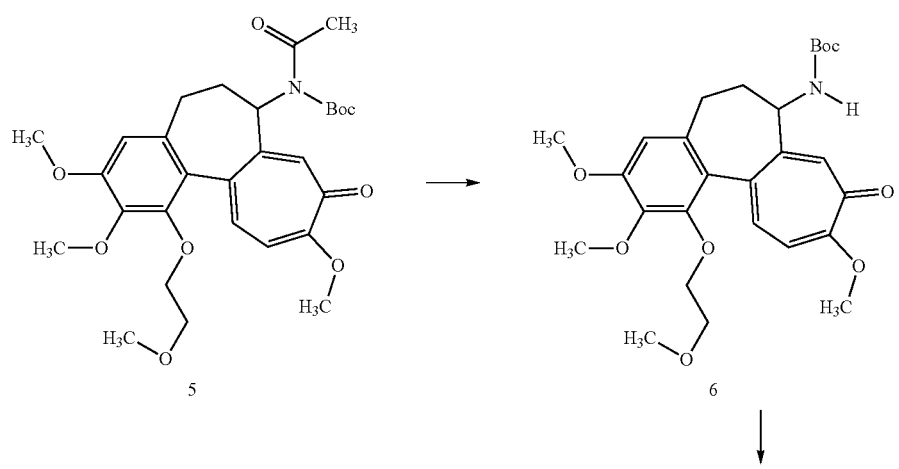

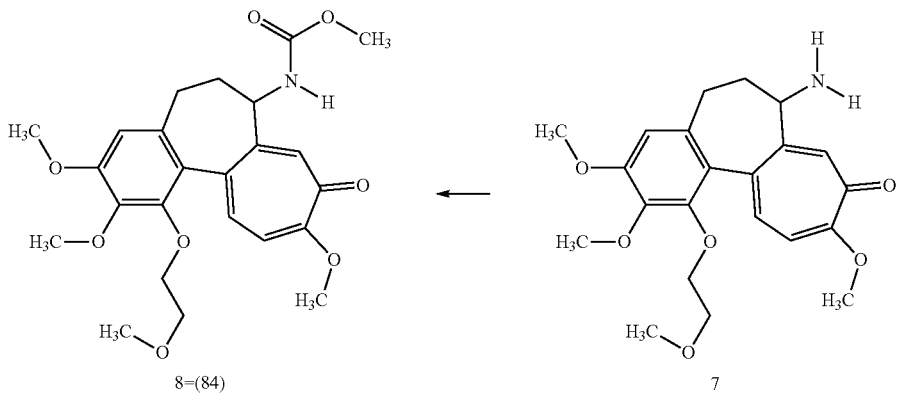

8=(84)

7

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), 1-bromo-2-methoxyethane (580 mg, 4.16 mmol) and potassium carbonate (1.15 g, 8.31 mmol) in DMF (20 mL) was stirred at 75° C. for 3 h. The reaction mixture was poured in water, extracted with ethyl acetate and concentrated to give the crude product. The crude product was purified by silica gel column chromatography to give the desired product (0.5 g, 54%)

A mixture of 4 (500 mg, 1.13 mmol), (Boc)2O (2.5 g, 11.29 mmol) and DMAP (55 mg, 0.45 mmol) in THF (10 mL) was refluxed overnight. The reaction mixture was vcashed with water, dried and concentrated to give the crude product which was used directly for the next step.

A solution of 5 (crude) and sodium methoxide (244.0 mg, 4.52 mmol) in methanol (15 mL) was stirred at rt for 2 h. Then water was added and extracted with dichloromethane. The extracts were concentrated to give the crude product. The crude product was purified by silica gel column chromatography to give the desired product (0.4 g).

A solution of 6 (0.6 g, 1.20 mmol) and trifluoroacetic acid (5 ml) in dichloromethane (5 mL) was stirred at rt for 3 hours. The reaction solution was concentrated to give the product (0.45 g, 94%).

To a solution of 7 (50 mg, 0.12 mmol) and triethylamine (25 mg, 0.25 mmol) in dichloromethane (3 mL) was added methyl carbonochloridate (18 mg, 0.19 mmol) at 0° C. The resulting solution was stirred at rt for 1 h. The reaction mixture was washed with water and concentrated to give the crude product. The crude product was purified by chromatography to give the desired product (16 mg, 28%).

Compound (85)

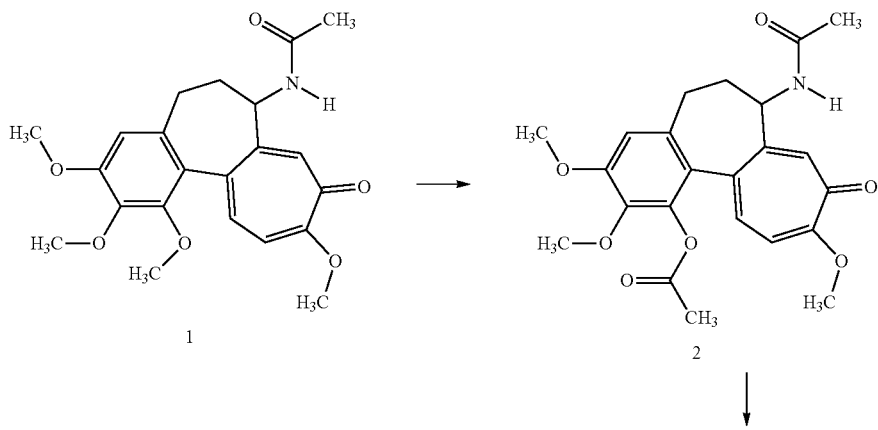

1

2

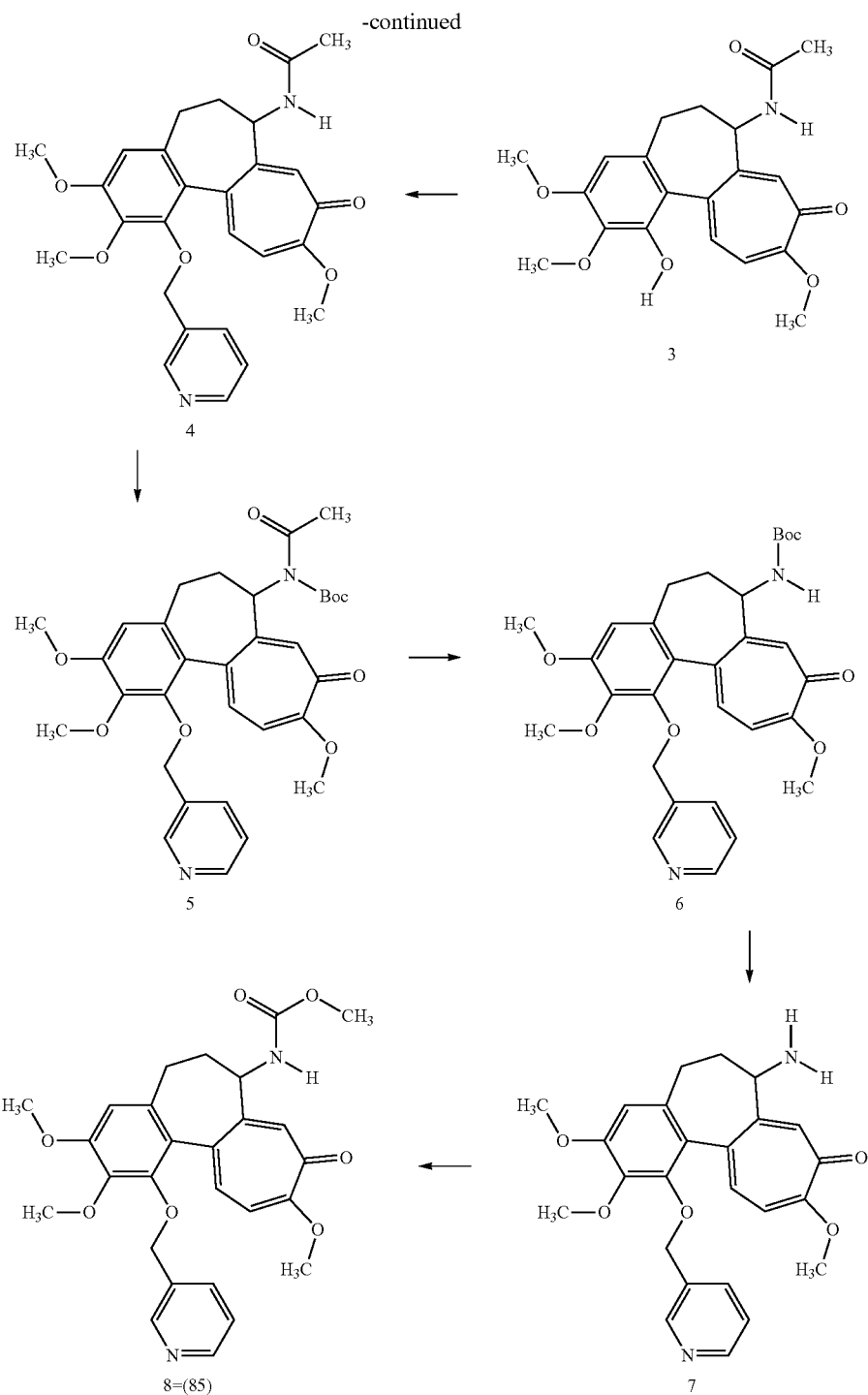

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stored at rt for an hour. The aqueous phase was extracted and concentrated to give the crude product. The product was obtained by recrystallization (0.2 g, 21%, two steps).

A mixture of 3 (1.0 g, 2.6 mmol), 3-(chloromethyl) pyridine (0.64 g, 3.9 mmol) and potassium carbonate (1.08 g, 7.8 mmol) in DMF (20 mL) was stared at 90° C. for 8 h. The reaction mixture was poured in water, extracted with ethyl acetate and concentrated to give the crude product. The crude product was purified by silica gel column chromatography to give the desired product (0.7 g, 58%)

A mixture of 4 (700 mg, 1.47 mmol), (Boc)2O (3.2 g, 14.71 mol) and DN P (72 neg. 0.59 mmol) in THF (20 mL)

was refluxed overnight. The reaction mixture was washed with water. dried and concentrated to give the crude product which was purified by silica gel column, chromatography to give the product (0.7 g, 87%).

A solution of 5 (0.7 g, 1.22 mmol) and sodium methoxide (131.0 mg, 2.43 mmol) in methanol (10 mL) was stirred at rt for 1 h. The reaction mixture was poured into water, extracted with dichloromethane, dried and concentrated to give the crude product which was used directly for the next step.

A solution of 6 (crude) and trifluoroacetic acid (10 ml) in dichloromethane (10 mL) was stirred at rt for 2 hours. The reaction solution was concentrated to give the product (0.3 g).

To a solution of 7 (50 mg, 0.12 mmol) and triethylamine (35 mg, 0.35 mmol) in dichloromethane (3 mL) was added methyl carbonochloridate (16 mg, 0.17 mmol) at 0° C. The resulting solution was stirred at rt for 1 h. The reaction mixture was washed with water and concentrated to give the crude product. The crude product was purified by chromatography to give the desired product (12 mg, 21%).

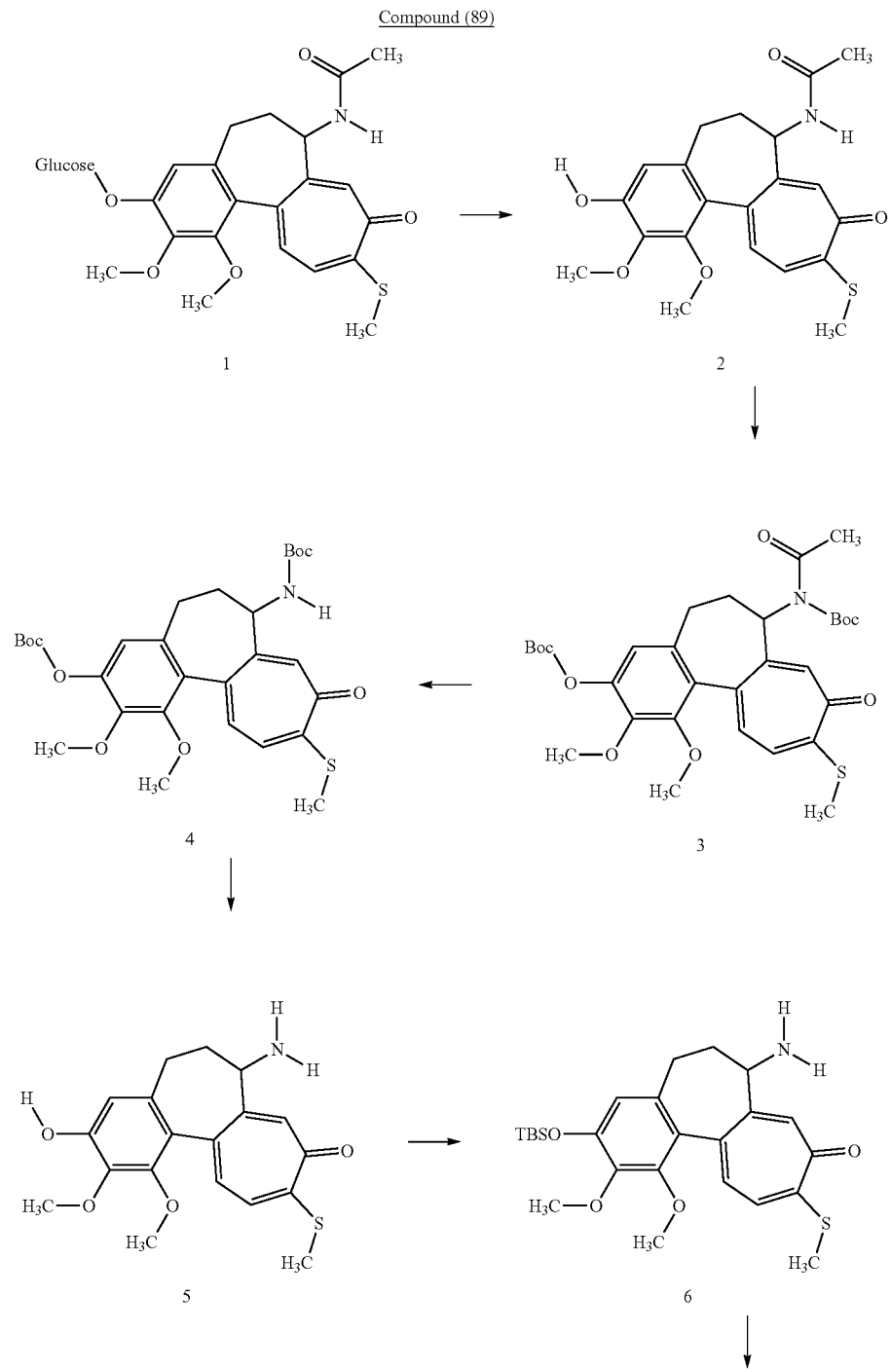

Compound (89)

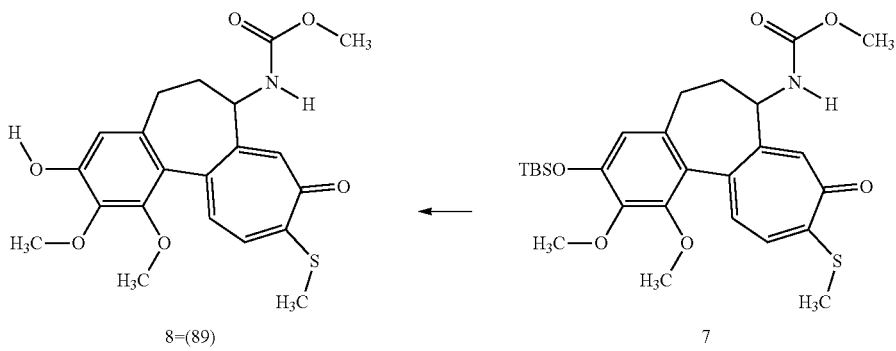

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (600 mg, 1.50 mmol), (Boc)2O (3.3 g, 14.96 mmol) and DMAP (73 mg, 0.60 mmol) in THF (20 mL) was refluxed overnight. The reaction mixture was washed with water, dried and concentrated to give the crude product which was directly used for the next.

A solution of 3 (crude) and sodium methoxide (120.0 mg, 2.3 mmol) in methanol (10 mL) was stirred at rt for 1 h. The reaction mixture was poured into water, extracted with dichloromethane, dried and concentrated to give the crude product which was used directly for the next.

A solution of 4 (crude) and trifluoroacetic acid (10 mL) in dichloromethane (10 mL) was stirred at rt for 2 hours. The reaction solution was concentrated to give the product (0.4 g).

To a solution of 5 (50 mg, 0.14 mmol) and Im (9 mg, 0.14 mmol) in dichloromethane (3 mL) cooled to 0° C. was added tert-butyldimethylchlorosilane (21 mg, 0.14 mmol). The resulting mixture was stirred at rt for 10 min. The reaction mixture was washed with water and concentrated to give the crude product. The crude product was purified by chromatoaraphy to give the desired product (30 mg, 45%).

To a solution of 6 (100 mg, 0.13 mmol) and triethylamine (64 mg, 0.64 mmol) in dichloromethane (3 mL) was added methyl carbonochloridate (40 mg, 0.42 mmol) at 0° C. The resulting solution was stirred at rt for 1 h. The reaction mixture was washed with water and concentrated to give the crude product. The crude product was purified by chromatography to give the desired product (50 mg, 45%).

To a solution of 7 (50 mg, 0.09 mmol) in tetrahydrofuran (3 mL) was added TBAF (29 mg, 0.11 mmol). The resulting mixture was stirred at rt for 30 min. The reaction mixture was concentrated and purified by chromatography to give the desired product (20 mg, 51%).

Compound 90

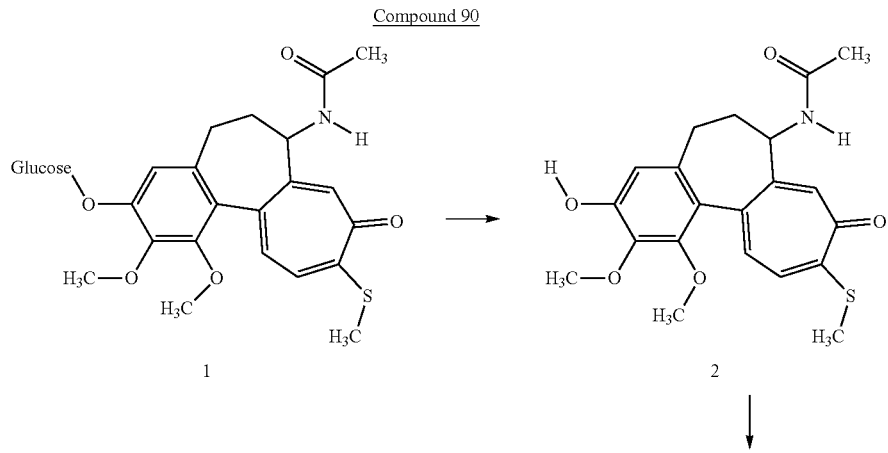

-continued

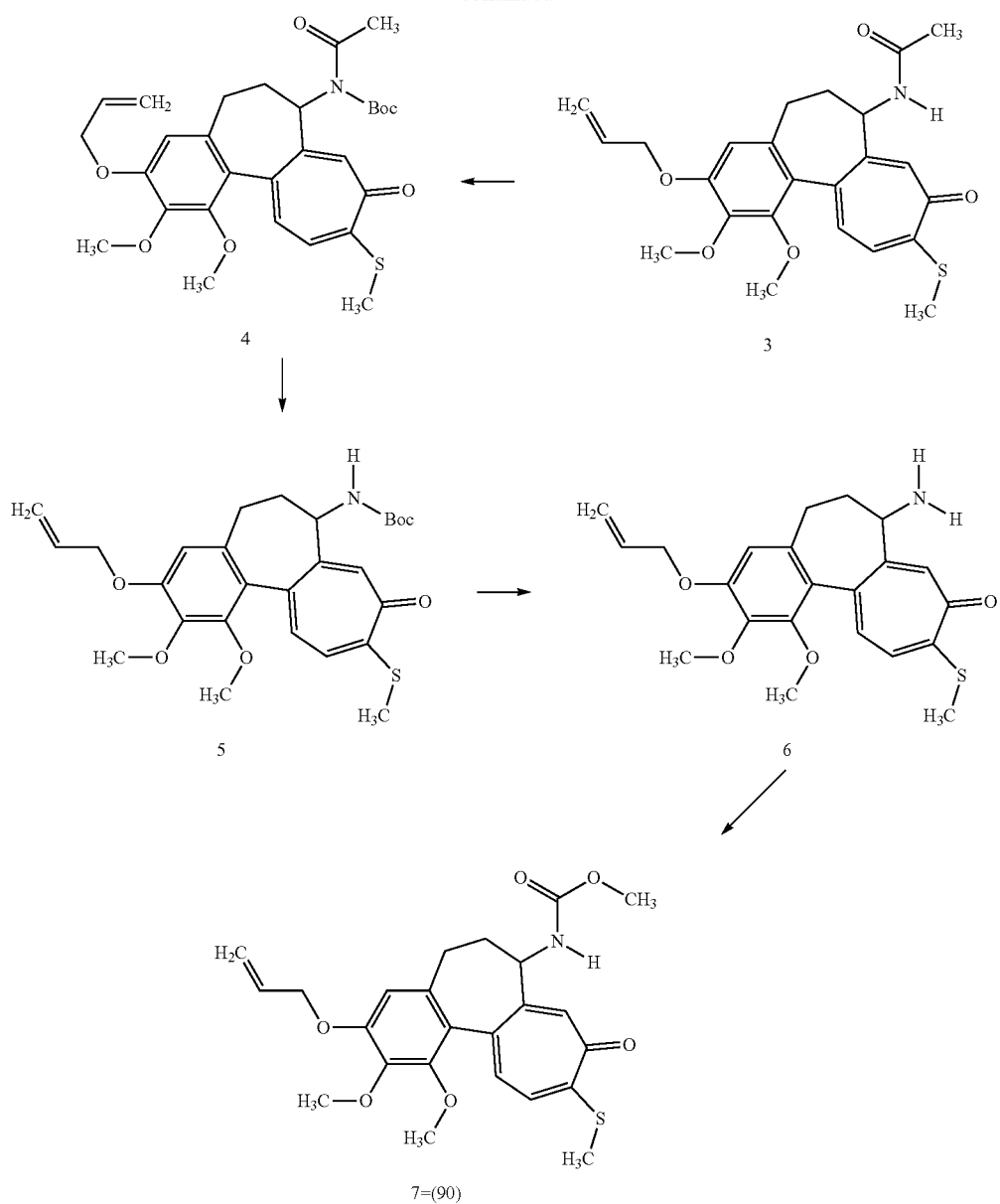

A mixture of 1 (4.0 g) in phosphoricacid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (50 mg, 0.12 mmol), 3-bromoprop-1-ene (23 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (30 mg, 55%).

A mixture of 3 (500 mg, 1.13 mmol), (Boc)2O (2.5 g, 11.31 mol) and DMAP (55 mg, 0.45 mmol) in THF (20 mL) was refluxed overnight. The reaction mixture was washed with water, dried and concentrated to give the crude product which was directly used for the next step.

A solution of 4 (crude) and sodium methoxide (120.0 mg, 2.21 mmol) in methanol (10 mL) was stirred at rt for 1 h. The reaction mixture was poured into water, extracted with dichloromethane, dried and concentrated to give the crude product which was used directly for the next step.

A solution of 5 (crude) and trifluoroacetic acid (10 mL) in dichloromethane (10 mL) was stirred at rt for 2 hours. The reaction solution was concentrated to give the product (04 g).

To a solution of 6 (50 mg, 0.13 mmol) and triethylamine (25 mg, 0.25 mmol) in dichloromethane (3 mL) was added methylcarbonochloridate (24 mg, 0.25 mmol) at 0° C. The resulting mixture was stirred at rt for 1 h. The reaction mixture was washed with water and concentrated to give the crude product. The crude product was purified by chromatography to give the desired product (20 mg, 35%).

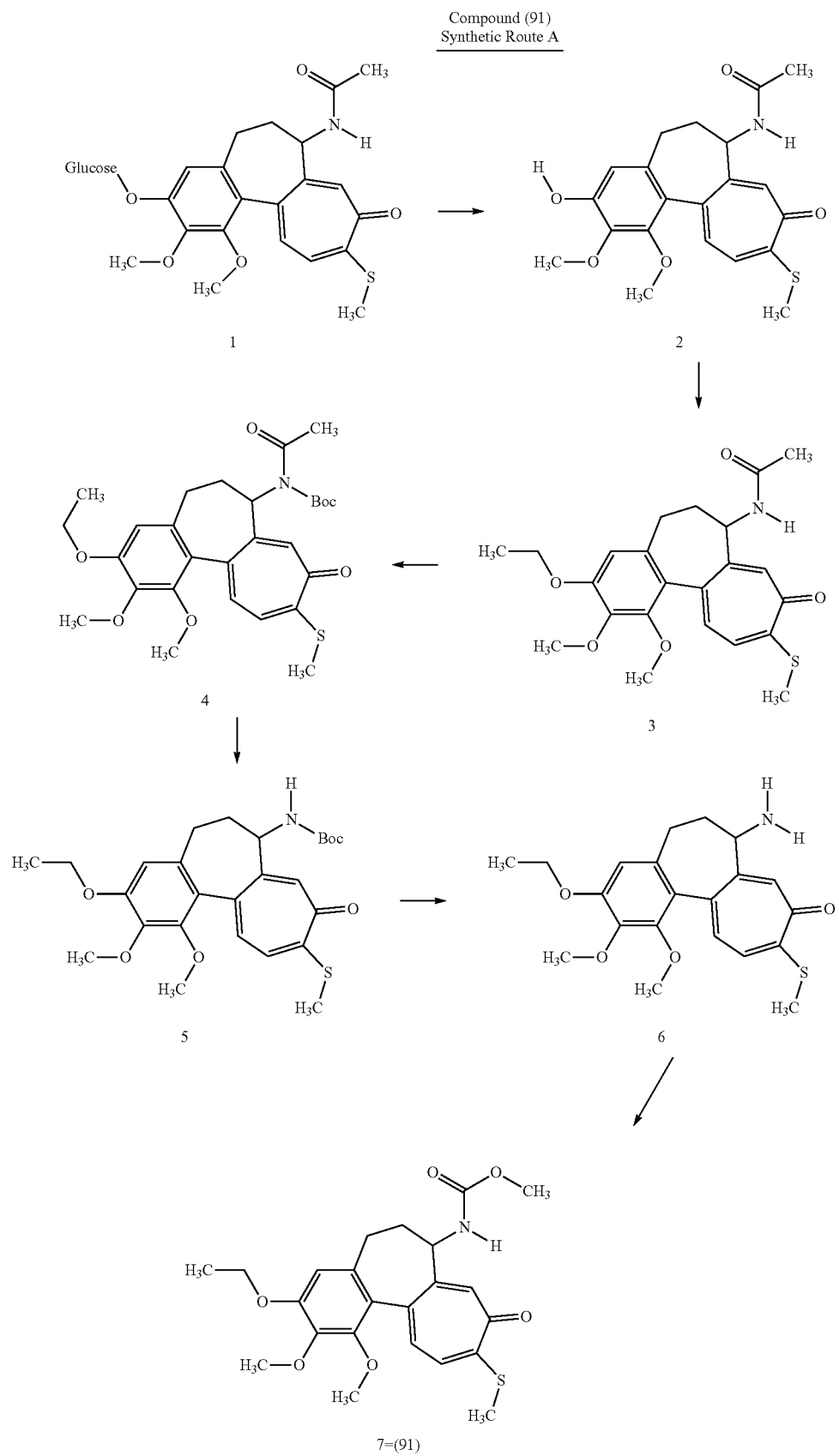

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (50 mg, 0.12 mmol), bromoethane (21 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (35 mg, 65%).

A mixture of 3 (500 mg, 1.16 mmol), (Boc)2O (2.5 g, 11.63 mol) and DMAP (57 mg, 0.47 mmol) in THF (20 mL) was refluxed overnight. The reaction mixture was washed with water, dried and concentrated to give the crude product which was directly used for the next step.

A solution of 4 (crude) and sodium methoxide (122.0 mg, 2.26 mmol) in methanol (10 mL) was stirred at rt for 1 h. The reaction mixture was poured into water, extracted with dichloromethane, dried and concentrated to give the crude product which was used directly for the next step.

A solution of 5 (crude) and triethylamine (10 mL) in dichloromethane (10 mL) was stirred at rt for 2 hours. The reaction solution was concentrated to give the product (0.4 g).

To a solution of 6 (50 mg, 0.13 mmol) and triethylamine (25 mg, 0.25 mmol) in dichloromethane (3 mL) was added methyl carbonochloridate (24 mg, 0.25 mmol) at 0° C. The resulting solution was stirred at rt for 1 h. The reaction mixture was washed with water and concentrated to give the crude product. The crude product was purified by chromatography to give the desired product (20 mg, 35%).

Synthetic Route B

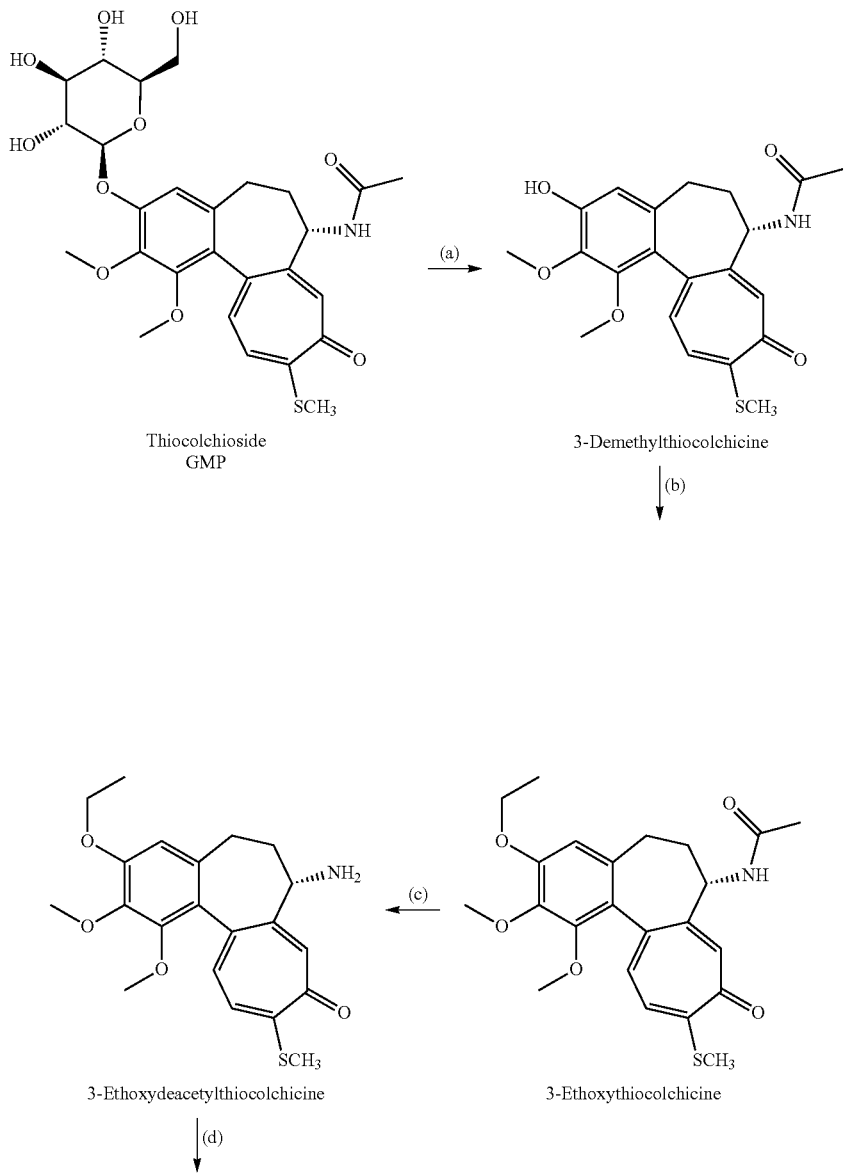

-continued
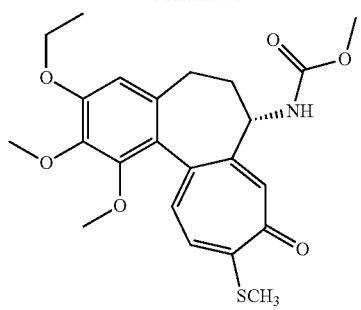
CR-42-024
(a) acid-catalyzed hydrolysis of glycosides
(b) Williamson ether synthesis
(c) acid-catalyzed amide hydrolysis
(d) rection with methyl chloroformate
Step 1- Acidolysis
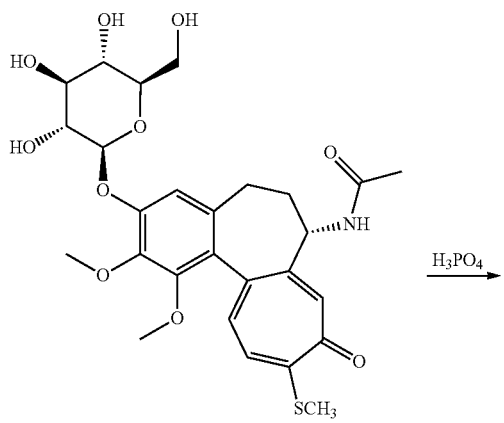
Thiocolchicoside
GMP
Chemical Formula:
$C_{27}H_{33}NO_{10}S$
Exact Mass: 563.2
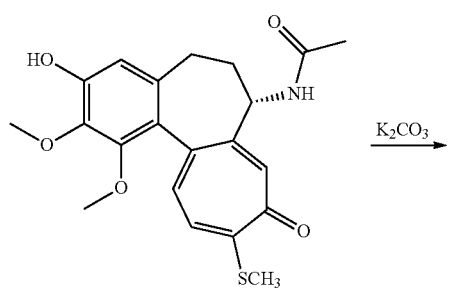
3-Demethylthiocolchicine
Chemical Formula: $C_{21}H_{23}NO_5S$
Exact Mass: 401.1
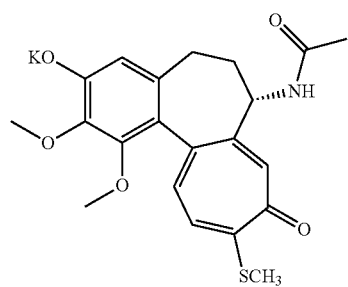

THC (1 g) was dissolved in warm concentrated phosphorous acid (85%) (40 ml) and stirred for about 12 h. The solution was extracted about five times with chloroform. The resultant chloroform fractions were washed with water and then evaporated using a rotary evaporator to provide a product from the hydrolysis.

The product of the hydrolysis was dissolved in acetone and an aqueous solution of $K_2CO_3$ of was added. The resulting solution was evaporated and then more acetone was added, followed by evaporation to yield potassium salt (3-Demethylthiocolchicine).

Step 2 - Synthesis of ether (3-Ethoxythiocolchicine)

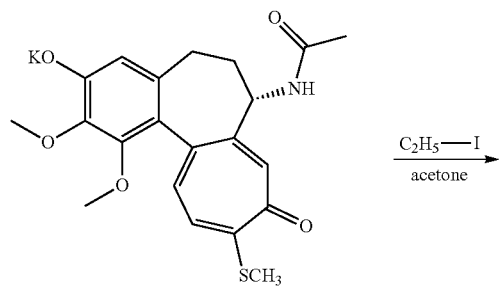

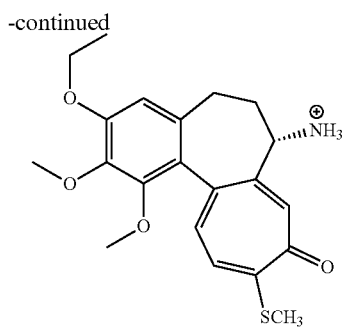

3-Ethoxydeacetylthiocolchicine
Chemical Formula: $C_{21}H_{26}NO_4S^+$
Exact Mass: 388,2

The 3-ethoxythiocolchicine was dissolved in 5M HCl (100 ml) and refluxed (boiled) and stirred boiling and monitored by TLC. After about 5 h, the reaction mixture was extracted seven times with chloroform. The resultant chloroform fractions were washed with water and evaporated to dryness. The product was dissolved in methanol and evaporated three times to remove traces of water. The product was dissolved in acetonitrile and evaporated to dryness to yield amine (3-ethoxydeacetylthiocolchicine).

Step 4

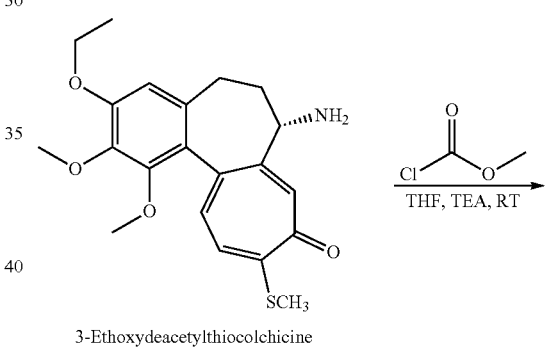

3-Ethoxydeacetylthiocolchicine
Chemical Formula: $C_{23}H_{27}NO_5S$
Exact Mass: 429,2

The potassium salt (3-Demethylthiocolchicine) from Step 1 was dissolved in acetone (75 ml) and two times a molar excess of ethyl iodide was added. The resulting solution was stirred and refluxed (boiled) under reflux for about 5 h. The solution was evaporated, and acetonitrile was added and the solution evaporated again to remove the remaining ethyl iodide to yield precipitation 3-ethoxythiocolchicine.

Step 3 - Hydrolysis of amide bond

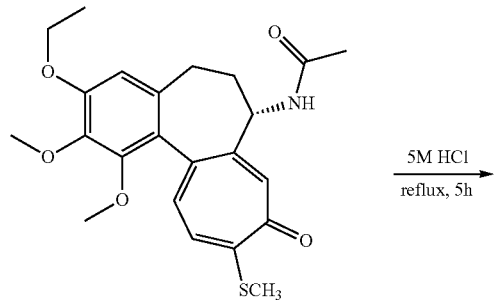

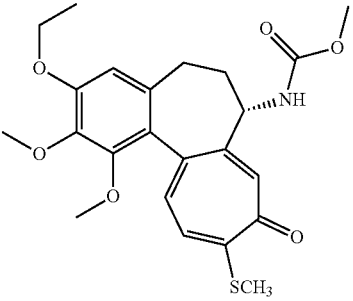

Chemical Formula: $C_{23}H_{27}NO_6S$
Exact Mass: 445,2
CR-42-024

Dry amine (3-ethoxydeacetylthiocolchicine) was dissolved in THF (50 ml) and TEA (triethylamine) (1.5 ml) was added. To this solution, methyl chloroformate (0.5 g) was added and stirred at RT (room temperature) for about 5 h and monitored by TLC. The resultant solution was evaporated to dryness and dissolved in chloroform and extracted twice with 0.2 M HCl, then once with water. The resultant chloroform fractions were evaporated to dryness, dissolved in acetonitrile and evaporated to dryness once again. The resultant product (CR-42-024=(91)) was purified by flash chromatography on silica gel. The eluent was a mixture of hexane/ethyl acetate containing 0-5% of hexane.

TPO

In some of the experiments described below, the colchicine derivative TPO (described in Kerekes P, Sharma P N, Brossi A, Chignell C F, Quinn F R (1985) Synthesis and biological effects of novel thiocolchicines. 3. Evaluation of N-acyldeacetylthiocolchicines, N-(alkoxycarbonyl) deacetylthiocolchicines, and O-ethyldemethylthiocolchicines. New synthesis of thiodemecolcine and antileukemic effects of 2-demethyl- and 3-demethylthiocolchicine. J Med Chem 28:1204-1208, herein incorporated in its entirety by reference) was used to determine its effectiveness against inflammation associated with gout in comparison to (91)

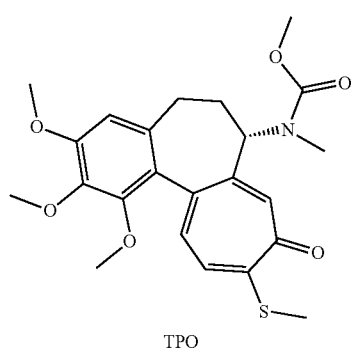 [SMILES: COC(=O)N(C)[C@H]1CCc2cc(OC)c(OC)c(OC)c2-c2ccc(SC)c(=O)cc21 ; "TPO"]

TPO

Example 2—In Vitro Studies of Gouty Inflammation

A series of in vitro experiments were conducted with (91) (referred to as "CCI" in some of the Figures), a colchicine derivative, in MSU-induced neutrophil activation. Experiments were also conducted to show the effect of colchicine derivatives that have a similar structure to (91), such as CH-35 (43) and CR42-003 (47a). The structure of colchicine, the scaffold used to generate the compounds, was modified at the positions indicated in Table 1 below to generate CCI (91), CH-35 (43) and CR-42-003 (47a). In summary, and as described in further detail below, human neutrophils were isolated from healthy donors and stimulated with the causative agent of gout, MSU, in the presence or absence of (91), (43) and (47a). The key neutrophil responses assessed were cytoplasmic calcium levels (FIG. 7), pro-inflammatory cytokine (e.g., IL-8 or IL-1) production (FIG. 8) and superoxide production (FIG. 9).

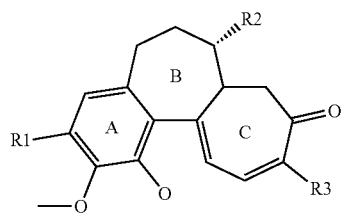

TABLE 1

| Compound | R1 | R2 | R3 | βVI binding free energy (kcal/mol) |
|---|---|---|---|---|
| Colchicine | —OCH₃ | —NHCOCH₃ | —OCH₃ | −42.03 |
| CR-42-003 | —OCH₃ | —NHCOCH₂NHCOCF₃ | —SCH₃ | −42.21 |
| CH-35 | —OCH₂CH₂CH₃ | —NHCOCH₃ | —SCH₃ | −47.63 |
| CCI | —OCH₂CH₃ | —NHCOOCH₃ | —SCH₃ | −51.70 |

Compounds were selected in an algorithmic approach to balance between a need for a high affinity interaction of the compound for the target isoform, βVI in the present case, with a lowest possible affinity for an off-target tubulin isoform in a sensitive organ or tissue, thus selecting for compounds having improved specificity/selectivity for the desired target. The key parameters used by this approach to identify the chemical modifications that are more likely to increase the affinity of colchicine for the β-tubulin isotypes in the cell of interest include: (i) the different affinities of colchicine for the β-tubulin isotypes and (ii) the quantitative and qualitative difference in the expression of these β-tubulin isotypes between different cell types.

Detailed knowledge of drug docking and the mode of interactions of the ligand with the individual residues of tubulin made it possible to determine modifications to lead to improved specificity and selectivity for a tubulin isotype of choice due to its expression in the target cell type. It should be noted that the computational work was based on the homology modeling of the human tubulin isotypes, which used bovine tubulin as a scaffold from which equilibrated human structures were generated. With a very high sequence similarity between human and bovine tubulin, the level of confidence in the obtained results is very high. The structures and predicted binding energies of the three compounds shown in Table 1 and the details of the chemical synthesis of the three compounds studied here as well as their closely structurally-related colchicine derivatives are described herein and also can be found in U.S. Pat. No. 9,458,101, the contents of which are incorporated by reference.

Materials and Methods

Materials

Antibodies against human β-tubulin isotypes β-I (MAB8527) and beta-III (MAB1195) were purchased from R&D System, beta-II (ab155311) and beta-V (ab82366) were obtained from Abcam, and the beta-IVb (WH0010383M2), anti-PI3 kinase p85 (ABS1856) antibodies were purchased from Sigma-Aldrich. The beta-VI (LS-C338196) antibody was obtained from LS Bio and the horseradish peroxidase-labeled donkey anti-mouse immunoglobulins (IgGs) (715-035-150) and horseradish peroxidase-labeled donkey anti-rabbit immunoglobulins (IgGs) (711-035-152) from Jackson Immunoresearch. Rat anti-mouse CD45 Fitc (11-0451-82) and Fura-2-acetoxymethyl ester (Fura-2AM) were purchased from Invitrogen. Colchicine, dextran T500, aprotinin, leupeptin and cytochrome C were obtained from Sigma-Aldrich. The Western Lightning Chemiluminescence Plus ECL kit was obtained from PerkinElmer and Ficoll-Paque from Wisent Bioproducts. Triclinic MSU crystals were synthesized in-house. Endotoxin contamination was ruled out by Limulus amebocyte lysate assay.

Isolation of Human Neutrophils

Neutrophils were isolated from venous blood of healthy adult volunteers. Briefly, venous blood was obtained in tubes containing isocitrate, red blood cells were sedimented in 2% dextran and neutrophils were aseptically purified by centrifugation on Ficoll-Paque cushions. Contaminating erythrocytes were removed by hypotonic lysis and neutrophils were resuspended in $Mg^{2+}$-free HBSS containing 1.6 mM of $CaCl_2$.

Figure 7C:
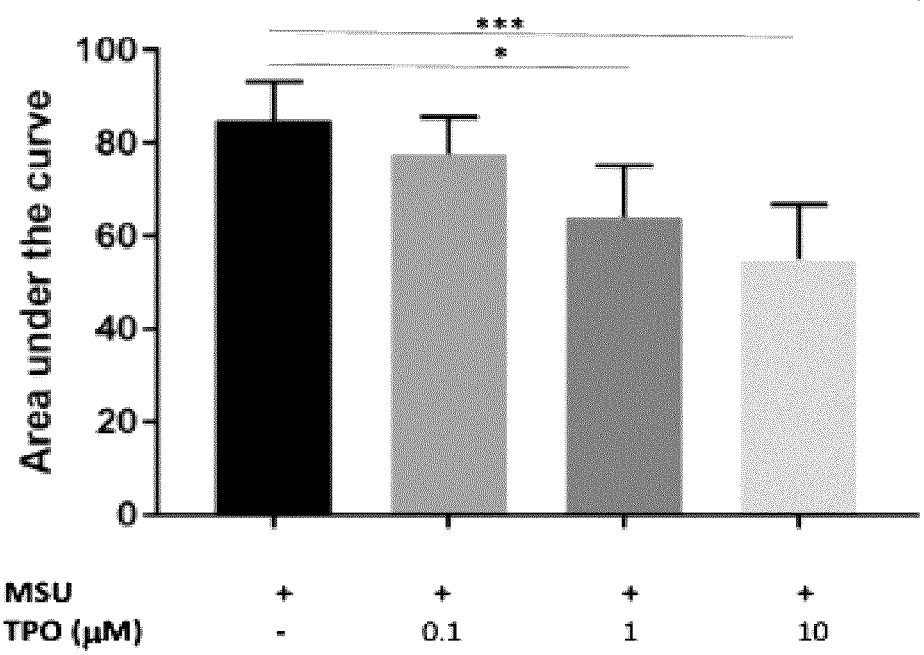
FIG. 7C shows the effect of colchicine derivative TPO.
Figure 7J:
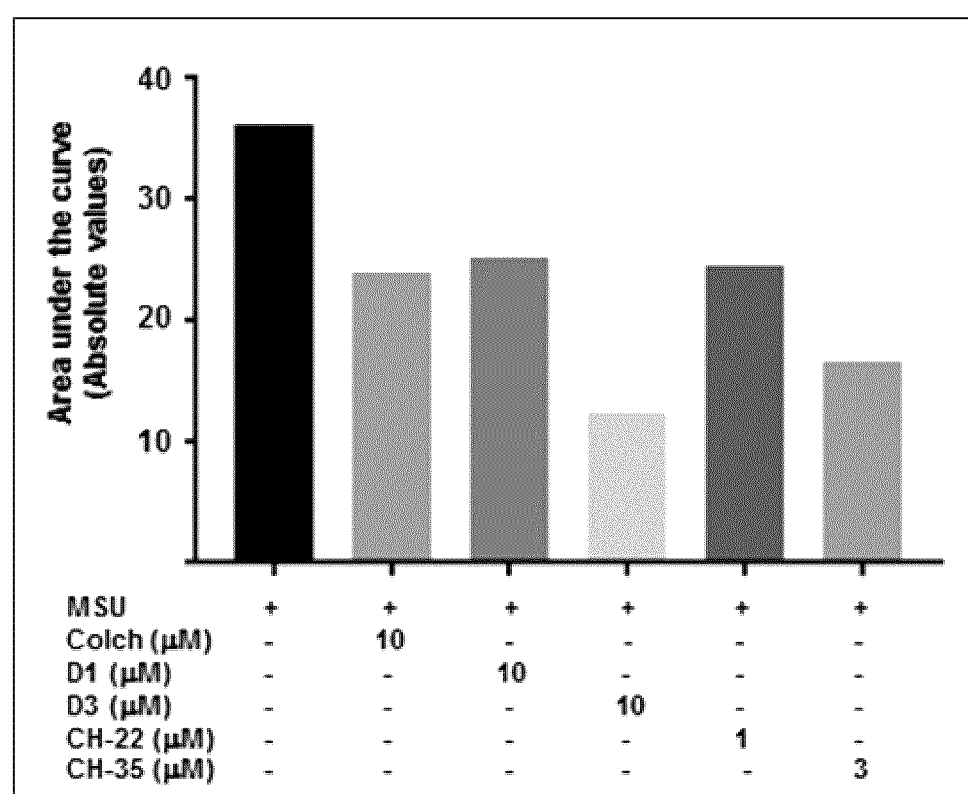
Figure 7M:
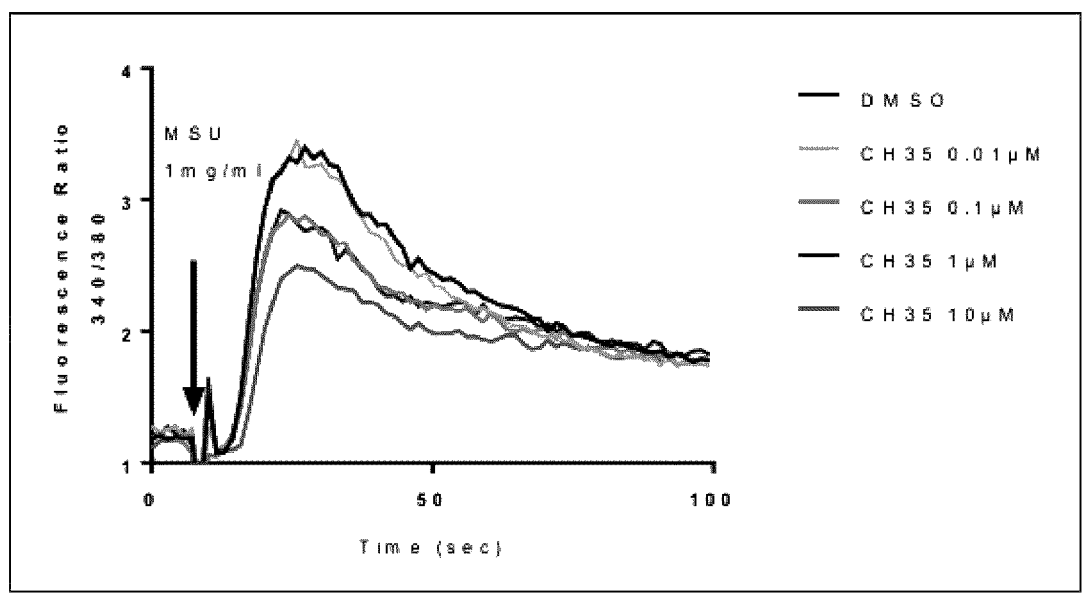
Figure 7N:
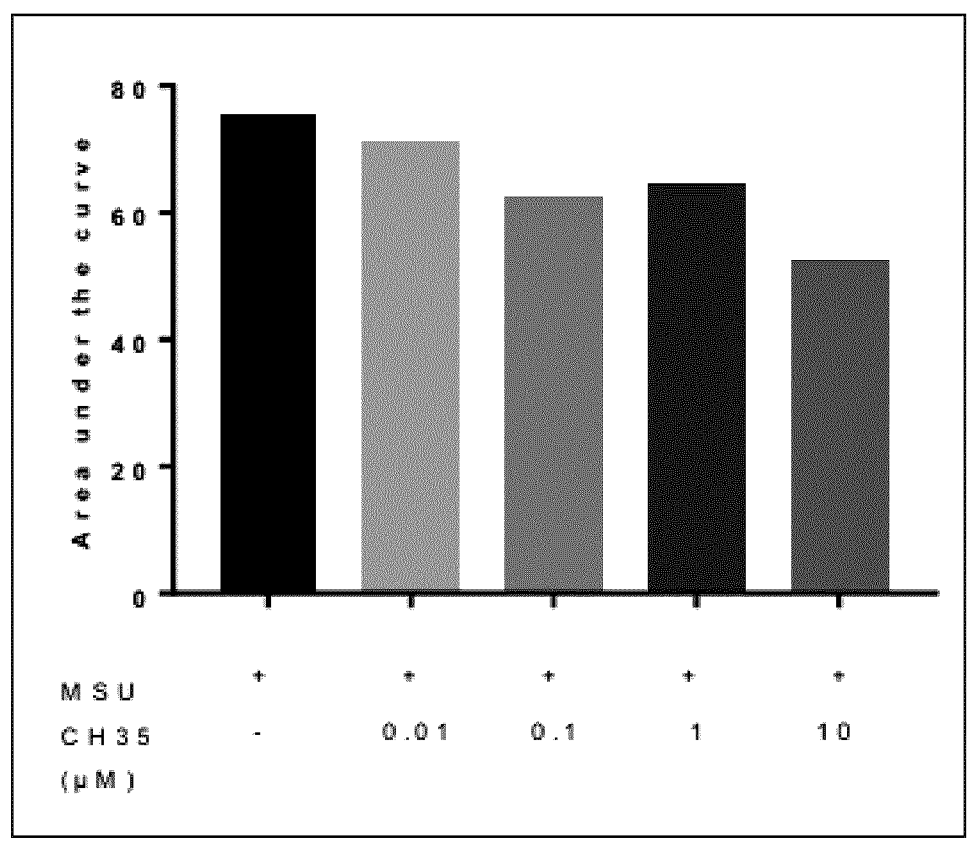
Figure 7S:
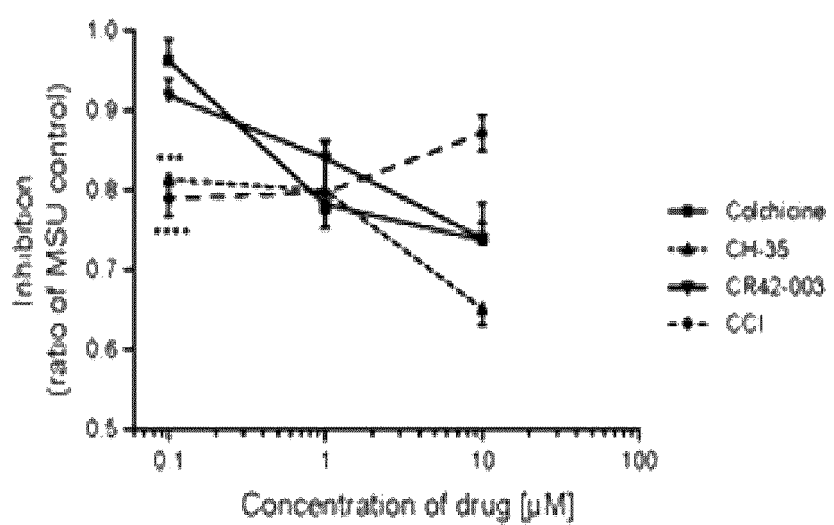
FIG. 7S shows a comparison of the inhibitory activity of the compounds tested in FIGS. 7A, 7B, 7Q and 7R.

Stimulation of Human Neutrophils with MSU and Colchicine or Colchicine Derivatives to Determine Intraceullar Calcium Mobilization Human neutrophils ($1 \times 10^7$ cells/ml) were pre-incubated with 1 µM Fura-2AM and the indicated concentrations of colchicine (FIG. 7A); (91) (CCI) (FIG. 7B), TPO (FIG. 7C) or diluent (DMSO) prior to the addition of 1 mg/ml MSU. In addition, similar experiments were conducted with respect to further colchicine derivatives. In particular, human neutrophils were stimulated with 10 µM of colchicine (FIG. 7D), D1=(28a) (FIGS. 7E and 7J), D2=(39) (FIG. 7F), D3=(47a) (FIGS. 7G and 7J), D4=(89) (FIG. 7H) prior to the addition of MSU (1 mg/ml). In further experiments, human neutrophils were stimulated with 10 µM of colchicine, 1 µM CH-22=(14), 3 µM CH-35=(43) or diluent DMSO (FIGS. 7I and 7J). In further experiments, human neutrophils were stimulated with 0.1 µM or 10 µM colchicine (FIGS. 7K and 7L), 0.01 µM, 0.1 µM or 1 µM or 10 µM of derivative (43) (FIGS. 7M and 7N), or 0.01 µM, 0.1 µM or 1 µM or 10 µM of derivative (47a) (FIGS. 7O and 7P). In further experiments, human neutrophils were stimulated with 0.1 µM or 1 µM or 10 µM of derivative (43) (FIG. 7Q), or with 0.1 µM or 1 µM or 10 µM of derivative (47a) (FIG. 7R), prior to the addition of 1 mg/ml MSU. FIG. 7S shows a plot of the potency of the compounds at the indicated concentrations, for the compounds tested in FIGS. 7A, 7B, 7Q and 7R.

Neutrophils ($1 \times 10^7$ cells/ml) were incubated for 30 min at 37° C. with 1 µM Fura-2AM and at the indicated concentrations of (91) (CCI), TPO, 28a, 39, 47a, 89, 14, 43 or colchicine, washed once in HBSS, resuspended to a concentration of $5 \times 10^6$ cells/ml and transferred to a temperature-controlled (37° C.) cuvette compartment of a spectrofluorometer (Fluorolog-SPEX from Jobin Yvon).

Measurement of Calcium Levels in Human Neutrophils

The intracellular calcium concentration was determined with a spectrofluorometer and is expressed as the area under the curve (from the MSU injection up to 100 sec).

Changes in cytoplasmic calcium were then measured after the addition of MSU or HBSS (the negative control) using two excitation wavelengths at 340 and 380 nm and an emission wavelength of 510 nm. The free internal calcium concentration was estimated from the ratio of the fluorescence values obtained at 340 and 380 nm. The results are calculated as the area under the curve of the intracellular calcium concentration as a function of time (0-100 sec relative to stimulus addition).

Determination of Specificity of Response to MSU: fMLP-Induced Increase in Cytoplasmic Calcium in Human Neutrophils Human neutrophils ($1 \times 10^7$ cells/ml) were isolated as described above and were pre-incubated with 1 µM Fura-2AM and the indicated concentrations of colchicine, CCI (91) or CH-35 (43) prior to the addition of $10^{-7}$ M fMLP (FIGS. 7T and 7U) or 1 mg/ml MSU (FIGS. 7V and 7W). The intracellular calcium concentration was determined with a spectrofluorometer and is expressed as the area under the curve.

Figure 8A:
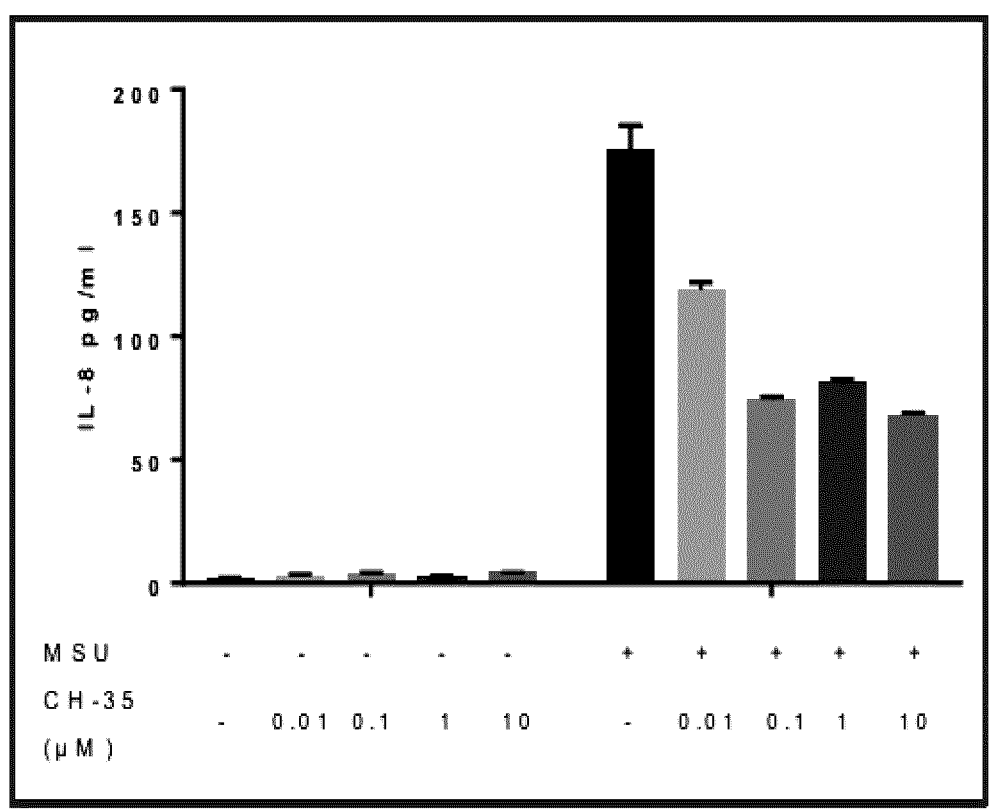
FIG. 8A shows the effect of colchicine derivative (43).

Stimulation of Human Neutrophils with MSU and Colchicine or Colchicine Derivatives to Determine CXCL8/IL-8 or IL-1 Release Human neutrophils were isolated as described above and were incubated with the indicated concentrations of colchicine (43) (FIG. 8A), (47a) (FIG. 8B) or DMSO for 30 min at 37° C. MSU (1 mg/ml) or buffer (RPMI) were then added to the cells and incubated for a further 3 h at 37° C. The cells were centrifuged (400×g for 2 min) and the supernatants harvested and centrifuged again at 16,000×g for 5 min. In further experiments, human neutrophils were incubated with the indicated concentrations of colchicine (FIG. 8C), CCI (91) (FIG. 8D), CR42-003 (47a) (FIG. 8E) or (43) (FIG. 8F), prior to the incubation with 1 mg/ml MSU for 3 h. FIG. 8G shows a plot of the potency of the compounds at the indicated concentrations tested in FIGS. 8C-F. Basal levels of IL-8 production in the presence of CR42-003 (47a) and CH-35 (43) was also determined, prior to MSU stimulation (FIG. 8L). For IL-1β, human neutrophils ($2 \times 10^7$ cells/ml) in white RPMI were primed with 250 U/ml TNFα and incubated with the indicated concentrations of colchicine (FIG. 8H), CCI (91) (FIG. 8I), CH-35 (43) (FIG. 8J), for 30 min at 37° C. prior to the addition of 1 mg/ml MSU and incubation for 3 h at 37° C. FIG. 8K shows a comparison of the potency of the compounds at the indicated concentrations for the compounds tested in FIGS. 8H-J. The cells were then centrifuged to harvest the supernatant as described above. Extracellular CXCL8/IL-8 or IL-1β were quantified by ELISA (Invitrogen). All samples were measured in duplicate.

Measurement of CXCL8/IL-8 or IL-1 Levels in Human Neutrophils

The quantity of CXCL8/IL-8 or IL-1 released by the stimulated neutrophils was determined by using commercially available enzyme-linked immunosorbent assay (ELISA) kits (human IL-8 cytoset, no. CHC1303 and IL-1β (no. 88-7261-88)) from Invitrogen.

Figure 9H:
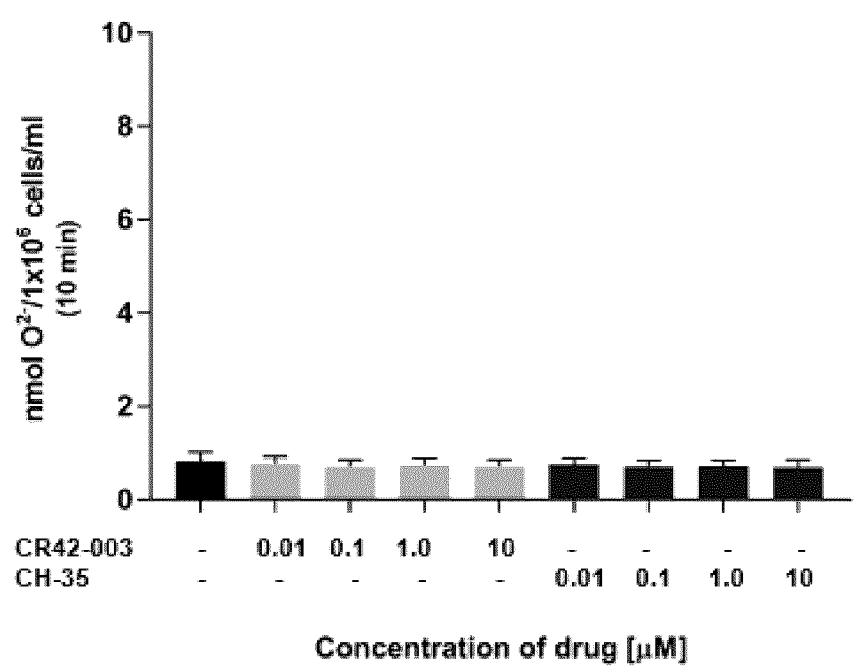
FIG. 9H shows the basal levels of superoxide production in human neutrophils stimulated with colchicine derivative (43) or (47a) in the absence of MSU.

Stimulation of Human Neutrophils with MSU and Colchicine or Colchicine Derivatives to Determine Superoxide Production Human neutrophils were isolated as described above and were incubated for 30 min at 37° C. with the indicated concentrations of colchicine (FIG. 9A), (91) (CCI) (FIG. 9B), or diluent (DMSO) prior to a stimulation with 1 mg/ml MSU for 10 min at 37° C. in the presence of 125 µM cytochrome C or buffer (HBSS). In further experiments, human neutrophils were incubated for 30 min at 37° C. with the indicated concentrations of colchicine (FIG. 9C), CCI (91) (FIG. 9D), (47a) (FIG. 9E) or (43) (FIG. 9F) prior to a stimulation with 1 mg/ml MSU. FIG. 9G shows a plot of the potency of the compounds at the indicated concentrations for the compounds tested in FIGS. 9C-9F. Basal levels of ROS production in the presence of (47a) and (43) was also determined, prior to MSU stimulation (FIG. 9H). The results are expressed as a ratio of the superoxide produced by the MSU control.

Measurement of Superoxide Levels in Human Neutrophils

Superoxide production was measured using the reduction of cytochrome C assay. The difference between the optical density readings at 550 nm and 540 nm read within the first 10 minutes was multiplied by the extinction coefficient of cytochrome C to obtain the number of nmol $O_2$ produced by $1 \times 10^6$ cells. The results are expressed as nmol $O_2/1 \times 10^6$ cells/ml.

Western Blot Analysis

Neutrophil suspensions ($2 \times 10^7$ cells/ml) were transferred directly into the same volume of 2× boiling modified Laemmli sample buffer (1× buffer: 62.5 mM Tris·HCl (pH 6.8), 4% (wt/vol) sodium dodecyl sulfate (SDS), 5% (vol/vol) β-mercaptoethanol, 8.5% (vol/vol), glycerol, 2.5 mM orthovanadate, 10 µg/ml leupeptin, 10 µg/ml aprotinin and 0.025% bromophenol blue) and boiled for 7 min. Proteins were separated by SDS-PAGE on 10% acrylamide gels under reducing conditions and transferred to polyvinylidene fluoride (PVDF) membranes. Blocking agents and antibodies were diluted in a Tris-buffered saline Tween 20 (TBST) solution (25 mM Tris·HCl, pH 7.8, 190 mM NaCl, 0.15% vol Tween-20). Primary and secondary antibodies were used at concentrations recommended by their manufacturers. PVDF membranes were incubated in blocking solution (5% wt/vol dried milk in TBST) prior to immunoblotting with the anti-β-tubulin isotype-specific antibodies. Horseradish peroxidase-labeled donkey anti-mouse IgG and donkey anti-rabbit IgG were diluted in TBST solution. Chemiluminescence reagents were used to detect antibodies with a maximal exposure time of 5 min. All the immunoblots presented were controlled for equal protein loading with an anti-PI3 kinase p85 antibody.

Results

(91) (CCI) Inhibits MSU-Induced Calcium Mobilization at a Lower Concentration than Colchicine Since one of the earliest molecular events in neutrophils that is initiated by MSU is the mobilization of intracellular calcium stores, the effect of (91) (CCI), (43) and (47a) was assessed on this early signalling event. Briefly, and as described in further detail above, human neutrophils were incubated with the fluorescent calcium indicator Fura-2 prior to incubation with a range of concentrations of (91) (CCI), (43) or (47a) and stimulated with MSU. Fura-2 monitors the increase in cytoplasmic calcium caused by its release from intracellular stores. The concentrations of (91) (CCI), (43) or (47a) tested ranged from 0.1 to 10 µM. For comparative purposes, the same experiment was performed with colchicine at the same concentrations.

As shown in FIGS. 7A-C, (91) (CCI) significantly inhibits the increase in intracellular calcium concentration at a dose as low as 0.1 µM, whereas TPO shows inhibition at higher concentrations. In contrast, colchicine is only able to induce a significant inhibition in the mobilization of calcium at a concentration of 10 µM. (91) is thus able to significantly reduce the mobilization of intracellular calcium stores at about 100-fold lower concentration than colchicine and is, thus, about 100-fold more potent than colchicine at inhibiting mobilization of calcium. Other colchicine derivatives 28a, 39, 47a, 14, and 43 showed neutrophil-inhibitory effects with respect to reducing calcium levels in human neutrophils (FIGS. 7E-J), with the exception of (89) (FIG. 7H), when compared to colchicine (FIG. 7E). This is noted by an increase in the slope of a graphed line (after the first spike) signifying an increase in the concentration of cytoplasmic-free calcium (FIGS. 7D-I).

Of note, findings similar to those for colchicine derivatives (91) were found for colchicine derivatives (43) (FIGS. 7M and 7N) and (47a) (FIGS. 7O and 7P) at concentrations as low as 0.1 µM, when compared to colchicine (FIGS. 7K and 7L). Thus, colchicine derivatives, such as 91, 47a and 43 demonstrate the ability to inhibit the MSU-induced increase in calcium mobilization in human neutrophils (FIG. 7) at much lower (e.g., about 100-fold lower) concentrations than required for colchicine.

In further experiments, and as shown in FIGS. 7B and 7Q-S, the derivatives were tested in a concentration range from 0.01 to 10 µM. For comparative purposes, the same experiments was performed with colchicine at the same concentrations. CCI (91) (FIG. 7B) and CH-35 (43) (FIG. 7R) were found to significantly diminish the increase in cytoplasmic calcium at a concentration of 0.1 µM. As shown in FIG. 7R, CH-35 (43) was able to significantly inhibit the increase in intracellular calcium concentration at 0.1 µM, 1 µM and 10 µM. CH-35 (43) has a classical monotonic dose response and its effect is concentration-dependent. In contrast, CCI (91) has a non-monotonic dose response and does not have a significant effect on the MSU-induced increase in cytoplasmic calcium at a 10 µM concentration. As shown in FIG. 7S, the comparison of the inhibitory activity of the derivatives and colchicine at 0.1 µM, confirmed that CCI (91) and CH-35 (43) were more potent than colchicine at significantly reducing the MSU-induced increase in cytoplasmic calcium. Thus, CCI (91) and CH-35 (43) preserve their inhibitor activity at lower concentrations compared to colchicine.

To assess the specificity of CCI (91) towards neutrophil activation by MSU, it was determined whether CCI (91) was able to inhibit neutrophil responses towards an unrelated stimulus. A bacterial stimulus was chosen because neutrophil activation in response to this stimulus affects the survival of the host. Briefly, human neutrophils were incubated with the 10 µM CCI (91) prior to the activation with the bacterial peptide fMLF. As shown in FIGS. 7T and 7U, neutrophil activation with fMLF induced a significant rise in the concentration of calcium in the cytoplasm. In the presence of CCI (91), however, the cytoplasmic calcium response was unaffected. These results revealed that the inhibition of neutrophil activation by CCI (91) exhibited a certain degree of selectivity towards MSU.

(91) (CCI) Inhibits MSU-Induced CXCL8/IL-8 or IL-1 Release at a Lower Concentration than Colchicine The ability of (91) (CCI), (43) or (47a) to dampen the mobilization of calcium in response to MSU prompted determination of the effect on neutrophil responses downstream of this signaling event. Since early signalling events such as calcium mobilization depend on the activation of Src kinases by MSU, it was determined whether the Src-dependent production of CXCL8/IL-8 induced by MSU is also inhibited by (91) (CCI). In addition, since IL-1 induces the expression of adhesion molecules on endothelial cells as well as the synthesis of pro-inflammatory cytokines, which together promote a massive recruitment of neutrophils, the ability of CCI (91) and CH-35 (43) to dampen the production of IL-1 was also assessed. Briefly, as described in further detail above, neutrophils were incubated with the indicated concentrations of (91) (CCI), (43), (47a) and colchicine or DMSO prior to stimulation with MSU or incubation in phenol-free RPMI (negative control) for 3 hrs. Cell-free supernatants were then harvested and the amount of CXCL8/IL-8 or IL-1 released by the activated neutrophils was determined by ELISA.

Figure 8B:
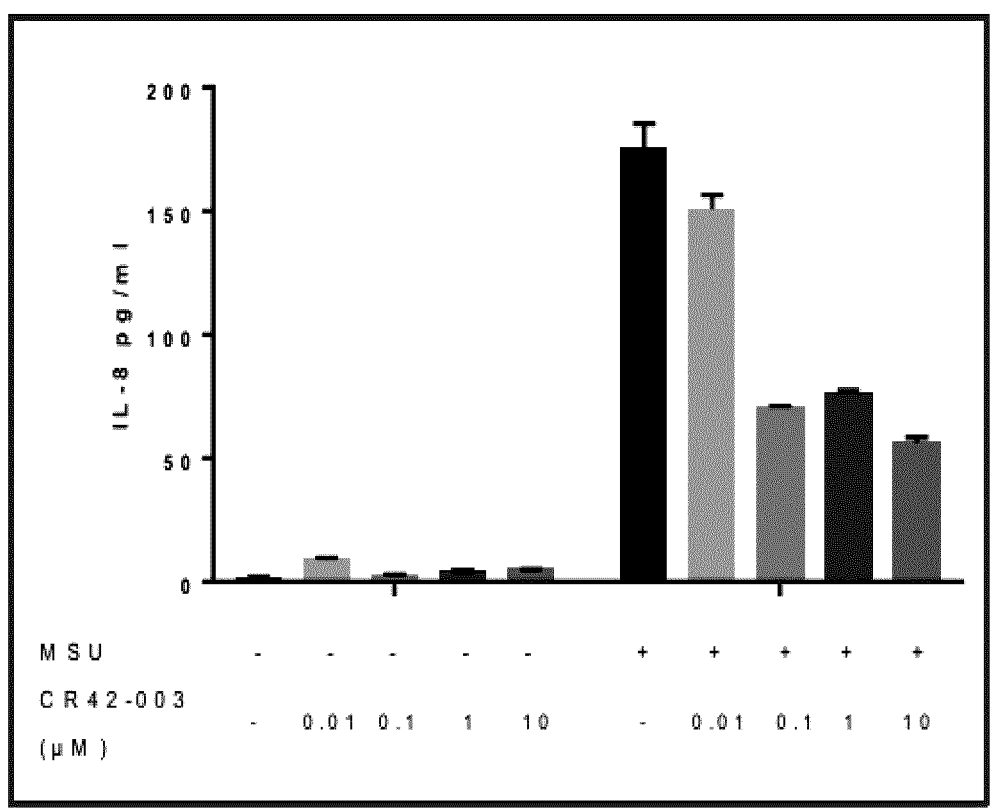
FIG. 8B shows the effect of colchicine derivative (47a).
Figure 8L:
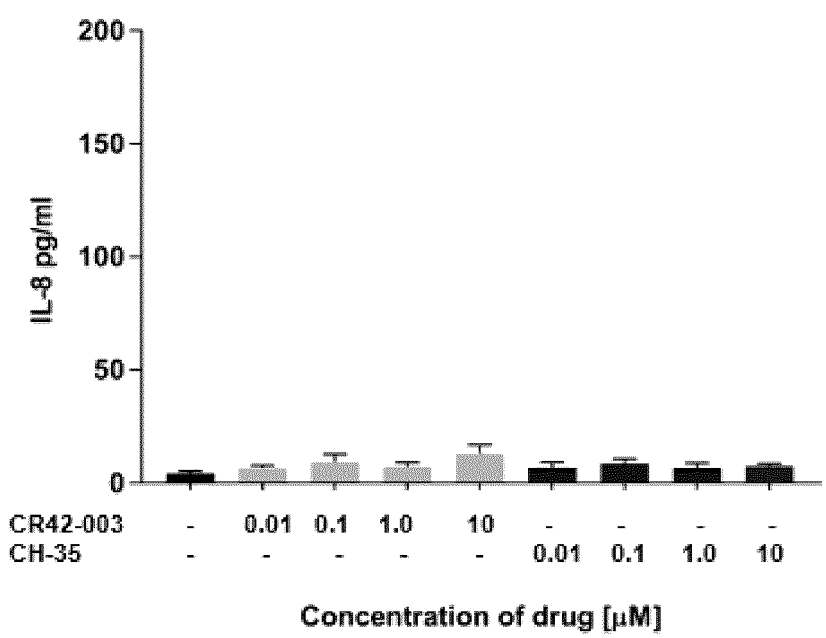
FIG. 8L shows the basal levels of IL-8 production in human neutrophils incubated with colchicine derivative (43) or (47a) in the absence of MSU.

As shown in FIGS. 8A-B, a significant decrease in the release of IL-8 by neutrophils pre-incubated with colchicine derivative (43)(FIG. 8A) or colchicine derivative (47a) (FIG. 8B) was observed from a concentration as low as 0.1 µM.

In further experiments and as shown in FIGS. 8D-F, a significant decrease was observed in the release of IL-8 by neutrophils pre-incubated with CCI (91), CR42-003 (47a) and CH-35 (43) from a concentration as low as 0.1 µM to 10 µM (FIG. 8D-F). In contrast, colchicine only significantly inhibited the release of IL-8 at 1 and 10 µM (FIG. 8C). A comparison of the inhibitory activity of the derivatives at 0.1 µM (FIG. 8G) revealed that CCI (91) was more potent than CH-35 (43) and CR42-003 (47a) at reducing the MSU-induced increase in IL-8 production, a concentration at which colchicine is no longer able to dampen this neutrophil effector function.

Since the in vitro assays revealed that CCI (91) and CH-35 (43) dampen the increase in cytoplasmic calcium and the production of ROS (see below) in response to MSU, this assay was performed with CCI (91) and CH-35 (43) in respect of IL-1 production. The effect of CCI (91) and CH-35 (43) on the MSU-induced synthesis of IL-1 was determined using the same experimental approach as described for IL-8 with a slight modification. The production and secretion of mature IL-1 requires two stimuli. Human neutrophils were, therefore, primed with TNF-α prior to stimulation with MSU. A diminution was observed in the production of IL-1 by cells treated with 10 µM of CCI (91), CH-35 (43) or colchicine (FIG. 8H-J). Markedly, CCI (91) was the most potent compound with a threshold concentration of 0.1 µM, whereas CH-35 (43) was effective at 1 µM (FIGS. 8I and 8J). When compared to colchicine, both derivatives are more potent (FIG. 8K). Together, the compounds have a high potency with regards to the inhibition of MSU-induced IL-1 production in neutrophils.

Moreover, as shown in FIG. 8L, the quantity of IL-8 measured in the supernatant of neutrophils incubated with either CR42-003 (47a) or CH-35 (43) alone is similar to that of the negative control (neutrophils included in HBSS). This suggests that neither CR42-003 (47a) nor CH-35 (43) exhibit a non-specific effect on neutrophils as determined by the release of IL-8.

Superoxide Levels in Human Neutrophils Stimulated with Colchicine or Colchine Derivatives An additional neutrophil effector function that is calcium-dependent, known to be activated by MSU and that can cause damage to the inflamed joint, is the production of ROS. Since (91) (CCI), (43) and (47a) inhibit the mobilization of calcium, (91) (CCI), (43) and (47a) may also modulate MSU-induced ROS production in neutrophils. Briefly, and as described in detail above, human neutrophils were incubated with (91) (CCI), (43) or (47a), or colchicine for comparative purposes prior to a stimulation with MSU.

As shown in FIGS. 9A-B, (91) (CCI) induced a significant decrease in the production of superoxide triggered by MSU. (91) (CCI) inhibits superoxide production at a concentration of 0.1 µM whereas the lowest dose at which colchicine can inhibit MSU-induced superoxide production is 1 µM. (91) (CCI) thus inhibits the MSU-induced superoxide production in human neutrophils at about a 10-fold lower concentration than colchicine and is thus, about 10-fold more potent than colchicine for inhibiting MSU-induced superoxide production in human neutrophils.

In further experiments, as shown in FIGS. 9D-9F, CCI (91), CR42-003 (47a) and CH-35 (43) induced a significant decrease in the production of superoxide triggered by MSU at a concentration of 0.1 µM. In contrast, colchicine inhibitory capacity has a higher threshold of 1 µM (FIG. 9C). The comparison of the inhibitory activity of the derivatives and colchicine at 0.1 µM (FIG. 9G) revealed that CCI (91) and CH-35 (43) are significantly more potent than colchicine and CR42-003 (47a) at reducing the MSU-induced increase in ROS production. Moreover, as shown in FIG. 9H, the quantity of superoxide measured when neutrophils are incubated with either CR42-003 (47a) or CH-35 (43) alone, is similar to that of the negative control (neutrophils included in HBSS). This suggests that neither CR42-003 (47a) nor CH-35 (43) exhibit a non-specific effect on neutrophils as determined by the production of superoxide.

Example 3—ADMET Prediction

Prior to evaluating the function of derivative (91) in vivo based on the above described in vitro findings and based on the diverging effects on the inflammatory responses of human neutrophils observed between derivative (91) and (89), ADMET predictions were determined between these derivatives, to assess the use of (91) as a potential drug for the treatment for gout.

ADMET Predictor 7.2 (Simulations Plus, CA) is an industry-standard prediction software for pharmacokinetics. It was run on the compound structures in order to predict ADMET properties. Table 2 below shows ADMET risk indices. Each risk index is a score where higher values indicate an increased risk that the compound will fail as a drug due to a pharmokinetic or toxicity problem. CYP_Risk is an aggregate of metabolic liability models. TOX_MU-T_Risk is an aggregate of models of mutagenicity in *S. typhimurium*. TOX_Risk is an aggregate of models of toxic liability. ADMET_Risk is an overall risk score combining multiple factors. Specific factors contributing to the scores are given in the notes. This analysis is a reliable in-silico proxy for in vivo behavior. In each risk index, the risk score of (89) was found to be higher than the score of (91). Therefore, (89) is predicted to be more likely to fail as a drug due to ADMET factors.

TABLE 2

| Name | CYP_Risk | TOX_MUT_Risk | TOX_Risk | ADMET_Risk |
|---|---|---|---|---|
| CCI-001 | $0.39^a$ | 0.0 | $1.0^b$ | $1.39^c$ |
| TP01 | $1.49^d$ | $1.0^e$ | $2.0^f$ | $3.49^g$ |

$^a$p450 oxidation
$^b$acute rat toxicity
$^c$P450 oxidation, acute rat toxicity
$^d$P450 oxidation, interactions with CYP1A2
$^e$Mutagenicity in one strain of *S. typhimurium*
$^f$Acute rat toxicity, SGOT and SGPT elevation
$^g$P450 oxidation, interactions with CYP1A2, acute rat toxicity, SGOT and SGPT elevation Thus, ADMET prediction shows a clearly elevated toxicity risk of (89) compared to (91) making it a high probability candidate for failure in animal trials.

Example 4—In Vivo Studies

Having shown an effect of colchicine derivatives in vitro (see above), a series of experiments were conducted with CCI (compound 91) in MSU-induced inflammation in vivo. In summary, and as described in further detail below, mice were injected with MSU to induce gout-like inflammation. Mice were further injected with CCI (compound 91) or CH-35 (compound 43), alone or before or after MSU injection, to determine the plasma half-life of CCI (compound 91; FIG. 10A), to determine plasma half-life of CH-35 (compound 43; FIG. 10B), to determine if CCI (compound 91) or CH-35 (compound 43) is taken up by circulating leukoctyes (FIGS. 11A and B, respectively) and to compare the effect of CCI (compound 91) or CH-35

Figure 12:
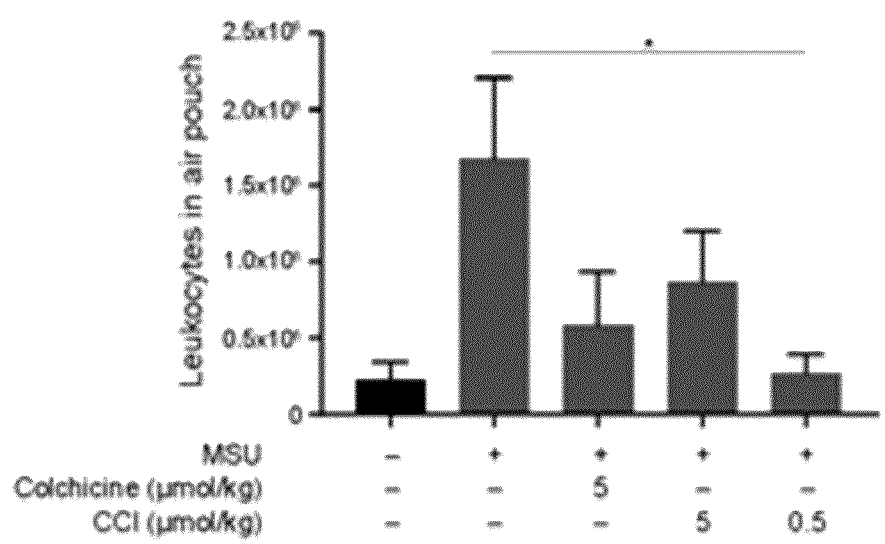
FIG. 12 shows the effect of colchicine and colchicine derivative (91) on leukocyte recruitment to the dorsal air-pouch of mice injected with monosodium uric acid (MSU)
Figure 13:
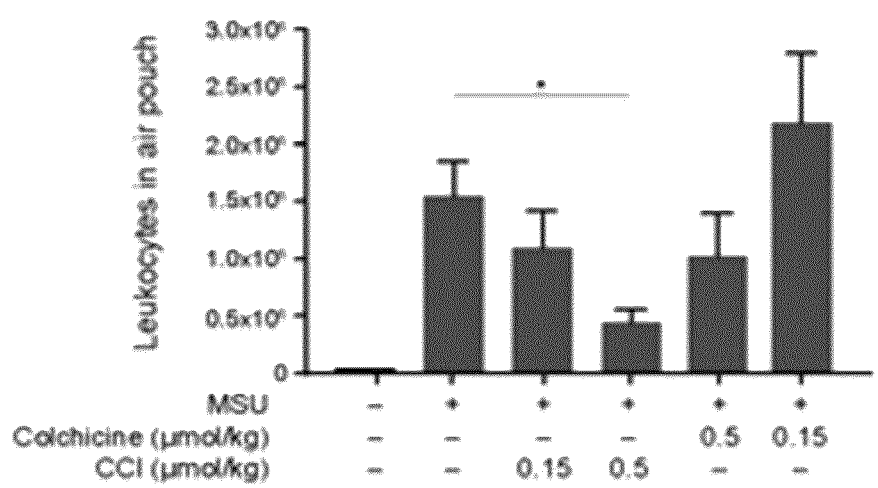
FIG. 13 shows the therapeutic effect of colchicine and colchicine derivative (91) on leukocyte recruitment to the dorsal air-pouch of mice injected with monosodium uric acid (MSU)

(compound 43) versus colchicine in relation to MSU-induced inflammatory responses (FIGS. 12, 13 and 14).

A. Determining the Plasma Half-Life of Colchicine Derivatives in Mice

Experimental Model Used and Measurement of Concentration of CCI or CH-35 in Plasma Mice were injected subcutaneously with 5 µmol/kg of (91) (CCI) or CH-35 (43) and sacrificed 15, 30, 45, 60 or 120 min post-injection. Blood was harvested by cardiac puncture with 35% Tyrode's buffer pH 6.5 and 20% citrate-dextrose solution (ACD) and centrifuged 2500×g for 15 min at RT to obtain plasma. The concentration of the compound in the plasma (FIGS. 10A and B) was determined by mass spectrometry. The concentration of (91) (CCI) or CH-35 (43) is expressed as the means of the amount of (91) (CCI) or CH-35 (43) measured in the plasma (ng/ml) of 5 mice harvested at the same time point.

B. Determining the Concentration of Colchicine Derivatives in Circulating Leukocytes Experimental Model Used and Measurement of Concentration of CCI or CH-35 in Circulating Leukocytes Mice were injected subcutaneously with 5 µmol/kg of (91) (CCI) or CH-35 (43) and sacrificed 15, 30, 45, 60 or 120 min post-injection. Blood was harvested by cardiac puncture and centrifuged to obtain circulating leukocytes. The concentration of the compound in the leukocytes (FIGS. 11A and B) was determined by mass spectrometry. The concentration of (91) (CCI) or CH-35 (43) is expressed as the means of the amount of (91) (CCI) or CH-35 (43) measured in circulating leukocytes (ng/ml) of 5 mice harvested at the same time point.

C. (91) (CCI) Inhibits MSU-Induced Leukocyte Recruitment in the Air-Pouch Model when Administered 5 Min Prior to the MSU Injection Experimental Model Used and Measurement of Leukocytes in the Air Pouch In vivo evaluation of the anti-inflammatory activity of colchicine and colchicine derivatives in wild-type mice (CD-1 mice) was performed. An air-pouch was generated on the dorsum of mice over a period of seven days by injecting air subcutaneously. Seven days after the first injection of air, 10 µl/g of HBSS containing the indicated amounts of (91) (CCI), colchicine or DMSO (vehicle) were injected subcutaneously 5 min prior to the injection of MSU (1.5 mg/ml) or diluent (PBS) in the air pouch. Seven hours after the administration of MSU, the exudate in the air pouches was harvested by two flushes with 2 ml and one with 1 ml of PBS+0.5 M EDTA and the number of recruited leukocytes determined by flow cytometry. Leukocytes were stained with an anti-CD45 and anti-Ly6G antibody.

D. (91) or (43) Inhibit MSU-Induced Leukocyte Recruitment in the Air-Pouch Model when Administered 1.5 Hours after the MSU Injection.

Experimental Model Used and Measurement of Leukocytes in the Air Pouch

In vivo evaluation of the anti-inflammatory activity of colchicine and colchicine derivatives in wild-type mice was performed. An air-pouch was generated on the dorsum of mice over a period of seven days by injecting air subcutaneously. Seven days after the first injection of air, 10 µl/g of HBSS containing the indicated amounts of (91), (43), colchicine or DMSO (vehicle) were injected subcutaneously 1.5 hours after the injection of MSU (1.5 mg/ml) or diluent (PBS) in the air pouch. Seven hours after the administration of MSU, the exudate in the air pouches was harvested by two flushes with 2 ml and one with 1 ml of PBS+0.5 M EDTA and the number of recruited leukocytes determined by flow cytometry. Leukocytes were stained with an anti-CD45 and anti-Ly6G antibody.

Results

The Half-Life of (91) (CCI) or (43) (CH-35) in Circulation and its Concentration in leukocytes Prior to testing the anti-inflammatory activity of CCI or CH-35 (43) in vivo, their half-lives in mouse plasma and concentrations in circulating leukocytes over a period of 2 hours were determined.

As shown in FIG. 10A, mass spectrometry of the plasma samples revealed that the concentration of (91) (CCI) peaked at 15 min (80 ng/ml) and then diminished to less than ¼ of this concentration by 60 minutes (t ½=13.3 min). Although a decline in the concentration of (91) (CCI) was observed, it persisted in the plasma for at least 2 hours. Similarly, the highest concentration of circulating CH-35 (43) peaked at 15 minutes post-injection (FIG. 10B). In contrast to CCI (91), however, the amount of CH-35 (43) in the plasma dropped to undetectable levels about 50 minutes after the injection of the drug. Thus, the concentration of CH-35 (43) diminished significantly in the plasma within 1 hour of its administration. Together, these results reveal that CCI (91) and CH-35 (43) have very short half-lives and suggest that their uptake into another compartment is rapid.

As shown in FIG. 11A, in circulating leukocytes, the concentration of (91) (CCI) peaked at 15 min and persisted in these cells up to the last time point analyzed (2 hours). Similarly, as shown in FIG. 11B, in circulating leukocytes, the concentration of CH-35 (43) peaked at 15 min and persisted in these cells up to the last time point analyzed (2 hours). Thus, CH-35 (43) can persist in circulating leukocytes for at least 2 hours after its subcutaneous injection.

(91) (CCI) or (43) CH-35 Reduces MSU-Induced Inflammation In Vivo

The in vivo anti-inflammatory activity of (91) (CCI) or CH-35 (43) was assessed in the air-pouch model of MSU-induced inflammation. This model was chosen since the dorsal air cavity shares essential cellular features with the synovial lining of joints (eg: fibroblasts and macrophages) and the same profile of leukocyte recruitment.

As shown in FIG. 12, MSU induced the recruitment of leukocytes to the air pouch at 7 hours which was inhibited by colchicine at a concentration of 5 µmol/kg. At about a 10-fold lower concentration, (91) (CCI) was still able to inhibit leukocyte recruitment when injected prior to the administration of MSU. As shown, the ability of CCI (91) to inhibit leukocyte recruitment at a significantly lower dose of 0.5 µmol/kg compared to 5 µmol/kg for colchicine was demonstrated, however, this dose of colchicine was not significant in this series. At a dose of 0.5 µmol/kg, colchicine lost its potency to significantly inhibit MSU-induced leukocyte recruitment in vivo. Conversely, CCI (91) may not be more effective than colchicine at a concentration of 5 µmol/kg, due to its non-monotonic dose response curve.

To determine the therapeutic potential of (91) (CCI), the air-pouch experiment was modified and 0.5 µmol/kg (91) (CCI) was injected after adding MSU to the air pouch. As shown in FIG. 13, a significant decrease in leukocyte recruitment was also observed under these experimental conditions, indicating that (91) (CCI) was still able to dampen MSU-induced inflammation when administered once MSU has already triggered the inflammatory process. In contrast, colchicine at a concentration of 0.5 µmol/kg was no longer able to significantly inhibit MSU-induced leukocyte recruitment in vivo (FIG. 13). Rather unexpectedly, (91) (CCI) thus inhibits MSU-induced leukocyte recruitment at a concentration of about 10-fold lower than the effective dose of colchicine. In further experiments, and as shown in FIG. 14, CH-35 (43) was similarly tested to compare the results obtained for CCI (91) shown in FIG. 13. The results of FIG. 14 reveal that CH-35 (43) was less potent than CCI (91) at inhibiting the influx of leukocytes to the air-pouch. The lowest concentration of CH-35 (43) that significantly dampened leukocyte recruitment was 2.5 µmol/kg. Thus, CH-35 (43) can inhibit the recruitment of leukocytes during inflammation induced by MSU. Together, these results indicate that while both CH-35 (43) and CCI (91) can inhibit leukocyte recruitment in vivo at lower concentrations than colchicine, CCI (91) is the most potent compound for the inhibition of MSU-induced leukocyte recruitment in vivo.

Example 5—Expression Profile of Beta-Tubulin Isotypes in Neutrophils

Methods

Neutrophil suspensions ($2 \times 10^7$ cells/ml) were transferred directly into the same volume of 2× boiling modified Laemmli sample buffer (1× buffer: 62.5 mM Tris·HCl (pH 6.8), 4% (wt/vol) sodium dodecyl sulfate (SDS), 5% (vol/vol) β-mercaptoethanol, 8.5% (vol/vol), glycerol, 2.5 mM orthovanadate, 10 µg/ml leupeptin, 10 µg/ml aprotinin and 0.025% bromophenol blue) and boiled for 7 min. Proteins were separated by SDS-PAGE on 10% acrylamide gels under reducing conditions and transferred to polyvinylidene fluoride (PVDF) membranes. Blocking agents and antibodies were diluted in a Tris-buffered saline Tween 20 (TBST) solution (25 mM Tris·HCl, pH 7.8, 190 mM NaCl, 0.15% vol Tween-20). Primary and secondary antibodies were used at concentrations recommended by their manufacturers. PVDF membranes were incubated in blocking solution (5% wt/vol dried milk in TBST) prior to immunoblotting with the anti-β-tubulin isotype-specific antibodies. Horseradish peroxidase-labeled donkey anti-mouse IgG and donkey anti-rabbit IgG were diluted in TBST solution. Chemiluminescence reagents were used to detect antibodies with a maximal exposure time of 5 min. All the immunoblots presented were controlled for equal protein loading with an anti-PI3 kinase p85 antibody.

Results

Figure 15:
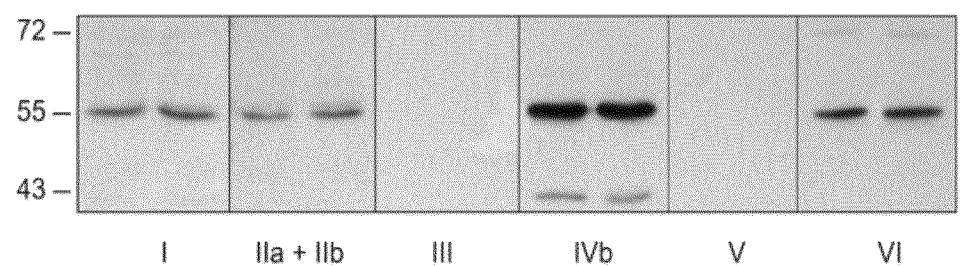
FIG. 15 shows a western blot of β-tubulin expression in human neutrophils.

The expression profile of β-tubulin isotypes in leukocytes has been investigated at the mRNA level. The expression of the mRNA of βVI is mostly restricted to hematopoietic cells, whereas β-tubulin I, IV and V mRNA is ubiquitously expressed and β-II and -III mRNAs are restricted to the brain. The rational design approach was used to develop colchicine derivatives based on the differential binding affinity of colchicine towards the various β-tubulin isotypes, and it was determined whether the mRNA expression profile of these isotypes in neutrophils correlated with their expression at the protein level. Briefly, freshly isolated human neutrophils were lysed and analyzed by Western blot with commercially available antibodies against beta-I, alpha/beta-II, beta-III, beta-IV, beta-V and beta-VI tubulin. It is of note that βII and µIV have two variants called βIIa, βIIb and βIVa, βIVb, respectively but their sequences are very similar and so are their structures. As shown in FIG. 15, human neutrophils express beta-I, alpha/beta-II, beta-IV and beta-VI but not beta-III and beta-V. The bands observed for βV are non-specific (verified with a positive control (data not shown)). Since the expression of β-VI is mostly limited to hematopoietic cells, colchicine derivatives with a higher affinity towards this β-tubulin isotype were selected for the analysis described herein.

To identify the β-tubulin isotypes that most likely confer upon CH-35 (43) the ability to inhibit MSU-induced responses at low concentrations, the binding free energies (kcal/mol) of colchine, CCI (91), CR42-003 (47a) and CH-35 (43) were compared in Table 3 below.

TABLE 3

|  | bI | bIIa | bIIb | bIII | bIVa | bIVb | bV | bVI |
|---|---|---|---|---|---|---|---|---|
| Colchicine | −29.596 | −37.899 | −32.519 | −38.816 | −30.962 | −37.443 | −51.387 | −42.031 |
| CR42-003 | −56.623 | −47.450 | −40.010 | −38.238 | −30.26 | −33.287 | −47.264 | −42.213 |
| CCI | −53.106 | −34.397 | −39.109 | −48.44 | −32.035 | −43.974 | −63.818 | −47.627 |
| CH-35 | −52.431 | −33.74 | −39.818 | −40.612 | −40.865 | −49.547 | −63.964 | −51.702 |

As shown in Table 3 above, CH-35 (43) has significantly lower binding free energies for βIVb and βVI as compared to those for colchicine and CR42-003 (47a). These data suggest that the higher affinity of CH-35 (43) for βIVb and βVI most likely renders CH-35 (43) active at lower concentrations compared to colchicine and CR42-003 (47a) in the assays tested. Moreover, with regards to CCI (91), it also has a higher affinity for βIVb and βVI compared to colchicine and CR42-003 (47a). A difference between CCI (91) and CH-35 (43) is that CH-35 (43) has a monotonic dose relationship which is not the case for CCI (91). The binding free energy data suggests that this may be due to the higher affinity of CH-35 (43) to either βIVb or µVI or both since these are the only two β-tubulin isotypes expressed in neutrophils for which the binding free energies are significantly higher for CH-35 (43) compared to CCI (91).

Discussion

Of the drugs used to treat gout, colchicine exhibits the most specificity with respect to the pathogenesis of this inflammatory disease since it dampens most of the inflammatory actions of the principal leukocyte involved in gout attacks, the neutrophil. Nevertheless, its administration remains challenging due to its low therapeutic index between efficacy and treatment-limiting side effects. Using a rational drug design approach, an analogue of colchicine, (91) (CCI), was developed that inhibits MSU-induced inflammation in vivo and MSU-induced neutrophil responses in vitro at concentrations of about 10- to about 100-fold lower than colchicine. Of note, other colchicine derivatives 43 and 47a were similarly effective at reducing neutrophil responses at the same dose as 91, as described herein.

CCI (91) and (43) retained their anti-inflammatory activity at about 10 to about 100-fold lower doses than colchicine in vitro and in vivo. Moreover, these compounds exhibit anti-inflammatory properties when administered after the initiation of the inflammatory reaction induced by MSU, indicative of their therapeutic potential.

(91) (CCI)'s ability to dampen MSU-induced neutrophil activation in vitro and in vivo at lower concentrations than colchicine can be explained, in part, by its tubulin isotype specificity. In silico analysis of (91) (CCI) revealed that it preferentially binds β-VI tubulin, one of the β-tubulin isotypes expressed in neutrophils. Moreover, the β-VI tubulin isotype is very distinct from others, especially in the colchicine binding area, offering a high level of specificity and selectivity for the drugs that bind it. In contrast to (91) (CCI), colchicine has the highest affinity for β-IV tubulin, a ubiquitously expressed β-tubulin isotype. Although colchicine is able to inhibit MSU-induced activation and leukocyte recruitment, it is associated with undesirable side effects that are most probably due to its ability to bind a β-tubulin isotype(s) that is expressed by many different cell types. It is thus highly likely that the specific binding of (91) (CCI) to β-VI tubulin minimizes off-target effects with non-hematopoietic cells since this isotype is not expressed in these cells, whilst maximizing its activity in neutrophils.

In vitro analysis revealed that (91) (CCI) inhibits one of the most upstream signalling events activated by MSU, the increase in cytoplasmic calcium. The ability of (91) (CCI) to inhibit this molecular event at a concentration at which colchicine is no longer effective (about 100-fold lower dose), strongly suggests that the β-tubulin isotypes bound preferentially by (91) (CCI) most likely play a more significant role in MSU-induced intracellular calcium store mobilization. (91) (CCI) binds preferentially to βVI, βV and with less affinity to βI-tubulin as predicted by our in silico analysis. The same line of reasoning can be extended to the effector functions downstream of the mobilization of intracellular calcium such as the MSU-induced production of superoxide. Direct evidence is provided herein that (91) (CCI) inhibits the production of superoxide by human neutrophils in response to MSU at about a 10-fold lower dose than colchicine. Similarly, the release of IL-8 induced by MSU is also dampened by (91) (CCI). (91) (CCI) is particularly effective at inhibiting the release of IL-8 at up to about 10-fold lower concentration than colchicine. (91) (CCI) could thus be administered at lower doses to treat MSU-induced inflammation, which diminishes the risk of drug-related side effects. The inhibition of IL-8 production by (91) (CCI) at low concentrations is highly pertinent to gout since IL-8 is one of the most potent chemoattractants for neutrophils. Similarly, the dampening of superoxide production is also relevant to gout pathogenesis since superoxide causes collateral damage to the joint.

The in vitro observations revealed that (91) (CCI) inhibits MSU-induced neutrophil responses and the ability of CCI to dampen MSU-induced inflammation in vivo was then determined. Shown herein is that (91) (CCI) inhibits MSU-induced leukocyte recruitment when administered prior to or after MSU. The latter indicates that (91) (CCI) may be used therapeutically since its anti-inflammatory activity was preserved when it was injected about 1 h30 after MSU was administered in the in vitro experiments. In the experiments herein, the lowest dose at which (91) (CCI) retained its anti-inflammatory activity in vivo was 0.5 μmol/kg.

To obtain an estimate of the human equivalent dose of a drug used in mice, in aspects, the concentration used in mice may be divided by about 12.3 (Nair, A. B. and Jacob, S. 2016. *A simple practice guide for dose conversion between animals and human, J Basic Clin Pharma:* 7: 27-31). The dose of colchicine that effectively dampens MSU-induced leukocyte recruitment in mice is 5 μmol/kg (Chia, E. W., Grainger, R. and Harper, J. L. 2008. *British Journal of Pharmacology:* 153: 1288-95). Since this dose is 10-fold higher than the human dose given to gout patients, it is considered the human equivalent dose. By extrapolation, and based on the experiments herein, (91) (CCI) would be expected to be able to dampen MSU-induced inflammation in humans at a dose that is about 10-fold lower than the dose of colchicine that is currently used to treat gout attacks.

The human neutrophil was targeted due to the massive influx of these cells into the joint during a gout attack and the expression of beta-tubulin isotypes in this leukocyte was determined. Neutrophils express β-I, β-II, β-IV and β-VI tubulin, but not β-III and β-V tubulin. This protein expression pattern correlates well with the mRNA expression profile of β-tubulin isotypes reported by others. The mRNA for β-VI tubulin is restricted to hematopoietic cells and organs that harbor large numbers of leukocytes such as the bone marrow, thymus and fetal liver. The mRNA for β-Ill and β-V tubulin is, however, undetectable in leukocytes. The levels of mRNA for the β-1, β-II, and β-IV tubulin isotypes is significantly lower than β-VI in leukocytes. Although the functional significance of the different β-tubulin isotypes in both neutrophils and most other cell types remains unknown, there is evidence for both functional redundancy and specificity. With regard to the former, the ability of most β-tubulin isotypes to polymerize into heterogeneous microtubules supports functional redundancy. Regarding the latter, the distinct phenotypes of the group of diseases known as the tubulinopathies is suggestive that tubulin isotypes play distinct functional roles. Tubulinopathies may be caused by mutations in different β-tubulin isotypes. Moreover, the tissue-specific as well as developmental stage-specific expression of β-tubulin isotypes is also suggestive of non-redundant, functional roles for these proteins.

Although the function of β-VI tubulin in leukocytes remains unknown, this isotype was targeted since it was reasoned that its leukocyte expression profile reflects a certain degree of functional specificity for leukocytes and that a β-VI tubulin-specific drug may exhibit fewer off-target effects on non-hematopoietic cells. The potency of three derivatives predicted to have a significantly higher, relative affinity for βVI tubulin than colchicine was tested to inhibit the activation of human neutrophils by MSU in vitro and in vivo. The effector functions investigated in vitro are those that play a role in the pathogenesis of gout, namely, the release of IL-1 and IL-8 as well as the production of superoxide. With regards to IL-8, a very effective neutrophil chemoattractant, neutralizing antibodies against this cytokine significantly diminish the neutrophil influx induced by MSU in a rabbit model. IL-1 on the other hand, plays a role in gout by inducing the expression of adhesion molecules and cytokines by endothelial cells and other cell types in the joint such as synoviocytes. Regarding superoxide, this reactive oxygen species is associated with co-lateral tissue damage in the joint. The data provided herein suggest that CCI (91) and CH-35 (43) dampen the production of ROS and release of IL-8 elicited by MSU at concentrations significantly lower than colchicine, from about 10 to about 100-fold lower concentrations in vitro. The ability of these derivatives to diminish these neutrophil responses is indicative that they may target key molecular events that drive a gout attack.

The observations in vitro prompted the determination of whether CCI (91) and CH-35 (43) are able to dampen MSU-induced inflammation in vivo with a significantly higher potency than colchicine. Using the air-pouch model of inflammation, the data provided herein suggest that the inhibitory activity of CCI (91) and CH-35 (43) in vitro reflects their ability to dampen MSU-induced inflammation in vivo. With regards to CCI (91), it inhibits the recruitment of leukocytes to air-pouches injected with MSU at a threshold dose about 10-fold lower than colchicine when injected prior to the administration of MSU. It is of note, however, that at higher concentrations, CCI (91) is less effective at inhibiting leukocyte influx. A similar non-monotonic trend was observed in the calcium and ROS in vitro assays. This non-monotonic dose response most likely reflects the binding of CCI (91) to ligands other than β-tubulin isotypes as has been reported for other drugs with non-monotonic dose responses resulting from off-target actions, such as, endocrine-disrupting drugs.

Having shown that CCI is more potent than colchicine at significantly diminishing the recruitment of leukocytes in response to MSU, its therapeutic potential was evaluated. The subcutaneous administration of CCI (91) 1.5 hrs post-MSU injection significantly diminished the recruitment of leukocytes to the air-pouch.

CCI (91) is thus also able to dampen MSU-induced inflammation after its initiation. Surprisingly, although colchicine shared this property with CCI (91), colchicine loses its anti-inflammatory activity at 0.5 μmol/kg, the concentration at which CCI (91) remains active. Similar observations were made for CH-35 (43) albeit at a higher concentration than CCI (91), 2.5 μmol/kg. Contrary to CCI (91), CH-35 (43) exhibits a monotonic dose-response both in vitro and in vivo. Together, these observations indicate that CCI (91) is more potent than CH-35 (43) at dampening MSU-induced inflammation in vivo.

Although the half-lives of CCI (91) and CH-35 (43) are short, both these derivatives are able to dampen MSU-induced leukocyte recruitment when administered 7 hours prior to the peak of leukocyte recruitment. This can be partly explained by uptake and retention of these compounds by leukocytes and most notably, neutrophils. Colchicine preferentially accumulates in neutrophils compared to mononuclear cells. The retention of CCI (91) was observed in circulating leukocytes up to 2 hours post-injection (preliminary data). The full characterisation of the pharmacokinetics of CCI (91) and CH-35 (43) may provide further insight into the mechanism of action of these compounds.

The targeting of the neutrophil to dampen inflammation has been a challenge since neutrophils are key players in protecting the host from infection. It was determined that CCI (91) selectively inhibits MSU-induced inflammation whilst sparing certain neutrophil anti-bacterial responses such as an increase in cytoplasmic calcium and the production of reactive oxygen species (data not shown). Using the bacterial peptide fMLF, evidence was provided for the ability of neutrophils to respond to this bacterial peptide in the presence of CCI (91). This observation suggests that CCI (91) should not increase the risk of bacterial infection while dampening neutrophil stimulation towards MSU and perhaps that the innate immunity mediated by the formyl peptide receptors does not fully rely on βVI tubulin. Either beta-VI tubulin plays a redundant role in bacterial defenses that it shares with other beta-tubulin isotypes, or beta-VI tubulin is not at all required for these defenses. It is of note that CCI (91) and CH-35 (43) also have an estimated increased affinity for other beta-tubulin isotypes.

In summary, a new, less toxic anti-inflammatory drug that inhibits MSU-induced inflammation and has the potential to relieve gout patients of their symptoms during gout attacks was developed. The development of such a drug addresses a major, unmet clinical need of gout patients. Colchicine has a very narrow therapeutic index and is associated with harmful side effects due to drug-drug interactions. Moreover, gout manifests itself more often in patients with co-morbidities (eg: chronic kidney disease (CKD)). Approximately 54% of gout patients suffer from CKD. This renders the use of colchicine challenging since CKD patients require careful dosing of colchicine as this drug accumulates more easily to toxic levels in these patients due to renal impairment. Co-morbidities also greatly limit the choice of medication other than colchicine that can be used to decrease the inflammation and pain associated with acute gout attacks. Patients who are unable to take current therapies due to intolerance and co-moribidities are a driving force for new and less-toxic therapeutic approaches. Although there are alternative anti-inflammatory drugs such as NSAIDs and corticosteroids, these compounds are themselves also associated with well-documented side effects. Thus, the findings presented herein show that the lower effective dose of CCI widens its therapeutic window and diminishes adverse side effects associated with colchicine and other anti-inflammatory drugs. An estimated 12% of gout patients are refractory to all available treatment modalities (unpublished observation). Since (91) (CCI) is active at very low doses, it is highly unlikely that (91) (CCI) will cause toxicity due to interactions with other drugs. This hypothesis is supported by our acute inflammation toxicity study in rats that indicated that (91) (CCI) is less toxic than colchicine and other colchicine derivatives, such as (89) as shown above. The maximal tolerable dose of (91) (CCI) is 3-fold higher than that of colchicine. Such a drug is of particular interest to gout patients, in particular those with CKD due to their inability to eliminate the drug due to diminished renal function.(91) (CCI) is thus a safer anti-inflammatory drug than colchicine and a safer alternative for gout patients.

Example 6—Tubulin Binding Studies

Materials and Methods

Tubulin Model Preparation

Figures 5A, 5B:
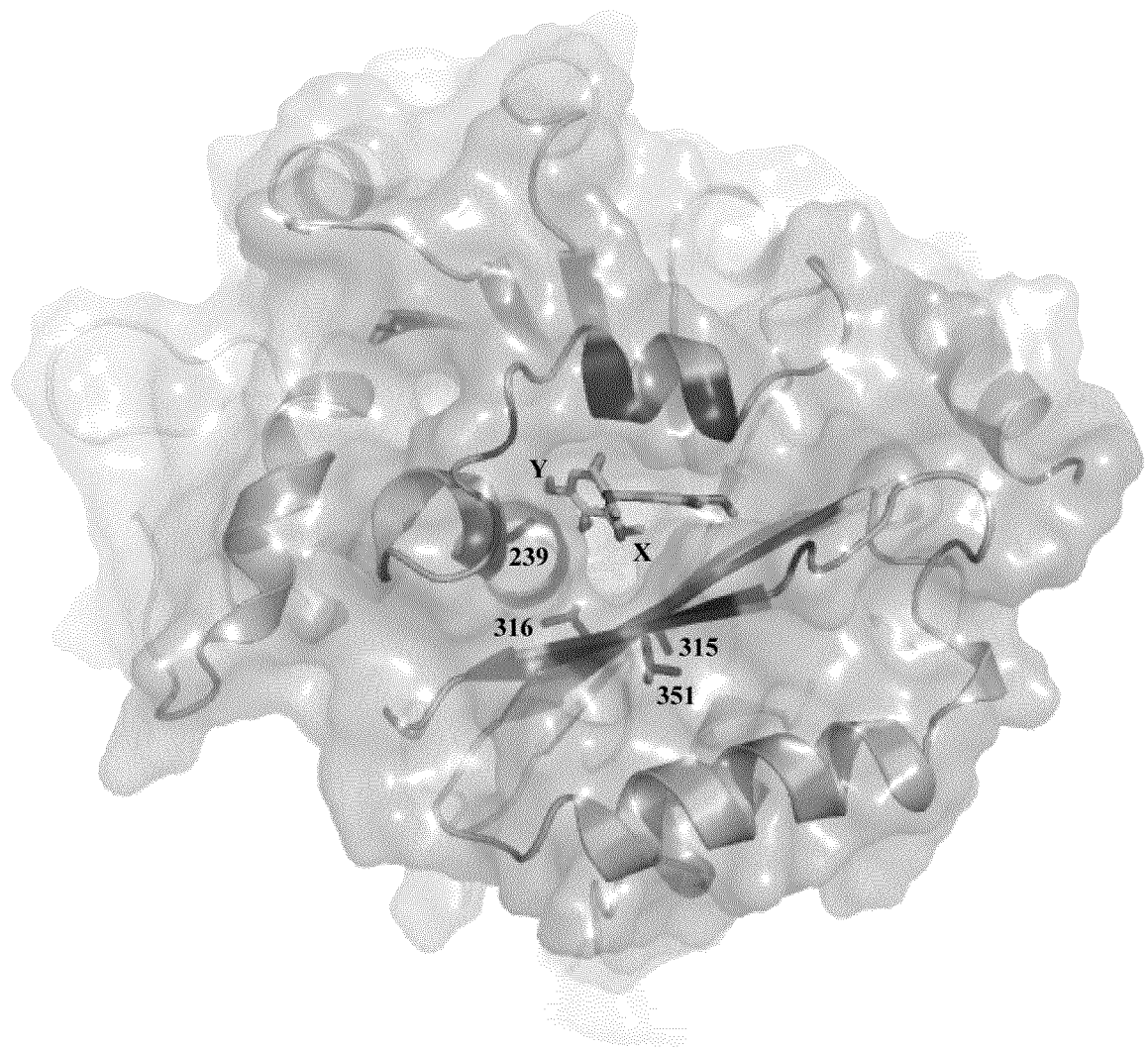
FIG. 5A shows residues contained within the binding surface for colchicine [pdb code 1SA0] that are shown as black letters on the canonical β1-tubulin sequence and differences between the three types of binding sites are shown as medium gray letters, the remaining letters are gray, and dashes represent identical positions between the sequences.
FIG. 5B shows a solvent accessible surface drawn onto β-tubulin [pdb code 1SA0] and the residues making up the colchicine binding surface are shown in black on the cartoon, while residues exhibiting differences between the three binding site models are shown as black sticks, and colchicine is shown as a molecular structure, with the A-ring and the X and Y positions clearly visible.

Consensus sequences for human β-tubulin isotypes have been previously described (Huzil J. T. et al., Nanotechnology. 2006:17:S90-S100). Residues making up the colchicine binding site were determined by examining the B chain within the 1SA0 pdb coordinates (Ravelli R. B. et al., Nature. 2004; 428:198-202.). Using PyMol v1.0 (Delano W L. The PyMOL Molecular Graphics System. 2002), residues with any atom found within 6 Å from colchicine were selected. From this subset of residues, a minimal set of contact residues found within the colchicine binding site was defined (FIGS. 5A and 5B). Examination of primary sequences for βI, βIIa, βIIb, βIII, βIVa, βIVb and βV, based on this reduced contact set, placed the tubulin isotypes into one of three colchicine binding sites; Type I (βI and βIV), Type II (βII) and Type III (βIII and βV) (FIG. 5A). The template β-tubulin structure obtained from the 1SA0 B chain coordinates (Ravelli et al., 2004, Nature, 428, 198-202), was then used to create the models by replacing appropriate residues from a standard conformer library using the mutate function found in PyMol v1.0 (Delano WL. The PyMOL Molecular Graphics System. 2002).

Minimization of each binding site models was performed in the GROMACS molecular dynamics (MD) package (version 3.2.1) (Lindahl F. et al., GROMACS 3.0: A package for molecular simulation and trajectory analysis. J Mol. Mod. 2001; 7:306-17) using the CHARMm (Chemistry at HARvard Molecular Mechanics) molecular force field (Brooks B. R., Brooks C L r, Mackerell A D. J. et al., CHARMM: The biomolecular simulation program. J. Comput. Chem. 2009). Convergence criteria for Steepest Descents and Conjugate Gradient minimization were set at a gradient of 0.05 kcal mol-1 Å-1. Following minimization, a short simulated annealing run (100 ps) was performed in a fully solvated periodic box (100×100×100 Å). Unconstrained charges were counterbalanced with sodium ions and long range electrostatics were calculated using particle-mesh Ewald's (PME).

Colchicine Derivatives

The structure of colchicine as bound to tubulin was extracted from the pdb structural file 1SA0 (Ravelli R. B. et al., Nature. 2004; 428:198-202) and imported into Marvin-Sketch (ChemAxon, Hungary). Derivatization of the C1 and C3 methoxy groups (FIGS. 2-4) was accomplished by building modifications using the 3D drawing tools. Each of the derivatives was then exported in 3D coordinates as MDL Molfiles (Symyx Technologies, U.S.A.).

Colchicine Parameterization and Minimization

Colchicine and its derivative structures were prepared and parameterized using the CHARMm force field (Brooks B. R., Brooks C L r, Mackerell A D. J. et al., CHARMM: The biomolecular simulation program. J. Comput. Chem. 2009) as implemented in Discovery Studio v2.1 (Accelrys, Inc., U.S.A.). Prior to the reintroduction of each derivative into the Type I, II and III binding site models, an in vacuo minimization step was performed. Because the initial colchicine coordinates were obtained from a crystallographic structure, harmonic restraints (10 kcal mol$^{-1}$) were placed on the carbon atoms contained in each of the three rings. Hydrogens were added, bond orders fixed and atomic positions optimized using the CHARMm forcefield and the Adopted Basis set Newton Raphson (ABNR) protocol until the root mean deviation (RMS) gradient was less than 0.05 kcal mol$^{-1}$ Å$^{-1}$. The certain colchicine derivatives were prepared slightly differently; individual systems were placed into a TIP3 water box using GROMACS and minimized. Following a short equilibration, system energies for three separate conditions were obtained. The energy for the solvated tubulin-colchicine complexes E(P+L) was subtracted from the energy obtained from a tubulin colchicine system, where colchicine was not bound to the colchicine binding site E(P-L). A large water box was used to ensure no non-bonded interactions between colchicine and tubulin were introduced in the E(P-L) case.

Computational Colchicine Screening

Docking of the 20 colchicine derivatives to the Type 1, 11 and III binding sites was performed using CDOCKER (Wu G. et al., J. Comput Chem. 2003; 24:1549-62), as implemented in Discovery Studio v2.1 (Accelrys, Inc., U.S.A.). Briefly, a conformational search of the derivatives was carried out using a simulated annealing MD approach with the CHARMm force field (Brooks B. R., Brooks C L r, Mackerell A D. J. et al., CHARMM: The biomolecular simulation program. J. Comput. Chem. 2009). Selection of an input site sphere was defined over the entire colchicine binding site. Each derivative was then heated to a temperature T=700K and annealed to T=300K. Ten such cycles were carried out for each of the 20 colchicine derivatives, producing 600 poses. Each conformation was then subjected to local energy minimization, using the ABNR method described above.

Binding Energy Evaluation

Using MM-GBSA (Molecular Mechanics-Generalized Born Surface Area), the binding energy was evaluated for each system using vacuum electrostatics and solvation was approximated using the Generalized Born model. Binding energies were calculated by obtaining the total potential energy of the system and subtracting the energy of the derivative and that of the empty dimer:

$$E_{bind} = E_{complex} - E_{tubulin} - E_{drug}$$

For certain colchicine derivatives, the energy was determined slightly differently:

$$E_{bind} = E(P-L) - E(P+L)$$

Drug-Binding to Purified Tubulin Isotypes

Tubulin was purified from bulk microtubule protein by phosphocellulose chromatography (Fellous A., et al., Eur. J. Biochem. 1977; 78:167–74). The αβII and αβIII tubulin dimers were subsequently purified by immunoaffinity chromatography using monoclonal antibodies as previously described (Banerjee A. et al., J. Biol. Chem. 1992; 267: 13335-9; and Baneljee A. et al., J. Biol. Chem. 1988; 263:3029-34). For kinetic fluorescence measurements, 500 μL aliquots of tubulin (0.1 mg/ml) were incubated at 37° C. in quartz fluorescence cuvettes (path length 0.5 cm) in the presence of a series of drug concentrations. Kinetics were performed under pseudo-first-order conditions using drugs in large excess over tubulin. The excitation and emission wavelengths used were 380 nm and 437 nm, respectively.

The corrected fluorescence values were plotted as a function of time (t) and fitted to the curve:

$$F_{max} - F_t = A e^{(-k_{on,app})(t)}$$

Under these conditions, $k_{on,app}$ is a good index of the degree of interaction between a drug and a tubulin isotype. An expected linear plot of $Ln(F_{max} - F_t)$ versus t has a slope $k_{on,app}$. The $k_{on,app}$ values were plotted as a function of the values previously reported for αβII, and αβIII, 132 and 30 M-1s1 respectively (Banerjee A. et al., J. Biol. Chem. 1992; 267:13335-9).

Results

Isotype Sequence Analysis

The tertiary structure of tubulin can be divided into three distinct domains: domain I (residues 1-198), domain II (residues 199-373) and domain III (residues 374-428) (Nogales E. et al., Nature. 1995; 375:424–7). The βI, βIIa, βIIb, βIII, βIVa, βIVb and βV isotypes respectively share 87.4%, 88.1% and 96.3% identity within these domains. For residues involved in paclitaxel binding (Nogales E. et al., Nature. 1995; 375:424-7), there was a greater than expected 91.7% sequence identity when compared to the overall identity between β-tubulin isotypes. This higher than average trend continues with the *Vinca* binding site (Gigant B. et al., Nature. 2005:435:519-22) (92.3% identity) and the GDP binding site (Nogales E. et al., Nature. 1995; 375:424-7) (100% identity). The colchicine binding surface (Ravelli R. B. et al., Nature. 2004; 428:198-202) was found to consist of 18 residues: V236, C239, L246, A248, K252, L253, N256, M257, T312, V313, A314, A315, V316, N348, K350, T351, A352 and 1368 (FIG. 5A) and in contrast to the paclitaxel and *Vinca* binding sites shares only 77.9% identity between the seven β-tubulin isotypes examined.

In general, the binding site is predominantly non-polar with a slight positive charge introduced to the outer lip of the surface by residues K252 and K350. Specific substitutions within the colchicine binding surface were found to be C236S (βIII and βV), A315T (βIII and βV), V316I (βII), and T351V (βIII and βV) (FIG. 5A). Based on the isotype distribution of the substitutions within this site, the β-tubulin isotypes were divided into three classes. The type-I binding site is characterized by the canonical βI sequence and contains, for the most part, the βII and the βIV isotypes. The type-II binding site is identical to the type-I site with the exception of a V316I substitution found within only the βII isotypes. The type-III binding site has the greatest variation (C236S, A315T and T351V) and includes the βIII and βV isotypes. When the substitutions found within the type-II and type-III binding sites were mapped onto the βI-tubulin structure (Lowe J. et al., J. Mol. Biol. 2001; 313:1045-57), all were observed to be located within a region surrounding the colchicine A-ring (FIG. 5B). While none of these substitutions alter the charge of the surface, C239S and A315T change the polarity of the surface interacting with the A-ring, specifically the three non-polar phenolic methoxy groups.

Colchicine Derivatives

Figure 3A:
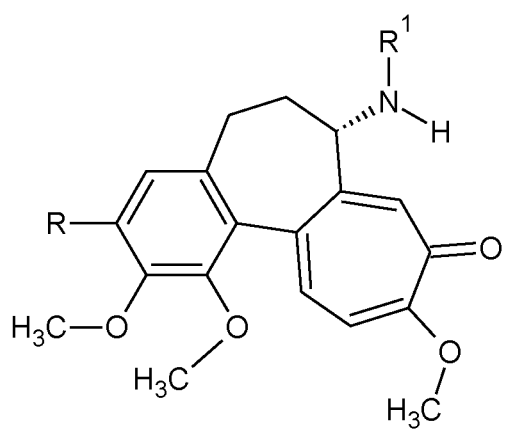
FIG. 3A shows the structure of colchicine with modifications (50) to (54) to colchicine at the R position.

As outlined in FIGS. 2-4, several modifications were made to the basic colchicine and thiocolchicine scaffolds. These modifications were composed of alkane/alkene, ester/ether, aromatic modifications to C1-demethylcolchicine and C3-demethylcolchicine (FIGS. 3 and 3A) or alkane/alkene modifications made to C3-demethylthiocolchicine (FIG. 4). Specific modifications were chosen to probe the spatial and chemical differences between the classes of isotype binding sites.

Modifications made at C1 were designed to probe differences found between residues 315, 316 and 351, while those made at $C_3$ were designed primarily to probe a non-polar cavity that is observed in the co-crystal and located beneath colchicine (Ravelli R. B. et al., Nature. 2004; 428:198-202).

Docking of Colchicine Derivatives

The basic strategy employed for computationally probing colchicine derivatives involved the generation of several ligand orientations, followed by MD-based simulated annealing and a final refinement step incorporating steepest descents and conjugate gradient minimization. Using CDOCKER (Accelrys, Inc., U.S.A.), a total of ten replicas for each of the colchicine derivatives were generated and randomly distributed around the center of the binding site models. Following the initial placement of the derivatives, they were each subjected to MD-based simulated annealing and final refinement by minimization, yielding ten docked poses for each derivative and colchicine in each of the three binding site models. The final step in the docking procedure was scoring of the refined docked poses using the Score Ligand Poses protocol of Discovery Studio. Note that the average energy values were used for the ten poses from each experiment to build the binding energy scores. This procedure yielded 630 ligand conformers, whose energy evaluations were performed.

Binding Enerqy Determination

Binding energies were determined by calculating the total potential energy of each complete systems determined in the docking steps and then subtracting the energy of the bound ligand and that of the apo-dimer (Tables 4 to 6). When the mean binding energies for each of the colchicine derivatives were plotted, trends were consistent across all of the models and there was no apparent differentiation between the type-I, type-II or type-III binding sites (FIG. 6; CH represents colchicine). However, in all of the models, the ester/ether and aromatic derivatives at position C1 exhibited elevated binding energies when compared to colchicine, while the alkane/alkene and thiocolchicine derivatives at positions C1 and C3 had superior binding affinities (Table 4 and FIG. 6). These plots also demonstrated the range of binding energies for each of the derivatives, which is suggestive of the overall appropriateness of the docking fit (FIG. 6). Specifically, those derivatives exhibiting higher binding energies than colchicine tended to have a larger distribution in their binding energies, while those with lower overall binding energies had a narrower distribution. This trend seemed to correlate with the polarity of each of the functional groups at the C1 position. To examine the role these modifications had in vitro, all of the colchicine derivatives were then synthesized and tested in tubulin binding assays.

From these calculations, it is clear that modification of the colchicine amide group increases binding with tubulin (Table 5 and 6). These results also suggest that, on average, modifications made to certain derivatives ((40), (42), (43)) had the lowest energies.

TABLE 4

Calculated and experimental values for colchicine derivative binding. CH is colchicines. The first three columns represent the mean value of ten computational docking experiments. The average binding energies (BE) [kcal mol − 1] for the three binding site models with standard errors are reported. Columns four and five are the kon rates [M − 1 s − 1] for αβII and αβIII isotypes.

| Drug | Type I (BE) | Type II (BE) | Type III (BE) | $k_{on}$ αβII | $k_{on}$ αβIII |
|---|---|---|---|---|---|
| CH | −14.47 ± 0.45 | −14.95 ± 0.36 | −16.29 ± 0.21 | 132 ± 5 | 30 ± 2 |
| (2) | −16.06 ± 0.18 | −18.78 ± 0.44 | −10.45 ± 1.24 | 35.9 | 9.4 ± 1.0 |
| (3) | −13.89 ± 1.08 | −11.42 ± 0.43 | −17.99 ± 0.57 | 36.6[†] | 12 ± 2.4 |
| (4) | −14.63 ± 1.45 | −14.65 ± 0.82 | −14.73 ± 1.60 | 33.2 | 21.3 ± 5.2 |
| (5) | −7.04 ± 1.36 | −10.09 ± 1.17 | −12.75 ± 1.93 | X[‡] | X |
| (6) | −16.15 ± 0.85 | −19.04 ± 0.31 | −16.36 ± 1.25 | 45.7 | 15.3 ± 2.2 |
| (7) | −18.72 ± 0.27 | −17.24 ± 1.33 | −20.92 ± 0.14 | 45.2 | 10.8 ± 0.7 |
| (7a) | −10.83 ± 1.07 | −15.75 ± 1.52 | −17.19 ± 1.69 | 41.9 ± 0.4 | 10 ± 0.4 |
| (8) | −17.9 ± 0.91 | −17.54 ± 0.73 | −21.52 ± 0.36 | 67.7 | 14.9 ± 0.6 |
| (9) | −16.27 ± 0.58 | −15.37 ± 0.57 | −15.32 ± 1.69 | 50.4 | 13.7 ± 0.7 |
| (10) | −12.92 ± 0.79 | −11.59 ± 1.08 | −14.2 ± 0.69 | 74.9 | 15.1 ± 0.4 |
| (11) | −13.44 ± 0.87 | −16.83 ± 0.63 | −16.44 ± 0.76 | 37.9 | 9.2 ± 0.7 |
| (12) | −9.07 ± 0.95 | −8.02 ± 0.70 | −15.42 ± 0.91 | 54.2 | 16 |
| (13) | −10.84 ± 1.15 | −6.91 ± 1.51 | −8.78 ± 1.63 | 35.1 | 11.6 |
| (14) | −11.85 ± 1.32 | −7.67 ± 0.91 | −10.65 ± 0.93 | X | 16.5 |
| (15) | −10.02 ± 0.97 | −7.24 ± 0.94 | −8.82 ± 0.22 | 49.4 | 14.1 |
| (16) | −8.9 ± 1.85 | −9.18 ± 1.08 | −7.32 ± 0.63 | 35.7 | 9.1 |
| (40) | −17.06 ± 0.33 | −10.15 ± 1.31 | −19.84 ± 0.32 | 201.2 ± 10.5 | 66.9 ± 1.4 |
| (41) | −12.2 ± 0.94 | −10.79 ± 0.86 | −12.7 ± 0.53 | 185.2 ± 7.8 | 65.5 ± 1.3 |
| (42) | −13.34 ± 0.42 | −12.3 ± 0.78 | −12.6 ± 1.52 | 138.3 ± 6.5 | 53.4 ± 0.8 |
| (43) | −14.51 ± 0.63 | −13.02 ± 1.05 | −17.25 ± 0.34 | 301.4 ± 20.1 | 98.5 ± 3.4 |

*Did not dissolve at normal pH
[†]Standard deviation not available
[‡]Insufficient data

TABLE 5

Calculated values for colchicine derivative binding. The average binding energies (BE) [kcal mol$^{-1}$] for the three binding site models are reported.

| Drug | Binding | Drug | Binding |
|---|---|---|---|
| (8) | −245.00 | (40) | −390.00 |
| (55) | −455.00 | (67) | −70.00 |
| (56) | −195.00 | (68) | −625.00 |
| (57) | −700.00 | (69) | −485.00 |
| (7) | −470.00 | (42) | −330.00 |
| (58) | −265.00 | (70) | −385.00 |
| (59) | 110.00 | (71) | −300.00 |

TABLE 5-continued

Calculated values for colchicine derivative binding. The average binding energies (BE) [kcal mol$^{-1}$] for the three binding site models are reported.

| Drug | Binding | Drug | Binding |
|---|---|---|---|
| (60) | −520.00 | (72) | −660.00 |
| (7a) | −575.00 | (43) | −290.00 |
| (61) | −515.00 | (73) | −455.00 |
| (62) | −505.00 | (74) | −415.00 |
| (63) | −475.00 | (75) | −665.00 |
| (9)  | −255.00 |      |         |
| (64) | −390.00 |      |         |
| (65) | −240.00 |      |         |
| (66) | −545.00 |      |         |

TABLE 6

Computed relative binding free energy of ChemRoutes colchicine derivatives in human β-tubulin isotypes (I, IIa, III, IVa) with respect to standard colchicine. Units in kJ/mol.

| Drug | Type I (BE) | Type IIa (BE) | Type III (BE) | Type IVa (BE) |
|---|---|---|---|---|
| (83) | 1.18 | −7.76 | −12.07 | −10.21 |
| (84) | 7.00 | −0.21 | −8.70 | 5.40 |
| (85) | 13.51 | −12.97 | 1.12 | 0.42 |
| (89) | 4.50 | −10.43 | −16.65 | −15.38 |
| (90) | 1.04 | −10.66 | −13.01 | −6.79 |
| (91) | −6.92 | −20.69 | −25.44 | −12.86 |

Example 7—Binding Kinetics

In an attempt to determine what aspect of (91) (CCI) may be contributing to the unexpected results described above, docking experiments (previously described in POT Publication No. WO2011022805, incorporated herein by reference) were performed to ascertain whether or not binding energies between the colchicine derivatives and Tubulin isotype β-III may with respect to modifications at the X1 position may contribute to the effects observed in vitro and in vivo.

3D structures of the colchicine derivatives shown in Table 7 below were docked into the colchicine binding site of βIII tubulin (which is structurally identical for beta VI in the colchicine binding site) using Autodock4 program under flexible ligand and rigid receptor condition. AutoDock4 is designed to predict how drug candidates bind to a receptor of known 3D structure and consists of two main programs: autodock performs the docking of the ligand to a set of grids describing the target protein and autogrid pre-calculates these grids. The initial structures of ligands were first minimized using the Amber12: EHT force field (in MOE2013.0802) and they were fully optimized based on RHF/cc-pVDZ level of theory in GAMESS-US version 2010-10-01. βIII Tubulin sequence data (TBB3_HUMAN) obtained from UniProt ID (Q13509) and a homology model was constructed to βIII Tubulin based on Tubulin structure in RCSB Protein Data Bank (1SA0.pdb) by MOE2013.0802.

TABLE 7

Compounds (or the structural modifications made to the colchicine or thiocolchcine backbone) are listed and structurally depicted.

| Compound Name/Structural modification | Structure |
|---|---|
| Colchicine | 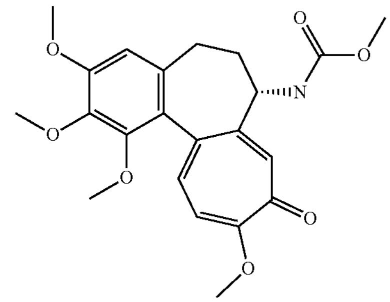 |
| (91) (CCI) | CR-42-024 |
| (89) | CR-42-022 |

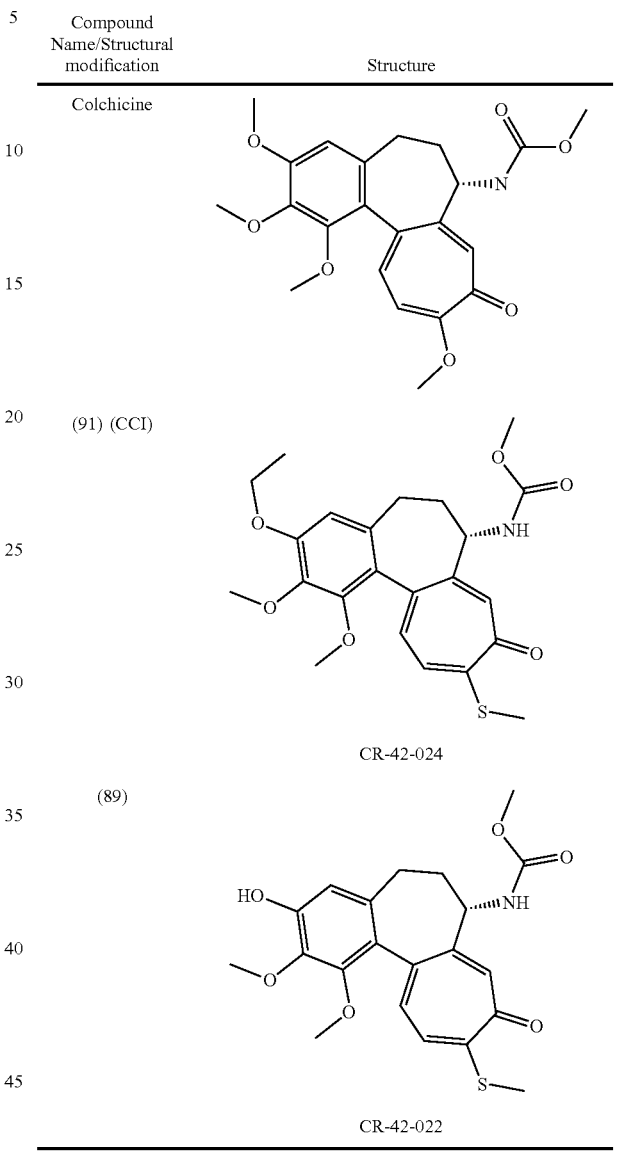

Results

The results of the docking experiments described above are shown in Table 8 below.

TABLE 8

Figure 16:
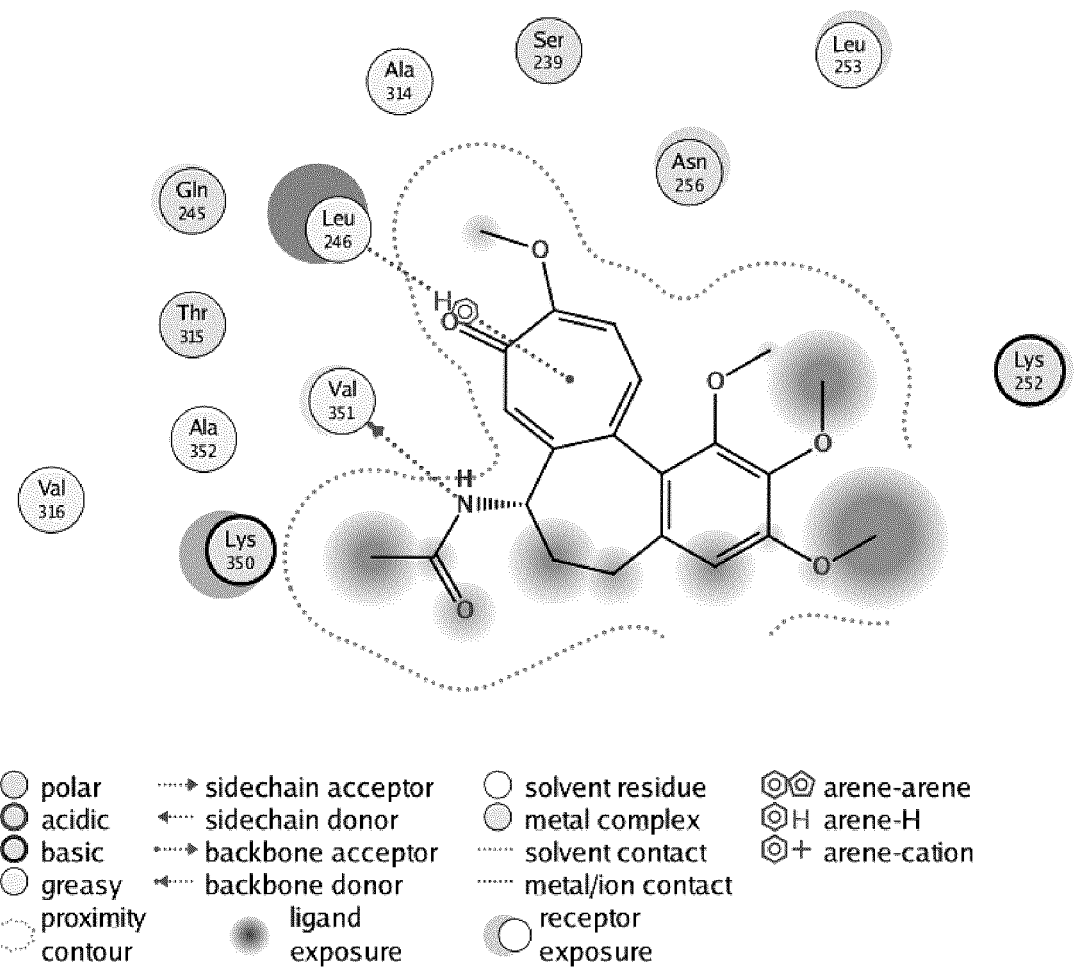
FIG. 16 shows how colchicine interacts with βIII tubulin.
Figure 17:
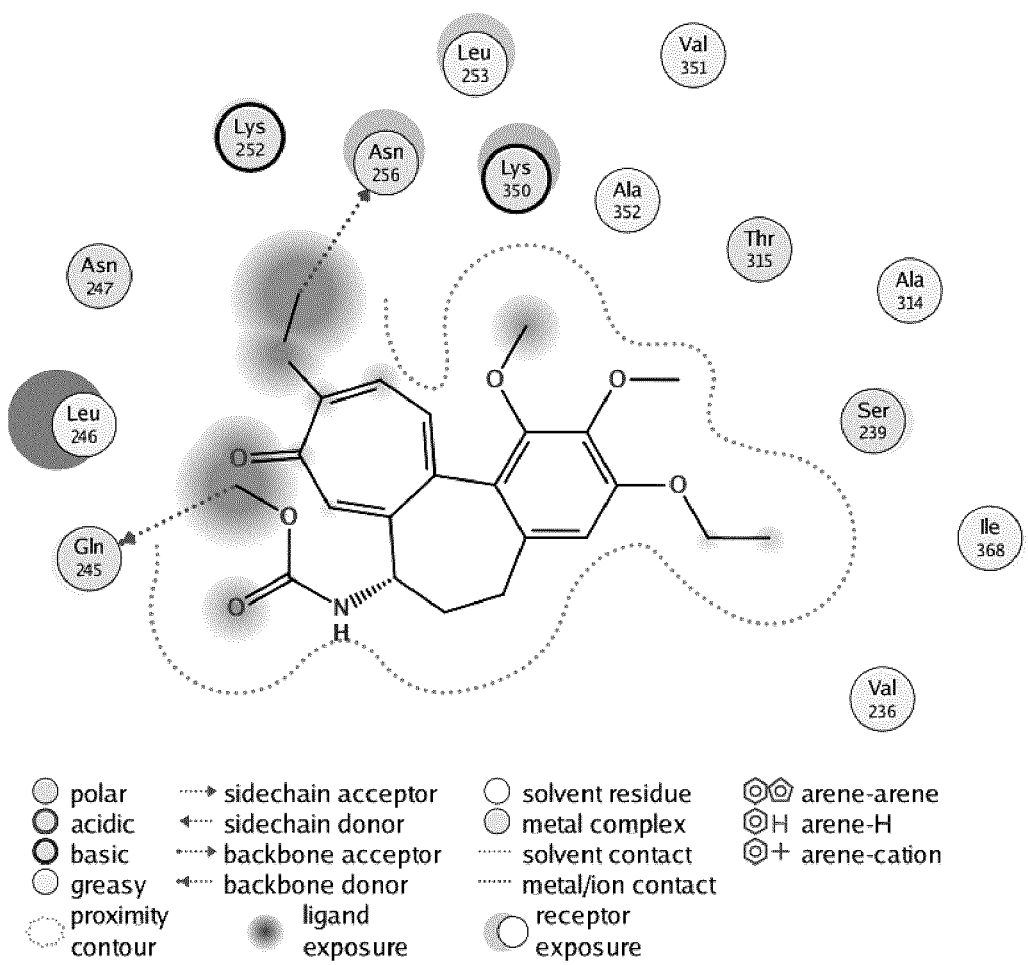
FIG. 17 shows how colchicine derivative (91) (CCI) interacts with βIII tubulin.
Figure 18:
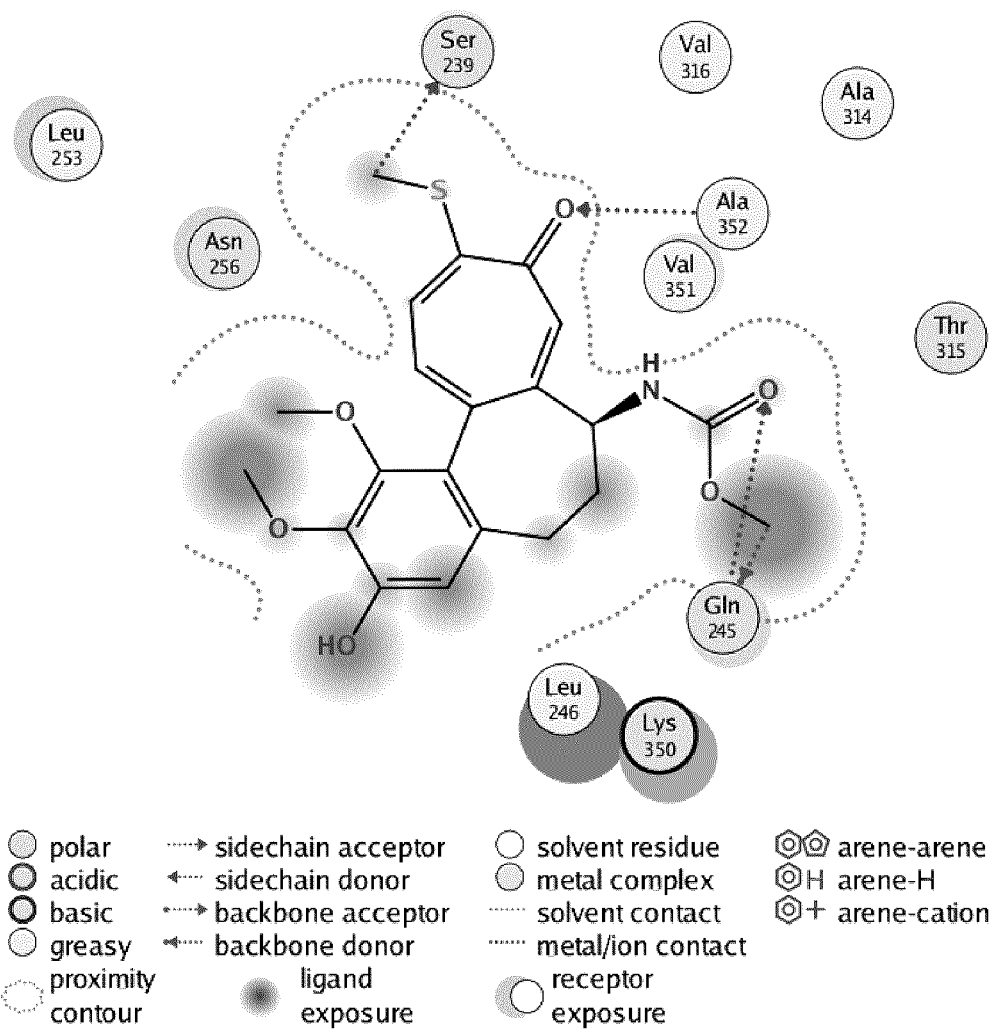
FIG. 18 shows how colchicine derivative (89) interacts with βIII tubulin.

| Name/ Structural modification | Binding energies (Kcal/mol) | Interaction with βIII |
|---|---|---|
| Colchicine | −5.97 | See FIG. 16 |
| (91) (CCI) | −6.2 | See FIG. 17 |
| (89) | −5.42 | See FIG. 18 |

As shown in the above Table 8, a comparison of colchicine and (91) (CCI) with (89) demonstrated that the OH group increased the binding energies to tubulin from −5.97 and −6.2 to −5.42 Kcal/mol. Therefore, having OH can be responsible for increasing the binding energy and reducing the affinity for tubulin. Accordingly, the (91) (CCI) lacking OH, has reduced binding energy and increased affinity for tubulin and therefore increased functional responses in the in vitro and in vivo results presented herein.

Example 8—Mouse Model of Atherosclerosis

Introduction

Atherosclerosis is a chronic inflammatory disease during which the narrowing of arteries occurs due to neo-intimal lesions (1). Immune cells such as neutrophils play a key role in the onset, progression and instability of atherosclerotic lesions (2). When these lesions rupture, they cause multiple cardiovascular complications including myocardial infarction and stroke. Since inflammation plays a key role in atherosclerosis, dampening inflammation is a therapeutic approach that has attracted much attention in the field. A drug that inhibits IL-1β, for instance, improves outcomes in atherosclerosis.

In this study, it is determined that the colchicine derivatives tested in the gout model could be used to treat atherosclerosis since inflammation involving neutrophils plays a role in the pathogenesis of both diseases. The advantage of using these derivatives for the treatment of atherosclerosis is that they are active at significantly lower doses than colchicine and consequently more likely to be less toxic.

Given this data, it is predicted that the colchicine derivatives described herein may play a role in other inflammation-mediated diseases, such as in diseases involving neutrophil-mediated inflammation.

Methods

Animals and Diets

LDLR KO mice were randomly divided into 4 groups and either fed a control (CD) diet (group 1 & 2) or high-fat (group 3 & 4) diet. The high-fat (HF) diet contained 0.2% total cholesterol, 21% total fat by weight (42% kcal from fat), >60% of total fatty acids) and was high in sucrose (34% by weight). The animals and their feed were weighed every week.

Treatment with CCI

Mice in group 2 & 4 were administered a dose of 0.5 μmol/kg CCI subcutaneously (s.c), 3 times a week for 8 weeks. This dose of CCI was chosen since it is the lowest dose that significantly diminishes leukocyte recruitment in the air-pouch model of gout.

Plasma Lipid Measurements

Blood was drawn from mice after the 8-week diet. Serum was prepared from the drawn blood and frozen until analysis. Serum triglycerides and cholesterol were measured in serum of mice by our Multidisciplinary and Microbiology Laboratory Service.

Quantification of the Gross Lesion Area

The aortic lesion 'en face' assay and Sudan IV staining was performed on aortas harvested from all mice. The percent lipid stained area in the aortic branch and the descending aorta was compared between mice using the 'region of interest' tool in ImageJ.

Cytokine Measurements

Blood was drawn from mice after the 8-week diet. Serum was prepared from the drawn blood and frozen until analysis. The levels of cytokines in the serum were measured by Luminex assay. The cytokines assayed were Eotaxin (CCL11), CCL21, G-CSF (CSF-3), RANKL, VEGF-A, IL-1 beta, IL-6 & MCP-1 (CCL2). These cytokines were chosen based on a cytokine signature that was reported to reflect the development of atherosclerosis in ApoE KO mice. The LDLR KO model was used since the inflammatory aspect of atherosclerosis is better represented in this model.

Results

Figure 19:
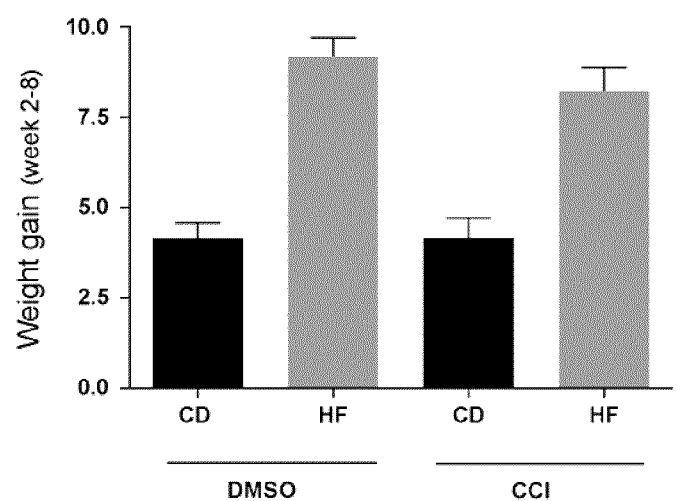
FIG. 19 shows the effect of a high-fat diet and CCI on the weight of wild-type and LDLR KO mice: C57BL/6 mice were fed a control diet (CD) or a high-fat diet (HF) for 8 weeks and subcutaneously injected with 0.5 μmol/kg CCI or vehicle (DMSO), 3 times a week. Mice were weighed 3 times a week. The weight gain of each group of mice between the second and 8th week is shown in the graph.

FIG. 19 shows that the mice treated with CCI and fed the CD or HF diet gained a similar amount of weight as mice not treated with the drug and fed with the same diets over the 8 week period. This is an indication that the mice tolerated the drug for 8 weeks at the dose used, the dose at which CCI dampens MSU-induced leukocyte recruitment in vivo. The mice behaved normally and did not show any signs of suffering.

A significant increase was observed in the amount of triglycerides in the serum of LDLR KO mice fed a HF diet for 8 weeks compared to mice fed the CD diet (FIG. 20). The levels of triglycerides were lower in CCI-treated mice fed the HF diet for 8 weeks than in mice fed the HF diet alone.

A significant increase was observed in the amount of cholesterol in the serum of LDLR KO mice fed a HF diet for 8 weeks compared to mice fed the CD diet (FIG. 21). The levels of cholesterol were lower in CCI-treated mice fed the HF diet than in mice fed the HF diet alone.

FIG. 22A shows that mice fed a HF diet for 8 weeks developed atherosclerotic lesions (stained in red). The percent stained lesion area in the aortic arch or descending aorta of CCI-treated mice on the HF diet was lower than in mice fed the HF diet alone. The percent of the total area of the aortic arch covered by the plaques stained in the 'en face assay' was determined for each mouse (FIG. 22B). The lesions covered a smaller percent of the total area of the aortic arch in LDLR KO mice fed the high-fat diet and our compound (HF+CCI) than in mice fed the HF diet (HF). The percent of the total area of the descending aorta covered by the plaques stained in the 'en face assay' was determined for each mouse (FIG. 22C). The lesions covered a smaller percent of the total area of the descending aorta in LDLR KO mice fed the high-fat diet and our compound (HF+CCI) than in mice fed the HF diet (HF). The majority of mice in the HF+CCI group cover less than 1% of the total area of the descending aorta. In contrast, in the HF diet group, the lesions cover an area between 1, 2 and 8%.

Figure 23:
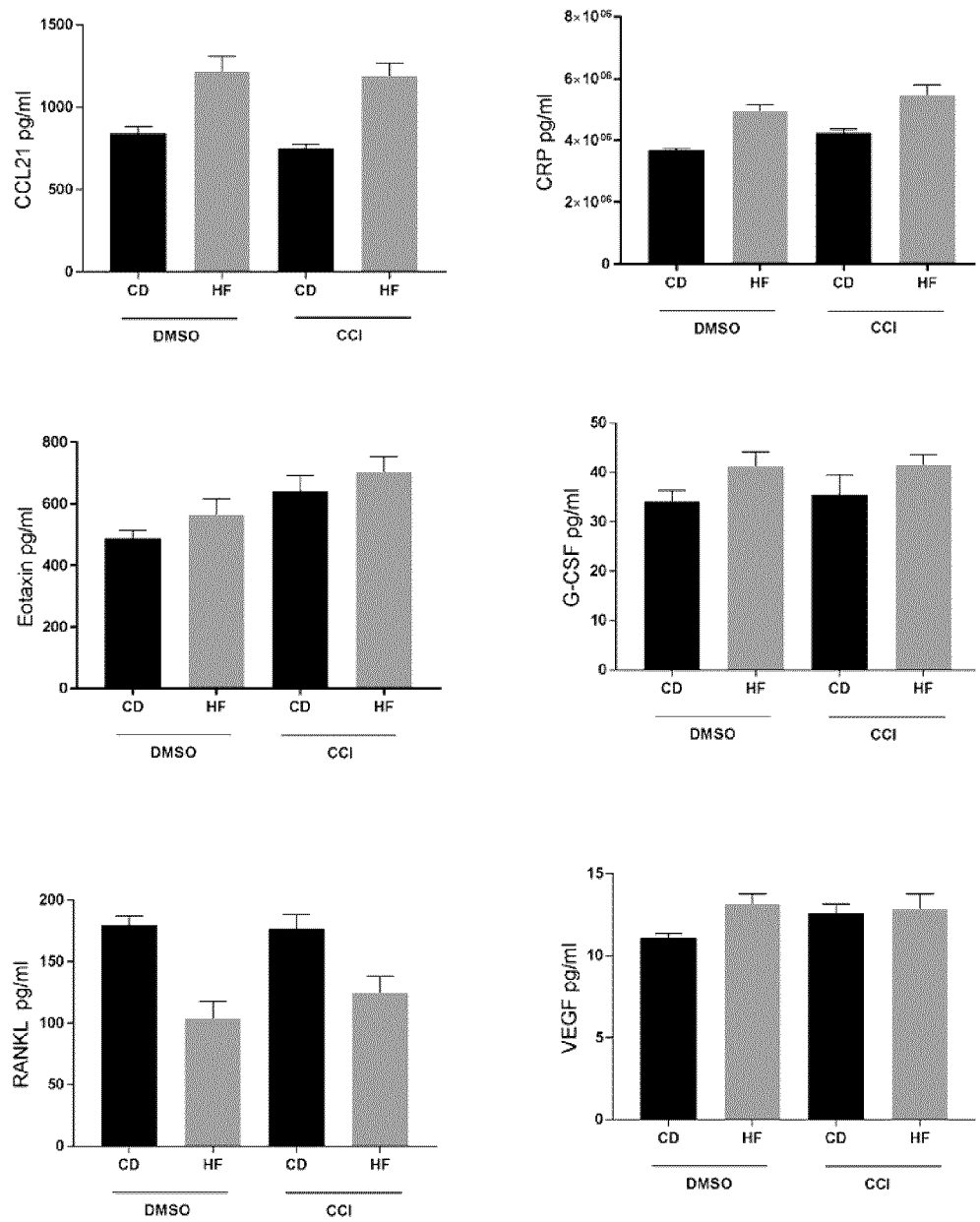

An increase in the levels of all cytokines was observed in the serum of mice fed the HF diet for 8 weeks compared to mice fed the CD with the exception of RANKL (FIG. 23). The level of RANKL decreased after the 8 week, HF diet. CCI had no significant effect on the levels of these cytokines in the serum of LDLR KO mice fed with the HF diet for 8 weeks.

Discussion

Atherosclerosis is a chronic inflammatory disease of the walls of arteries (1). Several inflammatory cells and mediators contribute to the initiation and progression of this disease (2-4). The inflammatory component of this disease is thus a potential therapeutic target. We tested the ability of the colchicine derivative, CCI, to slow the progression and/or development of atherosclerosis in the LDLR KO mouse model. Together, our findings indicate that CCI has the potential to affect the development and/or progression of atherosclerosis in that it diminishes several variables associated with this chronic inflammatory disease including serum levels of cholesterol and triglycerides as well as the percent area of the aorta stained for atherosclerotic plaques. Moreover, this study provides further evidence that CCI is well tolerated by mice for a period of at least 2 months. The lower toxicity of CCI compared to colchicine and the tendency for it to diminish several reliable indicators of atherosclerosis renders it a promising therapeutic alternative for the treatment of this disease in humans.

REFERENCES

1. Shapiro, M D and Fazio, S. From Lipids to Inflammation. 2016. Circulation Research 118:732–749.
2. Hartwig, H; Silvestre R; Daemen M; Lutgens, E and Soehnlein, O. Neutrophils in atherosclerosis. Hämostaseologie 2015; 35: 121-127.
3. Stefan Mark Nidorf and Peter Lindsay Thompson. Why Colchicine Should Be Considered for Secondary Prevention of Atherosclerosis: An Overview. 2019. Clinical Therapeutics 41: 41-48.
4. Lin B, Pillinger M, Shah B, et al. Use of colchicine in atherosclerotic heart disease. 2018. Curr Res Integr Med 3(S1):2-4.

What is claimed is:

1. A method for treating neutrophil-driven inflammation in a mammal, comprising administering to the mammal in need thereof a therapeutically effective amount of a compound of Formula I:

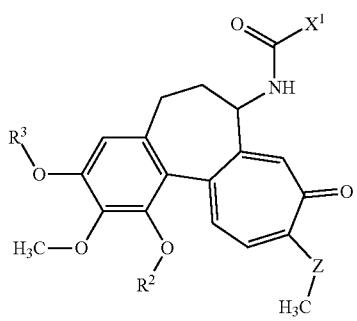

Formula I wherein:
Z is O or S;
$X^1$ is $OR^{10}$ and $R^{10}$ is selected from a substituted or unsubstituted $C_1$-$C_6$ alkyl, a substituted or unsubstituted $C_2$-$C_6$ alkenyl, or $C_2$-$C_6$ alkynyl or X1 is —$CR^4R^5R^6$, wherein $R^4$ and $R^5$ are each independently selected from H, or substituted or unsubstituted alkyl, and $R^6$ is —$NR(CO)CR^7R^8R^9$, wherein R is selected from H and a substituted or unsubstituted alkyl, and $R^7$, $R^8$, and $R^9$ are each selected from H, halo group, and a substituted or unsubstituted alkyl;
$R^2$ and $R^3$ are each independently selected from a substituted or unsubstituted alkyl, a substituted or unsubstituted aryl, or a substituted or unsubstituted alkylaryl;
Wherein the substituents are selected from a group consisting of cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, ialkylaminocarbonyl, arylcarbonyl, aryloxycarbonyl, alkylsulfonyl, and arylsulfonyl;
a pharmaceutically-acceptable salt thereof, hydrate thereof, solvate thereof, tautomer thereof, optical isomer thereof, or combination thereof;
wherein the compound of Formula I inhibits production of an inflammatory mediator at a lower dose than colchicine; and wherein the neutrophil-driven inflammation is associated with pseudogout, gout, cardiovascular disease, vasculitis, or combinations thereof.

2. The method according to claim 1, wherein the neutrophil-driven inflammation is associated with cardiovascular disease.

3. The method according to claim 2, wherein the cardiovascular disease is coronary atherosclerosis.

4. The method according to claim 1, wherein the neutrophil-driven inflammation is associated with gout.

5. The method according to claim 1, wherein $R^2$ and $R^3$ are each independently selected from a substituted or unsubstituted $C_1$-$C_6$ alkyl.

6. The method according to claim 5, wherein $R^2$ and $R^3$ are each independently selected from methyl, ethyl or propyl.

7. The method according to claim 6, wherein $R^2$ is methyl and $R^3$ is ethyl or propyl.

8. The method according to claim 1, wherein when $R^2$ and $R^3$ are both methyl, $X^1$ is not methyl.

9. The method according to claim 1, wherein $R^{10}$ is selected from methyl or ethyl.

10. The method according to claim 1, wherein the compound is:

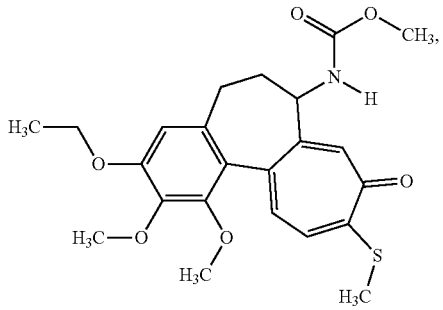

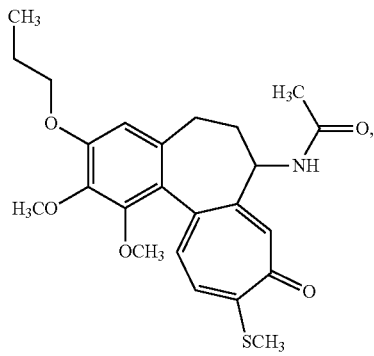

-continued

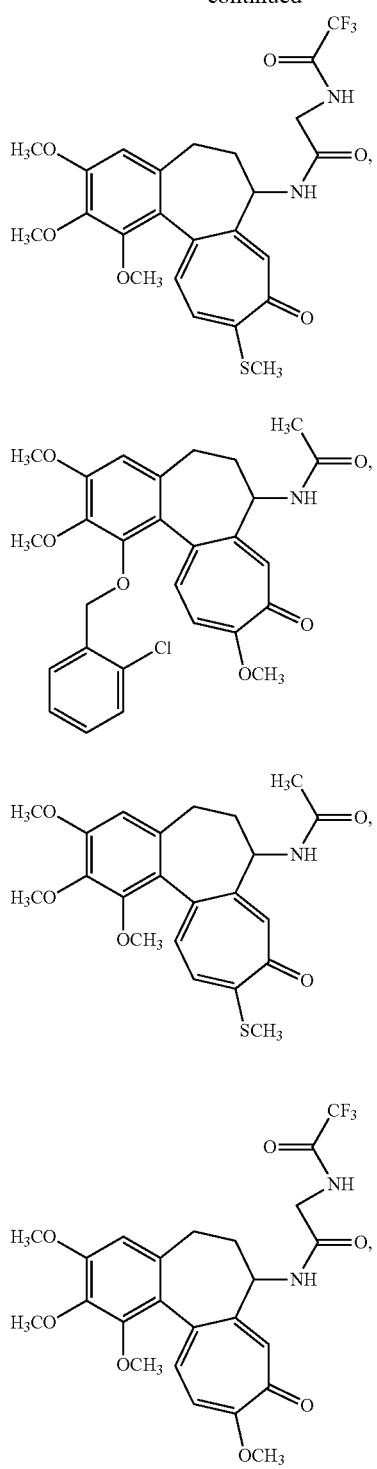

or a pharmaceutically-acceptable salt thereof, hydrate thereof, solvate thereof, tautomer thereof, optical isomer thereof, or combination thereof.

11. The method according to claim 1, wherein the compound binds to β-tubulin at a colchicine-binding site.

12. The method according to claim 11, wherein the β-tubulin is β-VI, β-V, β-I, or combinations thereof.

13. The method according to claim 11, wherein the compound:
has a binding energy that is less than the binding energy of colchicine;
is less toxic than colchicine;
more specifically targets neutrophils compared to colchicine;
inhibits the increase in intracellular calcium concentration at a lower dose than colchicine;
inhibits the increase in intracellular calcium concentration at a dose that is at least about 10-fold lower than colchicine;
inhibits the increase in intracellular calcium concentration at a dose that is about 10-fold to about 100-fold lower than a dose for colchicine;
inhibits the increase in intracellular calcium concentration at a dose of about 0.1 μM, or combinations thereof.

14. The method according to claim 1, wherein the compound inhibits the production of the inflammatory mediator at a dose that is about 10-fold to about 100-fold lower than a dose for colchicine.

15. The method according to claim 1, wherein the compound inhibits the production of the inflammatory mediator at a dose of about 0.1 μM.

16. The method according to claim 1, wherein the inflammatory mediator is selected from IL-8, IL-1, superoxide, or a combination thereof.

17. The method according to claim 1, wherein the compound has an inhibitory effect on immune function in response to monosodium uric acid (MSU)-induced inflammation.

18. The method according to claim 17, wherein the inhibitory effect is more potent than that of colchicine.

19. The method according to claim 18, wherein the inhibitory effect is at least about 10-fold greater than that of colchicine, the inhibitory effect occurs at a concentration of about 0.1p M, or combinations thereof.

20. The method according to claim 1, wherein $R^7$, $R^8$, and $R^9$ are a fluoro group.

21. The method according to claim 1, wherein:
$R^{10}$ is selected from $C_1$-$C_6$ alkyl, $C_2$-$C_6$ alkenyl, and $C_2$-$C_6$ alkynyl;
$R^4$ and $R^5$ are each independently selected from H and alkyl;
R is selected from H and alkyl;
$R^7$, $R^8$, and $R^9$ are each selected from H, halo group, and alkyl; and
$R^2$ and $R^3$ are each independently selected from alkyl, aryl, and alkylaryl.

22. A method for treating atherosclerosis in a mammal in need thereof, comprising administering to the mammal a therapeutically effective amount of:

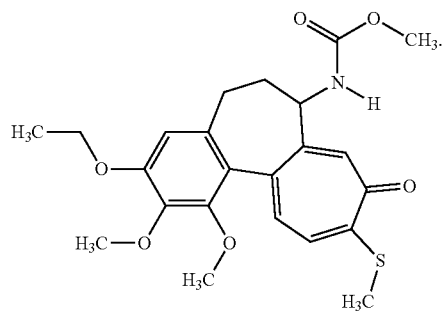 [SMILES: CCOc1cc2c(c(OC)c1OC)-c1ccc(SC)c(=O)cc1C(NC(=O)OC)CC2]

* * * * *